(12) United States Patent
Barlaam et al.

(10) Patent No.: US 8,569,298 B2
(45) Date of Patent: Oct. 29, 2013

(54) PYRIDINE COMPOUNDS

(75) Inventors: Bernard Christophe Barlaam, Reims (FR); Patrick Ple, Reims (FR); Kevin Michael Foote, Macclesfield (GB); Clifford David Jones, Macclesfield (GB)

(73) Assignee: Astrazeneca AB, Sodertalje (SE)

( * ) Notice: Subject to any disclaimer, the term of this patent is extended or adjusted under 35 U.S.C. 154(b) by 93 days.

(21) Appl. No.: 12/999,025

(22) PCT Filed: Jun. 15, 2009

(86) PCT No.: PCT/GB2009/050675
§ 371 (c)(1),
(2), (4) Date: Mar. 17, 2011

(87) PCT Pub. No.: WO2009/153589
PCT Pub. Date: Dec. 23, 2009

(65) Prior Publication Data
US 2011/0166139 A1    Jul. 7, 2011

Related U.S. Application Data

(60) Provisional application No. 61/073,055, filed on Jun. 17, 2008.

(51) Int. Cl.
*C07D 217/24* (2006.01)
*C07D 401/12* (2006.01)
*A61K 31/4709* (2006.01)

(52) U.S. Cl.
USPC ............. 514/236.5; 514/253.09; 514/309; 514/318; 514/341; 544/131; 544/311; 544/364; 546/141; 546/211; 546/275.4

(58) Field of Classification Search
None
See application file for complete search history.

(56) References Cited

FOREIGN PATENT DOCUMENTS

| WO | 01/64655 A1 | 9/2001 |
|---|---|---|
| WO | 2004/080980 A1 | 9/2004 |
| WO | 2005/016984 A1 | 2/2005 |
| WO | 2005/123191 A1 | 12/2005 |
| WO | 2006/021454 A2 | 3/2006 |
| WO | 2006/021457 A2 | 3/2006 |
| WO | 2006/074057 A2 | 7/2006 |
| WO | 2007/063384 A2 | 6/2007 |
| WO | 2007/072158 A2 | 6/2007 |
| WO | 2008/073687 A2 | 6/2008 |
| WO | 2008/115369 A2 | 9/2008 |

OTHER PUBLICATIONS

Wu et al., Toxicology, 236, pp. 1-6, 2007.*
Angelucci et al., "Targeting Vascular Cell Migration as a Strategy for Blocking Angiogenesis: The Central Role of Focal Adhesion Protein Tyrosine Kinase Family", Current Pharmaceutical Design (2007); vol. 13; pp. 2129-2145.
Braren et al., "Endothelial FAK is Essential for Vascular Network Stability, Cell Survival and Lamellipodial Formation", The Journal of Cell Biology (2006); vol. 172; No. 1; pp. 151-162.
Chatzizacharias et al., "Focal Adhesion Kinase: A Promising Target for Anticancer Therapy", Expert Opin. Ther. Targets (2007); vol. 11; No. 10; pp. 1315-1328.
Chatzizacharias et al., "Clinical Significance of FAK Expression in Human Neoplasia", Histology & Histopathology (2008); vol. 23; pp. 629-650.
Delvare et al, "Highly Regioselective Palladium-catalyzed C2-amination of 2,4-dichloropyridines: Scope and Limitations", Synthesis (2011); No. 15; pp. 2431-2436.
Mitra et al., "Integrin-regulated FAK-Src Signaling in Normal and Cancer Cells", Current Opinion in Cell Biology (2006); vol. 18; pp. 516-523.
Morgentin et al, "Two-Directional Approach for the Rapid Synthesis of 2,4-Bis-Aminoaryl Pyridine Derivatives", Synthetic Communications (2012); vol. 42; No. 1; pp. 8-24.

* cited by examiner

*Primary Examiner* — Zinna Northington Davis

(57) ABSTRACT

The present invention relates to compounds that inhibit of focal adhesion kinase function, processes for their preparation, pharmaceutical compositions containing them as the active ingredient, to their use as medicaments and to their use in the manufacture of medicaments for use in the treatment in warm-blooded animals such as humans of diseases such as cancer.

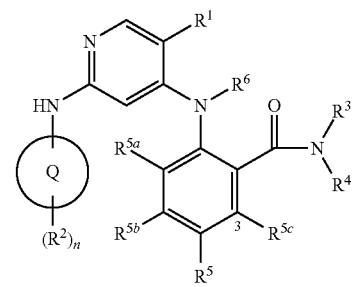

(I)

17 Claims, No Drawings

PYRIDINE COMPOUNDS

This application is a 35 U.S.C. §371 national stage filing of International Application No. PCT/GB2009/050675, filed Jun. 15, 2009, and claims priority under 35 U.S.C. §119(e) to U.S. provisional application Ser. No. 61/073,055, filed Jun. 17, 2008, entitled "COMPOUNDS 397", the contents of which are hereby incorporated by reference.

FIELD OF THE INVENTION

The present invention relates to novel pyridine derivatives, to processes for their preparation, and to compositions containing them. In addition, the present invention relates to the use of the pyridine derivatives in therapy, particularly methods for the treatment and prevention of cancers.

BACKGROUND OF THE INVENTION

Focal adhesion kinase (FAK) is a member of the non-receptor sub-family of protein tyrosine kinases and is expressed in various tissues and cell types. FAK acts as an early modulator in the integrin signalling cascade so that integrin clustering in response to various stimuli results in FAK autophosphorylation at Tyr397. This creates a motif that is recognised by various SH2 domain containing proteins, such as src. The FAK-src complex binds and phosphorylates many downstream molecules such as p130Cas, growth factor receptor bound protein-2 (Grb2) and phosphoinositide-3 kinase (PI3K) thereby transducing signals by many different, complex pathways which interact with each other[1].

In normal cells FAK regulates various basic cellular functions such as proliferation and growth, protection from apoptosis, adhesion and cell spreading, invasion and migration. Elevated FAK expression, activity or signalling is associated with malignancy in a variety of cancer cells leading to promotion of cancer cell proliferation, increased invasion in vitro and an increase in metastases in vivo[4].

Additionally FAK appears to be a key molecule in the activation of several signalling pathways initiated by angiogenic factors, including proliferation, migration and differentiation. Specific endothelial cell deletion of FAK revealed it to be crucial for vascular stability during vascular development[3]

Therefore FAK may be useful in the treatment of pathological angiogensis, for example as an anti-angiogenic therapy in diseases such as cancer and retinopathy. FAK inhibitors may also have beneficial effects on the proliferation or invasive ability of tumour cells[2]. There is emerging evidence of a potential correlation between FAK expression with malignant transformation and therefore FAK inhibition could slow down disease progression.

International Patent Applications WO2008/115369, WO2008/073687, WO2007/072158, WO2007/0633848, WO2006/074057, WO2006/021457, WO2006/021454, WO2005/123191, WO2005/016894, WO2004/080980 and WO2001/64655 disclose compounds that are stated to have FAK inhibitory properties. The compound PF-00562271 is in early development as a FAK inhibitor for use in the treatment of cancer.

There is however a need to find further compounds that are FAK inhibitors, particularly compounds with appropriate pharmacokinetic and pharmacodynamic drug properties, and also that exhibit appropriate selectivity profile(s) against other kinases and receptors.

1. Chatzizacharias, N. A. et al. Expert Opin. Ther. Targets. 2007; 11(10):1315-1328
2. Angelucci, A et al. Current Pharmaceutical Design. 2007; 13:2129-2145
3. Braren, R. et al. JCB 2006; 1:151-162
4. Mitra, S K. Current opinion in Cell Biology 2006; 18:516-523
5. Chatzizacharias, N. A. et al. Histology Histopathol. 2008; 23: 629-650

SUMMARY OF THE INVENTION

In accordance with the present invention, the applicants have hereby discovered novel pyridine compounds, or pharmaceutically acceptable salts thereof, which possess FAK inhibitory activity and are accordingly expected to be useful for their anti-proliferation and/or proapoptotic and/or anti-invasive and/or anti-cell motility and/or anti-angiogenic activity and in methods of treatment of the human or animal body, for example in inhibiting tumour growth and metastasis in cancers. The invention also relates to processes for the manufacture of said pyridine compounds, or pharmaceutically acceptable salts thereof, to pharmaceutical compositions containing them and to their use in the manufacture of medicaments for use in the production of anti-proliferation and/or proapoptotic and/or anti-invasive and/or anti-cell motility and/or anti-angiogenic activity in warm-blooded animals such as man.

Also in accordance with the present invention the applicants provide methods of using such pyridine compounds, or pharmaceutically acceptable salts thereof, in the treatment of cancer.

The properties of the compounds claimed in this invention are expected to be of value in the treatment of disease states associated with cell proliferation and pathological angiogenesis. By "pathological angiogenesis" is meant undesirable angiogenesis that results in an undesirable medical condition or disease such as ocular diseases with retinal vessel proliferation, for example age-related macular degeneration (AMD). Pathological angiogenesis also occurs in many solid tumours such as those mentioned herein and the compounds according to the invention may be useful in the inhibition of such angiogenesis. Particularly the compounds according to the invention, or pharmaceutically acceptable salts thereof, are expected to be useful in the treatment of cancers (solid tumours and leukaemia), for example in the treatment or prophylaxis of cancers selected from oesophageal cancer, myeloma, hepatocellular, pancreatic cancer, cervical cancer, ewings tumour, neuroblastoma, kaposis sarcoma, ovarian cancer, breast cancer, colorectal cancer, prostate cancer, bladder cancer, melanoma, lung cancer—non small cell lung cancer (NSCLC), and small cell lung cancer (SCLC), gastric cancer, head and neck cancer, renal cancer, lymphoma and leukaemia; particularly ovarian cancer, breast cancer, colorectal cancer, prostate cancer, pancreatic cancer and lung cancer—NSCLC and SCLC.

DETAILED DESCRIPTION OF THE INVENTION

According to a first aspect of the present invention there is provided a compound of formula I:

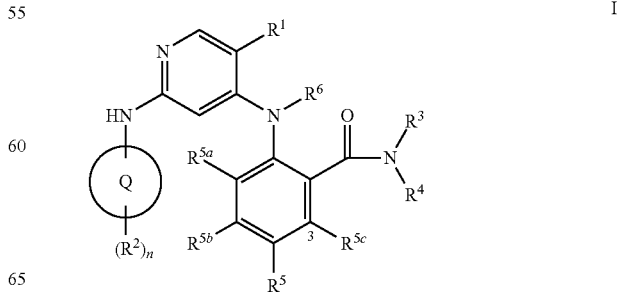

I wherein:

ring Q is selected from pyrazolyl and imidazolyl;

$R^1$ is selected from halo, trifluoromethyl, cyclopropyl, cyano, $C_{1-4}$alkyl and $C_{1-4}$alkoxy;

n is 0, 1, 2 or 3; wherein the values of $R^2$ may be the same or different;

$R^2$ is selected from halo, nitro, cyano, hydroxy, trifluoromethoxy, amino, carboxy, carbamoyl, mercapto, ureido, sulfonylamino, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$amino, N'—($C_{1-6}$alkyl)ureido, N',N'—($C_{1-6}$alkyl)$_2$ureido, N'—($C_{1-6}$alkyl)-N—($C_{1-6}$alkyl)ureido, N',N'—($C_{1-6}$alkyl)$_2$-N—($C_{1-6}$alkyl)ureido, $C_{1-6}$alkanoylamino, N—($C_{1-6}$alkyl)-$C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkylsulfonylamino, N—($C_{1-6}$alkyl)aminosulfonyl, N,N—($C_{1-6}$alkyl)$_2$aminosulfonyl, $C_{1-6}$alkoxycarbonyl, $C_{1-6}$alkoxycarbonylamino, N—($C_{1-6}$alkyl)$C_{1-6}$alkoxycarbonylamino, $C_{1-6}$alkylsulfonylaminocarbonyl, N—($C_{1-6}$alkyl) $C_{1-6}$alkylsulfonylaminocarbonyl, carbocyclyl-$X^1$—, heterocyclyl-$X^2$— and heteroaryl-$X^3$—;

wherein $R^2$ may be optionally substituted on carbon by one or more $R^7$; and wherein if a heterocyclyl or heteroaryl within $R^2$ contains an —NH— moiety that nitrogen may be optionally substituted by a group selected from $R^8$;

and wherein any heterocyclyl within $R^2$ optionally bears 1 or 2 oxo or thioxo substituents;

or two adjacent $R^2$ groups together with the carbon atoms to which they are attached form a carbocyclic, heteroaromatic or heterocyclic ring, which carbocyclic, heterocyclic or heteroaromatic ring may be optionally substituted on carbon by one or more $R^9$; and wherein if said heterocyclic or heteroaromatic ring so formed contains an —NH— moiety that nitrogen may be optionally substituted by a group selected from $R^{10}$; and wherein a carbocyclic or heterocyclic so formed optionally bears 1 oxo substituent;

$R^3$ is selected from hydrogen, hydroxy, $C_{1-4}$alkyl and $C_{1-4}$alkoxy; and wherein $R^3$ may be optionally substituted on carbon by one or more substituents selected from hydroxy, amino, $C_{1-4}$alkoxy, N—($C_{1-4}$alkyl)amino and N,N—($C_{1-4}$alkyl)$_2$amino;

$R^4$ is selected from hydrogen and $C_{1-4}$alkyl; and wherein $R^4$ may be optionally substituted on carbon by one or more substituents selected from hydroxy, amino, $C_{1-4}$alkoxy, N—($C_{1-4}$alkyl)amino and N,N—($C_{1-4}$alkyl)$_2$amino;

or $R^3$ and $R^4$ together with the nitrogen atom to which they are attached form a 4 or 5 membered heterocyclyl ring, which heterocyclyl ring may be optionally substituted on carbon by one or more $C_{1-4}$alkyl;

or the C(O)N$R^3R^4$ group together with the carbon atom to which it is attached and the $R^{5c}$ group together with the carbon atom to which it is attached (3-position of the phenyl ring) form a heterocyclic ring, which heterocyclic ring contains a —C(O)N($R^3$)— group as a ring member; wherein $R^3$ is as hereinbefore defined, or the N($R^3$) ring member together with an adjacent ring member together form a heterocyclic ring;

and wherein any heterocyclic ring so formed by the C(O)N$R^3R^4$ or N$R^3$ ring member may be optionally substituted on carbon by one or more $R^{3a}$ selected from $C_{1-4}$alkyl, $C_{1-4}$alkoxy, halo, cyano, hydroxy and oxo; and wherein if said heterocyclyl ring contains an —NH— moiety that nitrogen may be optionally substituted by $R^{3b}$ selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)carbamoyl;

$R^5$ is selected from hydrogen, halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_b$ wherein b is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl, $C_{1-6}$alkylsulfonylamino, carbocyclyl-$X^7$—, heterocyclyl-$X^8$— and heteroaryl-$X^9$—;

and wherein $R^5$ may be optionally substituted on carbon by one or more groups selected from halo, nitro, cyano, hydroxy, amino, $C_{1-4}$alkyl, $C_{1-4}$alkoxy, N—($C_{1-4}$alkyl)amino, N,N—($C_{1-4}$alkyl)$_2$amino, carbocyclyl-$X^{10}$—, heterocyclyl-$X^{11}$— and heteroaryl-$X^{12}$—; and wherein if a heterocyclyl or heteroaryl within $R^5$ contains an —NH— moiety that nitrogen may be optionally substituted by a group selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulfonyl;

and wherein any heterocyclyl within $R^5$ optionally bears 1 or 2 oxo or thioxo substituents;

$R^{5a}$ is selected from hydrogen and halo;

$R^{5b}$ and $R^{5c}$ are independently selected from hydrogen, halo, nitro, cyano, hydroxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_c$ wherein c is 0 to 2, $C_{1-4}$alkoxycarbonyl, $C_{1-4}$alkoxycarbonylamino, N—($C_{1-4}$alkyl)sulfamoyl, N,N—($C_{1-4}$alkyl)$_2$sulfamoyl and $C_{1-4}$alkylsulfonylamino;

and wherein $R^{5b}$ and $R^{5c}$ may be independently optionally substituted on carbon by one or more groups selected from halo, nitro, cyano, hydroxy, amino, $C_{1-4}$alkoxy, N—($C_{1-4}$alkyl)amino and N,N—($C_{1-4}$alkyl)$_2$amino;

$R^6$ is selected from hydrogen and $C_{1-4}$alkyl;

$R^7$ and $R^9$ are independently selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl, $C_{1-6}$alkylsulfonylamino, carbocyclyl-$X^4$—, heterocyclyl-$X^5$— and heteroaryl-$X^6$—; wherein $R^7$ may be optionally substituted on carbon by one or more $R^{11}$; and wherein if any heterocyclyl in $R^7$ and $R^9$ contains an —NH— moiety that nitrogen may be is optionally substituted by a group selected from $R^{12}$;

and wherein any heterocyclyl within $R^7$ and $R^9$ optionally bears 1 or 2 oxo or thioxo substituents;

$R^8$, $R^{10}$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulfonyl; wherein $R^8$, $R^{10}$ and $R^{12}$ may be optionally substituted on carbon by one or more $R^{13}$; and $R^{11}$ and $R^{13}$ are independently selected from halo, nitro, cyano, hydroxy, trifluoromethoxy, trifluoromethyl, amino, carboxy, carbamoyl, mercapto, sulfamoyl, methyl, ethyl, cyclopropyl, cyclobutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl and N-methyl-N-ethylsulfamoyl;

$X^1$, $X^2$ and $X^3$ are independently selected from a direct bond, —O—, —N($R^{22}$)—, —S—, —C(O)—, —N($R^{14}$)C(O)—, —C(O)N($R^{14}$)—, —N($R^{16}$)CON($R^{17}$)—, —OC($R^{18}$)$_2$—, —SC($R^{19}$)$_2$— and —N($R^{20}$)C($R^{21}$)$_2$—;

$X^4$, $X^5$ and $X^6$ are independently selected from a direct bond, —O—, —N($R^{22}$)—, —C(O)—, —N($R^{14}$)C(O)—, —C(O)N($R^{14}$)—, —S(O)$_e$—, —SO$_2$N($R^{15}$)—, —N($R^{15}$)SO$_2$—, —N($R^{16}$)CON($R^{17}$)—, —OC($R^{18}$)$_2$—, —SC($R^{19}$)$_2$— and —N($R^{20}$)C($R^{21}$)$_2$—;

$X^7$, $X^8$ and $X^9$ are independently selected from a direct bond, —O—, —N($R^{22}$)—, —S—, —C(O)—, —N($R^{14}$)C(O)—, —C(O)N($R^{14}$)—, —N($R^{16}$)CON($R^{17}$)—, —OC($R^{18}$)$_2$—, —SC($R^{19}$)$_2$— and —N($R^{20}$)C($R^{21}$)$_2$—;

$X^{10}$, $X^{11}$ and $X^{12}$ are independently selected from a direct bond, —O—, —N($R^{22}$)—, —C(O)—, —N($R^{14}$)C(O)—, —C(O)N($R^{14}$)—, —S(O)$_e$—, —SO$_2$N($R^{15}$)—, —N($R^{15}$)SO$_2$—, —N($R^{16}$)CON($R^{17}$)—, —OC($R^{18}$)$_2$—, —SC($R^{19}$)$_2$— and —N($R^{20}$)C($R^{21}$)$_2$—; and $R^{14}$, $R^{15}$, $R^{16}$, $R^{17}$, $R^{18}$, $R^{19}$, $R^{20}$, $R^{21}$ and $R^{22}$ are independently selected from hydrogen or $C_{1-6}$alkyl and e is independently 0-2;

or a pharmaceutically acceptable salt thereof.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl$C_{1-6}$alkyl" includes phenyl$C_{1-4}$alkyl, benzyl, 1-phenylethyl and 2-phenylethyl.

The term "$C_{m-n}$" or "$C_{m-n}$ group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "$C_{1-6}$alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene and the like.

"$C_{2-6}$alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene and the like.

"$C_{2-6}$alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"$C_{3-7}$cycloalkyl" means a hydrocarbon ring containing from 3 to 7 carbon atoms, for example, cyclopropyl, cyclobutyl, cyclopentyl, cyclohexyl, cycloheptyl or bicyclo[2.2.1]heptyl.

"$C_{3-7}$cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"$C_{3-7}$cycloalkyl$C_{1-6}$alkylene" means a $C_{3-7}$cycloalkyl group covalently attached to a $C_{1-6}$alkylene group, both of which are defined herein.

The term "halo" refers to fluoro, chloro, bromo and iodo.

"Haloalkyl" means alkyl substituted with one or more same or different halo atoms, e.g., —CH$_2$Cl, —CF$_3$, —CH$_2$CF$_3$, —CH$_2$CCl$_3$, and the like.

The term "heterocyclyl", "heterocyclic" or "heterocycle" means a non-aromatic is saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl and substituted cyclic ethers. Heterocycles containing nitrogen include, for example, azetidinyl, pyrrolidinyl, piperidinyl, piperazinyl, tetrahydrotriazinyl, tetrahydropyrazolyl and the like. Typical sulfur containing heterocycles include tetrahydrothienyl, dihydro-1,3-dithiol, tetrahydro-2H-thiopyran and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl and octahydrobenzothiazolyl. For heterocycles containing sulfur, the oxidized sulfur heterocycles containing SO or SO$_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl$C_{1-6}$alkyl" means a heterocyclyl group covalently attached to a $C_{1-6}$alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, t-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4] oxazinyl Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl$C_{1-6}$alkyl" means a heteroaryl group covalently attached to a $C_{1-6}$alkylene group, both of which are defined herein. Examples of heteroalkyl groups include pyridin-3-ylmethyl, 3-(benzofuran-2-yl)propyl and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like.

The term "aryl$C_{1-6}$alkyl" means an aryl group covalently attached to a $C_{1-6}$alkylene group, both of which are defined herein. Examples of aryl$C_{1-6}$alkyl groups include benzyl, phenylethyl and the like A "carbocyclyl", "carbocyclic" or "carbocycle" group is a saturated, partially saturated or unsaturated, mono or bicyclic carbon ring that contains 3-12 atoms; wherein a —$CH_2$— group within the carbocyclic can optionally be replaced by a —C(O)—. Particularly "carbocyclyl" is a monocyclic ring containing 5 or 6 atoms or a bicyclic ring containing 9 or 10 atoms. Suitable values for "carbocyclyl" include $C_{3-7}$cycloalkyl, $C_{3-7}$cycloalkenyl and aryl, for example "carbocyclyl" includes cyclopropyl, cyclobutyl, 1-oxocyclopentyl, cyclopentyl, cyclopentenyl, cyclohexyl, cyclohexenyl, cyclohexenyl, 4-oxocyclohex-1-yl, 3-oxocyclohept-5-en-1-yl, phenyl, naphthyl, tetralinyl, indanyl or 1-oxoindanyl.

This specification also makes use of several composite terms to describe groups comprising more than one functionality. Such terms are to be interpreted as is understood in the art. For example heterocyclyl$C_{m-n}$alkyl comprises $C_{m-n}$alkyl substituted by heterocyclyl and N—($C_{1-6}$alkyl)$C_{1-6}$alkoxycarbonylamino comprises an N—($C_{1-6}$alkyl)amino substituted by a carbonyl group which carbonyl is substituted by a $C_{1-6}$alkoxy group i.e. $C_{1-6}$alkoxy is linked to amino through a carbonyl group i.e.—N($C_{1-6}$alkyl)-C(O)—O$C_{1-6}$alkyl.

Examples for the substituents within the compound of formula I are listed below. Many of these examples will also apply for other $C_{m-n}$ values, for example, examples for $C_{1-4}$alkyl also include methyl, ethyl, propyl, isopropyl and tert-butyl. Examples include (but are not necessarily limited to):

for halo: fluoro, chloro, bromo and iodo;
for $C_{1-6}$alkyl: methyl, ethyl, propyl, isopropyl and tert-butyl;
for $C_{2-6}$alkenyl: vinyl, isopropenyl, allyl and but-2-enyl;
for $C_{2-6}$alkynyl: ethynyl, 2-propynyl and but-2-ynyl;
for $C_{1-6}$alkoxy: methoxy, ethoxy, propoxy, isopropoxy and butoxy;
for $C_{2-6}$alkenyloxy: vinyloxy and allyloxy;
for $C_{2-6}$alkynyloxy: ethynyloxy and 2-propynyloxy;
for $C_{1-6}$alkylthio: methylthio, ethylthio and propylthio;
for $C_{1-6}$alkylsulfinyl: methylsulfinyl and ethylsulfinyl;
for $C_{1-6}$alkylsulfonyl: methylsulfonyl and ethylsulfonyl;
for N—($C_{1-6}$alkyl)amino: methylamino, ethylamino, propylamino, isopropylamino and butylamino;
for N,N—($C_{1-6}$alkyl)$_2$amino: dimethylamino, diethylamino, N-ethyl-N-methylamino and diisopropylamino;
for $C_{1-6}$alkoxycarbonyl: methoxycarbonyl, ethoxycarbonyl, propoxycarbonyl and tert-butoxycarbonyl;
for N—($C_{1-6}$alkyl)carbamoyl: N-methylcarbamoyl, N-ethylcarbamoyl and N-propylcarbamoyl;
for N,N—($C_{1-6}$alkyl)$_2$carbamoyl: N,N-dimethylcarbamoyl, N-ethyl-N-methylcarbamoyl and N,N-diethylcarbamoyl;
for $C_{1-6}$alkanoyl: formyl, acetyl and propionyl;
for $C_{1-6}$alkanoyloxy: acetoxy and propionyloxy;
for $C_{1-6}$alkanoylamino: acetamido and propionamido;
for N—($C_{1-6}$alkyl)-$C_{1-6}$alkanoylamino: N-methylacetamido and N-methylpropionamido;
for N—($C_{1-6}$alkyl)sulfamoyl: N-methylsulfamoyl and N-ethylsulfamoyl;
for N,N—($C_{1-6}$alkyl)$_2$sulfamoyl: N,N-dimethylsulfamoyl;
for $C_{1-6}$alkylsulfonylamino: methanesulfonylamino and ethanesulfonylamino;
for N—($C_{1-6}$alkyl)$C_{1-6}$alkylsulfonylamino: N-methyl-methanesulfonylamino and N-methylethanesulfonylamino;
for $C_{1-6}$alkylsulfonylaminocarbonyl: methylsulfonylaminocarbonyl;
for N—($C_{1-6}$alkyl)$C_{1-6}$alkylsulfonylaminocarbonyl: N-methyl-methylsulfonylaminocarbonyl;
for N'—($C_{1-6}$alkyl)ureido: N'-methylureido and N'-ethylureido;
for N',N'—($C_{1-6}$alkyl)$_2$ureido: N',N'-dimethylureido and N'-methyl-N'-ethylureido;
for N—($C_{1-6}$alkyl)-,N'—($C_{1-6}$alkyl)ureido: N,N'-dimethylureido, N-methyl-N'-ethylureido and N-ethyl-N'-methylureido;
for N',N'—($C_{1-6}$alkyl)$_2$-N—($C_{1-6}$alkyl)ureido: N,N',N'-trimethylureido;
for $C_{1-6}$alkoxycarbonylamino: methoxycarbonylamino, ethoxycarbonylamino, and tert-butoxycarbonylamino;
for N—($C_{1-6}$alkyl)$C_{1-6}$alkoxycarbonylamino: N-methyl-methoxycarbonylamino and N-methyl-ethoxycarbonylamino.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups. "One or more" includes (but is not limited to) "1, 2 or 3", "1 or 2" and "1".

When, as defined herein that, for example, $R^2$ is carbocyclyl-$X^1$— and, for example, $X^1$, is a —N($R^{14}$)C(O)— linking group, it is the nitrogen atom, not the carbon atom, of the —N($R^{14}$)C(O)— linking group which is attached to the carbocyclyl group. The same principle applies to the other groups of the formula "carbocyclyl-X-", "heterocyclyl-X" and "heteroaryl-X—" defined herein, for example when, $R^2$ is heterocyclyl-$X^3$— and $X^3$ is —N($R^{20}$)C($R^{21}$)$_2$— the nitrogen atom of the —N($R^{20}$) C($R^{21}$)$_2$— linker group is attached to the heterocyclyl. It will be realised that when for example, heterocyclyl-$X^3$— is heterocyclyl-N($R^{14}$)C(O)— said heterocyclyl group is suitably attached to the —N($R^{14}$)C(O)— group by a ring carbon.

Where herein it is stated that the C(O)N$R^3R^4$ group together with the carbon atom to which it is attached and the $R^{5c}$ group together with the carbon atom to which it is attached (at the 3-position on the phenyl ring) form a heterocyclic ring, which heterocyclic ring contains a —C(O)N($R^3$)— group as a ring member, the ring so formed is fused to the phenyl ring such that the compound of the formula I so formed is of the formula I':

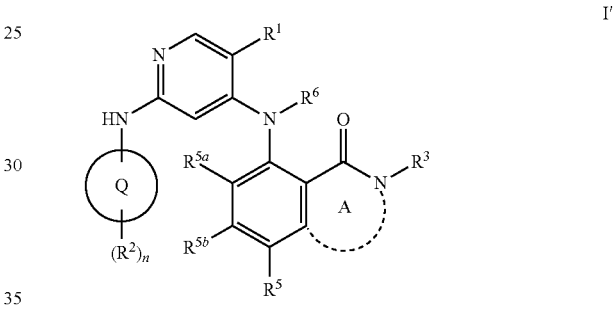

I' wherein:
ring Q, n, $R^1$, $R^2$, $R^5$, $R^{5a}$, $R^{5b}$ and $R^6$ are as hereinbefore defined; and
ring A is a heterocyclic containing the group C(O)N($R^3$) as a ring member; wherein $R^3$ is as hereinbefore defined; or the N($R^3$) ring member together with an adjacent ring member together form a heterocyclic ring;
and wherein ring A or any heterocyclic ring formed by the N$R^3$ ring member may be optionally substituted on carbon by one or more $R^{3a}$ selected from $C_{1-4}$alkyl, $C_{1-4}$alkoxy, halo, cyano, hydroxy and oxo; and wherein if said heterocyclyl ring contains an —NH-moiety that nitrogen may be optionally substituted by $R^{3b}$ selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$ alkyl)carbamoyl and N,N—($C_{1-4}$alkyl)carbamoyl.

Ring A is suitably a 5, 6 or 7 membered monocyclic heterocyclic ring fused to the phenyl ring, which heterocyclic ring is optionally substituted as hereinbefore defined. For example, in the compounds of the Formula I' the group of the formula:

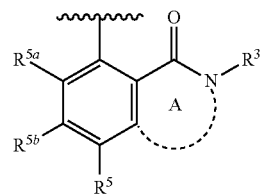

may be for example:

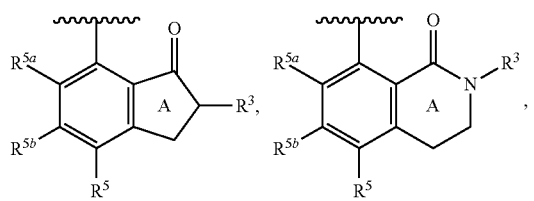

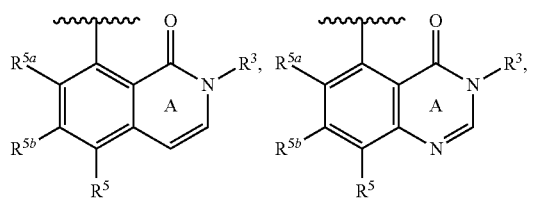

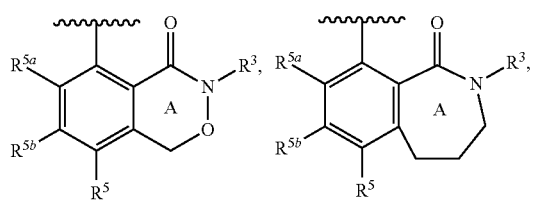

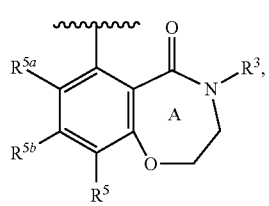

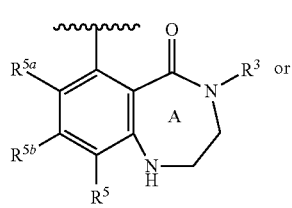 or

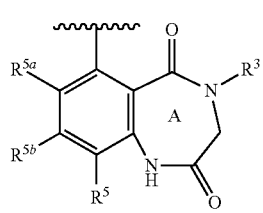

wherein in each case ring A is optionally substituted as hereinbefore defined;

$R^5$, $R^{5a}$ and $R^{5b}$ are as hereinbefore defined; and $R^3$ is as hereinbefore defined or the $N(R^3)$ ring member together with an adjacent ring member together form a heterocyclic ring, which heterocyclic ring is optionally substituted as hereinbefore defined.

When as hereinbefore defined or the $N(R^3)$ ring member together with an adjacent ring member together form a heterocyclic ring, the compound of formula I is of the formula I'':

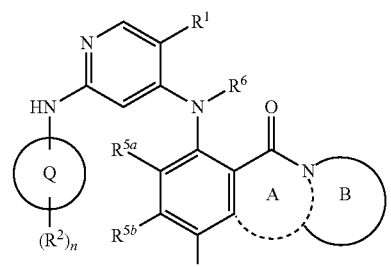

wherein:

ring Q, n, $R^1$, $R^2$, $R^5$, $R^{5a}$, $R^{5b}$ and $R^6$ are as hereinbefore defined;

ring A is a heterocyclyl containing the group $C(O)N(R^3)$ as a ring member (which ring is fused to the phenyl ring in formula I'');

ring B is a heterocyclyl ring (which ring is fused to ring A in formula I'');

and wherein ring A and ring B may be optionally substituted on carbon by one or more $R^{3a}$ selected from $C_{1-4}$alkyl, $C_{1-4}$alkoxy, halo, cyano, hydroxy and oxo; and wherein if said heterocyclyl ring contains an —NH— moiety that nitrogen may be optionally substituted by $R^{3b}$ selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)carbamoyl.

Suitably ring B is a 5 or 6 membered heterocyclic ring which is fused to ring A. For example, in the compounds of the Formula I'' the group of the formula:

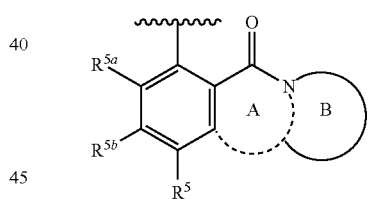

may be, for example:

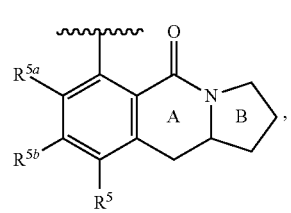

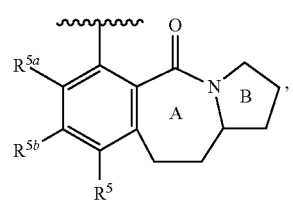

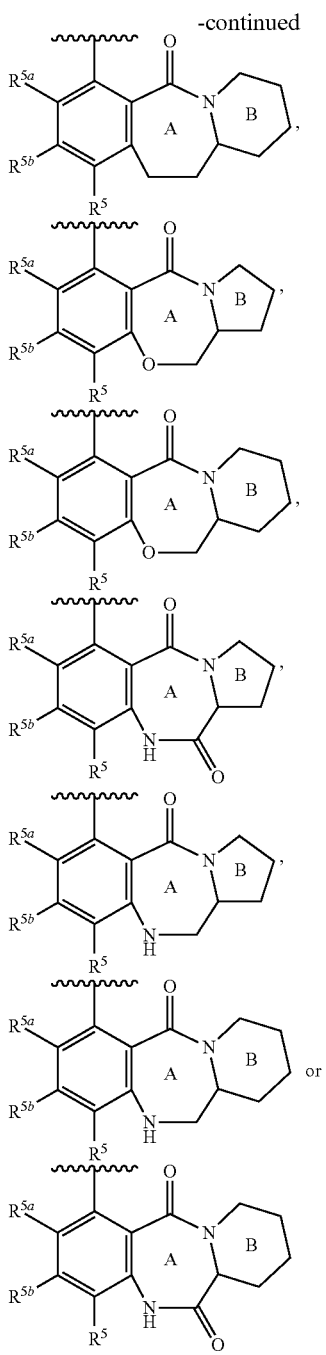

wherein in each case rings A and B are optionally substituted as hereinbefore defined; and $R^5$, $R^{5a}$ and $R^{5b}$ are as hereinbefore defined.

When $R^3$ and $R^4$ together with the nitrogen atom to which they are attached form a 4- or 5-membered heterocyclyl ring, the heterocyclyl ring so formed is a saturated or partially saturated 4 or 5 membered ring that is linked to the carbonyl group in formula I by a ring nitrogen. For example $R^3$ and $R^4$ together with the nitrogen atom to which they are attached form azetidin-1-yl or pyrrolidin-1-yl. As mentioned hereinbefore, the ring so formed is optionally substituted on carbon by $C_{1-4}$alkyl such as methyl.

The various functional groups and substituents making up the compounds of the formula I are typically chosen such that the molecular weight of the compound of the formula I does not exceed 1000. More usually, the molecular weight of the compound will be less than 750, for example less than 700, or less than 650, or less than 600, or less than is 550. More preferably, the molecular weight is less than 525 and, for example, is 500 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess FAK inhibitory activity.

It is also to be understood that certain compounds of the formula I may exist in solvated as well as unsolvated forms such as, for example, hydrated forms. It is to be understood that the invention encompasses all such solvated forms that possess FAK inhibitory activity.

It is also to be understood that certain compounds of the formula I may exhibit polymorphism, and that the invention encompasses all such forms that possess FAK inhibitory activity.

Compounds of the formula I may exist in a number of different tautomeric forms and references to compounds of the formula I include all such forms. For the avoidance of doubt, where a compound can exist in one of several tautomeric forms and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

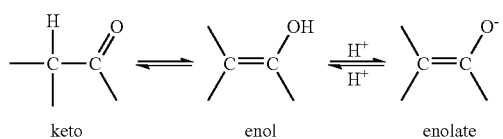

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

"Treating" or "treatment" of a disease includes:
1. preventing the disease, i.e. causing the clinical symptoms of the disease not to develop in a mammal that may be exposed to or predisposed to the disease but does not yet experience or display symptoms of the disease;
2. inhibiting the disease, i.e., arresting or reducing the development of the disease or its clinical symptoms; or
3. relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The phrase "compound of the invention" means those compounds which are disclosed herein, both generically and specifically.

Particular novel compounds of the invention include, for example, compounds of the formula I, or pharmaceutically acceptable salts thereof, wherein, unless otherwise stated, each of ring Q, $R^1$, $R^2$, $R^3$, $R^4$, $R^5$, $R^{5a}$, $R^{5b}$, $R^6$ and n has any of the meanings defined hereinbefore or in any of paragraphs (1) to (89) hereinafter:—

(1) $R^1$ is selected from halo, trifluoromethyl, cyclopropyl and cyano (particularly halo, trifluoromethyl and cyano).
(2) $R^1$ is selected from fluoro, chloro, bromo, trifluoromethyl and cyclopropyl.
(3) $R^1$ is selected from fluoro, chloro, cyano and trifluoromethyl.
(4) $R^1$ is halo.
(5) $R^1$ is selected from fluoro and chloro.
(6) $R^1$ is fluoro.
(7) $R^1$ is chloro.
(8) $R^1$ is cyano.
(9) $R^1$ is trifluoromethyl.
(10) $R^2$ is selected from halo, nitro, cyano, hydroxy, trifluoromethoxy, amino, carboxy, carbamoyl, mercapto, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)$C_{1-6}$alkanoylamino, N—($C_{1-6}$alkyl)carbamoyl, N,N—($C_{1-6}$alkyl)$_2$carbamoyl, $C_{1-6}$alkylthio, $C_{1-6}$alkoxycarbonyl, $C_{3-7}$cycloalkyl-$X^1$—, phenyl-$X^1$—, heterocyclyl-$X^2$— and heteroaryl-$X^3$—;

wherein $R^2$ may be optionally substituted on carbon by one or more $R^7$; and wherein if a heterocyclyl or heteroaryl within $R^2$ contains an —NH— moiety that nitrogen may be optionally substituted by a group selected from $R^8$;

and wherein any heterocyclyl within $R^2$ optionally bears 1 or 2 oxo substituents;

$R^7$ is selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl, $C_{1-6}$alkylsulfonylamino, $C_{3-7}$cycloalkyl-$X^{4-5}$ phenyl-$X^{4-5}$ heterocyclyl-$X^5$— and heteroaryl-$X^6$—;

wherein $R^7$ may be optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;

and wherein any heterocyclyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulfonyl;

wherein $R^8$ and $R^{12}$ may be optionally substituted on carbon by one or more $R^{13}$ selected from halo, amino, hydroxy, cyclopropyl, cyclobutyl, methoxy, ethoxy, methylamino, ethylamino, dimethylamino, diethylamino and N-methyl-N-ethylamino; and $X^1$, $X^2$ and $X^3$ are independently selected from a direct bond, —O—, —N($R^{22}$)—, —S—, —C(O)—, —N($R^{14}$)C(O)—, —C(O)N($R^{14}$)—, —N($R^{16}$)CON($R^{17}$)—, —OC($R^{18}$)$_2$—, —SC($R^{19}$)$_2$— and —N($R^{20}$)C($R^{21}$)$_2$—;

$X^4$, $X^5$ and $X^6$ are independently selected from a direct bond, —O—, —N($R^{22}$)—, —C(O)—, —N($R^{14}$)C(O)—, —C(O)N($R^{14}$)—, —S(O)$_e$—, —SO$_2$N($R^{15}$)—, —N($R^{15}$)SO$_2$—, —N($R^{16}$)CON($R^{17}$)—, —OC($R^{18}$)$_2$—, —SC($R^{19}$)$_2$— and —N($R^{20}$)C($R^{21}$)$_2$—; and $R^{14}$, $R^{15}$, $R^{16}$, $R^{17}$, $R^{18}$, $R^{19}$, $R^{20}$, $R^{21}$ and $R^{22}$ are independently selected from hydrogen or $C_{1-6}$alkyl and e is 0 to 2.

(11) $R^2$ is selected from halo, nitro, cyano, hydroxy, trifluoromethoxy, amino, carboxy, carbamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)-$C_{1-6}$alkanoylamino, N—($C_{1-6}$alkyl)carbamoyl, N,N—($C_{1-6}$alkyl)$_2$carbamoyl and $C_{1-6}$alkoxycarbonyl, or $R^2$ is selected from:
(i) $C_{3-7}$cycloalkyl-$X^1$—;
(ii) phenyl-$X^1$—;
(iii) heterocyclyl-$X^2$—, which heterocyclyl is a non-aromatic, saturated or partially saturated monocyclic 3 to 7 membered heterocyclyl ring or a bicyclic fused, spiro, or bridged heterocyclyl containing from 7 to 12 ring atoms, which heterocyclyl contains 1, 2 or 3 heteroatoms selected from nitrogen, oxygen and sulfur; and
(iv) heteroaryl-$X^3$—, which heteroaryl is a 5 or 6 membered monocyclic heteroaryl ring or a 9- or 10-membered bicyclic ring containing 1, 2 or 3 heteroatoms selected from nitrogen, oxygen and sulfur;

and wherein $R^2$ may be optionally substituted on carbon by one or more $R^7$; and wherein if a heterocyclyl or heteroaryl within $R^2$ contains an —NH— moiety that nitrogen may be optionally substituted by a group selected from $R^8$; and wherein any heterocyclyl within $R^2$ optionally bears 1 or 2 oxo substituents;

$R^7$ is selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl and $C_{1-6}$alkylsulfonylamino, or $R^7$ is selected from:
  (a) $C_{3-7}$cycloalkyl-$X^4$—;
  (b) phenyl-$X^4$—,
  (c) heterocyclyl-$X^5$—, which heterocyclyl is a non-aromatic saturated or partially saturated monocyclic 3 to 7 membered ring containing 1, 2 or 3 heteroatoms selected from nitrogen, oxygen and sulfur; and
  (d) heteroaryl-$X^6$—, which heteroaryl is a 5 or 6 membered monocyclic heteroaryl ring containing 1, 2 or 3 heteroatoms selected from nitrogen, oxygen and sulfur;
wherein $R^7$ may be optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;
and wherein any heterocyclyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl;
wherein $R^8$ and $R^{12}$ may be optionally substituted on carbon by one or more $R^{13}$ selected from halo, amino, hydroxy, cyclopropyl, cyclobutyl, methoxy, ethoxy, methylamino, ethylamino, dimethylamino, diethylamino and N-methyl-N-ethylamino;

$X^1$, $X^2$ and $X^3$ are independently selected from a direct bond, —O—, —N($R^{22}$)—, —C(O)—, —N($R^{14}$)C(O)— and —C(O)N($R^{14}$)—;
$X^4$, $X^5$ and $X^6$ are independently selected from a direct bond, —O—, —N($R^{22}$)—, —C(O)—, —N($R^{14}$)C(O)—, —C(O)N($R^{14}$)—, —S(O)$_e$—, —SO$_2$N($R^{15}$)— and —N($R^{15}$)SO$_2$—; and
$R^{22}$, $R^{14}$ and $R^{15}$ are independently selected from hydrogen or $C_{1-6}$alkyl and e is 0 to 2.

(12) $R^2$ is selected from halo, nitro, cyano, hydroxy, trifluoromethoxy, trifluoromethyl, amino, carboxy, carbamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)-$C_{1-6}$alkanoylamino, N—($C_{1-6}$alkyl)carbamoyl, N,N—($C_{1-6}$alkyl)$_2$carbamoyl and $C_{1-6}$alkoxycarbonyl, or $R^2$ is selected from:
  (i) $C_{3-7}$ cycloalkyl-$X^1$—;
  (ii) phenyl-$X^1$—;
  (iii) heterocyclyl-$X^2$—, which heterocyclyl is a non-aromatic, saturated or partially saturated monocyclic 3 to 7 membered heterocyclyl ring (for example selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl, diazepanyl, quinuclidinyl and tetrahydropyridazinyl (such as 1,4,5,6-tetrahydropyridazin-3-yl); and
  (iv) heteroaryl-$X^3$—, which heteroaryl is a 5 or 6 membered monocyclic heteroaryl ring containing 1, 2 or 3 heteroatoms selected from nitrogen, oxygen and sulfur (for example furanyl, thienyl, pyrrolyl, 1,3-oxazolyl, isoxazolyl, 1,3-thiazolyl, isothiazolyl, imidazolyl, 1,2,4-triazolyl, pyrazolyl, pyridyl, pyridazinyl, pyrimidinyl or pyrazinyl);
and wherein $R^2$ may be optionally substituted on carbon by one or more $R^7$; and wherein if a heterocyclyl or heteroaryl within $R^2$ contains an —NH— moiety that nitrogen may be optionally substituted by a group selected from $R^8$;
and wherein any heterocyclyl within $R^2$ optionally bears 1 or 2 oxo substituents;

$R^7$ are independently selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl and $C_{1-6}$alkylsulfonylamino, or $R^7$ is selected from:
  (ai) $C_{3-7}$cycloalkyl-$X^4$—;
  (bi) phenyl-$X^4$—,
  (ci) heterocyclyl-$X^5$—, which heterocyclyl is selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl and diazepanyl; and
  (di) heteroaryl-$X^6$—, which heteroaryl is a 5 or 6 membered monocyclic heteroaryl ring containing 1, 2 or 3 heteroatoms selected from nitrogen, oxygen and sulfur (for example furanyl, thienyl, pyrrolyl, 1,3-oxazolyl, isoxazolyl, 1,3-thiazolyl, isothiazolyl, imidazolyl, pyrazolyl, 1,2,4-triazolyl, pyridyl, pyridazinyl, pyrimidinyl or pyrazinyl);
wherein $R^7$ may be optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;
and wherein any heterocyclyl or cycloalkyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl;
wherein $R^8$ and $R^{12}$ may be optionally substituted on carbon by one or more $R^{13}$ selected from halo, amino, hydroxy, cyclopropyl, cyclobutyl, methoxy, ethoxy, methylamino, ethylamino, dimethylamino, diethylamino and N-methyl-N-ethylamino;

$X^1$, $X^2$, $X^3$, $X^4$, $X^5$ and $X^6$ are independently selected from a direct bond, —O—, —S—, —N($R^{22}$)—, —C(O)—, —N($R^{14}$)C(O)— and —C(O)N($R^{14}$)—; and
$R^{22}$ and $R^{14}$ are independently selected from hydrogen or $C_{1-6}$alkyl.

(13) $R^2$ is selected from halo, cyano, hydroxy, trifluoromethoxy, trifluoromethyl, amino, carboxy, carbamoyl, $C_{1-6}$alkyl, $C_{1-6}$alkoxy, $C_{1-6}$alkanoyl, N—($C_{1-6}$alkyl)amino, N,N—($C_{1-6}$alkyl)$_2$amino, $C_{1-6}$alkanoylamino, N—($C_{1-6}$alkyl)-$C_{1-6}$alkanoylamino, N—($C_{1-6}$alkyl)carbamoyl and N,N—($C_{1-6}$alkyl)$_2$carbamoyl or $R^2$ is selected from:
  (i) $C_{3-7}$cycloalkyl-$X^1$—; and
  (ii) heterocyclyl-$X^2$—, which heterocyclyl is selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl, quinuclidinyl and tetrahydropyridazinyl (such as 1,4,5,6-tetrahydropyridazin-3-yl);

and wherein $R^2$ may be optionally substituted on carbon by one or more $R^7$; and wherein if a heterocyclyl within $R^2$ contains an —NH— moiety that nitrogen may be optionally substituted by a group selected from $R^8$;

and wherein any heterocyclyl within $R^2$ optionally bears 1 or 2 oxo substituents;

$R^7$ is selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl and $C_{1-6}$alkylsulfonylamino, or $R^7$ is selected from:

(ai) $C_{3-7}$cycloalkyl-$X^4$—;
(bi) phenyl-$X^4$—,
(ci) heterocyclyl-$X^5$—, which heterocyclyl is selected from azetidinyl, tetrahydrofuranyl, tetrahydropyranyl, pyrrolidinyl, morpholinyl, piperidinyl, piperazinyl, homopiperidinyl, homopiperazinyl and diazepanyl; and
(di) heteroaryl-$X^6$—, which heteroaryl is selected from furanyl, thienyl, pyrrolyl, 1,3-oxazolyl, isoxazolyl, 1,3-thiazolyl, isothiazolyl, imidazolyl, pyrazolyl, 1,2,4-triazolyl, pyridyl, pyridazinyl, pyrimidinyl and pyrazinyl;

wherein $R^7$ may be optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;

and wherein any heterocyclyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl and N,N—($C_{1-6}$alkyl)$_2$carbamoyl;

wherein $R^8$ and $R^{12}$ may be optionally substituted on carbon by one or more $R^{13}$ selected from halo, hydroxy, cyclopropyl, cyclobutyl, methoxy and ethoxy; and $X^1$, $X^2$, $X^4$, $X^5$ and $X^6$ are independently selected from a direct bond, —O—, —N($R^{22}$)—, —C(O)—, —N($R^{14}$)C(O)— and —C(O)N($R^{14}$)—; and $R^{22}$ and $R^{14}$ are independently selected from hydrogen or $C_{1-6}$alkyl.

(14) $R^2$ is selected from cyano, $C_{1-6}$alkyl, $C_{1-6}$alkoxy, $C_{1-6}$alkanoylamino, N—($C_{1-6}$alkyl)-$C_{1-6}$alkanoylamino, N—($C_{1-6}$alkyl)carbamoyl and N,N—($C_{1-6}$alkyl)$_2$carbamoyl, or $R^2$ is selected from:
(i) $C_{3-7}$cycloalkyl-$X^1$—, wherein $X^1$ is selected from a direct bond, —N($R^{14}$)C(O)— and —C(O)N($R^{14}$)—, and $R^{14}$ is hydrogen or $C_{1-4}$alkyl;
(ii) heterocyclyl-$X^2$—, wherein $X^2$ is a direct bond, which heterocyclyl is carbon linked to $X^2$ and is a non-aromatic saturated or partially saturated heterocyclyl (for example a non-aromatic saturated or partially saturated monocyclic 3 to 7 membered heterocyclyl ring containing 1, 2 or 3 heteroatoms selected from nitrogen, oxygen and sulfur);
(iii) heterocyclyl-$X^2$—, wherein $X^2$ is —C(O)N($R^{14}$)— or —N($R^{14}$)C(O)—, and $R^{14}$ is hydrogen or $C_{1-4}$alkyl, which heterocyclyl is carbon or nitrogen linked to $X^2$ and is a non-aromatic saturated or partially saturated heterocyclyl (for example a non-aromatic saturated or partially saturated monocyclic 3 to 7 membered heterocyclyl ring containing 1, 2 or 3 heteroatoms selected from nitrogen, oxygen and sulfur);
(iv) heterocyclyl-$X^2$—, wherein $X^2$ is —C(O)—, which heterocyclyl is nitrogen-linked to $X^2$ and is a non-aromatic saturated or partially saturated heterocyclyl containing at least 1 nitrogen heteroatom (for example a non-aromatic saturated or partially saturated monocyclic 3 to 7 membered heterocyclyl ring containing 1 nitrogen heteroatom and optionally 1 or 2 additional heteroatoms selected from nitrogen, oxygen and sulfur; and
(v) heteroaryl-$X^3$—, wherein $X^3$ is selected from —N($R^{14}$)C(O)— and —C(O)N($R^{14}$)—, and $R^{14}$ is hydrogen or $C_{1-4}$alkyl, (for example the heteroaryl is a 5- or 6-membered monocyclic heteroaryl ring or a 9- or 10-membered bicyclic heteroaryl ring, particularly the heteroaryl is a 5- or 6-membered monocyclic heteroaryl ring containing 1, 2 or 3 heteroatoms selected from nitrogen, oxygen and sulfur);

and wherein $R^2$ may be optionally substituted on carbon by one or more $R^7$; and wherein if a heterocyclyl or heteroaryl within $R^2$ contains an —NH— moiety that nitrogen may be optionally substituted by a group selected from $R^8$;

and wherein any heterocyclyl within $R^2$ optionally bears 1 or 2 oxo substituents;

$R^7$ is selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_c$ wherein c is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl and $C_{1-6}$alkylsulfonylamino, or $R^7$ is selected from:

(ai) $C_{3-7}$cycloalkyl-$X^4$—;
(bi) phenyl-$X^4$—,
(ci) heterocyclyl-$X^5$—, which heterocyclyl is selected from a 4- to 7-membered heterocyclyl containing 1, 2 or 3 heteroatoms selected from nitrogen, oxygen and sulfur, for example, azetidinyl, tetrahydrofuranyl, tetrahydropyranyl, pyrrolidinyl, morpholinyl, piperidinyl, piperazinyl, homopiperidinyl, homopiperazinyl and diazepanyl; and
(di) heteroaryl-$X^6$—, which heteroaryl is selected from a 5 or 6-membered heteroaryl, for example furanyl, thienyl, pyrrolyl, 1,3-oxazolyl, isoxazolyl, 1,3-thiazolyl, isothiazolyl, imidazolyl, pyrazolyl, 1,2,4-triazolyl, pyridyl, pyridazinyl, pyrimidinyl and pyrazinyl;

wherein $R^7$ may be independently optionally substituted on carbon by one or more $R^{11}$; and wherein if any heterocyclyl or heteroaryl in $R^7$, contains an —NH— moiety that nitrogen may be optionally substituted by a group selected from $R^{12}$;

and wherein any heterocyclyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)$_2$carbamoyl, benzyl, benzyloxycarbonyl, benzoyl and phenylsulfonyl;

wherein $R^8$ and $R^{12}$ may be optionally substituted on carbon by one or more $R^{13}$;

$X^4$, $X^5$ and $X^6$ are independently selected from a direct bond, —O—, —N($R^{22}$)—, —C(O)—, —N($R^{14}$)C(O)—, —C(O)N($R^{14}$)—, —S(O)$_e$—, —SO$_2$N($R^{15}$)—, —N($R^{15}$)SO$_2$—, —N($R^{16}$)CON($R^{17}$)—, —OC($R^{18}$)$_2$—, —SC($R^{19}$)$_2$— and —N($R^{20}$)C($R^{21}$)$_2$—;

$R^{14}$, $R^{15}$, $R^{16}$, $R^{17}$, $R^{18}$, $R^{19}$, $R^{20}$, $R^{21}$ and $R^{22}$ are independently selected from hydrogen or $C_{1-6}$alkyl and e is 0 to 2; and $R^{11}$ and $R^{13}$ are independently selected from halo, nitro, cyano, hydroxy, trifluoromethoxy, trifluoromethyl, amino, carboxy, carbamoyl, mercapto, sulfamoyl, methyl, ethyl, cyclopropyl, cyclobutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl and N-methyl-N-ethylsulfamoyl.

(15) $R^2$ is selected from cyano, trifluoromethoxy, trifluoromethyl, $C_{1-6}$alkyl, $C_{1-6}$alkoxy, $C_{1-6}$alkanoylamino, N—($C_{1-6}$alkyl)$C_{1-6}$alkanoylamino, N—($C_{1-6}$alkyl)carbamoyl and N,N—($C_{1-6}$alkyl)$_2$carbamoyl, each of which may be optionally substituted on carbon by one or more $R^7$;

or $R^2$ is selected from:
(i) $C_{3-7}$cycloalkyl-$X^1$—, wherein $X^1$ is selected from a direct bond, —O—, —N($R^{14}$)C(O)— and —C(O)N($R^{14}$)—, and $R^{14}$ is hydrogen or $C_{1-4}$alkyl;
(ii) heterocyclyl-$X^2$—, wherein $X^2$ is a direct bond, which heterocyclyl is carbon linked to $X^2$ and is selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl, quinuclidinyl and tetrahydropyridazinyl (such as 1,4,5,6-tetrahydropyridazin-3-yl); and which cycloalkyl or heterocyclyl may be optionally substituted on carbon by one or more $R^7$; and wherein if a heterocyclyl within $R^2$ contains an —NH— moiety that nitrogen may be optionally substituted by a group selected from $R^8$;

and wherein any heterocyclyl within $R^2$ optionally bears 1 or 2 oxo substituents;

$R^7$ is selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl and $C_{1-6}$alkylsulfonylamino, or $R^7$ is selected from:
(ai) $C_{3-7}$cycloalkyl-$X^4$—;
(bi) phenyl-$X^4$—,
(ci) heterocyclyl-$X^5$—, which heterocyclyl is selected from azetidinyl, tetrahydrofuranyl, tetrahydropyranyl, pyrrolidinyl, morpholinyl, piperidinyl, is piperazinyl, homopiperidinyl, homopiperazinyl and diazepanyl; and
wherein $R^7$ may be independently optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;
and wherein any heterocyclyl or cycloalkyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl and N,N—($C_{1-6}$alkyl)$_2$carbamoyl;
wherein $R^8$ and $R^{12}$ may be optionally substituted on carbon by one or more $R^{13}$ selected from halo, hydroxy, cyclopropyl, cyclobutyl, methoxy and ethoxy;
$X^4$ and $X^5$ are independently selected from a direct bond, —O—, —N($R^{22}$)—, —C(O)—, —N($R^{14}$)C(O)— and —C(O)N($R^{14}$)—; and
$R^{22}$ and $R^{14}$ are independently selected from hydrogen or $C_{1-6}$alkyl.

(16) $R^2$ is selected from cyano, $C_{1-6}$alkyl and $C_{1-6}$alkoxy, wherein $C_{1-6}$alkyl and $C_{1-6}$alkoxy may be optionally substituted on carbon by one or more $R^7$;
or $R^2$ is selected from:
(i) $C_{3-7}$cycloalkyl-$X^1$—, wherein $X^1$ is selected from a direct bond, —O—, —N($R^{14}$)C(O)— and —C(O)N($R^{14}$)—, and $R^{14}$ is hydrogen or $C_{1-4}$alkyl;
(ii) heterocyclyl-$X^2$—, wherein $X^2$ is a direct bond, which heterocyclyl is carbon linked to $X^2$ and is selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl, quinuclidinyl and tetrahydropyridazinyl (such as 1,4,5,6-tetrahydropyridazin-3-yl); and which cycloalkyl or heterocyclyl may be optionally substituted on carbon by one or more $R^7$; and wherein if a heterocyclyl within $R^2$ contains an —NH— moiety that nitrogen may be optionally substituted by a group selected from $R^8$;

and wherein any heterocyclyl within $R^2$ optionally bears 1 or 2 oxo substituents;

$R^7$ is selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl and $C_{1-6}$alkylsulfonylamino, or $R^7$ is selected from:
(ai) $C_{3-7}$cycloalkyl-$X^4$—;
(bi) phenyl-$X^4$—,
(ci) heterocyclyl-$X^5$—, which heterocyclyl is selected from azetidinyl, tetrahydrofuranyl, tetrahydropyranyl, pyrrolidinyl, morpholinyl, piperidinyl, piperazinyl, homopiperidinyl, homopiperazinyl and diazepanyl;
wherein $R^7$ may be independently optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;
and wherein any heterocyclyl or cycloalkyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl and N,N—($C_{1-6}$alkyl)$_2$carbamoyl;
wherein $R^8$ and $R^{12}$ may be optionally substituted on carbon by one or more $R^{13}$ selected from halo, hydroxy, cyclopropyl, cyclobutyl, methoxy and ethoxy;
$X^4$ and $X^5$ are independently selected from a direct bond, —O—, —N($R^{22}$)—, —C(O)—, —N($R^{14}$)C(O)— and —C(O)N($R^{14}$)—;

$R^{22}$ and $R^{14}$ are independently selected from hydrogen or $C_{1-6}$alkyl.

(17) $R^2$ is selected from cyano, $C_{1-6}$alkyl and $C_{1-6}$alkoxy, wherein $C_{1-6}$alkyl and $C_{1-6}$alkoxy may be optionally substituted on carbon by one or more $R^7$;

or $R^2$ is selected from:
(i) $C_{3-7}$cycloalkyl-$X^1$—, wherein $X^1$ is selected from a direct bond, —O—, —N($R^{14}$)C(O)— and —C(O)N($R^{14}$)—, and $R^{14}$ is hydrogen or $C_{1-4}$alkyl;
(ii) heterocyclyl-$X^2$—, wherein $X^2$ is a direct bond, which heterocyclyl is carbon linked to $X^2$ and is selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl, quinuclidinyl and tetrahydropyridazinyl (such as 1,4,5,6-tetrahydropyridazin-3-yl); and which cycloalkyl or heterocyclyl may be optionally substituted on carbon by one or more $R^7$; and wherein if a heterocyclyl within $R^2$ contains an —NH— moiety that nitrogen may be optionally substituted by a group selected from $R^8$;

and wherein any heterocyclyl within $R^2$ optionally bears 1 or 2 oxo substituents;

$R^7$ is selected from halo, hydroxy, amino, carbamoyl, $C_{1-6}$alkyl, $C_{3-7}$cycloalkyl, $C_{1-6}$alkoxy, $C_{1-6}$alkanoyl, N—($C_{1-6}$ alkyl)amino, N,N—($C_{1-6}$alkyl)$_2$amino, N—($C_{1-6}$alkyl)carbamoyl, N,N—($C_{1-6}$alkyl)$_2$carbamoyl, $C_{3-7}$cycloalkyl and heterocyclyl, which heterocyclyl is selected from azetidinyl, tetrahydrofuranyl, tetrahydropyranyl, pyrrolidinyl, morpholinyl, piperidinyl, piperazinyl, homopiperidinyl, homopiperazinyl and diazepanyl;

and wherein $R^7$ may be independently optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$;

and wherein any heterocyclyl or cycloalkyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl and N,N—($C_{1-6}$alkyl)$_2$carbamoyl;

wherein $R^8$ and $R^{12}$ may be optionally substituted on carbon by one or more $R^{13}$ selected from halo, hydroxy, cyclopropyl, cyclobutyl, methoxy and ethoxy; and $R^{14}$ is selected from hydrogen or $C_{1-6}$alkyl.

(18) $R^2$ is selected from cyano, methyl, methoxy, cyclopropyl, which methyl may be optionally substituted on carbon by one or more $R^{7a}$; or $R^2$ is $C_{1-4}$alkyl (preferably methyl, ethyl, isopropyl, isobutyl or tert-butyl), which $C_{1-4}$alkyl may be optionally substituted by 1, 2 or 3 halo, hydroxy or methoxy groups; or $R^2$ is heterocyclyl-$X^2$—, wherein $X^2$ is a direct bond, which heterocyclyl is carbon linked to $X^2$ and is selected from tetrahydropyranyl, piperidinyl and piperazinyl which heterocyclyl may be optionally substituted on carbon by one or more $R^{7b}$ and wherein if a heterocyclyl within $R^2$ contains an —NH— moiety that nitrogen may be optionally substituted by a group selected from $R^8$; and wherein any heterocyclyl within $R^2$ optionally bears an oxo substituents;

$R^{7a}$ is selected from N—($C_{1-6}$alkyl)carbamoyl or N,N—($C_{1-6}$alkyl)$_2$carbamoyl, or $R^{7a}$ is heterocyclyl-$X^5$—, which heterocyclyl is selected from pyrrolidinyl, morpholinyl, piperidinyl, piperazinyl and diazepanyl;

wherein $R^{7a}$ may be optionally substituted on carbon by one or more $R^{11}$ selected from methyl, methoxy, methylamino, dimethylamino, diethylamino; and $R^{7a}$ may be optionally substituted on nitrogen by methyl;

$R^{7b}$ is methyl or acetyl;

$R^8$ is selected from selected from methyl, ethyl, acetyl, methyl, methoxycarbonyl, carbamoyl, N-(methyl)carbamoyl and N,N-(methyl)$_2$carbamoyl;

$X^5$ is —C(O)— or —C(O)N$R^{14}$; and
$R^{14}$ is hydrogen, methyl or ethyl.

(19) $R^2$ is selected from cyano, methyl, methoxy, cyclopropyl, which methyl may be optionally substituted on carbon by one or more $R^{7a}$; or $R^2$ is heterocyclyl-$X^2$—, wherein $X^2$ is a direct bond, which heterocyclyl is carbon linked to $X^2$ and is selected from tetrahydropyranyl, piperidinyl and piperazinyl which heterocyclyl may be optionally substituted on carbon by one or more $R^{7b}$ and wherein if a heterocyclyl within $R^2$ contains an —NH— moiety that nitrogen may be optionally substituted by a group selected from $R^8$; and wherein any heterocyclyl within $R^2$ optionally bears an oxo substituents;

$R^{7a}$ is selected from N—($C_{1-6}$alkyl)carbamoyl or N,N—($C_{1-6}$alkyl)$_2$carbamoyl, or $R^{7a}$ is heterocyclyl-$X^5$—, which heterocyclyl is selected from pyrrolidinyl, morpholinyl, piperidinyl, piperazinyl and diazepanyl;

wherein $R^{7a}$ may be optionally substituted on carbon by one or more $R^{11}$ selected from methyl, methoxy, methylamino, dimethylamino, diethylamino; and $R^{7a}$ may be optionally substituted on nitrogen by methyl;

$R^8$ is selected from selected from methyl, ethyl, acetyl, methyl, methoxycarbonyl, carbamoyl, N-(methyl)carbamoyl and N,N-(methyl)$_2$carbamoyl;

wherein $X^5$ is —C(O)— or —C(O)N$R^{14}$; and
$R^{14}$ is hydrogen, methyl or ethyl.

(20) $R^2$ is selected from $C_{1-4}$alkyl (optionally substituted by 1, 2 or 3 halo, hydroxy or $C_{1-4}$alkoxy), $C_{1-4}$alkoxy, cyano, cyclopropyl, $C_{1-4}$alkylaminocarbonyl, N,N—($C_{1-4}$alkyl)$_2$amino carbonyl; or $R^2$ is a heterocyclic ring selected from piperidyl, piperazinyl and tetrahydropyranyl which ring is itself optionally substituted by methyl or acetyl and optionally bears an oxo substituent; or $R^2$ is 2-oxoethyl optionally substituted (preferably at the 2-position) by a heterocyclic ring selected from pyrrolidinyl, piperidyl, piperazinyl, morpholino and 1,4-diazepanyl which ring itself is optionally substituted by methyl, methylamino, or dimethylamino; or $R^2$ is carbamoylmethyl optionally substituted on nitrogen by 2-methoxyethyl, 2-dimethylaminoethyl, 3-dimethylaminopropyl, piperidyl or 1-methylpiperidyl, and which carbamoylmethyl is further optionally substituted on nitrogen by methyl.

(21) $R^2$ is selected from methyl, methoxy, cyano and cyclopropyl; or $R^2$ is a heterocyclic ring selected from piperidyl, piperazinyl and tetrahydropyranyl which ring is itself optionally substituted by methyl or acetyl and optionally bears an oxo substituent; or $R^2$ is 2-oxoethyl optionally substituted (preferably at the 2-position) by a heterocyclic ring selected from pyrrolidinyl, piperidyl, piperazinyl, morpholino and 1,4-diazepanyl which ring itself is optionally substituted by methyl, methylamino, or dimethylamino; or $R^2$ is carbamoylmethyl optionally substituted on nitrogen by 2-methoxyethyl, 2-dimethylaminoethyl, 3-dimethylaminopropyl, piperidyl or 1-methylpiperidyl, and which carbamoylmethyl is further optionally substituted on nitrogen by methyl.

(22) $R^2$ is selected from methyl, ethyl, isopropyl, isobutyl, tert-butyl, difluoromethyl, trifluoromethyl, methoxymethyl, 2-hydroxyethyl, methoxy, cyano, cyclopropyl, methylaminocarbonyl, dimethylaminocarbonyl, piperid-4-yl, 1-methylpiperid-4-yl, 1-acetylpiperid-4-yl, piperid-3-yl, 6-oxopiperidin-3-yl, 1-methylpiperazin-4-yl, tetrahydropyran-4-yl, 2-oxo-2-pyrrolidin-1-ylethyl, 2-(3-methylaminopyrrolidin-1-yl)-2-oxoethyl, 2-(4-dimethylaminopiperid-1-yl)-2-oxoethyl, 2-(4-methylpiperazin-1-yl)-2-oxoethyl, 2-morpholino-2-oxoethyl, 2-(4-methyl-1,4-diazepan-1-yl)-2-oxoethyl, 2-{N-[2-(dimethylamino)ethyl]amino}-2-oxoethyl, 2-{N-[3-(dimethylamino)propyl]amino}-2-oxoethyl, 2-[N-(2-methoxyethyl)amino]-2-oxoethyl, 2-[N-(2-methoxyethyl)-N-methylamino]-2-oxoethyl and 2-[methyl-(1-methylpiperid-4-yl)amino]-2-oxoethyl.

(23) $R^2$ is selected from methyl, methoxy, cyano, cyclopropyl, piperid-4-yl, 1-methylpiperid-4-yl, 1-acetylpiperid-4-yl, piperid-3-yl, 6-oxopiperidin-3-yl, 1-methylpiperazin-4-yl, tetrahydropyran-4-yl, 2-oxo-2-pyrrolidin-1-ylethyl, 2-(3-methylaminopyrrolidin-1-yl)-2-oxoethyl, 2-(4-dimethylaminopiperid-1-yl)-2-oxoethyl, 2-(4-methylpiperazin-1-yl)-2-oxoethyl, 2-morpholino-2-oxoethyl, 2-(4-methyl-1,4-diazepan-1-yl)-2-oxoethyl, 2-{N-[2-(dimethylamino)ethyl]amino}-2-oxoethyl, 2-{N-[3-(dimethylamino)propyl]amino}-2-oxoethyl, 2-[N-(2-methoxyethyl)amino]-2-oxoethyl, 2-[N-(2-methoxyethyl)-N-methylamino]-2-oxoethyl and 2-[methyl-(1-methyl-4-piperidyl)amino]-2-oxoethyl.

(24) $R^2$ is methyl.
(25) n is 1, 2 or 3.
(26) n is 2 or 3.
(27) n is 1 or 2.
(28) n is 3
(29) n is 2
(30) n is 1.
(31) Ring Q is selected from pyrazole and imidazole.
(32) Ring Q is selected from:

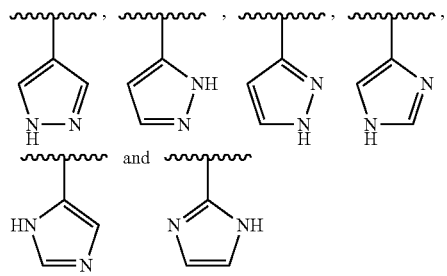

wherein ⁓ shows the point of attachment of ring Q to the NH group in formula I.
(33) Ring Q is selected from

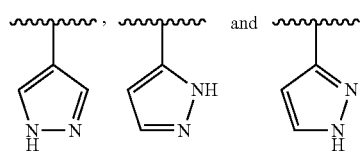

wherein ⁓ shows the point of attachment of ring Q to the NH group in formula I.
(34) Ring Q is selected from

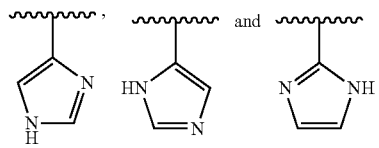

wherein ⁓ shows the point of attachment of ring Q to the NH group in formula I.
(35) Ring Q is

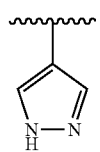 [SMILES: *c1cn[nH]c1]

wherein ⁓ shows the point of attachment of ring Q to the NH group in formula I.
(36) Ring Q is

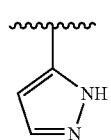

wherein ⁓ shows the point of attachment of ring Q to the NH group in formula I.
(37) Ring Q is

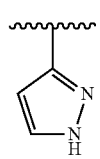 [SMILES: *c1cc[nH]n1]

wherein ⁓ shows the point of attachment of ring Q to the NH group in formula I.
(38) Ring Q is

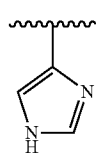

wherein ⁓ shows the point of attachment of ring Q to the NH group in formula I.

As will be appreciated ring Q in (31) to (38) above is optionally substituted by n $R^2$ groups as hereinbefore defined, for example n and $R^2$ are as defined in any of (10) to (30) above.

(39) The group in formula I of the formula:

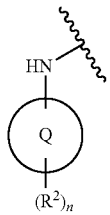

is selected from 1,3-dimethylpyrazol-4-yl, 5-methoxy-2-methylpyrazol-3-yl, 1-methylpyrazol-4-yl, 1,5-dimethylpyrazol-3-yl, 1-(1-methylpiperid-4-yl)pyrazol-4-yl, 1-(2-oxo-2-pyrrolidin-1-ylethyl)pyrazol-4-yl, 1-[2-(4-methyl-1,4-diazepan-1-yl)-2-oxo-ethyl]pyrazol-4-yl, 1-(2-morpholino-2-oxo-ethyl)pyrazol-4-yl, 1-{2-[2-methoxyethyl(methyl)amino]-2-oxoethyl}pyrazol-4-yl, 1-[2-(4-methylpiperazin-1-yl)-2-oxoethyl]pyrazol-4-yl, 2,5-dimethylpyrazol-3-yl, 1-(1-acetylpiperid-4-yl)pyrazol-4-yl, 1-tetrahydropyran-4-ylpyrazol-4-yl, 5-methyl-1H-pyrazol-3-yl, 5-cyclopropyl-1H-pyrazol-3-yl, 1-methylimidazol-4-yl, 1-(piperidin-4-yl)pyrazol-4-yl, 1-(1-methylpiperid-4-yl)pyrazol-4-yl, 1-[N-(2-methoxyethyl)carbamoylmethyl]pyrazol-4-yl, 1-[N-(2-methoxyethyl)-N-methylcarbamoylmethyl]pyrazol-4-yl, 1-[N-(2-dimethylaminoethyl)carbamoylmethyl]pyrazol-4-yl, 1-(2-morpholino-2-oxoethyl)pyrazol-4-yl, 1-(piperid-3-yl)pyrazol-4-yl, 1-[2-[methyl(1-methylpiperid-4-yl)amino]-2-oxo-ethyl]pyrazol-4-yl, 1-[2-(4-dimethylaminopiperidin-1-yl)-2-oxoethyl]pyrazol-4-yl, 1-[(3R)-6-oxopiperidin-3-yl]pyrazol-4-yl, 1-[N-(3-dimethylaminopropyl)carbamoylmethyl]pyrazol-4-yl and 1-[2-(3-methylaminopyrrolidin-1-yl)-2-oxoethyl]pyrazol-4-yl.

The group in formula I of the formula:

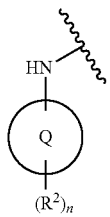

is additionally selected from 1,5-dimethylpyrazol-4-yl, 1-ethyl-3-methylpyrazol-4-yl, 1-isobutylpyrazol-4-yl, 1-ethylpyrazol-4-yl, 1,3,5-trimethylpyrazol-4-yl, 1-isopropylpyrazol-4-yl, 1-methyl-3-trifluoromethylpyrazol-4-yl, 1,3-dimethylpyrazol-5-yl, 1-methylpyrazol-5-yl, 1-methyl-3-cyclopropylpyrazol-5-yl, 1-ethylpyrazol-5-yl, 1-tertbutyl-3-ethyl-4-methylpyrazol-5-yl, 1-piperidin-4-ylpyrazol-3-yl, 4-cyano-5-(4-methylpiperazidin-1-yl)pyrazol-3-yl, 1-methylpyrazol-3-yl, 1-ethylpyrazol-3-yl, 1-methyl-3-methoxypyrazol-5-yl, 3-methylpyrazol-4-yl, 1-methyl-3-methoxypyrazol-4-yl, 1-methyl-3-cyanopyrazol-4-yl, 1-methyl-3-(methoxymethyl)pyrazol-4-yl, 1-methyl-3-(methylaminocarbonyl)pyrazol-4-yl, 1-methyl-3-(dimethylaminocarbonyl)pyrazol-4-yl, 1-(2-hydroxyethyl)pyrazol-4-yl, 1-difluoromethyl-3-methylpyrazol-4-yl and 1-isopropyl-3-methylpyrazol-4-yl.

(40) The group in formula I of the formula:

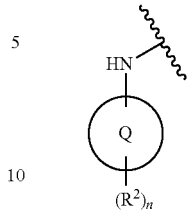

is 1,3-dimethylpyrazol-4-yl, 1,3-dimethylpyrazol-5-yl or 1,3,5-trimethylpyrazol-4-yl.

(41) $R^3$ is selected from hydrogen, hydroxy, $C_{1-4}$alkyl and $C_{1-4}$alkoxy.
(42) $R^3$ is selected from hydrogen and $C_{1-4}$alkyl.
(43) $R^3$ is selected from hydroxy and $C_{1-4}$alkoxy (particularly $R^3$ is $C_{1-4}$alkoxy such as methoxy).
(44) $R^3$ is $C_{1-4}$alkyl.
(45) $R^3$ is methyl.
(46) $R^3$ is hydrogen.
(47) $R^3$ is $C_{1-4}$alkyl and $R^4$ is hydrogen.
(48) $R^3$ is $C_{1-4}$alkoxy.
(49) $R^3$ is methoxy.
(50) $R^3$ is ethoxy.
(51) $R^3$ is $C_{1-4}$alkoxy and $R^4$ is hydrogen.
(52) $R^3$ is methoxy and $R^4$ is hydrogen.
(53) $R^3$ is ethoxy and $R^4$ is hydrogen.
(54) $R^3$ is methoxy and $R^4$ is methyl.
(55) $R^3$ is selected from hydroxy and $C_{1-4}$alkoxy (particularly $R^3$ is $C_{1-4}$alkoxy such as methoxy) and $R^4$ is selected from hydrogen and $C_{1-4}$alkyl.
(56) $R^3$ and $R^4$ are both hydrogen.
(57) $R^3$ and $R^4$ are both independently $C_{1-4}$alkyl.
(58) $R^3$ is methyl and $R^4$ is hydrogen.
(59) $R^4$ is hydrogen.
(60) $R^4$ is methyl.
(61) The $C(O)NR^3R^4$ group together with the carbon atom to which it is attached and the $R^{5c}$ group together with the carbon atom (at the 3-position on the phenyl ring) form a heterocyclic ring fused to the phenyl ring such that the aniline at the 4-position on the pyridine ring in Formula I is of the formula:

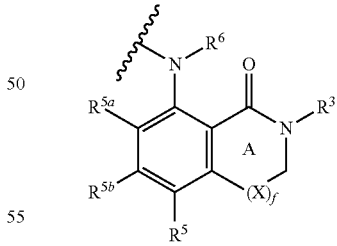

wherein:
$R^3$, $R^5$, $R^{5a}$, $R^{5b}$ and $R^6$ have any of the values defined herein;
f is 0 or 1;
X is selected from —O—, —S—, —S(O)—, —S(O$_2$)—, —N(R$^x$)—, —OCH$_2$, —SCH$_2$, —S(O)CH$_2$, —S(O$_2$)CH$_2$, —N(R$^x$)CH$_2$, —CH$_2$— and —(CH$_2$)$_2$— wherein R$^x$ is selected from hydrogen, $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)carbamoyl;

and wherein ring A may be optionally substituted on carbon by one or more $R^{3a}$ selected from $C_{1-4}$alkyl, $C_{1-4}$alkoxy, halo, cyano, hydroxy and oxo (preferably $C_{1-4}$alkyl such as methyl).

As will be realised when f is 0, ring A is a 5-membered heterocyclyl ring such that the aniline at the 4-position on the pyridine ring in Formula I is of the formula:

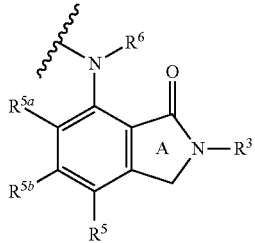

(62) The $C(O)NR^3R^4$ group together with the carbon atom to which it is attached and the $R^{5c}$ group together with the carbon atom to which it is attached (at the 3-position on the phenyl ring) form a heterocyclic ring fused to the phenyl ring such that the aniline at the 4-position on the pyridine ring in Formula I is of the formula:

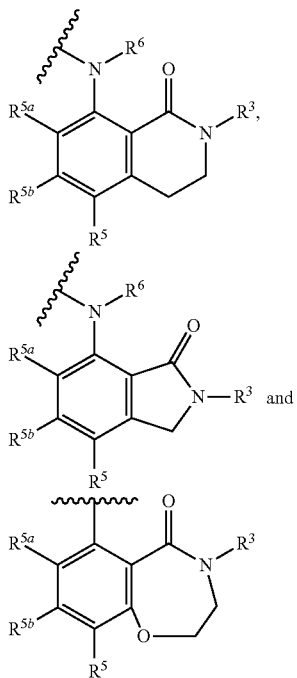

wherein the heterocyclic ring so formed by the C(O)NR³R⁴ ring member may be optionally substituted on carbon by one or more $R^{3a}$ selected from $C_{1-4}$alkyl, $C_{1-4}$alkoxy, halo, cyano, hydroxy and oxo; and $R^3$, $R^5$, $R^{5a}$, $R^{5b}$ and $R^6$ have any of the values defined herein.

(63) The $C(O)NR^3R^4$ group together with the carbon atom to which it is attached and the $R^{5c}$ group together with the carbon atom to which it is attached (at the 3-position on the phenyl ring) form a heterocyclic ring fused to the phenyl ring such that the aniline at the 4-position on the pyridine ring in Formula I is of the formula:

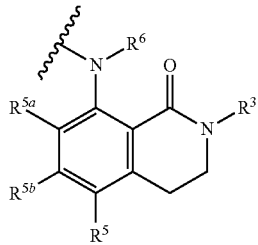

wherein the heterocyclic ring so formed by the $C(O)NR^3R^4$ ring member may be optionally substituted on carbon by one or more $R^{3a}$ as defined herein and $R^3$, $R^5$, $R^{5a}$, $R^{5b}$ and $R^6$ have any of the values defined herein.

(64) The $C(O)NR^3R^4$ group together with the carbon atom to which it is attached and the is $R^{5c}$ group together with the carbon atom to which it is attached (at the 3-position on the phenyl ring) form a heterocyclic ring fused to the phenyl ring such that the aniline at the 4-position on the pyridine ring in Formula I is of the formula:

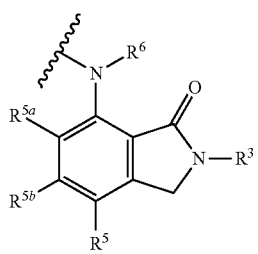

wherein the heterocyclic ring so formed by the $C(O)NR^3R^4$ ring member may be optionally substituted on carbon by one or more $R^{3a}$ as defined herein and $R^3$, $R^5$, $R^{5a}$, $R^{5b}$ and $R^6$ have any of the values defined herein.

(65) The $C(O)NR^3R^4$ group together with the carbon atom to which it is attached and the $R^{5c}$ group together with the carbon atom to which it is attached (at the 3-position on the phenyl ring) form a heterocyclic ring fused to the phenyl ring such that the aniline at the 4-position on the pyridine ring in Formula I is of the formula:

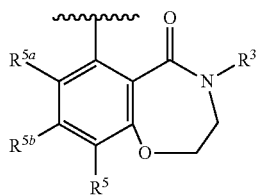

wherein the heterocyclic ring so formed by the $C(O)NR^3R^4$ ring member may be optionally substituted on carbon by one or more $R^{3a}$ as defined herein and $R^3$, $R^5$, $R^{5a}$, $R^{5b}$ and $R^6$ have any of the values defined herein.

(66) $R^5$ is hydrogen, halo, cyano, sulfamoyl, sulfonylamino, $C_{1-4}$alkyl, $C_{1-4}$alkoxy, $C_{1-4}$alkylthio or heterocyclyl-$X^8$— wherein $X^8$ is a direct bond and which heterocyclyl is selected from azetidinyl, tetrahydrofuranyl, tetrahydropyranyl, pyrrolidinyl, morpholinyl, piperidinyl, piperazinyl, homopiperidinyl and homopiperazinyl and wherein heterocyclyl may be optionally substituted on carbon by one or more groups selected from halo, amino, hydroxy, methyl, ethyl, prop-2-yl, cyclopropyl, cyclobutyl, methoxy, ethoxy, methylamino, ethylamino, dimethylamino, diethylamino and N-methyl-N-ethylamino; and wherein if a heterocyclyl contains an —NH— moiety that nitrogen may be optionally substituted by a group selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)carbamoyl.

(67) $R^5$ is hydrogen, halo, cyano, sulfamoyl, sulfonylamino, $C_{1-4}$alkyl, $C_{1-4}$alkoxy or heterocyclyl-$X^8$— wherein $X^8$ is a direct bond and which heterocyclyl is selected from azetidinyl, tetrahydrofuranyl, tetrahydropyranyl, pyrrolidinyl, morpholinyl, piperidinyl, piperazinyl, homopiperidinyl and homopiperazinyl and wherein heterocyclyl may be optionally substituted on carbon by one or more groups selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if a heterocyclyl contains an —NH— moiety that nitrogen may be optionally substituted by a group selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$alkyl)carbamoyl.

(68) $R^5$ is hydrogen, halo, $C_{1-4}$alkyl, $C_{1-4}$alkoxy, $C_{1-4}$alkylS(O)$_j$ (where j is 0, 1 or 2) or heterocyclyl which heterocyclyl may be optionally substituted on nitrogen by $C_{1-4}$alkyl.

(69) $R^5$ is hydrogen, halo, methyl, methoxy, methylthio, morpholino or piperazinyl wherein piperazinyl may be optionally substituted on nitrogen by $C_{1-4}$alkyl.

(70) $R^5$ is hydrogen, halo or piperazinyl wherein piperazinyl may be optionally substituted on nitrogen by $C_{1-4}$alkyl.

(71) $R^5$ is hydrogen, fluoro, chloro, methyl, methoxy, methylthio, morpholino, 4-methylpiperazinyl or 4-isopropylpiperazinyl.

(72) $R^5$ is hydrogen, fluoro, 4-methylpiperazinyl or 4-isopropylpiperazinyl.

(73) $R^5$ is hydrogen or fluoro.

(74) $R^5$ is hydrogen.

(75) $R^{5a}$ is hydrogen or halo.

(76) $R^{5a}$ is hydrogen or fluoro.

(77) $R^{5a}$ is hydrogen.

(78) $R^{5b}$ is selected from hydrogen, halo, $C_{1-4}$alkyl, $C_{1-4}$alkoxy and $C_{1-4}$alkylsulphonyl.

(79) $R^{5b}$ is hydrogen, fluoro, chloro, methyl, methoxy or methylsulphonyl.

(80) $R^{5b}$ is hydrogen, fluoro, chloro or methyl.

(81) $R^{5b}$ is hydrogen or fluoro.

(82) $R^{5b}$ is hydrogen.

(83) $R^{5c}$ is hydrogen, halo or $C_{1-4}$alkoxy.

(84) $R^{5c}$ is hydrogen, fluoro or methoxy.

(85) $R^{5c}$ is hydrogen or fluoro (particularly hydrogen).

(86) $R^{5c}$ is hydrogen or methoxy.

(87) $R^6$ is hydrogen.

(88) $R^6$ is $C_{1-4}$alkyl, for example methyl.

(89) $R^6$ is hydrogen or methyl.

In an embodiment of the invention there is provided a compound of the formula I, or a pharmaceutically acceptable salt thereof, wherein:

ring Q is pyrazolyl;

$R^1$ is selected from fluoro and chloro (particularly $R^1$ is chloro, more particularly $R^1$ is fluoro);

n is 1 or 2;

$R^2$ is as defined hereinbefore, for example as defined in any one of (10) to (24) above;

$R^3$ is selected from hydrogen, $C_{1-3}$alkyl and $C_{1-3}$alkoxy (particularly $R^3$ is hydrogen or $C_{1-3}$alkyl);

$R^4$ is selected from hydrogen and $C_{1-3}$alkyl (for example $R^3$ is $C_{1-3}$alkyl such as methyl and $R^4$ is hydrogen); or the C(O)NR$^3$R$^4$ group together with the carbon atom to which it is attached and the R$^{5c}$ group together with the carbon atom to which it is attached (at the 3-position on the phenyl ring) form a heterocyclic ring fused to the phenyl ring such that the aniline at the 4-position on the pyridine ring in Formula I is selected from:

wherein the heterocyclic ring so formed by the C(O)NR$^3$R$^4$ ring member may be optionally substituted on carbon by one or more R$^{3a}$ selected from $C_{1-4}$alkyl, $C_{1-4}$alkoxy, halo, cyano, hydroxy and oxo;

$R^5$, $R^{5a}$, $R^{5b}$ and $R^{5c}$ are as hereinbefore defined; and $R^6$ is hydrogen.

In this embodiment, n may also be 3.

In a further embodiment of the invention there is provided a compound of the formula I, or a pharmaceutically acceptable salt thereof, wherein:

ring Q is pyrazolyl;

$R^1$ is cyano;

n is 1 or 2;

$R^2$ is as defined hereinbefore, for example as defined in any one of (10) to (24) above;

$R^3$ is selected from hydrogen, $C_{1-3}$alkyl and $C_{1-3}$alkoxy (particularly $R^3$ is hydrogen or $C_{1-3}$alkyl);

$R^4$ is selected from hydrogen and $C_{1-3}$alkyl (for example $R^3$ is $C_{1-3}$alkyl such as methyl and $R^4$ is hydrogen); or the C(O)NR$^3$R$^4$ group together with the carbon atom to which it is attached and the R$^{5a}$ group together with the carbon atom to which it is attached (at the 3-position on the phenyl ring) form a heterocyclic ring fused to the phenyl ring such that the aniline at the 4-position on the pyridine ring in Formula I is selected from:

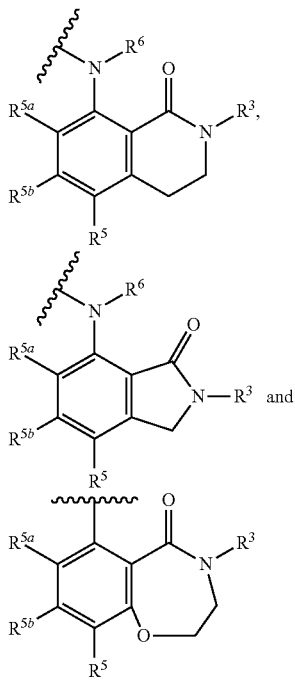

wherein the heterocyclic ring so formed by the C(O)NR³R⁴ ring member may be optionally substituted on carbon by one or more R³ᵃ selected from $C_{1-4}$alkyl, $C_{1-4}$alkoxy, halo, cyano, hydroxy and oxo; and R³, R⁵, R⁵ᵃ, R⁵ᵇ and R⁶ have any of the values defined herein. R⁵, R⁵ᵃ, R⁵ᵇ and R⁵ᶜ are as hereinbefore defined; and R⁶ is hydrogen.

In this embodiment, n may also be 3.

In another embodiment of the invention there is provided a compound of the formula I, or a pharmaceutically acceptable salt thereof, wherein:

ring Q is pyrazolyl;

R¹ is trifluoromethyl;

n is 1 or 2;

R² is as defined hereinbefore, for example as defined in any one of (10) to (24) above;

R³ is selected from hydrogen, $C_{1-3}$alkyl and $C_{1-3}$alkoxy (particularly R³ is hydrogen or $C_{1-3}$alkyl);

R⁴ is selected from hydrogen and $C_{1-3}$alkyl (for example R³ is $C_{1-3}$alkyl such as methyl and R⁴ is hydrogen); or the C(O)NR³R⁴ group together with the carbon atom to which it is attached and the R⁵ᶜ group together with the carbon atom to which it is attached (at the 3-position on the phenyl ring) form a heterocyclic ring fused to the phenyl ring such that the aniline at the 4-position on the pyridine ring in Formula I is selected from:

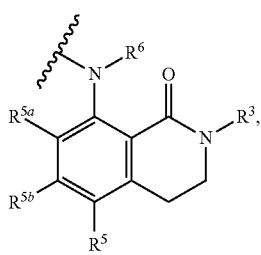

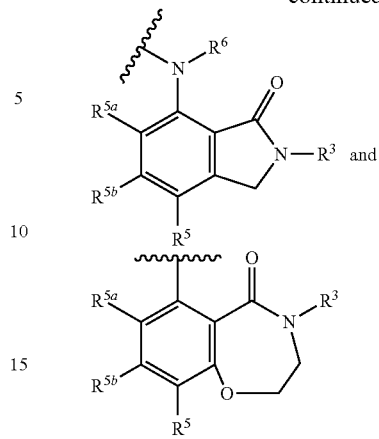

wherein the heterocyclic ring so formed by the C(O)NR³R⁴ ring member may be optionally substituted on carbon by one or more R³ᵃ selected from $C_{1-4}$alkyl, $C_{1-4}$alkoxy, halo, cyano, hydroxy and oxo; R⁵, R⁵ᵃ, R⁵ᵇ and R⁵ᶜ are as hereinbefore defined;

R⁶ is hydrogen.

In this embodiment, n may also be 3.

In another embodiment of the invention there is provided a compound of the formula I, or a pharmaceutically acceptable salt thereof of the formula Ia:

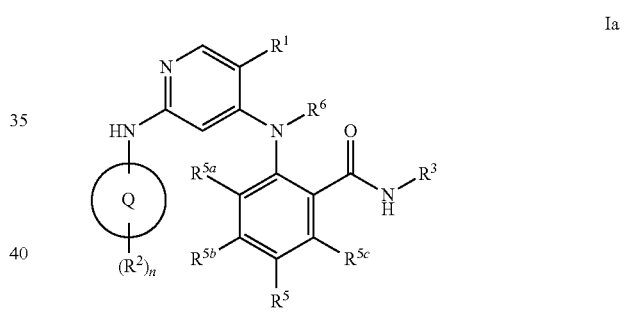

Ia wherein:

ring Q, R¹, R², R⁵, R⁵ᵃ, R⁵ᵇ, R⁵ᶜ and n have any of the values defined herein;

R³ is selected from hydrogen, $C_{1-4}$alkyl and $C_{1-4}$alkoxy (particularly R³ is selected from hydrogen and $C_{1-4}$alkyl, more particularly R³ is $C_{1-4}$alkyl such as methyl); and R⁶ is hydrogen.

In a particular embodiment in the compound of formula Ia, R³ is $C_{1-4}$alkyl such as methyl and R⁴ is hydrogen.

In another embodiment of the invention there is provided a compound of the formula Ia (as shown above), or a pharmaceutically acceptable salt thereof wherein:

ring Q is selected from:

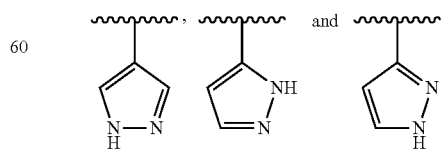

R¹ is trifluoromethyl; R² is as defined in (20) above, and more particularly as defined in (22) above; n is 1, 2 or 3; R³ is selected from hydrogen, $C_{1-4}$alkyl and $C_{1-4}$alkoxy (particularly $R^3$ is selected from $C_{1-4}$alkyl such as methyl and $C_{1-4}$alkoxy such as methoxy); $R^5$ is hydrogen, halo or piperazinyl wherein piperazinyl may be optionally substituted on nitrogen by $C_{1-4}$alkyl; $R^{5a}$ is hydrogen or halo; $R^{5b}$ is selected from hydrogen, halo, $C_{1-4}$alkyl, $C_{1-4}$alkoxy and $C_{1-4}$alkylsulphonyl; $R^{5c}$ is hydrogen, halo or $C_{1-4}$alkoxy; and $R^6$ is hydrogen.

In another embodiment of the invention there is provided a compound of the formula Ia (as shown above), or a pharmaceutically acceptable salt thereof wherein:
ring Q is selected from:

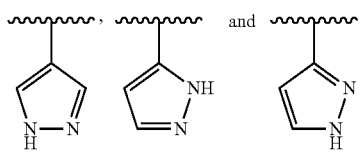

$R^1$ is trifluoromethyl; $R^2$ is methyl; n is 2 or 3; $R^3$ is methyl or methoxy; $R^5$ hydrogen or fluoro; $R^{5a}$ is hydrogen or fluoro; $R^{5b}$ is selected from hydrogen, fluoro, chloro or methyl (particularly hydrogen or fluoro); $R^{5c}$ is hydrogen or methoxy; and $R^6$ is hydrogen.

In another embodiment of the invention there is provided a compound of the formula Ia (as shown above), or a pharmaceutically acceptable salt thereof wherein:
the group in formula Ia of the formula:

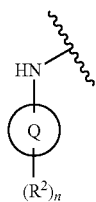

is selected from 1,3-dimethylpyrazol-4-yl, 1,3-dimethylpyrazol-5-yl or 1,3,5-trimethylpyrazol-4-yl; $R^1$ is trifluoromethyl; $R^3$ is methyl or methoxy; $R^5$ hydrogen or fluoro; $R^{5a}$ is hydrogen or fluoro; $R^{5b}$ is selected from hydrogen or fluoro; $R^{5c}$ is hydrogen or methoxy; and $R^6$ is hydrogen.

In another embodiment of the invention there is provided a compound of the formula I, or a pharmaceutically acceptable salt thereof of the formula Ib:

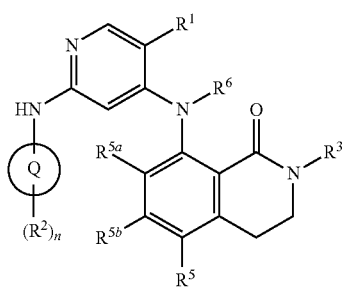

wherein:
ring Q, $R^1$, $R^2$, $R^5$, $R^{5a}$, $R^{5b}$ and n have any of the values defined herein;

$R^3$ is selected from hydrogen and $C_{1-4}$alkyl; and $R^6$ is hydrogen. In another embodiment of the invention there is provided a compound of the formula I, or a pharmaceutically acceptable salt thereof of the formula Ic:

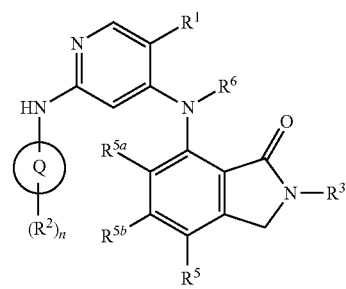

wherein:
ring Q, $R^1$, $R^2$, $R^5$, $R^{5a}$, $R^{5b}$ and n have any of the values defined herein;
$R^3$ is selected from hydrogen and $C_{1-4}$alkyl; and $R^6$ is hydrogen.

In another embodiment of the invention there is provided a compound of the formula I, or a pharmaceutically acceptable salt thereof of the formula Id:

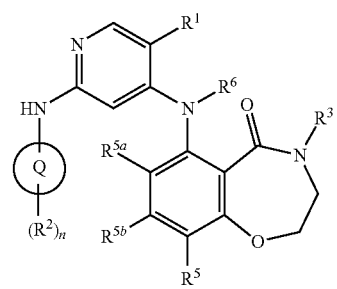

wherein:
ring Q, $R^1$, $R^2$, $R^5$, $R^{5a}$, $R^{5b}$ and n have any of the values defined herein;
$R^3$ is selected from hydrogen and $C_{1-4}$alkyl; and $R^6$ is hydrogen.

In the compounds of formulae Ia, Ib, Ic, Id a particular value for $R^1$ is halo (For example $R^1$ is chloro. Alternatively $R^1$ is fluoro).

In the compounds of formulae Ia, Ib, Ic, Id (particularly Ib, Ic, Id) a particular value for $R^1$ is cyano.

In the compounds of formulae Ia, Ib, Ic, Id a particular value for $R^1$ is trifluoromethyl.

In the compounds of formulae Ia, Ib, Ic, Id a particular value for $R^5$ is hydrogen.

In the compounds of formulae Ia, Ib, Ic, Id a particular value for $R^5$ is fluoro.

In the compounds of formulae Ia, Ib, Ic, Id a particular value for $R^5$ is piperazinyl optionally substituted by $C_{1-4}$alkyl.

In the compounds of formulae Ia, Ib, Ic, Id a particular value for $R^{5a}$ is hydrogen or fluoro.

In the compounds of formulae Ia, Ib, Ic, Id a particular value for $R^{5a}$ is hydrogen.

In the compounds of formulae Ia, Ib, Ic, Id a particular value for $R^{5b}$ is hydrogen.

In the compounds of formulae Ia, Ib, Ic, Id a particular value for $R^{5b}$ is fluoro.

In the compounds of formulae Ia, Ib, Ic, Id a particular value for $R^{5c}$ is hydrogen or fluoro.

In the compounds of formulae Ia, Ib, Ic, Id a particular value for $R^{5c}$ is hydrogen.

In the compounds of formulae Ia, Ib, Ic, Id a particular value for $R^{5c}$ is methoxy.

In the compounds of formulae Ia, Ib, Ic, Id a particular value for $R^3$ is hydrogen or $C_{1-3}$alkyl. Particularly, $R^3$ is $C_{1-3}$alkyl such as methyl or ethyl (particularly $R^3$ is methyl). Particularly, $R^3$ is $C_{1-3}$alkoxy such as methoxy.

In a further embodiment in the compounds of formulae Ia, Ib, Ic, Id a particular value for n is 1 or 2 and $R^2$ has any of the values defined hereinbefore. For example $R^2$ is as defined in any one of (10) to (24) above.

In another embodiment in the compounds of formulae Ia, Ib, Ic, Id a particular value for n is 1, and $R^2$ has any of the values defined hereinbefore. For example $R^2$ is as defined in any one of (10) to (24) above.

In another embodiment in the compounds of formulae Ia, Ib, Ic ring Q is

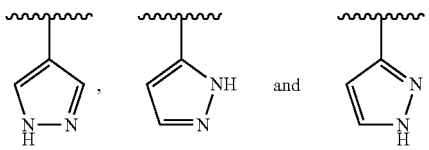 [SMILES: *c1cn[nH]c1 ; *c1ccn[nH]1 ; *c1cc[nH]n1]

wherein ⌇ shows the point of attachment of ring Q to the NH group in formulae Ia, Ib, Ic and Id and ring Q is optionally substituted by n $R^2$ groups as defined herein, such as n is 2 or 3, and $R^2$ is any one of (20) or (22).

In another embodiment in the compounds of formulae Ia, Ib, Ic ring Q is selected from

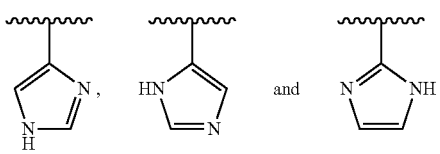 [SMILES: *c1c[nH]cn1 ; *c1cnc[nH]1 ; *c1ncc[nH]1]

wherein ⌇ shows the point of attachment of ring Q to the NH group in formulae Ia, Ib, Ic and Id and ring Q is optionally substituted by n $R^2$ groups as defined herein.

Accordingly in a further embodiment there is provided a compound of the formula I of the formula Ia, Ib, Ic or Id as hereinbefore defined, or a pharmaceutically acceptable salt thereof, wherein:
ring Q is selected from

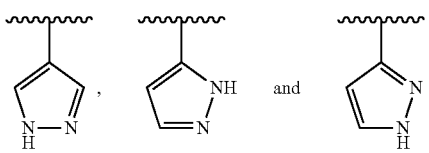 [SMILES: *c1cn[nH]c1 ; *c1ccn[nH]1 ; *c1cc[nH]n1]

wherein ⌇ shows the point of attachment of ring Q to the NH group in formulae Ia, Ib, Ic and Id and ring Q is optionally substituted by n $R^2$ groups;

$R^1$ is selected from chloro and fluoro (Particularly $R^1$ is chloro. More particularly $R^1$ is fluoro);

$R^3$ is $C_{1-3}$alkyl such as methyl;

$R^5$ is hydrogen or piperazinyl optionally substituted by $C_{1-4}$alkyl;

$R^{5a}$, $R^{5b}$ and $R^{5c}$ (where present) are hydrogen;

$R^6$ is hydrogen;

n is 1, 2 or 3; and $R^2$ has any of the values defined herein, for example as defined in any one of (10) to (24). Particularly in this embodiment the group in formula Ia, Ib, Ic and Id of the formula:

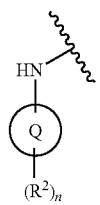

is as defined in (39) or (40) above.

Accordingly in a further embodiment there is provided a compound of the formula I of the formula Ia, Ib. Ic or Id as hereinbefore defined, or a pharmaceutically acceptable salt thereof, wherein:
ring Q is selected from

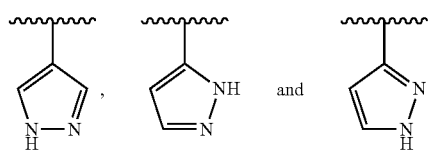 [SMILES: *c1cn[nH]c1 ; *c1ccn[nH]1 ; *c1cc[nH]n1]

wherein ⌇ shows the point of attachment of ring Q to the NH group in formulae Ia, Ib and Ic; and ring Q is optionally substituted by n $R^2$ groups as defined herein;

$R^1$ is cyano;

$R^3$ is $C_{1-3}$alkyl such as methyl;

$R^5$ is hydrogen or piperazinyl optionally substituted by $C_{1-4}$alkyl;

$R^{5a}$, $R^{5b}$ and $R^{5c}$ (where present) are hydrogen;

$R^6$ is hydrogen;

n is 1, 2 or 3; and $R^2$ has any of the values defined herein, for example as defined in any one of (10) to (24). Particularly in this embodiment the group in formula Ia, Ib, Ic and Id of the formula:

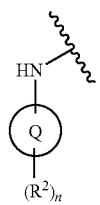

is as defined in (39) or (40) above.

Accordingly in a further embodiment there is provided a compound of the formula I of the formula Ia, Ib, Ic or Id as hereinbefore defined, or a pharmaceutically acceptable salt thereof, wherein:

ring Q is selected from

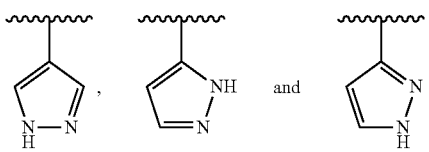

wherein ⁓⁓⁓ shows the point of attachment of ring Q to the NH group in formulae Ia, Ib and Ic; and ring Q is optionally substituted by n $R^2$ groups as defined herein;

$R^1$ is trifluoromethyl;
$R^3$ is $C_{1-3}$alkyl such as methyl or $C_{1-3}$alkoxy such as methoxy;
$R^5$ is hydrogen, fluoro or piperazinyl optionally substituted by $C_{1-4}$alkyl;
$R^{5a}$ and $R^{5b}$ are independently hydrogen or fluoro;
$R^{5c}$ (where present) is hydrogen, fluoro or methoxy;
$R^6$ is hydrogen;
n is 2 or 3; and
$R^2$ has any of the values defined herein, for example as defined in any one of (10) to (24). Particularly in this embodiment the group in formula Ia, Ib, Ic and Id of the formula:

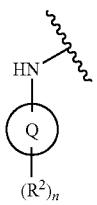

is as defined in (39) or (40) above.

In another embodiment of the invention there is provided a compound of the formula I selected from:
2-[[5-cyano-2-[(1,3-dimethylpyrazol-4-yl)amino]-4-pyridyl]amino]-N-methyl-benzamide;
2-[[5-cyano-2-[(5-methoxy-2-methylpyrazol-3-yl)amino]pyridin-4-yl]amino]-N-methylbenzamide;
2-[[5-cyano-2-[(1,3-dimethylpyrazol-4-yl)amino]-4-pyridyl]amino]-N-methoxy-N-methyl-benzamide;
4-[(2-methyl-1-oxo-3,4-dihydroisoquinolin-8-yl)amino]-6-[(1-methylpyrazol-4-yl)amino]pyridine-3-carbonitrile;
6-[(1,5-dimethylpyrazol-3-yl)amino]-4-[(2-methyl-1-oxo-3,4-dihydroisoquinolin-8-yl)amino]pyridine-3-carbonitrile;
6-[(5-methoxy-2-methylpyrazol-3-yl)amino]-4-[(2-methyl-1-oxo-3,4-dihydroisoquinolin-8-yl)amino]pyridine-3-carbonitrile;
4-[(2-methyl-1-oxo-3,4-dihydroisoquinolin-8-yl)amino]-6-[[1-(1-methyl-4-piperidyl)pyrazol-4-yl]amino]pyridine-3-carbonitrile;
6-[(1,3-dimethylpyrazol-4-yl)amino]-4-[(2-methyl-1-oxo-3,4-dihydroisoquinolin-8-yl)amino]pyridine-3-carbonitrile;
6-[(1,3-dimethylpyrazol-4-yl)amino]-4-[[7-(4-isopropylpiperazin-1-yl)-2-methyl-3-oxo-isoindolin-4-yl]amino]pyridine-3-carbonitrile;
2-[[2-[(1,5-dimethylpyrazol-3-yl)amino]-5-(trifluoromethyl)-4-pyridyl]amino]-N-methyl-benzamide;
2-[[2-[(1,3-dimethylpyrazol-4-yl)amino]-5-(trifluoromethyl)-4-pyridyl]amino]-N-methyl-benzamide;
2-[[5-chloro-2-[(1,3-dimethylpyrazol-4-yl)amino]-4-pyridyl]amino]-N-methoxy-benzamide;
2-[[5-chloro-2-[(1,5-dimethylpyrazol-3-yl)amino]-4-pyridyl]amino]-N-methoxy-benzamide;
2-[[5-chloro-2-[[1-(2-oxo-2-pyrrolidin-1-yl-ethyl)pyrazol-4-yl]amino]-4-pyridyl]amino]-N-methyl-benzamide;
2-[[5-chloro-2-[[1-[2-(4-methyl-1,4-diazepan-1-yl)-2-oxo-ethyl]pyrazol-4-yl]amino]-4-pyridyl]amino]-N-methyl-benzamide;
2-[[5-chloro-2-[[1-(2-morpholino-2-oxo-ethyl)pyrazol-4-yl]amino]-4-pyridyl]amino]-N-methyl-benzamide;
2-[[5-chloro-2-[[1-[2-(2-methoxyethyl-methyl-amino)-2-oxo-ethyl]pyrazol-4-yl]amino]-4-pyridyl]amino]-N-methyl-benzamide;
2-[[5-chloro-2-[[1-[2-(4-methylpiperazin-1-yl)-2-oxo-ethyl]pyrazol-4-yl]amino]-4-pyridyl]amino]-N-methyl-benzamide;
2-[[5-chloro-2-[(5-methoxy-2-methylpyrazol-3-yl)amino]pyridin-4-yl]amino]-N-methylbenzamide;
2-[[5-chloro-2-[(2,5-dimethylpyrazol-3-yl)amino]-4-pyridyl]amino]-N-methyl-benzamide;
2-[[5-chloro-2-[(1,5-dimethylpyrazol-3-yl)amino]-4-pyridyl]amino]-N-methyl-benzamide;
2-[[5-chloro-2-[(1-methylpyrazol-4-yl)amino]-4-pyridyl]amino]-N-methyl-benzamide;
2-[[5-chloro-2-[[1-(1-methyl-4-piperidyl)pyrazol-4-yl]amino]-4-pyridyl]amino]-N-methyl-benzamide;
2-[[2-[[1-(1-acetyl-4-piperidyl)pyrazol-4-yl]amino]-5-chloro-4-pyridyl]amino]-N-methyl-benzamide;
2-[[5-chloro-2-[(1,3-dimethylpyrazol-4-yl)amino]-4-pyridyl]amino]-N-methyl-benzamide;
2-[[5-chloro-2-[(1-tetrahydropyran-4-ylpyrazol-4-yl)amino]-4-pyridyl]amino]-N-methyl-benzamide;
2-[[5-chloro-2-[(5-methyl-1H-pyrazol-3-yl)amino]pyridin-4-yl]amino]-N-methylbenzamide;
2-[[5-chloro-2-[(5-cyclopropyl-1H-pyrazol-3-yl)amino]-4-pyridyl]amino]-N-methyl-benzamide;
2-[[5-chloro-2-[(1-methylimidazol-4-yl)amino]-4-pyridyl]amino]-N-methyl-benzamide;
2-[[5-chloro-2-[[1-(4-piperidyl)pyrazol-4-yl]amino]-4-pyridyl]amino]-N-methyl-benzamide;
2-[[5-chloro-2-[[1-(1-methyl-4-piperidyl)pyrazol-4-yl]amino]-4-pyridyl]amino]-N-methoxy-N-methyl-benzamide;
2-[[5-chloro-2-[(1,3-dimethylpyrazol-4-yl)amino]-4-pyridyl]amino]-N-methoxy-N-methyl-benzamide;
6-[[5-chloro-2-[(1,3-dimethylpyrazol-4-yl)amino]-4-pyridyl]amino]-4-methyl-2,3-dihydro-1,4-benzoxazepin-5-one;
8-[[5-chloro-2-[[1-(2-oxo-2-pyrrolidin-1-yl-ethyl)pyrazol-4-yl]amino]-4-pyridyl]amino]-2-methyl-3,4-dihydroisoquinolin-1-one;
2-[4-[[5-chloro-4-[(2-methyl-1-oxo-3,4-dihydroisoquinolin-8-yl)amino]-2-pyridyl]amino]pyrazol-1-yl]-N-(2-methoxyethyl)acetamide;
2-[4-[[5-chloro-4-[(2-methyl-1-oxo-3,4-dihydroisoquinolin-8-yl)amino]-2-pyridyl]amino]pyrazol-1-yl]-N-(2-methoxyethyl)-N-methyl-acetamide;
2-[4-[[5-chloro-4-[(2-methyl-1-oxo-3,4-dihydroisoquinolin-8-yl)amino]-2-pyridyl]amino]pyrazol-1-yl]-N-(2-dimethylaminoethyl)acetamide;
8-[[5-chloro-2-[[1-(2-morpholino-2-oxo-ethyl)pyrazol-4-yl]amino]-4-pyridyl]amino]-2-methyl-3,4-dihydroisoquinolin-1-one;
8-[[5-chloro-2-[(1-methylpyrazol-4-yl)amino]-4-pyridyl]amino]-2-methyl-3,4-dihydroisoquinolin-1-one;
8-[[5-chloro-2-[[1-(1-methyl-4-piperidyl)pyrazol-4-yl]amino]-4-pyridyl]amino]-2-methyl-3,4-dihydroisoquinolin-1-one;

8-[[5-chloro-2-[(1,5-dimethylpyrazol-3-yl)amino]-4-pyridyl]amino]-2-methyl-3,4-dihydroisoquinolin-1-one;
8-[[2-[[1-(1-acetyl-4-piperidyl)pyrazol-4-yl]amino]-5-chloro-4-pyridyl]amino]-2-methyl-3,4-dihydroisoquinolin-1-one;
8-[[5-chloro-2-[(1,3-dimethylpyrazol-4-yl)amino]-4-pyridyl]amino]-2-methyl-3,4-dihydroisoquinolin-1-one;
8-[[5-chloro-2-[[1-(4-piperidyl)pyrazol-4-yl]amino]-4-pyridyl]amino]-2-methyl-3,4-dihydroisoquinolin-1-one;
8-[[5-chloro-2-[[1-(3-piperidyl)pyrazol-4-yl]amino]-4-pyridyl]amino]-2-methyl-3,4-dihydroisoquinolin-1-one;
7-[[5-chloro-2-[(1,3-dimethylpyrazol-4-yl)amino]-4-pyridyl]amino]-2-methyl-isoindolin-1-one;
2-[[5-chloro-2-[(1,5-dimethylpyrazol-3-yl)amino]-4-pyridyl]amino]-N-methyl-5-(4-methylpiperazin-1-yl)benzamide;
2-[[5-chloro-2-[(1,3-dimethylpyrazol-4-yl)amino]-4-pyridyl]amino]-N-methyl-5-(4-methylpiperazin-1-yl)benzamide;
7-[[5-chloro-2-[(1,3-dimethylpyrazol-4-yl)amino]-4-pyridyl]amino]-4-(4-isopropylpiperazin-1-yl)-2-methyl-isoindolin-1-one;
2-[[5-chloro-2-[(1,3-dimethylpyrazol-4-yl)amino]-4-pyridyl]amino]-3-fluoro-N-methyl-benzamide;
2-[[5-chloro-2-[(1,3-dimethylpyrazol-4-yl)amino]-4-pyridyl]amino]-6-fluoro-N-methyl-benzamide;
2-[[5-fluoro-2-[[1-(2-oxo-2-pyrrolidin-1-yl-ethyl)pyrazol-4-yl]amino]-4-pyridyl]amino]-N-methyl-benzamide;
2-[[5-fluoro-2-[[1-[2-[methyl-(1-methyl-4-piperidyl)amino]-2-oxo-ethyl]pyrazol-4-yl]amino]-4-pyridyl]amino]-N-methyl-benzamide;
2-[[5-fluoro-2-[[1-[2-(2-methoxyethyl-methyl-amino)-2-oxo-ethyl]pyrazol-4-yl]amino]-4-pyridyl]amino]-N-methyl-benzamide;
2-[[5-fluoro-2-[[1-[2-(4-methyl-1,4-diazepan-1-yl)-2-oxo-ethyl]pyrazol-4-yl]amino]-4-pyridyl]amino]-N-methyl-benzamide;
2-[[5-fluoro-2-[[1-(2-morpholino-2-oxo-ethyl)pyrazol-4-yl]amino]-4-pyridyl]amino]-N-methyl-benzamide;
2-[[2-[[1-[2-(4-dimethylamino-1-piperidyl)-2-oxo-ethyl]pyrazol-4-yl]amino]-5-fluoro-4-pyridyl]amino]-N-methyl-benzamide;
2-[[5-fluoro-2-[[1-[2-(4-methylpiperazin-1-yl)-2-oxo-ethyl]pyrazol-4-yl]amino]-4-pyridyl]amino]-N-methyl-benzamide;
2-[[5-fluoro-2-[(1-methylpyrazol-4-yl)amino]-4-pyridyl]amino]-N-methyl-benzamide;
2-[[5-fluoro-2-[(1-tetrahydropyran-4-ylpyrazol-4-yl)amino]-4-pyridyl]amino]-N-methyl-benzamide;
2-[[2-[(1,3-dimethylpyrazol-4-yl)amino]-5-fluoro-4-pyridyl]amino]-N-methyl-benzamide;
2-[[5-fluoro-2-[[1-(1-methyl-4-piperidyl)pyrazol-4-yl]amino]-4-pyridyl]amino]-N-methyl-benzamide;
8-[[2-[(1,3-dimethylpyrazol-4-yl)amino]-5-fluoro-4-pyridyl]amino]-2-methyl-3,4-dihydroisoquinolin-1-one;
8-[[5-fluoro-2-[[1-[(3R)-6-oxopiperidin-3-yl]pyrazol-4-yl]amino]pyridin-4-yl]amino]-2-methyl-3,4-dihydroisoquinolin-1-one;
8-[[5-fluoro-2-[(1-methylpyrazol-4-yl)amino]-4-pyridyl]amino]-2-methyl-3,4-dihydroisoquinolin-1-one;
8-[[5-fluoro-2-[(1-tetrahydropyran-4-ylpyrazol-4-yl)amino]-4-pyridyl]amino]-2-methyl-3,4-dihydroisoquinolin-1-one;
8-[[5-fluoro-2-[[1-(1-methyl-4-piperidyl)pyrazol-4-yl]amino]-4-pyridyl]amino]-2-methyl-3,4-dihydroisoquinolin-1-one;
8-[[5-fluoro-2-[[1-(4-piperidyl)pyrazol-4-yl]amino]-4-pyridyl]amino]-2-methyl-3,4-dihydroisoquinolin-1-one;
8-[[5-fluoro-2-[[1-(3-piperidyl)pyrazol-4-yl]amino]-4-pyridyl]amino]-2-methyl-3,4-dihydroisoquinolin-1-one;
8-[[5-fluoro-2-[[1-(4-piperidyl)pyrazol-3-yl]amino]-4-pyridyl]amino]-2-methyl-3,4-dihydroisoquinolin-1-one;
8-[[5-fluoro-2-[[1-(2-oxo-2-pyrrolidin-1-yl-ethyl)pyrazol-4-yl]amino]-4-pyridyl]amino]-2-methyl-3,4-dihydroisoquinolin-1-one;
N-(3-dimethylaminopropyl)-2-[4-[[5-fluoro-4-[(2-methyl-1-oxo-3,4-dihydroisoquinolin-8-yl)amino]-2-pyridyl]amino]pyrazol-1-yl]acetamide;
N-(2-dimethylaminoethyl)-2-[4-[[5-fluoro-4-[(2-methyl-1-oxo-3,4-dihydroisoquinolin-8-yl)amino]-2-pyridyl]amino]pyrazol-1-yl]acetamide;
2-[4-[[5-fluoro-4-[(2-methyl-1-oxo-3,4-dihydroisoquinolin-8-yl)amino]-2-pyridyl]amino]pyrazol-1-yl]-N-(2-methoxyethyl)acetamide;
2-[4-[[5-fluoro-4-[(2-methyl-1-oxo-3,4-dihydroisoquinolin-8-yl)amino]-2-pyridyl]amino]pyrazol-1-yl]-N-(2-methoxyethyl)-N-methyl-acetamide;
8-[[5-fluoro-2-[[1-(2-morpholino-2-oxo-ethyl)pyrazol-4-yl]amino]-4-pyridyl]amino]-2-methyl-3,4-dihydroisoquinolin-1-one;
8-[[5-fluoro-2-[[1-[2-(4-methylpiperazin-1-yl)-2-oxo-ethyl]pyrazol-4-yl]amino]-4-pyridyl]amino]-2-methyl-3,4-dihydroisoquinolin-1-one;
8-[[5-fluoro-2-[[1-[2-(3-methylaminopyrrolidin-1-yl)-2-oxo-ethyl]pyrazol-4-yl]amino]-4-pyridyl]amino]-2-methyl-3,4-dihydroisoquinolin-1-one;
7-[[2-[(1,3-dimethylpyrazol-4-yl)amino]-5-fluoro-4-pyridyl]amino]-4-(4-isopropylpiperazin-1-yl)-2-methyl-isoindolin-1-one; and
3-[[5-fluoro-4-[(2-methyl-1-oxo-3,4-dihydroisoquinolin-8-yl)amino]-2-pyridyl]amino]-5-(4-methylpiperazin-1-yl)-1H-pyrazole-4-carbonitrile;
or a pharmaceutically acceptable salt thereof.

In addition, the invention also provides a compound of formula (I) selected from any one of:

2-[[5-chloro-2-[(1,3-dimethylpyrazol-4-yl)amino]-4-pyridyl]amino]-5-fluoro-N-methyl-benzamide;
2-[[5-chloro-2-[(1,3-dimethylpyrazol-4-yl)amino]-4-pyridyl]amino]-4-fluoro-N-methyl-benzamide;
8-[[2-[(1,3-dimethylpyrazol-4-yl)amino]-5-(trifluoromethyl)-4-pyridyl]amino]-2-methyl-3,4-dihydroisoquinolin-1-one;
2-[[2-[(1,3-dimethylpyrazol-4-yl)amino]-5-(trifluoromethyl)-4-pyridyl]amino]-6-methoxy-N-methyl-benzamide;
6-[[2-[(1,3-dimethylpyrazol-4-yl)amino]-5-(trifluoromethyl)-4-pyridyl]amino]-4-methyl-2,3-dihydro-1,4-benzoxazepin-5-one;
8-[[5-chloro-2-[(2-methylpyrazol-3-yl)amino]-4-pyridyl]amino]-2-methyl-3,4-dihydroisoquinolin-1-one;
8-[[5-chloro-2-[(2,5-dimethylpyrazol-3-yl)amino]-4-pyridyl]amino]-2-methyl-3,4-dihydroisoquinolin-1-one;
8-[[5-chloro-2-[(1,5-dimethylpyrazol-4-yl)amino]-4-pyridyl]amino]-2-methyl-3,4-dihydroisoquinolin-1-one;
8-[[5-chloro-2-[(1-ethyl-3-methyl-pyrazol-4-yl)amino]-4-pyridyl]amino]-2-methyl-3,4-dihydroisoquinolin-1-one;
8-[[5-chloro-2-[(5-cyclopropyl-2-methyl-pyrazol-3-yl)amino]-4-pyridyl]amino]-2-methyl-3,4-dihydroisoquinolin-1-one;
8-[[5-chloro-2-[(2-ethylpyrazol-3-yl)amino]-4-pyridyl]amino]-2-methyl-3,4-dihydroisoquinolin-1-one;
8-[[5-chloro-2-[(1-methylpyrazol-3-yl)amino]-4-pyridyl]amino]-2-methyl-3,4-dihydroisoquinolin-1-one;

8-[[2-[(2-tert-butyl-5-ethyl-4-methyl-pyrazol-3-yl)amino]-5-chloro-4-pyridyl]amino]-2-methyl-3,4-dihydroisoquinolin-1-one;
8-[[5-chloro-2-[(1-isobutylpyrazol-4-yl)amino]-4-pyridyl]amino]-2-methyl-3,4-dihydroisoquinolin-1-one;
N-methyl-2-[[2-[(2-methylpyrazol-3-yl)amino]-5-(trifluoromethyl)-4-pyridyl]amino]benzamide;
2-[[2-[(2,5-dimethylpyrazol-3-yl)amino]-5-(trifluoromethyl)-4-pyridyl]amino]-N-methyl-benzamide;
2-[[2-[(1,5-dimethylpyrazol-4-yl)amino]-5-(trifluoromethyl)-4-pyridyl]amino]-N-methyl-benzamide;
2-[[2-[(1-ethyl-3-methyl-pyrazol-4-yl)amino]-5-(trifluoromethyl)-4-pyridyl]amino]-N-methyl-benzamide;
2-[[2-[(1-ethylpyrazol-4-yl)amino]-5-(trifluoromethyl)-4-pyridyl]amino]-N-methyl-benzamide;
2-[[2-[(1-ethylpyrazol-3-yl)amino]-5-(trifluoromethyl)-4-pyridyl]amino]-N-methyl-benzamide;
2-[[2-[(5-cyclopropyl-2-methyl-pyrazol-3-yl)amino]-5-(trifluoromethyl)-4-pyridyl]amino]-N-methyl-benzamide;
2-[[2-[(2-ethylpyrazol-3-yl)amino]-5-(trifluoromethyl)-4-pyridyl]amino]-N-methyl-benzamide;
2-[[2-[(1-isobutylpyrazol-4-yl)amino]-5-(trifluoromethyl)-4-pyridyl]amino]-N-methyl-benzamide;
N-methyl-2-[[5-(trifluoromethyl)-2-[(1,3,5-trimethylpyrazol-4-yl)amino]-4-pyridyl]amino]benzamide;
2-[[2-[(1-isopropylpyrazol-4-yl)amino]-5-(trifluoromethyl)-4-pyridyl]amino]-N-methyl-benzamide;
N-methyl-2-[[2-[[1-methyl-3-(trifluoromethyl)pyrazol-4-yl]amino]-5-(trifluoromethyl)-4-pyridyl]amino]benzamide;
2-[[2-[(1,3-dimethylpyrazol-4-yl)amino]-5-(trifluoromethyl)-4-pyridyl]amino]-5-methoxy-N-methyl-benzamide;
2-[[2-[(1,3-dimethylpyrazol-4-yl)amino]-5-(trifluoromethyl)-4-pyridyl]amino]-N,4-dimethyl-benzamide;
2-[[2-[(1,3-dimethylpyrazol-4-yl)amino]-5-(trifluoromethyl)-4-pyridyl]amino]-N,5-dimethyl-benzamide;
2-[[2-[(1,3-dimethylpyrazol-4-yl)amino]-5-(trifluoromethyl)-4-pyridyl]amino]-4-methoxy-N-methyl-benzamide;
2-[[2-[(1,3-dimethylpyrazol-4-yl)amino]-5-(trifluoromethyl)-4-pyridyl]amino]-4-fluoro-N-methyl-benzamide;
2-[[2-[(1,3-dimethylpyrazol-4-yl)amino]-5-(trifluoromethyl)-4-pyridyl]amino]-3-fluoro-N-methyl-benzamide;
5-chloro-2-[[2-[(1,3-dimethylpyrazol-4-yl)amino]-5-(trifluoromethyl)-4-pyridyl]amino]-N-methyl-benzamide;
2-[[2-[(1,3-dimethylpyrazol-4-yl)amino]-5-(trifluoromethyl)-4-pyridyl]amino]-N-methoxy-benzamide;
4-chloro-2-[[2-[(1,3-dimethylpyrazol-4-yl)amino]-5-(trifluoromethyl)-4-pyridyl]amino]-N-methyl-benzamide;
2-[[2-[(1,3-dimethylpyrazol-4-yl)amino]-5-(trifluoromethyl)-4-pyridyl]amino]-N-methyl-5-methylsulfanyl-benzamide;
2-[[2-[(1,3-dimethylpyrazol-4-yl)amino]-5-(trifluoromethyl)-4-pyridyl]amino]-N-methyl-5-morpholino-benzamide;
2-[[2-[(1,3-dimethylpyrazol-4-yl)amino]-5-(trifluoromethyl)-4-pyridyl]amino]-N-methyl-4-methylsulfonyl-benzamide;
2-[[2-[(2,5-dimethylpyrazol-3-yl)amino]-5-(trifluoromethyl)-4-pyridyl]amino]-6-methoxy-N-methyl-benzamide;
4-[[5-chloro-4-[(2-methyl-1-oxo-3,4-dihydroisoquinolin-8-yl)amino]-2-pyridyl]amino]-N,1-dimethyl-pyrazole-3-carboxamide;
4-[[5-chloro-4-[(2-methyl-1-oxo-3,4-dihydroisoquinolin-8-yl)amino]-2-pyridyl]amino]-N,N,1-trimethyl-pyrazole-3-carboxamide;
8-[[5-chloro-2-[(3-methyl-1H-pyrazol-4-yl)amino]-4-pyridyl]amino]-2-methyl-3,4-dihydroisoquinolin-1-one;
8-[[5-chloro-2-[3-(methoxymethyl)-1-methyl-pyrazol-4-yl]amino]-4-pyridyl]amino]-2-methyl-3,4-dihydroisoquinolin-1-one;
4-[[5-chloro-4-[(2-methyl-1-oxo-3,4-dihydroisoquinolin-8-yl)amino]-2-pyridyl]amino]-1-methyl-pyrazole-3-carbonitrile;
8-[[5-chloro-2-[(3-methoxy-1-methyl-pyrazol-4-yl)amino]-4-pyridyl]amino]-2-methyl-3,4-dihydroisoquinolin-1-one;
N,1-dimethyl-4-[[4-[[2-(methylcarbamoyl)phenyl]amino]-5-(trifluoromethyl)-2-pyridyl]amino]pyrazole-3-carboxamide;
N,N,1-trimethyl-4-[[4-[[2-(methylcarbamoyl)phenyl]amino]-5-(trifluoromethyl)-2-pyridyl]amino]pyrazole-3-carboxamide;
N-methyl-2-[[2-[(3-methyl-1H-pyrazol-4-yl)amino]-5-(trifluoromethyl)-4-pyridyl]amino]benzamide;
2-[[2-[[3-(methoxymethyl)-1-methyl-pyrazol-4-yl]amino]-5-(trifluoromethyl)-4-pyridyl]amino]-N-methyl-benzamide;
2-[[2-[(3-cyano-1-methyl-pyrazol-4-yl)amino]-5-(trifluoromethyl)-4-pyridyl]amino]-N-methyl-benzamide;
2-[[2-[(3-methoxy-1-methyl-pyrazol-4-yl)amino]-5-(trifluoromethyl)-4-pyridyl]amino]-N-methyl-benzamide;
8-[[5-chloro-2-[(1-isopropyl-3-methyl-pyrazol-4-yl)amino]-4-pyridyl]amino]-2-methyl-3,4-dihydroisoquinolin-1-one;
2-[[2-[(1-isopropyl-3-methyl-pyrazol-4-yl)amino]-5-(trifluoromethyl)-4-pyridyl]amino]-N-methyl-benzamide;
2-[[2-[[1-(difluoromethyl)-3-methyl-pyrazol-4-yl]amino]-5-(trifluoromethyl)-4-pyridyl]amino]-N-methyl-benzamide;
8-[[5-chloro-2-[[1-(difluoromethyl)-3-methyl-pyrazol-4-yl]amino]-4-pyridyl]amino]-2-methyl-3,4-dihydroisoquinolin-1-one;
8-[[5-chloro-2-[[1-(2-hydroxyethyl)-3-methyl-pyrazol-4-yl]amino]-4-pyridyl]amino]-2-methyl-3,4-dihydroisoquinolin-1-one;
2-[[2-[[1-(2-hydroxyethyl)-3-methyl-pyrazol-4-yl]amino]-5-(trifluoromethyl)-4-pyridyl]amino]-N-methyl-benzamide;
2-[[2-[(1,3-dimethylpyrazol-4-yl)amino]-5-(trifluoromethyl)-4-pyridyl]amino]-N,6-dimethoxy-benzamide;
2-[[2-[(2,5-dimethylpyrazol-3-yl)amino]-5-(trifluoromethyl)-4-pyridyl]amino]-N-methoxy-benzamide;
2-[[2-[(2,5-dimethylpyrazol-3-yl)amino]-5-(trifluoromethyl)-4-pyridyl]amino]-N,6-dimethoxy-benzamide;
2-[[2-[(1,3-dimethylpyrazol-4-yl)amino]-5-(trifluoromethyl)-4-pyridyl]amino]-4-fluoro-N-methoxy-benzamide;
2-[[2-[(2,5-dimethylpyrazol-3-yl)amino]-5-(trifluoromethyl)-4-pyridyl]amino]-4-fluoro-N-methoxy-benzamide;
2-[[2-[(2,5-dimethylpyrazol-3-yl)amino]-5-(trifluoromethyl)-4-pyridyl]amino]-4-fluoro-N-methyl-benzamide;
2-methoxy-N-methyl-6-[[5-(trifluoromethyl)-2-[(1,3,5-trimethylpyrazol-4-yl)amino]-4-pyridyl]amino]benzamide;
N,2-dimethoxy-6-[[5-(trifluoromethyl)-2-[(1,3,5-trimethylpyrazol-4-yl)amino]-4-pyridyl]amino]benzamide;
N-methoxy-2-[[5-(trifluoromethyl)-2-[(1,3,5-trimethylpyrazol-4-yl)amino]-4-pyridyl]amino]benzamide;
2-[[2-[(2,5-dimethylpyrazol-3-yl)amino]-5-(trifluoromethyl)-4-pyridyl]amino]-N-ethoxy-benzamide;
2-[[2-[(2,5-dimethylpyrazol-3-yl)amino]-5-(trifluoromethyl)-4-pyridyl]amino]-N-(2-hydroxyethoxy)benzamide;

2-[[2-[(2,5-dimethylpyrazol-3-yl)amino]-5-(trifluoromethyl)-4-pyridyl]amino]-5-fluoro-N-methoxy-benzamide; and 2-[[2-[(1,3-dimethylpyrazol-4-yl)amino]-5-(trifluoromethyl)-4-pyridyl]amino]-5-fluoro-N-methoxy-benzamide;

or a pharmaceutically acceptable salt thereof.

Synthesis

The compounds of the present invention can be prepared in a number of ways using methods analogous to well known methods of organic synthesis. More specifically, the novel compounds of this invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, are chosen to be the conditions standard for that reaction. It is understood by one skilled in the art of organic synthesis that the functionality present on various portions of the molecule must be compatible with the reagents and reactions proposed. Such restrictions to the substituents, which are not compatible with the reaction conditions, will be apparent to one skilled in the art and alternate methods must then be used.

It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

Compounds of the formula I, or pharmaceutically acceptable salts or prodrugs thereof, may be prepared by any process known to be applicable to the preparation of chemically-related compounds. Such processes, when used to prepare a compound of the formula I, or a pharmaceutically acceptable salt or prodrug thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist.

The present invention also provides that compounds of the formula I, or pharmaceutically acceptable salts or prodrugs thereof, can be prepared by a process (a) to (d) as follows (wherein the variables are as defined above unless otherwise stated):

Process (a)

The palladium catalysed coupling in the presence of a suitable base of a compound of the formula II:

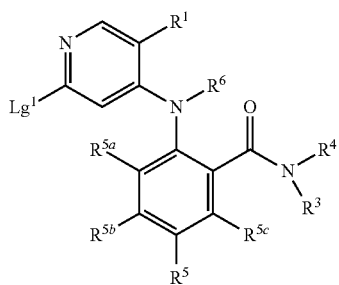

wherein $R^1$, $R^3$, $R^4$, $R^5$, $R^{5a}$, $R^{5b}$, $R^{5c}$ and $R^6$ are as hereinbefore defined, except any functional group is protected if necessary, and $Lg^2$ is a suitable displaceable group, with a compound of the formula III:

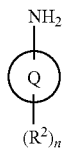

III wherein ring Q, $R^2$ and n are as hereinbefore defined, except any functional group is protected if necessary; or Process (b)

the palladium catalysed coupling in the presence of a suitable base of a compound of the formula IV:

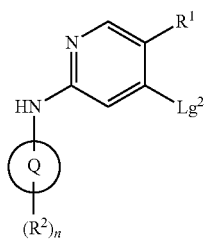

IV wherein ring Q, $R^1$, $R^2$ and n are as hereinbefore defined, except any functional group is protected if necessary, and $Lg^2$ is a suitable displaceable group, with a compound of the formula V:

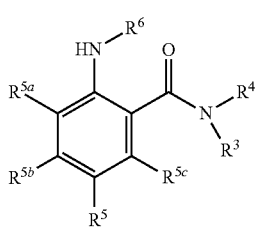

V wherein $R^3$, $R^4$, $R^5$, $R^{5a}$, $R^{5b}$, $R^{5c}$ and $R^6$ are as hereinbefore defined, except any functional group is protected if necessary; or Process (b')

the coupling of a compound of the formula IV (as shown above) with a compound of formula V (as shown above) under acidic conditions; or Process (c)

the coupling of a compound of the formula VI or a reactive derivative thereof:

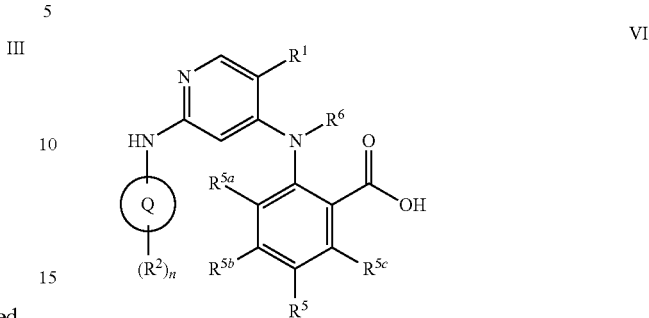

VI wherein ring Q, $R^1$, $R^2$, $R^5$, $R^{5a}$, $R^{5b}$, $R^{5c}$, $R^6$ and n are as hereinbefore defined, except any functional group is protected if necessary, with an amine of the formula VII:

$HNR^3R^4$    VII wherein $R^3$ and $R^4$ are as hereinbefore defined, except any functional group is protected if necessary; or Process (d)

for the preparation of those compounds of the formula I wherein an $R^2$ is linked to ring Q by a —$N(R^{14})C(O)$— group or a —$N(R^{14})C(O)CH_2$— group the coupling of a compound of the formula VIII, or a reactive derivative thereof:

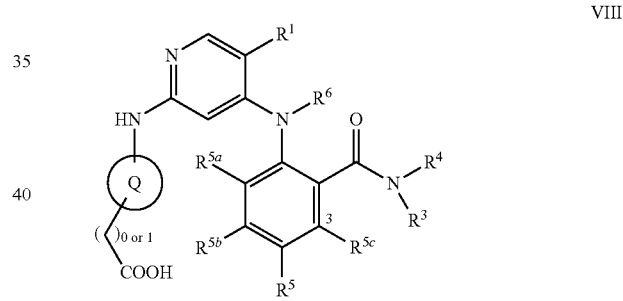

VIII wherein ring Q, $R^1$, $R^2$, $R^3$, $R^4$, $R^5$, $R^{5a}$, $R^{5b}$, $R^{5c}$ and $R^6$ are as hereinbefore defined, except any functional group is protected if necessary, with an appropriate amine such that the coupling with the compound of formula VIII gives an amide linked $R^2$ substituent as hereinbefore defined; and thereafter, if necessary (in any order):

(i) converting a compound of the formula I into another compound of the formula I;
(ii) removing any protecting groups; and
(iii) forming a pharmaceutically acceptable salt of the compound of formula I.

Reaction Conditions for Process (a)

A convenient displaceable group $Lg^1$ is, for example, a halo, alkanesulfonyloxy or arylsulfonyloxy group, for example a chloro, bromo, methanesulfonyloxy, trifluoromethanesulfonyloxy, 4-nitrobenzenesulfonyloxy or toluene-4-sulfonyloxy group. $Lg^1$ is selected such that it is more labile than the group $R^1$. For example when $R^1$ is fluoro a suitable $Lg^1$ is chloro.

The reaction is advantageously carried out in the presence of base. A suitable base is, for example, an organic amine base such as, for example, an alkali metal or alkaline earth metal carbonate or hydroxide, for example sodium carbonate, potassium carbonate, cesium carbonate or calcium carbonate. Alternatively such a base is, for example, an alkali metal tert-butoxide such as sodium or potassium tert-butoxide. A particular base is cesium carbonate.

The coupling reaction is performed in the presence of a suitable palladium catalyst. Suitably the catalyst is formed in situ by reacting a palladium source such as palladium(II) acetate with a suitable ligand, particularly a phosphorus containing ligand such as 9,9-dimethyl-4,5-bis(diphenylphosphino)xanthene (Xantphos).

The reaction is suitably effected in the presence of an inert solvent or diluent, for example a dipolar aprotic solvent such as N,N-dimethylformamide, N-dimethylacetamide, N-methylpyrrolidin-2-one or dimethylsulfoxide; a hydrocarbon such as toluene; or an ether such as dioxane. The reaction is conveniently effected at elevated temperature for example in the range, of for example, 50 to 180° C. (or the boiling point of the solvent), suitably at about 150° C.

Compounds of the formula II may be prepared using methods well known to those skilled in organic chemistry. Representative methods are illustrated in the Examples described herein. For example compounds of the formula II may be prepared according to Reaction Scheme 1

Reaction Scheme 1

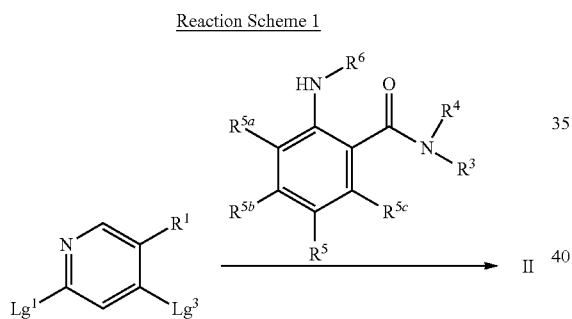

wherein $Lg^3$ is a suitable displaceable group such as iodo or chloro.

The reaction is performed under analogous conditions to those described for Process (a) above or under strongly basic conditions (such as using sodium hydride in THF at typically 60° C.). The conditions chosen should allow for formation of the anion of the aniline.

Compounds of the formula III are commercially available, known in the literature, or can be prepared by standard processes known in the art.

Reaction Conditions for Process (b)

$Lg^2$ is a suitable displaceable group such as iodo or chloro.

The reaction is performed under analogous conditions to those described for Process (a) above.

Compounds of the formula IV may be prepared using methods well known to those skilled in organic chemistry. Representative methods are illustrated in the Examples described herein. For example compounds of the formula IV may be prepared according to Reaction Scheme 2:

Reaction Scheme 2

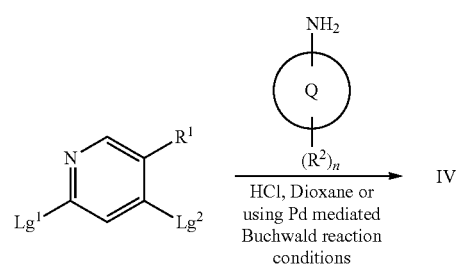

wherein $Lg^1$ is as hereinbefore defined, for example fluoro or chloro.

The reaction is suitably performed at elevated temperature, for example at about 80° C.

Compounds of formula IV may also be prepared according to Reaction Scheme 3:

Reaction Scheme 3

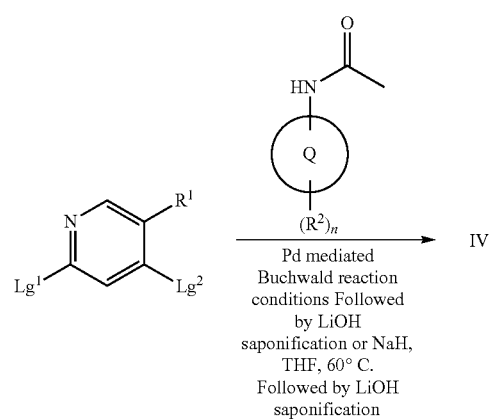

Compounds of the formula V are commercially available, or they are known in the literature, or they can be prepared by standard processes known in the art.

Reaction Conditions for Process (b')

The coupling of a compound of formula IV with a compound of formula V under acidic conditions may involve, for example, p-toluene sulfonic acid in solvents such as cyclohexanol. Such a reaction is suitably performed at an elevated temperature such as 160° C. For reactions of this type, $Lg^2$ is typically chloro and $R^1$ is typically cyano.

Reaction Conditions for Process (c)

The coupling reaction may be carried out using standard methods for the coupling of acids and amines. The coupling reaction is conveniently carried out in the presence of a suitable coupling reagent. Standard peptide coupling reagents known in the art can be employed as suitable coupling reagents for example O-(Benzotriazol-1-yl)-N,N,N',N'-tetramethyluronium tetrafluoroborate (TBTU) or O-(7-Azabenzotriazol-1-yl)-N,N,N',N'-tetramethyluronium hexafluorophosphate (HATU), or for example carbonyldiimidazole or a carbodimide such as dicyclohexylcarbodiimide or N-ethyl-N'-(3-dimethylaminopropyl)carbodiimide (EDCI), optionally in the presence of a catalyst such as dimethylaminopyridine, 4-pyrrolidinopyridine or 2-hydroxy-pyridine-N-oxide, optionally in the presence of a base for example a tri-alkylamine such as triethylamine or N-ethyldiisopropylamine, N-methylmorpholine, is pyridine, or 2,6-di-alkyl-pyridines such as 2,6-lutidine or 2,6-di-tert-butylpyridine.

The reaction is conveniently performed in the present of a suitable inert solvent. Suitable solvents include for example a dipolar aprotic solvent such as N,N-dimethylformamide, N,N-dimethylacetamide, N-methylpyrrolidin-2-one or dimethylsulfoxide; dichloromethane; benzene or tetrahydrofuran. The coupling reaction is conveniently performed at a temperature in the range of −40 to 40° C., suitably at about room temperature.

A "reactive derivative" of the acid of the formula VI is a carboxylic acid derivative that will react with the amine of the formula VII to give the corresponding amide. A suitable reactive derivative of a carboxylic acid of the formula VI is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; or an acyl azide, for example an azide formed by the reaction of the acid and azide such as diphenylphosphoryl azide; an acyl cyanide, for example a cyanide formed by the reaction of an acid and a cyanide such as diethylphosphoryl cyanide. The reaction of such reactive derivatives of carboxylic acid with amines is well known in the art, for example they may be reacted in the presence of a base, such as those described above, and in a suitable solvent, such as those described above. The reaction with a reactive derivative may conveniently be performed at a temperature as described above.

Compounds of the formula VI may be prepared using methods well known to those skilled in organic chemistry. Representative methods are illustrated in the Examples described herein.

Compounds of the formula VII are commercially available, known in the literature, or they can be prepared by standard processes known in the art.

Reaction Conditions for Process (d)

The coupling reaction may be carried out using analogous conditions to those described in process (c) above. Process (d) is suitable for preparing compounds of the formula I wherein an $R^2$ substituent is linked to ring Q by an amide link (—N($R^{14}$)C(O)— or —N($R^{14}$)C(O)CH$_2$). Accordingly process (c) is suitable for preparing compounds of the formula I where $R^2$ is, for example carbamoyl, N—(C$_{1-6}$alkyl)carbamoyl, N,N—(C$_{1-6}$alkyl)$_2$carbamoyl, carbocyclyl-X$^1$—, heterocyclyl-X$^2$— and heteroaryl-X$^3$—, wherein X$^1$, X$^2$ and X$^3$ are —N($R^{14}$)C(O)—; which groups may be optionally substituted as described herein. As will be understood, the corresponding amine is reacted with the compound of formula VIII to give the desired amide. For example where $R^2$ is heterocyclyl-N($R^{14}$)C(O)—, the compound of formula VIII is reacted with an amine of formula heterocyclyl-NH($R^{14}$) to give the required amide linked $R^2$.

It is expected that analogous methods could be used to prepare $R^2$ substituents that are linked to ring B by a —C(O)N($R^{14}$)— link by reacting a compound of the formula VIII wherein the carboxy group is replaced by an amine, with an appropriate carboxylic acid.

Compounds of the formula VIII may be prepared using methods well known to those skilled in organic chemistry. Representative methods are illustrated in the Examples.

Compounds of the formula I may also be obtained by modifying a substituent in or introducing a substituent into another compound of formula I or a pharmaceutically acceptable salt or prodrug thereof. Suitable chemical transformations are well known to those in the art of organic chemistry.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulfinyl or alkylsulfonyl.

When a pharmaceutically acceptable salt of a compound of the formula I is required, for example an acid or base addition salt, it may be obtained by, for example, reaction of the compound of formula I with a suitable acid or base using a conventional procedure. Methods for the preparation of pharmaceutically acceptable salts are well known in the art. For example, following reaction of a compound of the formula I with an acid or base the required salt may be precipitated from solution by supersaturating the solution containing the compound of the formula I. Super saturation may be achieved using well-known techniques, for example by cooling the solution, by removing solvent by evaporation or by the addition of a suitable anti-solvent to precipitate the salt.

To facilitate isolation of a compound of the formula I during its preparation, the compound may be prepared in the form of a salt that is not a pharmaceutically acceptable salt. The resulting salt can then be modified by conventional techniques to give a pharmaceutically acceptable salt of the compound. Such salt modification techniques are well known and include, for example ion exchange techniques or re-precipitation of the compound from solution in the presence of a pharmaceutically acceptable counter ion as described above, for example by re-precipitation in the presence of a suitable pharmaceutically acceptable acid to give the required pharmaceutically acceptable acid addition salt of a compound of the formula I.

Stereoisomers of compounds of formula I may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. When a specific stereoisomer is isolated it is suitably isolated substantially free from other stereoisomers, for example containing less than 20%, particularly less than 10% and more particularly less than 5% by weight of other stereoisomers.

In the synthesis section above and hereafter, the expression "inert solvent" refers to is a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Certain of the intermediates used in the above described processes for the preparation of compounds of the formula I form a further aspect of the invention Biological Activity The following assays can be used to measure the effects of the compounds of the present invention as FAK inhibitors.

(a) In Vitro Enzyme Assay

Assay Principle

A sandwich ELISA assay with a 3,3',5,5'-tetramethyl benzidine (TMB) colorimetric endpoint was used in order to determine the level of effect of selected compounds on inhibition of FAK protein tyrosine kinase enzyme activity. A synthetic tyrosine containing peptide is coated onto a plastic surface, the level of phosphorylation of these tyrosine residues by the kinase enzyme in the presence of inhibitors is measured using an antibody that binds specifically to phosphorylated tyrosine residues. The amount of antibody bound to substrate is proportional to the level of enzyme catalysis.

Assay Protocol to Identify Inhibitors of Focal Adhesion Kinase (FAK).

A PlateMate Plus™ 384 automated liquid handling unit with a 100 µl disposable tip head was used to make all the non compound reagent additions and a Tecan 384PW plate washer with 384 head was used for all wash steps. Initially Matrix 384 well polystyrene plates (Cat #:4311) were coated with 40 µl/well of a 0.0375 mg/ml solution of synthetic poly peptide (polyGAT, Sigma Cat #:P3899) dissolved in phosphate buffered saline (PBS). Plates were stored overnight at 4° C. Immediately before use the coating solution was aspirated out and each well washed with 2×100 µl of PBS+0.05% Tween 20. To remove surplus phosphate, the wells were then washed with 2×100 µl 50 mM HEPES buffer pH 7.4. Plates were blotted dry before the addition of compounds. Compounds were tested over a 12 point dose range, a Labcyte Echo 550 was used to dispense compounds in nl volumes and back fill with DMSO. The final concentration of compound in the assay was dependent on the starting concentration of compound. For a 10 mM stock compound the final assay dose ranged from 100 µM down to 0.1 nM in half log unit steps, the final dose point contained compound at 0.01 nM. Control wells containing 120 nl DMSO (Max) or 120 nl of 10 mM staurosporine (LC Laboratories, Boston, USA Cat #: S-9300) (Min) were included in each plate. 10 ul of 5% dimethyl sulfoxide v/v (DMSO, Fisher Scientific) was added to each well immediately prior to addition of 10 µl of a co-factor solution containing 80 mM $MgCl_2$ (Sigma Cat #: M1028); 80 mM $MnCl_2$ (Sigma Cat #: M1787); ATP at a concentration calculated to enable the initial reaction velocity to progress at half the maximum velocity ($K_m$ for ATP) (Sigma Cat #: A7699). A final addition of 20 µl of enzyme solution containing 100 mM HEPES pH7.4; 0.2 mM sodium vanadate (Sigma Cat #:S6508); 0.2 g/l bovine serum albumin (BSA, Sigma Cat #: A7888); 0.2 mM dithioreitol (Sigma Cat #: 5545); 0.1% Triton X100 (Sigma Cat #:X100); FAK enzyme (20 µl/ml) was made to each well to start the assay running FAK enzyme was generated from an insect culture infected with baculo virus containing the DNA sequence encoding the 6 His tagged kinase domain (GenBank NP_722560).

Plates were left at room temperature for 25 minutes before 10 µl of 500 mM ethylenediaminetetraacetic acid (EDTA) was added to stop the assay and the wells were immediately washed 3×100 µl with PBS+0.05% Tween 20. A 4G10 antibody (Millipore Cat #: 16-105; 16-184) with a directly conjugated horse radish peroxidase (HRP) was used to detect the phosphorylation of the substrate by the FAK. 40 µl of PBS+ 0.05% Tween 20 containing 0.5% BSA and 0.1 µl/ml antibody was added to each well and left for 1 hour at room temperature to allow the antibody to bind. After this period the wells were again washed with 3×100 µl of PBS+0.05% Tween 20. TMB (Sigma Cat #: T2885) was used as a substrate for the HRP. Phosphate-citrate buffer was made up using capsules provided by Sigma (Cat #: P4922) following the manufacturers guidelines. TMB was dissolved at a concentration of 1 mg/ml in DMSO and let down to a final concentration of 0.05 mg/ml with the phosphor-citrate buffer. 40 µl of the TMB solution was added to each assay well and left for 30 minutes for the blue colour to develop. To fix the colour 20 µl of 2M sulphuric acid was added to each well, the colour changes from blue to yellow. The plates were read in a Perkin Elmer Envision using 450 nM wavelength optical density filters. Automated data analysis was carried out by importing the raw data files from the reader into Origin™. Using the mean Max and mean Min signal on each plate to anchor the curve top and bottom, the optical density was plotted against compound concentration. The $IC_{50}$ was then extrapolated from the shape of the curve.

(b) In Vitro Cell Assay

Assay Principle

This assay uses HEK293 which are transiently transfected with a plasmid coding for cMyc-tagged full length human FAK, using lipofectamine 2000. Cells are transfected overnight, prior to treatment with compound for one hour. Cells are then lysed and taken through to the next phase of the assay, which is a solid phase sandwich Enzyme Linked-Immuno-Sorbent Assay. The assay uses plates pre-coated with anti-cMyc antibody to pull down the cMyc tagged-kinase, and then detects with an anti-p$Y^{397}$ FAK antibody. Upon further incubation with anti-rabbit IgG-HRP, and subsequent incubation with QuantaBlu, a fluorescent product is formed, which can be measured on an optical reader. The intensity of this fluorescent product is directly proportional to the concentration of FAK [p$Y^{397}$] present in the original lysate.

Assay Protocol to Identify Inhibitors of Focal Adhesion Kinase (FAK).

A Tecan Power washer was used for all wash steps and either a Wellmate or Multidrop was used to make all non-compound reagent additions.

HEK293 cells were routinely cultured in 10% FCS (Sigma F7524) plus 1% L-glutamine (Gibco 25030) in Earle's MEM (Gibco 21090). Cells were seeded at a density of 3–4×10$^6$ cells per T175 flask to be about 85% confluent after 2 to 3 days in culture. On the first assay day cells were detached from their culture support by rinsing the cells in the flasks once with 12 ml HBSS (Gibco 14170) before lifting with 2 ml Accutase/flask (Innovative Cell Technologies Inc Cat # AT104). Pre-warmed Plating Media (1% FCS (Sigma F7524) plus 1% L-glutamine (Gibco 25030) in Earle's MEM (Gibco 21090)) was added to each flask (13 ml per flask) and the cells pooled. Cells were counted using a Coulter Counter and diluted with Plating Media to $3.6 \times 10^5$ cells/ml. Cells were transfected in suspension by adding transfection mix at a 5:1 v/v ratio (for a 96-well plate 10 ml cell suspension+2 ml transfection mix) and swirling gently to mix. The transfection mix was prepared by incubating 24 µl Lipofectamine 2000 (Invitrogen Cat #11668019) with 809 µl OptiMEM (Gibco 31985) per plate, at room temperature for 5 minutes. Meanwhile the DNA mix was prepared by adding 20 ug pcDNA3.2 Fak_cmyc plasmid (GenBank NP_722560) to 816 µl OptiMEM (Gibco 31985) per plate. An equal quantity (v/v) of Lipofectamine 2000/OptiMEM was added to the DNA/OptiMEM solutions to form the transfection mix, which was incubated at room temperature for 20 minutes prior to added to the cells. A sterile head was used to seed cells/transfection mixture at 100 µl/well at a final cell concentration of $3 \times 10^5$ cells/ml into poly-D-lysine coated BD Biocoat plates (Becton Dickinson Cat #35 6461). Cells were allowed to settle in the plates for about 2 minutes before placing in the incubator. Plates were incubated at 37° C. in a 5% $CO_2$ incubator overnight.

ELISA plates were prepared by diluting c-myc 9E10 mouse monoclonal antibody (generated in house) in phosphate buffered saline (PBS) to a final concentration of 5 µg/ml, 50 µl per well was added to black high-bind 96-well plates (Greiner 655077). Plates were sealed and incubated over night at 4° C. The following day ELISA plates were washed with 2×400 µl PBS-Tween to remove unbound antibody. Plates were blocked at room temperature for >1 hour by adding 500 µl/well 3% BSA (Sigma A8022) in PBS-Tween.

Compounds were dosed to cells over a 6 or 8-point dose range, a Labcyte Echo 500 was used to dispense compounds in nl volumes and back fill with DMSO. The top concentration was 3 µM decreasing in half log steps. Control wells containing DMSO or compound were included in each plate. Following dosing cell plates were returned to the incubator for 1 hour. Media/compound solution was aspirated from the wells and the cells lysed by adding 70 µl/well lysis buffer (final concentration 25 mM Tris/HCl (in house), 3 mM EDTA (in house), 3 mM EGTA (Sigma E4378), 50 mM NaF (Sigma S6508), 2 mM Orthovanadate (Sigma S6508), 0.27M Sucrose (Sigma S0389), 10 mM Beta-glycerophosphate (Sigma G6251), 5 mM Sodium pyrophosphate (Sigma S6422), 0.5% Triton X-100 (Sigma X100), Complete Protease Inhibitor Cocktail tablets (Roche #1 697 498 or #1 836 153)). Plates were incubated at room temperature for 10-30 minutes. 50 µl cell lysate was transferred to pre-washed ELISA plates (2×400 µl PBS-Tween) using a PlateMate Plus. Plates were sealed and incubated at 4° C. over night.

The following day the ELISA plates were washed with 2×400 µl PBS-Tween. 50 µl Primary antibody solution ($pY^{397}$ FAK (Biosource 44-624G (polyclonal) or 44-625G (monoclonal)) diluted 1/2000 in 3% BSA (Sigma A8022) in PBS-0.05%) was added per well and incubated at room temperature for 1 hour. Unbound antibody was removed by washing with 2×400 µl PBS-Tween. 50 µl secondary antibody solution (Goat anti-rabbit HRP (Cell Signalling CS7074) diluted 1/5000 in 3% BSA (Sigma A8022) in PBS-0.05%) was added per well and incubated at room temperature for 1 hour. Unbound antibody was removed by washing with 2×400 µl PBS-Tween. QuantaBlu fluorogenic peroxidase substrate kit (Pierce #15169) was used as the substrate for HRP.

Peroxide Solution was diluted 1/10 with Substrate Solution. 35 µl/well Working Solution was added per well and incubate at room temperature for 90 minutes. The reaction was stopped by the addition of 35 µl Stop Solution (provided in the kit). Fluorescence was read on a Tecan Ultra using an Excitation Filter of 340 nm and an Emission Filter of 465 nm.

A variant of the in vitro Cell Assay (b) is as follows:
Assay Principle

This assay uses HEK293 which are transiently transfected with a plasmid coding for cMyc-tagged full length human FAK, using lipofectamine 2000. Cryopreserved cells that have been transfected for 5 hours are cultured overnight, prior to treatment with compound for 1½-2 hours. Cells are then lysed and taken through to the next phase of the assay, which is a solid phase sandwich Enzyme Linked-Immuno-Sorbent Assay. The assay uses plates pre-coated with anti-cMyc antibody to pull down the cMyc tagged-kinase and then detects with an anti-$pY^{397}$ FAK antibody. Upon further incubation with anti-rabbit IgG-HRP and subsequent incubation with QuantaBlu, a fluorescent product is formed, which can be measured on an optical reader. The intensity of this fluorescent product is directly proportional to the concentration of FAK [$pY^{397}$] present in the original lysate.

Assay Protocol to Identify Inhibitors of Focal Adhesion Kinase (FAK).

A Tecan Power washer was used for all wash steps and either a Wellmate or Multidrop was used to make all non-compound reagent additions.

HEK293 cells grown in 10-layer cell factories were transiently transfected with a plasmid coding for 3' cMyc-tagged, full-length FAK (GenBank NP_722560) using Lipofectamine 2000 (Invitrogen Cat #11668019). 5 hours post-transfection, the cells were detached from their culture support and cryopreserved. For each assay, the required number of vials were thawed, resuspended in cell assay media (DMEM (Gibco #41966) containing 1% FCS (Sigma F7524) and HEPES (Gibco #15630)) and spun down to remove DMSO in the cryo-preservation media. The cells were resuspended in cell assay media and the cell count adjusted to $1.25 \times 10^5$/ml. Cells were seeded using a Wellmate into poly-D-lysine coated BD Biocoat plates (Becton Dickinson Cat # 35 6461) 384 well plates and were allowed to adhere overnight in 37° C. in a 5% $CO_2$ incubator.

ELISA plates were prepared by diluting c-myc 9B11 (Cell Signaling #cs2276) mouse monoclonal antibody in phosphate buffered saline (PBS/A) to a final concentration of 1 µg/ml, 20 µl per well was added to black high-bind 384-well plates (Greiner 781077). Plates were sealed and incubated over night at 4° C. The following day ELISA plates were washed with 3×400 µl PBS-Tween to remove unbound antibody. Plates were blocked at room temperature for >1 hour by adding 400 µl/well 3% BSA (Sigma A8022) in PBS-Tween.

Compounds were dosed to cells over a 8-point dose range, a Labcyte Echo 500 was used to dispense compounds in nl volumes and back fill with DMSO. The top concentration was 3.125 µM decreasing in half log steps. Control wells containing DMSO or compound were included in each plate. Following dosing cell plates were returned to the incubator for 1½-2 hours. Media/compound solution was aspirated from the wells and the cells lysed by adding 40 µl/well lysis buffer (final concentration 25 mM Tris/HCl (in house), 3 mM EDTA (in house), 3 mM EGTA (Sigma E4378), 50 mM NaF (Sigma S6508), 2 mM Orthovanadate (Sigma S6508), 0.27M Sucrose (Sigma S0389), 10 mM Beta-glycerophosphate (Sigma G6251), 5 mM Sodium pyrophosphate (Sigma S6422), 0.5% Triton X-100 (Sigma X100), Complete Protease Inhibitor Cocktail tablets (Roche #1 697 498 or #1 836 153)). Plates were incubated at room temperature for 10-30 minutes. 15 µl cell lysate was transferred to pre-washed ELISA plates (3×400 µl PBS-Tween) using a PlateMate Plus. Plates were sealed and incubated at 4° C. over night.

The following day the ELISA plates were washed with 3×400 µl PBS-Tween. 20 µl is Primary antibody solution (pY$^{397}$ FAK (Biosource 44-624G (polyclonal)) diluted 1/2000 in 3% BSA (Sigma A8022) in PBS-Tween) was added per well and incubated at room temperature for 1 hour. Unbound antibody was removed by washing with 3×400 µl PBS-Tween. 20 µl secondary antibody solution (Goat anti-rabbit HRP (Cell Signalling CS7074) diluted 1/5000 in 3% BSA (Sigma A8022) in PBS-Tween) was added per well and incubated at room temperature for 1 hour. Unbound antibody was removed by washing with 3×400 µl PBS-Tween. QuantaBlu fluorogenic peroxidase substrate kit (Pierce #15169) was used as the substrate for HRP.

Peroxide Solution was diluted 1/10 with Substrate Solution. 20 µl/well Working Solution was added per well and incubate at room temperature for 90 minutes. The reaction was stopped by the addition of 20 µl Stop Solution (provided in the kit). Fluorescence was read on a Tecan SafireExcitation wavelength of 325 nm and an Emission wavelength of 425 nm.

Although the pharmacological properties of the compounds of the formula I vary with structural change as expected, compounds of the formula I, were found to be active in the above screens. In general activity possessed by compounds of the formula I, may be demonstrated at the following concentrations or doses in one or more of the above tests (a) and (b):

Test (a):—IC$_{50}$ less than 25 µM (preferred compounds have an IC$_{50}$ of less than 5 µM, more preferably less than 1 µM);

Test (b):—The maximum concentration of the compounds used in Test (b) was 3 µM. Accordingly, preferred compounds have an IC$_{50}$ of less than 3 µM. Certain compounds tested would require concentrations greater than 3 µM to determine the IC$_{50}$. For such compounds the IC$_{50}$ was not determined.

By way of example, activity for the following compounds was observed when measured in an assay substantially as described above in relation to in vitro Enzyme Assay test (a):

| Example | IC$_{50}$ µM | Example | IC$_{50}$ µM | Example | IC$_{50}$ µM |
|---|---|---|---|---|---|
| 1.01 | 0.065 | 3.40 | 0.122 | 8.07 | 0.026 |
| 1.02 | 0.102 | 3.41 | 0.087 | 8.08 | 0.010 |
| 1.03 | 0.554 | 3.42 | 0.005 | 8.09 | 0.069 |
| 1.04 | 0.014 | 4.01 | 1.505 | 8.10 | 0.013 |
| 1.05 | 0.004 | 4.02 | 1.325 | 8.11 | 0.034 |
| 1.06 | 0.020 | 4.03 | 2.117 | 8.12 | 0.018 |
| 1.07 | 0.128 | 4.04 | 0.967 | 10.01 | 0.008* |
| 1.08 | 0.006 | 4.05 | 1.299 | 10.02 | 0.013* |
| 1.09 | 0.019 | 4.06 | 1.050 | 10.03 | 0.002* |
| 2.01 | 0.019 | 4.07 | 0.577 | 10.04 | 0.053* |
| 2.02 | 0.008 | 4.08 | 2.187 | 10.05 | 0.009* |
| 3.01 | 0.044 | 4.09 | 3.378 | 10.06 | 0.010* |
| 3.02 | 0.041 | 4.10 | 1.771 | 10.07 | 0.014* |
| 3.03 | 0.080 | 4.11 | 2.082 | 10.08 | 0.005 |
| 3.04 | 0.068 | 4.12 | 0.121 | 10.09 | 0.007* |
| 3.05 | 0.090 | 4.13 | 1.034 | 10.10 | 0.011* |
| 3.06 | 0.099 | 4.14 | 0.408 | 10.11 | 0.026* |
| 3.07 | 0.048 | 4.15 | 0.454 | 10.13 | 0.462* |
| 3.08 | 0.060 | 4.16 | 0.465 | 11.01 | 0.005 |
| 3.09 | 0.029 | 4.17 | 0.189* | 12.01 | 0.915* |
| 3.10 | 0.045 | 4.18 | 0.676 | 12.02 | 1.358* |
| 3.11 | 0.439 | 4.19 | 0.083 | 12.03 | 0.002* |
| 3.12 | 0.195 | 4.20 | 0.304 | 12.04 | 0.022* |
| 3.13 | 0.128 | 4.21 | 0.188 | 12.05 | 0.020* |
| 3.14 | 0.045 | 4.22 | 0.364 | 12.06 | 0.008* |
| 3.15 | 0.670 | 4.23 | 0.449 | 12.07 | 0.171* |
| 3.16 | 0.093 | 4.24 | 0.294 | 12.08 | 0.482* |
| 3.17 | 0.093 | 4.25 | 0.204 | 12.09 | 0.003* |
| 3.18 | 0.275 | 4.26 | 0.199 | 12.10 | 0.010* |
| 3.19 | 0.686 | 4.27 | 0.072 | 12.11 | 0.015* |
| 3.20 | 1.230 | 4.28 | 1.118 | 12.12 | 0.003* |
| 3.21 | 0.324 | 4.29 | 22.682 | 13.01 | 0.013* |
| 3.22 | 0.025 | 5.01 | 0.006 | 13.02 | 0.021* |
| 3.23 | 0.020 | 5.02 | 0.009 | 13.03 | 0.050* |
| 3.24 | 0.018 | 5.03 | 0.006 | 13.04 | 0.023* |
| 3.25 | 0.027 | 6.01 | 0.006* | 13.05 | 0.004* |
| 3.26 | 0.038 | 6.02 | 0.007* | 13.06 | 0.006* |
| 3.27 | 0.011 | 6.03 | 0.005* | 14.01 | 0.004* |
| 3.28 | 0.041 | 6.04 | 0.006* | 14.02 | 0.002* |
| 3.29 | 0.118* | 6.05 | 0.010* | 14.03 | 0.006* |
| 3.30 | 0.059 | 6.06 | 0.004* | 15.01 | 0.004* |
| 3.31 | 0.171 | 6.07 | 0.009* | 15.02 | 0.003* |
| 3.32 | 0.009 | 6.08 | 5.623* | 15.03 | 0.006* |
| 3.33 | 0.191 | 6.09 | 0.071* | 15.04 | 0.024* |
| 3.34 | 0.160 | 8.01 | 0.006* | 15.05 | 0.010* |
| 3.35 | 0.036 | 8.02 | 0.008 | 15.06 | 0.005* |
| 3.36 | 0.249 | 8.03 | 0.006* | 15.07 | 0.113* |
| 3.37 | 1.054 | 8.04 | 0.006* | 15.08 | 0.620* |
| 3.38 | 0.036 | 8.05 | 0.014* | 16.01 | 0.012* |
| 3.39 | 0.055 | 8.06 | 0.011 | 16.02 | 0.006* |

Unless otherwise indicated in the table above (indicated by *) each compound was tested at least twice in the assay (n > 1) and the IC$_{50}$ value quoted is the geometric mean of the measured IC$_{50}$ values. Therefore, as will be understood, the IC$_{50}$ values quoted above are not absolute and further measurements of the IC$_{50}$ value for a compound may result in a different geometric mean IC$_{50}$ value.

Pharmaceutical Compositions

According to a further aspect of the invention there is provided a pharmaceutical composition which comprises a compound of the invention, or a pharmaceutically acceptable salt thereof, as defined hereinbefore in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of infection is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active ingredient, (suitable from 0.5 mg to 1 g of active ingredient, for example from 0.5 mg to 0.5 g of active agent, and more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention and a unit dose may be administered once, twice, three or four times a day or more often if required.

The compounds of the present invention are expected to possess, amongst others, anti-tumour properties that are believed to arise from the inhibition of FAK, for example the compounds may exhibit anti-proliferation and/or proapoptotic and/or anti-invasive and/or anti-cell motility and/or anti-angiogenic activity. Such compounds are likely to be useful in the treatment of, for example FAK driven tumours, particularly as an anti-cancer agent.

Accordingly, the compounds of the present invention are expected to be useful in the treatment of diseases or medical conditions mediated alone or in part by FAK, i.e. the compounds may be used to produce an FAK inhibitory effect in a warm-blooded animal in need of such treatment. Thus the compounds of the present invention provide a method for the treatment of malignant cells characterised by inhibition of FAK. Particularly the compounds of the invention may be used to produce anti-proliferation and/or proapoptotic and/or anti-invasive and/or anti-cell motility and/or anti-angiogenic activity effect mediated alone or in part by the inhibition of FAK function. Particularly, the compounds of the present invention are expected to be useful in the prevention or treatment of those tumours that are sensitive to inhibition of FAK that are involved in for example, angiogenesis, proliferation and the signal transduction steps which drive proliferation, invasion, migration and particularly angiogenesis of these tumour cells. Accordingly the compounds of the present invention may be useful in the treatment of hyperproliferative disorders, including cancer. Benign or malignant tumours may affect any tissue and include non-solid tumours such as leukemia, multiple myeloma or lymphoma, and also solid tumours, for example bile duct, bone (including ewings tumour), bladder, brain/CNS, breast, colorectal, endometrial, gastric, head and neck, hepatic, lung (including non small cell lung cancer and small cell ling cancer), neuronal (including neuroblasoma), oesophageal, ovarian, pancreatic, prostate, renal, skin, testicular, thyroid, uterine, cervical and vulval cancers and kaposis sarcoma. The compounds of the invention are expected to be useful in the treatment of pathogenic angiogenesis (pathological angiogenesis), for example in the treatment of cancers as hereinbefore described and other diseases in which inappropriate, or pathogenic angiogenesis occurs such as age-related macular degeneration (AMD) as well as cancers involving a solid tumour.

In another aspect of the present invention there is provided a compound of formula I, or a pharmaceutically acceptable salt thereof, as defined hereinbefore for use as a medicament.

In another embodiment the present invention provides the use of a compound of formula I or a pharmaceutically acceptable salt thereof in the preparation of a medicament.

In another embodiment the present invention provides a compound of formula I or a pharmaceutically acceptable salt thereof for use in the treatment or prophylaxis of a cancer, for example a cancer involving a solid tumour.

In another embodiment the present invention provides a compound of formula I or a pharmaceutically acceptable salt thereof for use in the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors.

In still another embodiment the present invention provides a compound of formula I or a pharmaceutically acceptable salt thereof for use in the treatment or prophylaxis of pathological angiogenesis.

In another embodiment the present invention provides a compound of formula I or a pharmaceutically acceptable salt thereof for use in the inhibition FAK.

In another embodiment the present invention provides a compound of formula I or a pharmaceutically acceptable salt thereof for use as an antiangiogenic agent in the treatment of a solid tumour.

In another embodiment the present invention provides the use of a compound of formula I or a pharmaceutically acceptable salt thereof in the preparation of a medicament for the treatment or prophylaxis of a cancer, for example a cancer involving a solid tumour.

In another embodiment the present invention provides the use of a compound of formula I or a pharmaceutically acceptable salt thereof in the preparation of a medicament for the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, esophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors.

In still another embodiment the present invention provides the use of a compound of formula I or a pharmaceutically acceptable salt thereof in the preparation of a medicament for the treatment or prophylaxis of pathological angiogenesis.

In another embodiment the present invention provides the use of a compound of formula I or a pharmaceutically acceptable salt thereof in the preparation of a medicament for use in the inhibition of FAK.

In another embodiment the present invention provides the use of a compound of formula I or a pharmaceutically acceptable salt thereof in the manufacture of a medicament for use as an antiangiogenic agent in the treatment of a solid tumour.

In a further aspect of the invention there is provided a pharmaceutical composition which comprises a compound of the formula I, or a pharmaceutically acceptable salt thereof, as defined herein before in association with a pharmaceutically acceptable diluent or carrier for use in the production of a FAK inhibitory effect in a warm-blooded animal such as man.

In a further aspect of the invention there is provided a pharmaceutical composition which comprises a compound of the formula I, or a pharmaceutically acceptable salt thereof, as defined herein before in association with a pharmaceutically acceptable diluent or carrier for use in the production of an anti-cancer effect in a warm-blooded animal such as man.

In a further aspect of the invention there is provided a pharmaceutical composition which comprises a compound of the formula I, or a pharmaceutically acceptable salt thereof, as defined herein before in association with a pharmaceutically acceptable diluent or carrier for use as an antiangiogenic agent in the treatment of a solid tumour.

In a further aspect of the invention there is provided a pharmaceutical composition which comprises a compound of the formula I, or a pharmaceutically acceptable salt thereof, as defined herein before in association with a pharmaceutically acceptable diluent or carrier for use in the treatment or prophylaxis of pathological angiogenesis.

In another embodiment the present invention provides a method of inhibiting pathological angiogenesis in a human or animal comprising administering to said human or animal in need of said inhibiting a therapeutically effective amount of a compound of formula I or a pharmaceutically acceptable salt thereof.

In a further embodiment the present invention provides a method of inhibiting FAK comprising administering to an animal or human in need of said inhibiting a therapeutically effective amount of a compound of formula I, or a pharmaceutically acceptable salt thereof.

In a further embodiment the present invention provides a method of prophylaxis or treatment of a disease mediated in part or alone by FAK comprising administering to an animal or human in need of said prophylaxis or treatment a therapeutically effective amount of a compound of formula I, or a pharmaceutically acceptable salt thereof.

In another embodiment the present invention provides a method of treatment of a human or animal suffering from cancer comprising administering to said human or animal a therapeutically effective amount of a compound of formula I, or a pharmaceutically acceptable salt thereof.

In further embodiment the present invention provides a method of prophylaxis or treatment of cancer comprising administering to a human or animal in need of such prophylaxis or treatment a therapeutically effective amount of a compound of formula I, or a pharmaceutically acceptable salt thereof.

In another embodiment the present invention provides a method of prophylaxis or treatment of a human or animal suffering from a neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumours of the central and peripheral nervous system, and other tumour types such as melanoma, multiple myeloma, fibrosarcoma and osteosarcoma, and malignant brain tumours, comprising administering to said human or animal a therapeutically effective amount of a compound of formula I, or a pharmaceutically acceptable salt thereof.

In another embodiment the present invention provides a method of prophylaxis or treatment of pathological angiogenesis comprising administering to said human or animal a therapeutically effective amount of a compound of formula I or a pharmaceutically acceptable salt thereof.

Combination Therapies

The anti-cancer treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin $\alpha v\beta 3$ function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of formula I as defined hereinbefore or a pharmaceutically acceptable salt thereof and any one of the anti-tumour agents listed under (i)-(ix) above.

In a further aspect of the invention there is provided a compound of formula I or a pharmaceutically acceptable salt thereof in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of formula I or a pharmaceutically acceptable salt thereof in combination with an anti-tumour agent selected from one listed under (i)-(ix) herein above, in association with a pharmaceutically acceptable diluent or carrier.

According to a further aspect of the invention there is provided a pharmaceutical composition which comprises a compound of formula I or a pharmaceutically acceptable salt thereof in combination with an anti-tumour agent selected from one listed under (i)-(ix) herein above, in association with a pharmaceutically acceptable diluent or carrier for use in the production of FAK inhibitory effect in a warm-blooded animal such as man. According to a further aspect of the invention there is provided a pharmaceutical composition which comprises a compound of formula I or a pharmaceutically acceptable salt thereof in combination with an anti-tumour agent selected from one listed under (i)-(ix) herein above, in association with a pharmaceutically acceptable diluent or carrier for use as an antiangiogenic agent in the treatment of a solid tumour.

According to a further aspect of the invention there is provided a pharmaceutical composition which comprises a compound of formula I or a pharmaceutically acceptable salt thereof in combination with an anti-tumour agent selected from one listed under (i)-(ix) herein above, in association with a pharmaceutically acceptable diluent or carrier for use in the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, is cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors.

According to another feature of the invention there is provided the use of a compound of the formula I or a pharmaceutically acceptable salt thereof in combination with an anti-tumour agent selected from one listed under (i)-(ix) herein above, in the manufacture of a medicament for use in the treatment of a cancer in a warm-blooded animal, such as man.

According to another feature of the invention there is provided the use of a compound of the formula I or a pharmaceutically acceptable salt thereof in combination with an anti-tumour agent selected from one listed under (i)-(ix) herein above, in the manufacture of a medicament for use in the production of a FAK inhibitory effect in a warm-blooded animal, such as man.

According to another feature of the invention there is provided the use of a compound of the formula I or a pharmaceutically acceptable salt thereof in combination with an anti-tumour agent selected from one listed under (i)-(ix) herein above, in the manufacture of a medicament for use as an antiangiogenic agent in the treatment of a solid tumour in a warm-blooded animal, such as man.

According to another feature of the invention there is provided the use of a compound of the formula I or a pharmaceutically acceptable salt thereof in combination with an anti-tumour agent selected from one listed under (i)-(ix) herein above, in the manufacture of a medicament for use in the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors in a warm-blooded animal, such as man.

According to another feature of the invention there is provided a compound of the formula I or a pharmaceutically acceptable salt thereof in combination with an anti-tumour agent selected from one listed under (i)-(ix) herein above for use in the treatment of a cancer in a warm-blooded animal, such as man.

According to another feature of the invention there is provided a compound of the formula I or a pharmaceutically acceptable salt thereof in combination with an anti-tumour agent selected from one listed under (i)-(ix) herein above for use in the production of a FAK inhibitory effect in a warm-blooded animal, such as man.

According to another feature of the invention there is provided a compound of the formula I or a pharmaceutically acceptable salt thereof in combination with an anti-tumour agent selected from one listed under (i)-(ix) herein above for use as an antiangiogenic agent in the treatment of a solid tumour in a warm-blooded animal, such as man.

According to another feature of the invention there is provided a compound of the formula I or a pharmaceutically acceptable salt thereof in combination with an anti-tumour agent selected from one listed under (i)-(ix) herein above for use in the treatment or prophylaxis of neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumors of the central and peripheral nervous system, and other tumor types such as melanoma, multiple myeloma, fibrosarcoma and osteosarcoma, and malignant brain tumors in a warm-blooded animal, such as man.

Therefore in an additional feature of the invention, there is provided a method of treating a cancer in a warm-blooded animal, such as man, in need of such treatment which comprises administering to said animal an effective amount of a compound of formula I or a pharmaceutically acceptable salt thereof in combination with an anti-tumour agent selected from one listed under (i)-(ix) herein above.

In an additional feature of the invention, there is provided the production of a FAK inhibitory effect in a warm-blooded animal, such as man, in need of such treatment which comprises administering to said animal an effective amount of a compound of formula I or a pharmaceutically acceptable salt thereof in combination with an anti-tumour agent selected from one listed under (i)-(ix) herein above.

In an additional feature of the invention, there is provided a method of treating pathogenic angiogenesis in a warm-blooded animal, such as man, in need of such treatment which comprises administering to said animal an effective amount of a compound of formula I or a pharmaceutically acceptable salt thereof in combination with an anti-tumour agent selected from one listed under (i)-(ix) herein above. In an additional feature of the invention, there is provided a method of treating neoplastic disease such as carcinoma of the breast, ovary, lung (including small cell lung cancer, non-small cell lung cancer and bronchioalveolar cancer), colon, rectum, prostate, bile duct, bone, bladder, head and neck, kidney, liver, gastrointestinal tissue, oesophagus, pancreas, skin, testes, thyroid, uterus, cervix, vulva or other tissues, as well as leukemias and lymphomas including CLL and CML, tumours of the central and peripheral nervous system, and other tumour types such as melanoma, multiple myeloma, fibrosarcoma and osteosarcoma, and malignant brain tumours in a warm-blooded animal, such as man, in need of such treatment which comprises administering to said animal an effective amount of a compound of formula I or a pharmaceutically acceptable salt thereof in combination with an anti-tumour agent selected from one listed under (i)-(ix) herein above.

According to a further aspect of the present invention there is provided a kit comprising a compound of formula I or a pharmaceutically acceptable salt thereof in combination with an anti-tumour agent selected from one listed under (i)-(ix) herein above.

According to a further aspect of the present invention there is provided a kit comprising:
a) a compound of formula I or a pharmaceutically acceptable salt thereof, in a first unit dosage form;
b) an anti-tumour agent selected from one listed under (i)-(ix) herein above; in a second unit dosage form; and
c) container means for containing said first and second dosage forms.

EXAMPLES

The invention will now be illustrated in the following Examples in which, generally:
(i) operations were carried out at ambient temperature, i.e. in the range 17 to 25° C. and under an atmosphere of an inert gas such as nitrogen or argon unless otherwise stated;
(ii) in general, the course of reactions were followed by liquid chromatography mass spectrometry (LCMS); the reaction times that are given are not necessarily the minimum attainable;
(iii) when necessary, organic solutions were dried over anhydrous magnesium sulfate, work-up procedures were carried out using traditional layer separating techniques, evaporations were carried out either by rotary evaporation in vacuo or in a Genevac HT-4/EZ-2.

(iv) yields, where present, are not necessarily the maximum attainable, and when necessary, reactions were repeated if a larger amount of the reaction product was required;

(v) in general, the structures of the end-products of the formula I were confirmed by nuclear magnetic resonance (NMR) and/or mass spectral techniques; electrospray mass spectral data were obtained using a Waters ZMD or Waters ZQ LC/mass spectrometer acquiring both positive and negative ion data, generally, only ions relating to the parent structure are reported; unless otherwise stated, proton NMR chemical shift values were measured on the delta scale at 300 or 400 MHz using a Bruker DPX300, a Bruker AV400, a Bruker 33 DRX400, or a Bruker DPX400 with QNP probes. The following abbreviations have been used: s, singlet; d, doublet; t, triplet; q, quartet; m, multiplet; br, broad;

(vi) unless stated otherwise compounds containing an asymmetric carbon and/or sulfur atom were not resolved;

(vii) intermediates were not necessarily fully purified but their structures and purity were assessed by TLC, analytical HPLC, infra-red (IR) and/or NMR analysis;

(viii) unless otherwise stated, column chromatography (by the flash procedure) and medium pressure liquid chromatography (MPLC) were performed on Merck Kieselgel silica (Art. 9385);

(ix) the following analytical HPLC methods were used; in general, reversed-phase silica was used with a flow rate of about 1 ml per minute and detection was by Electrospray Mass Spectrometry and by UV absorbance at a wavelength of 254 nm;

(x) where certain compounds were obtained as an acid-addition salt, for example a mono-hydrochloride salt or a di-hydrochloride salt, the stoichiometry of the salt was based on the number and nature of the basic groups in the compound, the exact stoichiometry of the salt was generally not determined, for example by means of elemental analysis data;

(xi) compounds were purified by i) flash silica chromtaography using Merck Kieselgel silica (Art. 9385); ii) strong cation exchange (SCX) chromatography using Isolute SPE flash SCX-2 column (International Sorbent Technology Limited, Mid Glamorgan, UK) or iii) reverse phase HPLC using a Waters FractionLynx XBridge C18 OBD column (5μ silica, 19 mm diameter, 100 mm length) eluting with decreasingly polar mixtures of water (containing 1-5% ammonia) and MeCN with either ultra violet or MS detection;

(xii) where stated, reactions were carried out in the one of the following microwave reactors: Biotage Initiator, Personal Chemistry Emrys Optimizer, Personal Chemistry Smithcreator or CEM Explorer;

(xiii) the following abbreviations have been used:
EtOAc: ethyl acetate
DCM dichloromethane
DMA: N-dimethylacetamide
DMF: N,N-dimethylformamide
MeOH: methanol
THF: tetrahydrofuran
DIAD: Diisopropyl azodicarboxylate
DIPEA: N,N-Diisopropylethylamine
HATU: O-(7-Azabenzotriazol-1-yl)-N,N,N',N'-tetramethyluronium hexafluorophosphate
DME: dimethoxyethane
Et$_2$O: diethyl ether
tBuOMe: methyl tert-butyl ether Example 1.01

2-[[5-Cyano-2-[(1,3-dimethylpyrazol-4-yl)amino]-4-pyridyl]amino]-N-methyl-benzamide

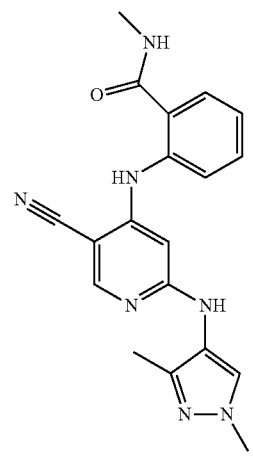 [SMILES: CNC(=O)c1ccccc1Nc1cc(Nc2cn(C)nc2C)ncc1C#N]

2-[(2-Chloro-5-cyanopyridin-4-yl)amino]-N-methylbenzamide (200 mg, 0.70 mmol), palladium(II) acetate (12.53 mg, 0.06 mmol), 1,3-dimethylpyrazol-4-amine (155 mg, 1.40 mmol), 9,9-dimethyl-4,5-bis(diphenylphosphino)xanthene (48.4 mg, 0.08 mmol) and cesium carbonate (273 mg, 0.84 mmol) were suspended in dioxane (5 mL). The mixture was purged for 5 minutes with nitrogen and then heated at 90° C. for 24 hours. The mixture was allowed to cool to room temperature and then loaded onto an SCX column. The mixture was eluted first with MeOH and then with a solution of 7N NH$_3$ in MeOH. Fractions containing product were combined and then evaporated. The residue was purified by preparative HPLC and fractions containing product were combined and evaporated to afford example 1.01 (126 mg, 50% yield); $^1$H NMR spectrum: (300 MHz, DMSO) δ 2.12 (3H, s), 2.84 (3H, d), 3.77 (3H, s), 6.60 (1H, s), 7.21 (1H, ddd), 7.58 (2H, d), 7.79 (1H, d), 7.88 (1H, s), 8.35 (1H, s), 8.66 (1H, s), 8.72 (1H, d), 10.28 (1H, s); Mass spectrum: m/z (ESI+) (M+H)+= 362.11.

The 2-[(2-chloro-5-cyanopyridin-4-yl)amino]-N-methyl-benzamide, used as starting material, was prepared as follows:

a) Sodium hydride (2.345 g, 58.64 mmol) was added portionwise to a mixture of 2-amino-N-methylbenzamide (2.201 g, 14.66 mmol), in THF (40 mL) at room temperature under an atmosphere of nitrogen. The resulting suspension was stirred at room temperature for 30 minutes and then 4,6-dichloropyridine-3-carbonitrile (2.536 g, 14.66 mmol) was added portionwise (caution—exotherm and effervescence); the mixture was then heated overnight at 60° C. The mixture was allowed to cool to room temperature and then diluted with EtOAc (200 mL). The mixture was washed sequentially with water (200 mL), water (150 mL), and finally with a saturated solution of NaCl (200 mL). The organic layer was filtered and the residue washed with water followed by EtOAc and then allowed to dry to leave 2-[(2-chloro-5-cyanopyridin-4-yl) amino]-N-methylbenzamide (0.687 g, 16% yield). The filtrate was dried over MgSO$_4$ and then evaporated to leave a solid. The solid was crystallised from MeOH/Et$_2$O to afford a second crop of 2-[(2-chloro-5-cyanopyridin-4-yl)amino]-N-methylbenzamide (2.471 g, 59% yield); $^1$H NMR spectrum: (300 MHz, DMSO) δ 2.76 (3H, t), 7.10 (1H, d), 7.26-7.32 (1H, m), 7.57 (2H, dd), 7.72-7.74 (1H, m), 8.56 (1H, s), 8.68 (1H, d), 10.63 (1H, s); Mass spectrum: m/z (ESI+) (M+H)+= 286.98 and 288.94.

The following compounds were prepared in an analogous way to example 1.01.

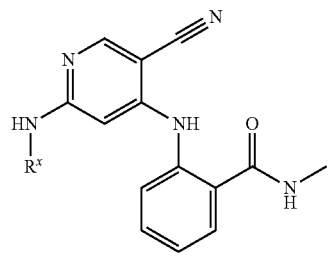

| # | R$^x$ | Name | $^1$H NMR spectrum (300 MHz, DMSO): δ | Mass spectrum m/z (ESI+) (M + H)$^+$ |
|---|---|---|---|---|
| 1.02$^a$ | | 2-[[5-cyano-2-[(5-methoxy-2-methylpyrazol-3-yl)amino]pyridin-4-yl]amino]-N-methylbenzamide | 2.78 (3H, d), 3.48 (3H, s), 3.71 (3H, s), 5.70 (1H, d), 6.63 (1H, d), 7.19 (1H, dd), 7.49-7.58 (2H, m), 7.73 (1H, dd), 8.35 (1H, s), 8.67 (1H, d), 9.19 (1H, s), 10.31 (1H, s) | 378.32 |

$^a$The 5-methoxy-2-methylpyrazol-3-amine, used as starting material, was prepared as follows:
i) A mixture of 5-amino-2H-pyrazol-3-ol (49.55 g, 0.50 mol) in CH$_2$Cl$_2$ (1000 mL was heated at reflux for 15 minutes and then cooled in an ice-bath. Triphenylphosphine (157.38 g, 0.60 mol) was added followed by the dropwise addition of DIAD (118.95 mL, 0.60 mol) over a period of 50 minutes, maintaining the temperature between −5 to 2° C. The mixture was stirred for an hour at 0° C. and then MeOH (24.305 mL, 0.60 mol) was added dropwise at 0° C. and the mixture stirred for 1 hour. The mixture was allowed to warm to room temperature and then stirred overnight. The mixture was filtered and the residue washed with CH$_2$Cl$_2$. The filtrate was extracted with 2N HCl (2 x 300 mL) and the aqueous phase was adjusted to pH 9 by the addition of a sodium hydroxide solution. The aqueous mixture was extracted with EtOAc (3x 500 mL) and the combined organic extracts were evaporated to leave an orange oil. The oil was purified by chromatography on silica eluting with a mixture of 5-10% MeOH in CH$_2$Cl$_2$. The less polar fractions were combined and evaporated and the residue repurified by chromatography on silica eluting with a mixture of 5% MeOH in CH$_2$Cl$_2$. Fractions containing product were combined and evaporated to leave 5-methoxy-2-methylpyrazol-3-amine (3.982 g, 6% yield); $^1$H NMR spectrum: (300 MHz, DMSO) δ 3.34 (s, 3H), 3.63 (s, 3H), 4.70 (s, 1H), 5.13 (s, 2H).

Example 1.03

2-[[5-Cyano-2-[(1,3-dimethylpyrazol-4-yl)amino]-4-pyridyl]amino]-N-methoxy-N-methyl-benzamide

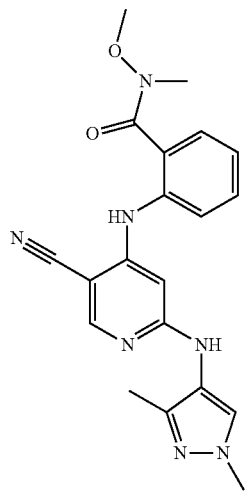 [SMILES: CON(C)C(=O)c1ccccc1Nc1cc(Nc2cn(C)nc2C)ncc1C#N]

A mixture of 2-[(2-chloro-5-cyanopyridin-4-yl)amino]-N-methoxy-N-methylbenzamide (100 mg, 0.32 mmol), palladium(II) acetate (5.67 mg, 0.03 mmol), 9,9-dimethyl-4,5-bis(diphenylphosphino)xanthene (21.92 mg, 0.04 mmol), 1,3-dimethylpyrazol-4-amine (70.2 mg, 0.63 mmol) and cesium carbonate (123 mg, 0.38 mmol) were suspended in dioxane (2 mL). The mixture was purged for 5 minutes with nitrogen and then heated at 90° C. for 1 hour. The mixture was allowed to cool to room temperature and then loaded onto an SCX column. The mixture was eluted first with MeOH and then using a solution of 7N NH$_3$ in MeOH. Fractions containing product were combined and then evaporated. The residue was purified by preparative HPLC and fractions containing product were combined and evaporated to afford example 1.03 (37 mg, 30% yield); $^1$H NMR spectrum: (300 MHz, DMSO) δ 2.02 (3H, s), 3.21 (3H, s), 3.47 (3H, s), 3.69 (3H, s), 6.08 (1H, s), 7.28 (1H, td), 7.41 (1H, d), 7.48-7.56 (2H, m), 7.77 (1H, s), 8.12 (1H, s), 8.22 (1H, s), 8.49 (1H, s); Mass spectrum: m/z (ESI+) (M+H)+=392.49.

The 2-[(2-chloro-5-cyanopyridin-4-yl)amino]-N-methoxy-N-methylbenzamide, used as starting material, was prepared as follows:

a) Sodium hydride (0.888 g, 22.20 mmol) was added portionwise to a mixture of 2-amino-N-methoxy-N-methylbenzamide (1.00 g, 5.55 mmol), in THF (30 mL) cooled to 0° C. under an atmosphere of nitrogen. The resulting suspension was stirred at room temperature for 20 minutes and then 4,6-dichloropyridine-3-carbonitrile (0.960 g, 5.55 mmol) was added portionwise and the mixture heated overnight at 60° C. The mixture was allowed to cool to room temperature and then diluted with EtOAc (50 mL). The mixture was washed sequentially with water (50 mL), a saturated solution of NaHCO$_3$ (50 mL), water (25 mL) and finally with a saturated solution of NaCl (20 mL). The organic layer was dried over Na$_2$SO$_4$ and then evaporated. The residue was crystallised from Et₂O/MeOH to afford 2-[(2-chloro-5-cyanopyridin-4-yl)amino]-N-methoxy-N-methylbenzamide (0.602 g, 34% yield); ¹H NMR spectrum: (300 MHz, DMSO) δ 3.15 (3H, s), 3.47 (3H, s), 6.56 (1H, s), 7.39-7.44 (2H, m), 7.52-7.56 (2H, m), 8.45 (1H, s), 9.33 (1H, s); Mass spectrum: m/z (ESI+) (M+H)+=317.28 and 319.30.

The 2-amino-N-methoxy-N-methylbenzamide can be prepared as described in the literature (Frye, S. V.; Johnson, M. C.; Valvano, N. L. Synthesis of 2-aminobenzophenones via rapid halogen-lithium exchange in the presence of a 2-amino-N-methoxy-N-methylbenzamide. *JOC*, 1991, 56(11), 3750-2).

Example 1.04

4-[(2-Methyl-1-oxo-3,4-dihydroisoquinolin-8-yl)amino]-6-[(1-methylpyrazol-4-yl)amino]pyridine-3-carbonitrile

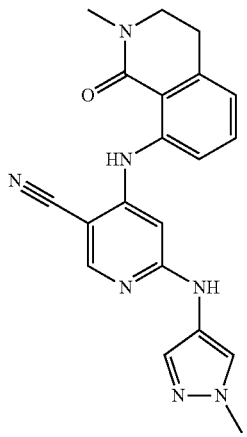 [SMILES: CN1CCc2cccc(Nc3cc(Nc4cnn(C)c4)ncc3C#N)c2C1=O]

6-Chloro-4-[(2-methyl-1-oxo-3,4-dihydroisoquinolin-8-yl)amino]pyridine-3-carbonitrile (100 mg, 0.32 mmol), palladium(II) acetate (5.74 mg, 0.03 mmol), 9,9-dimethyl-4,5-bis(diphenylphosphino)xanthene (22.20 mg, 0.04 mmol), 1-methylpyrazol-4-amine (62.1 mg, 0.64 mmol) and cesium carbonate (125 mg, 0.38 mmol) were suspended in dioxane (2 mL). The mixture was purged for 5 minutes with nitrogen and then heated at 90° C. for 1 hour. The mixture was allowed to cool to room temperature and then loaded onto an SCX column. The mixture was eluted first with MeOH and then with a solution of 7N NH₃ in MeOH. Fractions containing product were combined and then evaporated. The residue was purified by preparative HPLC and fractions containing product were combined and evaporated to afford example 1.04 (12.30 mg, 10% yield); ¹H NMR spectrum: (300 MHz, DMSO) δ 2.96 (2H, t), 3.05 (3H, s), 3.57 (2H, t), 3.79 (3H, s), 6.63 (1H, s), 6.94 (1H, t), 7.42 (3H, dd), 7.87 (1H, s), 8.35 (1H, s), 9.25 (1H, s), 11.40 (1H, s); Mass spectrum: m/z (ESI+) (M+H)+=374.41.

The 6-chloro-4-[(2-methyl-1-oxo-3,4-dihydroisoquinolin-8-yl)amino]pyridine-3-carbonitrile, used as starting material, was prepared as follows:

a) Sodium hydride (2.78 g, 69.46 mmol) was added portionwise to 8-amino-2-methyl-3,4-dihydroisoquinolin-1-one (3.06 g, 17.37 mmol), in THF (8 mL) under an atmosphere of nitrogen. The resulting suspension was stirred at room temperature for 20 minutes and then 4,6-dichloropyridine-3-carbonitrile (3.00 g, 17.37 mmol) was added portionwise and the mixture heated overnight at 60° C. The mixture was allowed to cool to room temperature and then diluted with EtOAc (100 mL). The mixture was washed sequentially with water (100 mL), a saturated solution of NaHCO₃ (100 mL), and finally with a saturated solution of NaCl (100 mL). The organic layer was dried over MgSO₄ and then evaporated. The residue was loaded onto an SCX column and the product was eluted using a mixture of MeOH in CH₂Cl₂. Fractions containing product were combined and evaporated. The residue was purified by chromatography on silica, eluting with a gradient of 50-70% EtOAc in isohexane. Fractions containing the required product were combined and evaporated to afford 6-chloro-4-[(2-methyl-1-oxo-3,4-dihydroisoquinolin-8-yl)amino]pyridine-3-carbonitrile (1.149 g, 21% yield). The mixed fractions were combined and repurified by silica chromatography, eluting with a gradient of 0-20% EtOAc in CH₂Cl₂. Fractions containing the required product were combined and evaporated to leave 6-chloro-4-[(2-methyl-1-oxo-3,4-dihydroisoquinolin-8-yl)amino]pyridine-3-carbonitrile (1.287 g, 24% yield); ¹H NMR spectrum: (300 MHz, DMSO) δ 2.98 (2H, t), 3.06 (3H, s), 3.58 (2H, t), 7.07 (1H, dd), 7.36 (1H, s), 7.48-7.52 (2H, m), 8.63 (1H, s), 12.00 (1H, s); Mass spectrum: m/z (ESI+) (M+H)+=313.34 and 315.33.

The 8-amino-2-methyl-3,4-dihydroisoquinolin-1-one, used as starting material, can be prepared as described in the literature (Glossop, S. C. A microwave-assisted alternative synthesis of 8-amino-2-methyl-3,4-dihydroisoquinolin-1-one. *Synthesis*, 2007, 7, 981-983) or as follows:

a) A mixture of 1-tent-butoxy-N,N,N',N'-tetramethyl-methanediamine (300 mL, 1452.80 mmol) and 2-methyl-6-nitrobenzonitrile (75 g, 462.55 mmol) was heated at 100° C. for 4 hours. The mixture was evaporated and the residue stirred vigorously in isohexane (1500 mL) for 2 hours. The mixture was filtered and the residue washed with isohexane (2×500 mL) and then air-dried to afford (E)-2-(2-(dimethylamino)vinyl)-6-nitrobenzonitrile (96 g, 95% yield); ¹H NMR spectrum (300 MHz, CDCl₃): δ 2.98 (6H, s), 5.52 (1H, d), 7.11 (1H, d), 7.40 (1H, t), 7.60-7.70 (2H, m); Mass spectrum: m/z (ESI+) (M+H)+=218.50.

b) Methylamine hydrochloride (131 g, 1933.49 mmol) was added to a suspension of (E)-2-(2-(dimethylamino)vinyl)-6-nitrobenzonitrile (84 g, 386.70 mmol) in MeOH (840 mL) and water (840 mL). The mixture was heated at 50° C. for 17 hours and then allowed to cool to room temperature. The mixture was poured into water (1000 mL), stirred for 30 minutes and then filtered. The solid was air-dried to afford (E)-2-(2-(methylamino)vinyl)-6-nitrobenzonitrile (71.1 g, 90% yield) which was used in the next step without further purification; ¹H NMR spectrum (300 MHz, DMSO): δ 2.74 (3H, d), 5.41 (1H, d), 6.93-7.03 (1H, m), 7.50-7.70 (3H, m), 7.96-8.01 (1H, m).

c) Sulfuric acid (26.2 ml, 492.13 mmol) was added in one portion to a stirred solution of (E)-2-(2-(methylamino)vinyl)-6-nitrobenzonitrile (50 g, 246.07 mmol) and sodium triacetoxyborohydride (78 g, 369.10 mmol) in DME (1000 mL) cooled to −10° C. The mixture was stirred at −10° C. for 10 minutes and then allowed to warm to room temperature and stirred for a further 20 minutes. The mixture was poured into water (1000 mL), basified to ~pH 10 with a 2N solution of NaOH and then extracted with EtOAc (3×750 mL). The combined organics were dried over MgSO₄ and then evaporated to afford 2-methyl-8-nitro-3,4-dihydroisoquinolin-1(2H)-imine (45.5 g) which was used in the next stage without further purification.

d) The following step was carried out in 9 separate batches. 2-Methyl-8-nitro-3,4-dihydroisoquinolin-1(2H)-imine (5 g, 24.36 mmol) and Montmorillonite K10 clay (2.5 g) were suspended in a mixture of water (20 mL) and acetonitrile (30 mL). The mixture was heated at 150° C. for 90 minutes in a microwave reactor and then allowed to cool to room temperature. The separate batches were combined and the mixture was then filtered and evaporated. The residue was purified by chromatography on silica, eluting with a gradient of 0-100% EtOAc in isohexane. Fractions containing product were combined and evaporated to afford 2-methyl-8-nitro-3,4-dihydroisoquinolin-1(2H)-one (23.00 g, 51% yield); $^1$H NMR spectrum (300 MHz, DMSO): δ 3.00-3.08 (5H, m), 3.60 (2H, t), 7.53-7.67 (3H, m); Mass spectrum: m/z (ES+) (M+H)+= 207.58.

e) A mixture of 2-methyl-8-nitro-3,4-dihydroisoquinolin-1 (2H)-one (23 g, 111.54 mmol) and 5% palladium on carbon (4.6 g, 1.08 mmol) in MeOH (230 mL) was stirred under an atmosphere of hydrogen at 5 atm and 25° C. for 18 hours. The mixture was filtered through Dicalite™ and the filtrate was evaporated. The residue was purified by chromatography on silica, eluting with a gradient of 0-100% EtOAc in isohexane. Fractions containing product were combined and evaporated to afford 8-amino-2-methyl-3,4-dihydroisoquinolin-1(2H)-one (17.33 g, 88% yield); $^1$H NMR spectrum (300 MHz, DMSO): δ 2.80 (2H, t), 2.96 (3H, s), 3.43 (2H, t), 6.26-6.32 (1H, m), 6.50-6.55 (1H, m), 6.84 (2H, s), 7.00-7.06 (1H, m); Mass spectrum m/z (ES+) (M+H)+=177.44.

The following compounds were prepared in an analogous way to example 1.04.

| # | R$^x$ | Name | $^1$H NMR spectrum (300 MHz, DMSO): δ | Mass spectrum m/z (ESI+) (M + H)$^+$ |
|---|---|---|---|---|
| 1.05 | 1,5-dimethylpyrazol-3-yl | 6-[(1,5-dimethylpyrazol-3-yl)amino]-4-[(2-methyl-1-oxo-3,4-dihydroisoquinolin-8-yl)amino]pyridine-3-carbonitrile | 2.19 (3H, s), 2.97 (2H, t), 3.06 (3H, s), 3.54-3.61 (5H, m), 5.95 (1H, s), 6.96 (1H, dd), 7.44-7.55 (2H, m), 7.67 (1H, s), 8.32 (1H, s), 9.59 (1H, s), 11.57 (1H, s) | 388.39 |
| 1.06 | 5-methoxy-2-methylpyrazol-3-yl | 6-[(5-methoxy-2-methylpyrazol-3-yl)amino]-4-[(2-methyl-1-oxo-3,4-dihydroisoquinolin-8-yl)amino]pyridine-3-carbonitrile | 2.96 (2H, t), 3.05 (3H, s), 3.49 (3H, s), 3.56 (2H, t), 3.72 (3H, s), 5.71 (1H, d), 6.76 (1H, d), 6.98 (1H, dd), 7.40-7.46 (2H, m), 8.37 (1H, s), 9.22 (1H, s), 11.50 (1H, s) | 404.39 |
| 1.07$^a$ | 1-(1-methyl-4-piperidyl)pyrazol-4-yl | 4-[(2-methyl-1-oxo-3,4-dihydroisoquinolin-8-yl)amino]-6-[[1-(1-methyl-4-piperidyl)pyrazol-4-yl]amino]pyridine-3-carbonitrile | 1.86-2.06 (6H, m), 2.19 (3H, s), 2.83 (2H, d), 2.96 (2H, t), 3.05 (3H, s), 3.56 (2H, t), 4.00-4.11 (1H, m), 6.61 (1H, s), 6.93 (1H, t), 7.43 (3H, d), 7.92 (1H, s), 8.34 (1H, s), 9.22 (1H, s), 11.41 (1H, s) | 457.42 |

-continued

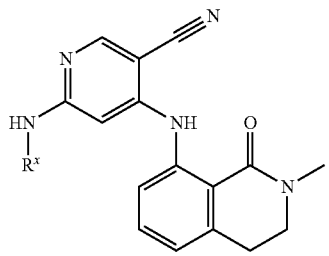

| # | R$^x$ | Name | $^1$H NMR spectrum (300 MHz, DMSO): δ | Mass spectrum m/z (ESI+) (M + H)$^+$ |
|---|---|---|---|---|
| 1.08$^b$ |  | 6-[(1,3-dimethylpyrazol-4-yl)amino]-4-[(2-methyl-1-oxo-3,4-dihydroisoquinolin-8-yl)amino]pyridine-3-carbonitrile | 2.13 (3H, s), 3.01 (2H, t), 3.11 (3H, s), 3.62 (2H, t), 3.77 (3H, s), 6.71 (1H, s), 6.99 (1H, d), 7.42-7.53 (2H, m), 7.89 (1H, s), 8.36 (1H, s), 8.68 (1H, s), 11.43 (1H, s) | 388.39 |

$^a$The 1-(1-methylpiperidin-4-yl)pyrazol-4-amine, used as starting material, was prepared as follows:
a) DIAD (84 mL, 424.76 mmol) was added dropwise to a cooled solution of 1-methylpiperidin-4-ol (39.1 g, 339.81 mmol), triphenylphosphine (111 g, 424.76 mmol) and 4-nitro-1H-pyrazole (32.02 g, 283.18 mmol) in THF (550 mL) at 0° C. (Care: exotherm). The resulting solution was stirred for 5 minutes, allowed to warm to room temperature and then stirred for 16 hours. The mixture was partitioned between CH$_2$Cl$_2$ (600 mL) and 1M HCl (400 mL). The organic phase was separated and then washed with 1M HCl (2 x 250 mL). The combined aqueous phases were made basic by the addition of 40% NaOH solution and then extracted with CH$_2$Cl$_2$ (2 x 500 mL). The combined organic phases were washed with a saturated solution of NaCl, dried over MgSO$_4$ and then evaporated. The residue was purified by chromatography on silica, eluting with a gradient of 0-10% MeOH in CH$_2$Cl$_2$. Fractions containing product were combined and evaporated to afford 1-methyl-4-(4-nitropyrazol-1-yl)piperidine (28.5 g, 48% yield); $^1$H NMR spectrum (300 MHz, DMSO): δ 1.94-2.07 (6H, m), 2.21 (3H, s), 2.85-2.87 (2H, m), 4.20-4.27 (1H, m), 8.27 (1H, s), 8.93 (1H, s); Mass spectrum: m/z (ESI+) (M + H)+ = 211.30.
b) A mixture of 1-methyl-4-(4-nitro-1H-pyrazol-1-yl)piperidine (24.05 g, 114.40 mmol) and 5% palladium on carbon (5 g, 2.4 mmol) in EtOH (240 mL) was stirred under an atmosphere of hydrogen (1 atm) at 25° C. for 16 hours. The mixture was filtered and the filtrate evaporated to leave 1-(1-methylpiperidin-4-yl)pyrazol-4-amine (16.39 g, 79% yield); $^1$H NMR spectrum (300 MHz, DMSO): δ 1.93-2.03 (3H, m), 2.10-2.16 (4H, m), 2.33 (3H, s), 2.79 (1H, br s), 2.94-2.97 (2H, m), 3.97-4.05 (1H, m), 7.06 (1H, s), 7.14 (1H, s); Mass spectrum: m/z (ESI+) (M + H)+ = 181.29.
$^b$Alternatively example 1.08 may be prepared as follows: 8-Amino-2-methyl-3,4-dihydroisoquinolin-1-one (5.36 g, 30.44 mmol), 4-chloro-6-(1,3-dimethylpyrazol-4-ylamino)pyridine-3-carbonitrile (5.8 g, 23.42 mmol) and 4-toluenesulfonic acid hydrate (4.90 g, 25.76 mmol) were suspended in cyclohexanol (56.9 ml, 538.59 mmol). The reaction was heated to 160° C. for 2.5 hours. The reaction mixture was allowed to cool to room temperature under stirring and tBuOMe (200 mL) was added. The resulting precipitate was collected by filtration, washed with tBuOMe and redissolved in DCM (400 mL). The solution was washed with a 0.5N aqueous solution of sodium hydroxide (400 mL) and the aqueous phase extracted with DCM. The combined organic phases were washed with water, dried over magnesium sulfate and concentrated. The crude product (15 g) was purified by flash chromatography on silica gel eluting with 0 to 6% MeOH in EtOAc/DCM (1/1). The solvent was evaporated to dryness to afford a solid (7.3 g) and stirred in tBuOMe (100 mL) overnight. The resulting precipitate was collected by filtration, washed with tBuOMe and dried to a constant weight to afford the title compound (7.50 g, 83%) as a white solid.

4-Chloro-6-(1,3-dimethylpyrazol-4-ylamino)pyridine-3-carbonitrile was prepared as follows:

4,6-Dichloropyridine-3-carbonitrile (9.60 g, 55.49 mmol), N-(1,3-dimethylpyrazol-4-yl)acetamide (8.5 g, 55.49 mmol, see Example 2.02), palladium(II) acetate (0.374 g, 1.66 mmol), 9,9-dimethyl-4,5-bis(diphenylphosphino)xanthene (1.926 g, 3.33 mmol) and cesium carbonate (27.1 g, 83.23 mmol) were weighed out in a flask. Dioxane (110 mL) was added and argon was bubbled through the reaction mixture for 5 minutes at room temperature. The resulting suspension was stirred at 90° C. for 2 hours. The reaction mixture was allowed to cool to room temperature with stirring, water (275 mL) was added followed by the portionwise addition of lithium hydroxide hydrate (6.99 g, 166.47 mmol). The solution was left to stir at room temperature for 30 minutes. The resulting precipitate was collected by filtration, washed with water and dried. The crude product was purified by flash chromatography on silica gel eluting with 0 to 5% MeOH in EtOAc/DCM (1:1). The solvent was evaporated to dryness. The residue was triturated in Et$_2$O, and the resulting precipitate was collected by filtration, washed with Et$_2$O and dried to a constant weight to afford 4-chloro-6-(1,3-dimethylpyrazol-4-ylamino)pyridine-3-carbonitrile (6 g, 43.7%) as a pale yellow solid. $^1$H NMR spectrum (500 MHz, CDCl$_3$): δ 2.15 (s, 3H), 2.88 (s, 3H), 6.43 (s, 1H), 6.45 (s, 1H), 7.44 (s, 1H), 8.36 (s, 1H); Mass spectrum: m/z (ESI+) (M+H)+=248.

Example 1.09

6-[(1,3-Dimethylpyrazol-4-yl)amino]-4-[[7-(4-isopropylpiperazin-1-yl)-2-methyl-3-oxo-isoindolin-4-yl]amino]pyridine-3-carbonitrile

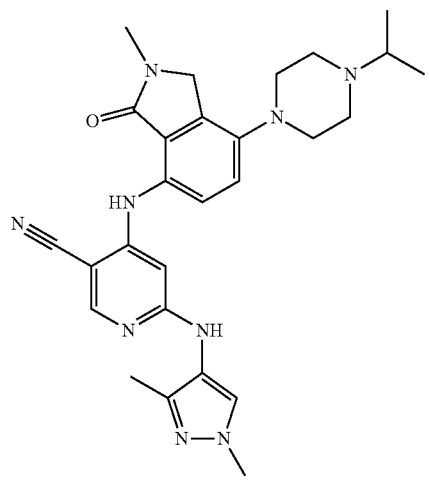 [SMILES: Cc1nn(C)cc1Nc1cc(Nc2ccc(N3CCN(C(C)C)CC3)c3c2C(=O)N(C)C3)c(C#N)cn1]

6-Chloro-4-[[2-methyl-3-oxo-7-(4-propan-2-ylpiperazin-1-yl)-1H-isoindol-4-yl]amino]pyridine-3-carbonitrile (100 mg, 0.24 mmol), palladium(II) acetate (4.23 mg, 0.02 mmol), 9,9-dimethyl-4,5-bis(diphenylphosphino)xanthene (16.34 mg, 0.03 mmol), 1,3-dimethylpyrazol-4-amine (52.3 mg, 0.47 mmol) and cesium carbonate (92 mg, 0.28 mmol) were suspended in dioxane (2 mL). The mixture was purged for 5 minutes with nitrogen and then heated at 90° C. for 1 hour. The mixture was allowed to cool to room temperature and then loaded onto an SCX column. The mixture was eluted first with MeOH and then with a solution of 7N $NH_3$ in MeOH. Fractions containing product were combined and then evaporated. The residue was purified by preparative HPLC and fractions containing product were combined and evaporated to afford example 1.09 (31 mg, 26% yield); $^1$H NMR spectrum: (300 MHz, DMSO) δ 1.02 (6H, d), 2.09 (3H, s), 2.60 (4H, t), 2.68-2.73 (1H, m), 3.01 (4H, t), 3.06 (3H, s), 3.72 (3H, s), 4.49 (2H, s), 6.72 (1H, s), 7.14 (1H, d), 7.39 (1H, d), 7.86 (1H, s), 8.30 (1H, s), 8.65 (1H, s), 9.26 (1H, s); Mass spectrum: m/z (ESI+) (M+H)+=500.33.

The 6-chloro-[[2-methyl-3-oxo-7-(4-propan-2-ylpiperazin-1-yl)-1H-isoindol-4-yl]amino]pyridine-3-carbonitrile, used as starting material, was prepared as follows:

a) Sodium hydride (0.557 g, 13.93 mmol) was added portionwise to 7-amino-2-methyl-4-(4-propan-2-ylpiperazin-1-yl)-3H-isoindol-1-one (1.004 g, 3.48 mmol), in THF (30 mL) at room temperature under an atmosphere of nitrogen. The resulting suspension was stirred at room temperature for 30 minutes and then 4,6-dichloropyridine-3-carbonitrile (0.602 g, 3.48 mmol) was added portionwise and the mixture heated overnight at 60° C. The mixture was allowed to cool to room temperature and then diluted with EtOAc (50 mL). The mixture was washed sequentially with water (50 mL), a saturated solution of $NaHCO_3$ (50 mL), water (25 mL) and finally with a saturated solution of NaCl (20 mL). The mixture was filtered and the organic layer separated, dried over $Na_2SO_4$ and then evaporated. The residue was triturated in $Et_2O$ and MeOH and the mixture filtered. The filtrate was evaporated and the residue purified by chromatography on silica, eluting with a gradient of 5-10% MeOH in $CH_2Cl_2$. Fractions containing product were combined and evaporated to leave 6-chloro-[[2-methyl-3-oxo-7-(4-propan-2-ylpiperazin-1-yl)-1H-isoindol-4-yl]amino]pyridine-3-carbonitrile (316 mg, 21% yield); $^1$H NMR spectrum: (300 MHz, DMSO) δ 1.02 (6H, d), 2.60 (4H, t), 2.70 (1H, t), 3.02-3.08 (7H, m), 4.51 (2H, s), 7.04 (1H, d), 7.15 (1H, dd), 7.44 (1H, dd), 8.53 (1H, d), 9.68 (1H, s); Mass spectrum: m/z (ESI+) (M+H)+=425.30.

The 7-amino-2-methyl-4-(4-propan-2-ylpiperazin-1-yl)-3H-isoindol-1-one, used as starting material, can be prepared as described in the literature (Kawahara, E.; Miyake, T.; Roesel, J. Preparation of pyrimidine compounds as FAK and/or ALK inhibitors, WO2006021457).

Example 2.01

2-[[2-[(1,5-Dimethylpyrazol-3-yl)amino]-5-(trifluoromethyl)-4-pyridyl]amino]-N-methyl-benzamide

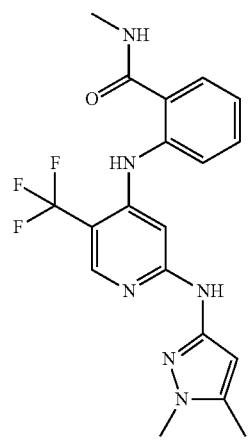 [SMILES: CNC(=O)c1ccccc1Nc1cc(Nc2cc(C)n(C)n2)ncc1C(F)(F)F]

1,5-Dimethylpyrazol-3-amine (50.6 mg, 0.45 mmol), 2-[[2-chloro-5-(trifluoromethyl)pyridin-4-yl]amino]-N-methylbenzamide (100 mg, 0.30 mmol), sodium tert-butoxide (43.7 mg, 0.45 mmol), 9,9-dimethyl-4,5-bis(diphenylphosphino)xanthene (35.1 mg, 0.06 mmol) and bis(dibenzylideneacetone)palladium (27.8 mg, 0.048 mmol) were suspended in dioxane (3 mL) and the mixture heated at 150° C. for 30 minutes in a microwave reactor. The mixture was allowed to cool to room temperature and then loaded onto an SCX column. The mixture was eluted first with MeOH and then with a solution of 7N $NH_3$ in MeOH. Fractions containing product were combined and then evaporated. The residue was purified by preparative HPLC and fractions containing product were combined and evaporated to leave example 2.01 (28.4 mg, 23% yield); $^1$H NMR spectrum: (300 MHz, DMSO) δ 2.18 (3H, s), 2.77 (3H, d), 3.55 (3H, s), 5.93 (1H, s), 7.08-7.11 (1H, m), 7.52-7.55 (1H, m), 7.61-7.63 (2H, m), 7.69-7.72 (1H, m), 8.21 (1H, d), 8.64 (1H, q), 9.36 (1H, s), 10.25 (1H, s); Mass spectrum: m/z (ESI+) (M+H)+=405.07.

The 2-[[2-chloro-5-(trifluoromethyl)pyridin-4-yl]amino]-N-methylbenzamide, used as starting material, was prepared as follows:

a) Cesium carbonate (3.40 g, 10.43 mmol) was added to 2-chloro-4-iodo-5-(trifluoromethyl)pyridine (1.604 g, 5.22 mmol), palladium(II) acetate (0.094 g, 0.42 mmol), 9,9-dimethyl-4,5-bis(diphenylphosphino)xanthene (0.362 g, 0.63 mmol) and 2-amino-N-methylbenzamide (0.784 g, 5.22 mmol) in dioxane (40 mL). The resulting suspension was heated at 80° C. for 24 hours under an argon atmosphere. The mixture was filtered through Celite and then purified directly by chromatography on silica eluting with a mixture of 50% EtOAc in isohexane. Fractions containing product were combined and evaporated to leave 2-[[2-chloro-5-(trifluoromethyl)pyridin-4-yl]amino]-N-methylbenzamide (1.168 g, 68% yield); $^1$H NMR spectrum: (300 MHz, DMSO) δ 2.76 (3H, d), 7.24 (2H, dd), 7.57 (2H, ddd), 7.74 (1H, dd), 8.49 (1H, d), 8.71 (1H, d), 10.54 (1H, s); Mass spectrum: m/z (ESI+) (M+H)+=329.99 and 331.95.

The following compounds were prepared in an analogous way to example 2.01.

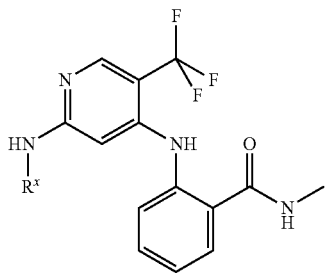

| # | R$^x$ | Name | $^1$H NMR spectrum (300 MHz, DMSO): δ | Mass spectrum m/z (ESI+) (M + H)$^+$ |
|---|---|---|---|---|
| 2.02$^a$ | (1,3-dimethylpyrazol-4-yl, N-methyl) | 2-[[2-[(1,3-dimethylpyrazol-4-yl)amino]-5-(trifluoromethyl)-4-pyridyl]amino]-N-methyl-benzamide | 2.05 (3H, s), 2.69-2.77 (3H, m), 3.70 (3H, s), 6.62 (1H, s), 7.06-7.11 (1H, m), 7.48-7.50 (2H, m), 7.69 (1H, dd), 7.82 (1H, s), 8.19 (1H, s), 8.38 (1H, s), 8.63 (1H, q), 10.09 (1H, s) | 405.07 |

$^a$Alternatively example 2.02 may be prepared as follows:
9,9-Dimethyl-4,5-bis(diphenylphosphino)xanthene (0.606 g, 1.05 mmol), palladium (II) acetate (0.118 g, 0.52 mmol), 2-amino-N-methylbenzamide (2.67 g, 17.80 mmol) and N-(1,3-dimethylpyrazol-4-yl)-4-iodo-5-(trifluoromethyl)pyridin-2-amine (4 g, 10.47 mmol) were dissolved in dioxane (120 mL) and argon was bubbled through the mixture for 5 minutes. Cesium carbonate (6.82 g, 20.94 mmol) was added and argon bubbled through the mixture for a further 5 minutes. The reaction was stirred at 90° C. for 2 hours. The reaction mixture was allowed to cool to room temperature with stirring, diluted with DCM, filtered and the filtrate concentrated. The crude product was purified by flash chromatography on silica gel eluting with 0 to 5% MeOH in EtOAc/DCM (1:1). The solvent was evaporated to dryness, giving a gummy foam. 60 mL of tBuOMe was added and the resulting solution was stirred at room temperature for 15 minutes. The resulting precipitate was collected by filtration, washed with tBuOMe and dried to a constant weight to afford the title compound (3.60 g, 85%) as a pale beige solid. Melting onset of 203° C.

The most prominent X-ray powder diffraction peaks for this crystalline material are listed below:

| Angle 2-Theta ° | Intensity % |
|---|---|
| 9.763 | 11.7 |
| 11.693 | 10.2 |
| 12.058 | 14.3 |
| 13.538 | 22.5 |
| 13.76 | 17.8 |
| 14.599 | 39.5 |
| 14.883 | 12.9 |
| 16.377 | 37.1 |
| 18.288 | 39.2 |
| 19.438 | 33.9 |
| 20.044 | 15.5 |
| 20.494 | 100 |
| 21.124 | 23.7 |
| 21.707 | 32.2 |
| 22.279 | 12 |
| 23.608 | 13.5 |
| 24.186 | 26 |
| 24.887 | 9.6 |
| 25.428 | 9.4 |
| 25.836 | 16.4 |
| 26.734 | 7.9 |
| 28.064 | 8.2 |
| 28.704 | 8.5 |
| 29.81 | 12.9 |
| 30.826 | 5.6 |
| 33.239 | 8.5 |
| 38.767 | 7.6 |
| 6.884 | 18.7 |

The N-(1,3-dimethylpyrazol-4-yl)-4-iodo-5-(trifluoromethyl)pyridin-2-amine used as starting material was made as follows:

Acetic anhydride (27.2 mL, 243.89 mmol) was dropwise added to a stirred suspension of 1,3-dimethyl-pyrazol-4-amine hydrochloride (12 g, 81.30 mmol) and potassium acetate (7.98 g, 81.30 mmol) in EtOAc (250 mL) at 25° C. The suspension was stirred for 1 hour and the insoluble was removed by filtration. After evaporation of the solvent, the resulting crude material was purified by chromatography on silica gel eluting with 0% to 10% of MeOH in DCM. After evaporation of the solvent, the residue was triturated in Et$_2$O. The resulting precipitate was collected by filtration, washed with Et$_2$O and dried to a constant weight to afford N-(1,3-dimethylpyrazol-4-yl)acetamide. The filtrate was concentrated and purified by flash chromatography on silica gel eluting with 0 to 10% MeOH in DCM. The solvent was evaporated to dryness to afford more N-(1,3-dimethylpyrazol-4-yl)acetamide. The two batches were combined to give N-(1,3-dimethylpyrazol-4-yl)acetamide (6.40 g, 51.4%) as a off-white solid.

$^1$H NMR spectrum: (500 MHz, DMSO) δ1.99 (s, 3H), 2.08 (s, 3H), 3.69 (s, 3H), 7.80 (s, 1H), 9.28 (s, 1H); Mass spectrum: m/z (ESI+) (M+H)+=154.

Sodium hydride (1.732 g, 41.13 mmol) was added to N-(1,3-dimethylpyrazol-4-yl)acetamide (6.3 g, 41.1 mmol) dissolved in THF (80 mL) under nitrogen. The resulting light suspension was stirred at room temperature for 15 minutes then at 35° C. for 15 minutes and then 2-chloro-4-iodo-5-(trifluoromethyl)pyridine (6.02 g, 19.6 mmol) was added. The mixture was stirred at 35° C. for 20 minutes then at 45° C. for 30 minutes, giving a light purple solution. The resulting mixture was allowed to cool to room temperature, quenched with water (30 mL) and lithium hydroxide hydrate (2.466 g, 58.75 mmol) was added. The mixture was stirred at room temperature for 1.5 hours. The mixture was extracted twice with DCM. The combined organic phases were washed with water, brine, dried over magnesium sulfate and concentrated to afford the crude product. The crude product was purified by flash chromatography on silica gel eluting with 0 to 50% EtOAc in DCM. The fractions containing pure product were evaporated to dryness, sonicated in petroleum ether then collected by filtration, washed with petroleum ether and dried to a constant weight to afford N-(1,3-dimethylpyrazol-4-yl)-4-iodo-5-(trifluoromethyl)pyridin-2-amine (3.5 g, 9.16 mmol, 46.8%) as a white solid.

Further purification of impure fractions by flash chromatography on silica gel eluting with 0 to 20% EtOAc in DCM to afforded more N-(1,3-dimethylpyrazol-4-yl)-4-iodo-5-(trifluoromethyl)pyridin-2-amine (0.59 g, 1.544 mmol, 7.88%) as a colorless oil which solidified on standing. $^1$H NMR spectrum: (500 MHz, CDCl$_3$) δ 2.16 (s, 3H), 3.87 (s, 3H), 6.22 (bs, 1H), 7.01 (s, 1H), 7.44 (s, 1H), 8.25 (s, 1H); Mass spectrum: m/z (ESI+) (M+H)+=383

Example 3.01

2-[[5-Chloro-2-[(1,3-dimethylpyrazol-4-yl)amino]-4-pyridyl]amino]-N-methoxy-benzamide

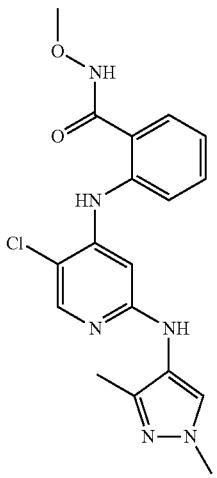 [SMILES: CONC(=O)c1ccccc1Nc1cc(Nc2cn(C)nc2C)ncc1Cl]

2-[(2,5-dichloropyridin-4-yl)amino]-N-methoxybenzamide (0.1 g, 0.32 mmol), 1,3-dimethylpyrazol-4-amine (0.053 g, 0.48 mmol), 9,9-dimethyl-4,5-bis(diphenylphosphino)xanthene (0.037 g, 0.06 mmol) and sodium tert-butoxide (0.046 g, 0.48 mmol) were suspended in dioxane (5 mL) and purged with nitrogen. Bis(dibenzylideneacetone)palladium (0.029 g, 0.050 mmol) was added and the mixture was heated at 150° C. for 30 minutes in a microwave reactor. The mixture was allowed to cool to room temperature and then loaded onto an SCX column. The mixture was eluted first with MeOH and then with a solution of 0.35N NH$_3$ in MeOH. Fractions containing product were combined and then evaporated. The residue was purified by preparative HPLC and fractions containing product were combined and evaporated to afford example 3.01 (6.0 mg, 5% yield); $^1$H NMR spectrum: (300 MHz, DMSO) δ 2.06 (3H, s), 3.69-3.71 (6H, m), 6.66 (1H, s), 7.08-7.13 (1H, m), 7.50-7.60 (4H, m), 7.80 (1H, s), 7.95-7.99 (2H, m), 9.43 (1H, s), 11.87 (1H, s); Mass spectrum: m/z (ESI+) (M+H)+=387.03 and 389.02.

The 2-[(2,5-dichloropyridin-4-yl)amino]-N-methoxybenzamide, used as starting material, was prepared as follows:

a) Palladium acetate (0.071 g, 0.32 mmol) was added under a nitrogen atmosphere to 2-amino-N-methoxybenzamide (1.32 g, 7.94 mmol) in dioxane (80 mL) containing 2,5-dichloro-4-iodopyridine (2.176 g, 7.94 mmol), 9,9-dimethyl-4,5-bis(diphenylphosphino)xanthene (0.276 g, 0.48 mmol) and cesium carbonate (5.18 g, 15.89 mmol). The resulting suspension was heated at 80° C. for 18 hours and then at 85° C. for a further 24 hours. The mixture was filtered through Celite and then concentrated in vacuo. The residue was diluted with MeOH and then loaded onto an SCX column. The mixture was eluted first with MeOH and then with a 7N solution of NH$_3$ in MeOH. Fractions containing product were combined and then evaporated. The residue was triturated with Et$_2$O to leave 2-[(2,5-dichloropyridin-4-yl)amino]-N-methoxybenzamide (0.823 g, 33% yield); $^1$H NMR spectrum: (300 MHz, DMSO) δ 3.66 (3H, s), 7.02 (1H, s), 7.26 (1H, m), 7.38 (1H, m), 7.56-7.64 (2H, m), 8.27 (1H, s), 9.66 (1H, s), 11.88 (1H, s); Mass spectrum: m/z (ESI+) (M+H)+=311.93 and 313.96 and 315.92.

The 2,5-dichloro-4-iodopyridine, used as starting material, was prepared as follows:

a) A solution of 2,5-dichloropyridine (10 g, 67.57 mmol) in THF (17 mL) was added dropwise to a stirred solution of n-BuLi in isohexane (33.8 mL, 67.57 mmol) and diisopropylamine (9.63 mL, 67.57 mmol) in THF (68.0 mL) cooled to −78° C., over a period of 1 hour under a nitrogen atmosphere. The resulting mixture was stirred at −78° C. for 30 minutes and then a solution of I$_2$ (17.49 g, 68.92 mmol) in THF (17.0 mL) was added dropwise. The resulting solution was stirred at −78° C. for 1 hour and then quenched with water (75 mL) and allowed to warm to room temperature. The mixture was extracted with Et$_2$O (3×100 mL) and the combined organic layers were dried over MgSO$_4$, and then evaporated. The residue was triturated with CH$_2$Cl$_2$ to give a solid which was dried under vacuum to afford 2,5-dichloro-4-iodopyridine (9.72 g, 53% yield). The filtrate was evaporated and the residue purified by chromatography on silica, eluting with a gradient of 50-100% CH$_2$Cl$_2$ in isohexane. Fractions containing product were combined and evaporated and the residue triturated with MeOH to leave a second crop of 2,5-dichloro-4-iodopyridine (5.74 g, 31% yield); $^1$H NMR spectrum: (300 MHz, DMSO) δ 7.85 (1H, s), 8.34 (1H, s).

The 2-amino-N-methoxybenzamide, used as starting material, was prepared as follows:

a) O-Methylhydroxylamine hydrochloride (1.253 g, 15.00 mmol) was added to 1H-3,1-benzoxazine-2,4-dione (isatoic anhydride) (1.631 g, 10 mmol) in THF (50 mL) containing DIPEA (2.79 ml, 16.00 mmol). The resulting solution was stirred at room temperature for 4 hours and then heated to reflux for 17 hours. The mixture was allowed to cool to room temperature, filtered and then evaporated. The residue was dissolved in MeOH (20 mL) and then loaded onto an SCX column. The mixture was eluted first with MeOH and then with a 7N solution of NH$_3$ in MeOH. Fractions containing product were combined and then evaporated to afford 2-amino-N-methoxybenzamide (1.410 g, 85% yield); $^1$H NMR spectrum: (300 MHz, DMSO) δ 3.67 (3H, s), 6.26 (2H, s), 6.48 (1H, m), 6.70 (1H, dd), 7.15 (1H, m), 7.31 (1H, dd), 11.36 (1H, s); Mass spectrum: m/z (ESI+) (M+H)+=167.41.

The following compounds were prepared in an analogous way to example 3.01.

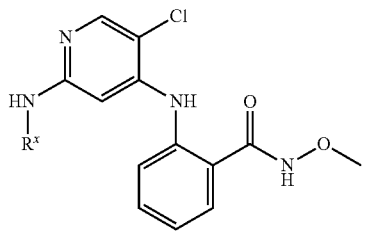

| # | R$^x$ | Name | $^1$H NMR spectrum (300 MHz, DMSO): δ | Mass spectrum m/z (ESI+) (M + H)$^+$ |
|---|---|---|---|---|
| 3.02 | | 2-[[5-chloro-2-[(1,5-dimethylpyrazol-3-yl)amino]-4-pyridyl]amino]-N-methoxy-benzamide | 2.18 (3H, s), 3.56 (3H, s), 3.71 (3H, s), 5.88 (1H, s), 7.09-7.15 (1H, m), 7.58 (2H, t), 7.68-7.70 (2H, m), 7.98 (1H, s), 8.98 (1H, s), 9.60 (1H, s), 11.89 (1H, s) | 387.03 and 389.02 |

Example 3.03

2-[[5-Chloro-2-[[1-(2-oxo-2-pyrrolidin-1-yl-ethyl) pyrazol-4-yl]amino]-4-pyridyl]amino]-N-methyl-benzamide

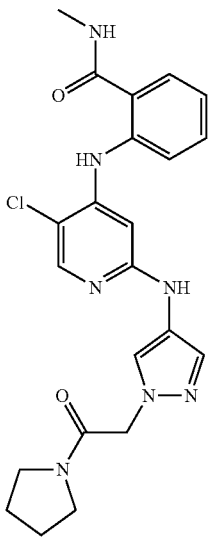 [SMILES: CNC(=O)c1ccccc1Nc1cc(Nc2cnn(CC(=O)N3CCCC3)c2)ncc1Cl]

2-[4-[[5-Chloro-4-[[2-(methylcarbamoyl)phenyl]amino] pyridin-2-yl]amino]pyrazol-1-yl]acetic acid (50 mg, 0.125 mmol) was dissolved in DMA (4 mL). Pyrrolidine (0.083 mL, 1.00 mmol) was added, followed by dropwise addition of a solution of HATU (57 mg, 0.150 mmol) in DMA (1 mL). The mixture was stirred at 22° C. for 16 hours. The mixture was evaporated and the residue was partitioned between CH$_2$Cl$_2$ (10 mL) and water (10 mL). The aqueous layer was separated and then extracted with CH$_2$Cl$_2$ (10 mL). The combined organics were evaporated and the residue purified by chromatography on silica, eluting with a mixture of 2-4% MeOH (containing 10% aqueous NH$_3$) in CH$_2$Cl$_2$. Fractions containing product were combined and evaporated to afford example 3.03 (12 mg, 21% yield); $^1$H NMR spectrum: (400 MHz, DMSO) δ 1.79 (2H, m), 1.91 (2H, m), 2.79 (3H, d), 3.31 (2H, t), 3.46 (2H, t), 4.94 (2H, s), 6.69 (1H, s), 7.11 (1H, dd), 7.36 (1H, s), 7.52 (1H, dd), 7.59 (1H, d), 7.71 (1H, d), 7.86 (1H, s), 8.00 (1H, s), 8.65 (1H, q), 8.70 (1H, s), 10.06 (1H, s); Mass spectrum: m/z (ESI+) (M+H)+=454.4 and 456.3.

The 2-[4-[[5-chloro-4-[[2-(methylcarbamoyl)phenyl] amino]pyridin-2-yl]amino]pyrazol-1-yl]acetic acid, used as starting material, was prepared as follows:

a) Sodium tert-butoxide (876 mg, 9.12 mmol) was added to a suspension of 2-(4-aminopyrazol-1-yl)acetic acid dihydrochloride (542 mg, 2.53 mmol) in 1,4-dioxane (15 mL). 2-[(2, 5-Dichloropyridin-4-yl)amino]-N-methylbenzamide (300 mg, 1.01 mmol) and 9,9-dimethyl-4,5-bis(diphenylphosphino)xanthene (94 mg, 0.16 mmol) were added and the resulting suspension was purged with nitrogen. Tris(dibenzylideneacetone)dipalladium(0) (74.2 mg, 0.08 mmol) was added and the mixture was again purged with nitrogen. The mixture was heated at 150° C. for 60 minutes in a microwave reactor and then allowed to cool to room temperature. The mixture was evaporated and the residue partitioned between CH$_2$Cl$_2$ (60 mL) and a 0.1N solution of NaOH (60 mL). The aqueous layer was separated, washed with CH$_2$Cl$_2$ (30 mL) and then adjusted to pH4 by the addition of a 2N solution of HCl. The mixture was filtered and the filtrate evaporated. The residue was triturated with a 1:1 mixture of CH$_2$Cl$_2$/MeOH (150 mL), filtered and the solid washed with a 1:1 mixture of CH$_2$Cl$_2$/MeOH (3×150 mL). The combined filtrates were evaporated to afford 2-[4-[[5-chloro-4-[[2-(methylcarbamoyl)phenyl]amino]pyridin-2-yl]amino]pyrazol-1-yl]acetic acid (300 mg, 74% yield) which was used in the next step without further purification; $^1$H NMR spectrum: (300 MHz, DMSO) δ 2.78 (3H, d), 4.41 (2H, s), 6.68 (1H, s), 7.10 (1H, dd), 7.28 (1H, s), 7.51 (1H, dd), 7.57 (1H, d), 7.73 (1H, d), 7.77 (1H, s), 7.98 (1H, s), 8.66 (1H, s), 8.75 (1H, q), 10.04 (1H, s); Mass spectrum: m/z (ESI+) (M+H)+=401.3 and 403.3.

The 2-[(2,5-dichloropyridin-4-yl)amino]-N-methylbenzamide, used as starting material, was prepared as follows:

a) Palladium(II) acetate (0.393 g, 1.75 mmol) was added to 2,5-dichloro-4-iodopyridine (12 g, 43.81 mmol), 2-amino-N-methylbenzamide (6.58 g, 43.81 mmol), cesium carbonate (28.6 g, 87.63 mmol) and 9,9-dimethyl-4,5-bis(diphenylphosphino)xanthene (1.521 g, 2.63 mmol) in dioxane (600 mL) under an atmosphere of nitrogen. The resulting suspension was heated at 80° C. for 18 hours, allowed to cool to room temperature and then filtered. The filtrate was evaporated and the residue triturated with CH$_2$Cl$_2$ to leave 2-[(2,5-dichloropyridin-4-yl)amino]-N-methylbenzamide (6.306 g, 48% yield). The CH$_2$Cl$_2$ solution was evaporated and the residue triturated with CH$_2$Cl$_2$ to leave a second crop of 2-[(2,5-dichloropyridin-4-yl)amino]-N-methylbenzamide (1.87 g, 14% yield); $^1$H NMR spectrum: (300 MHz, DMSO) δ 2.78 (2H, d), 7.19-7.21 (2H, m), 7.54-7.60 (2H, m), 7.73 (1H, d), 8.28 (1H, s), 8.70 (1H, d), 10.41 (1H, s); Mass spectrum: m/z (ESI+) (M+H)+=296.0 and 298.0 and 300.0.

The following compounds were prepared in an analogous way to example 3.03.

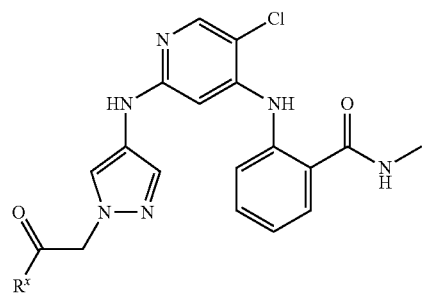

| # | R$^x$ | Name | $^1$H NMR spectrum (300 MHz, DMSO): δ | Mass spectrum m/z (ESI+) (M + H)$^+$ |
|---|---|---|---|---|
| 3.04 | 4-methyl-1,4-diazepan-1-yl | 2-[[5-chloro-2-[[1-[2-(4-methyl-1,4-diazepan-1-yl)-2-oxo-ethyl]pyrazol-4-yl]amino]-4-pyridyl]amino]-N-methyl-benzamide | | 497.4 and 499.3 |
| 3.05 | piperazin-1-yl | 2-[[5-chloro-2-[[1-(2-morpholino-2-oxo-ethyl)prazol-4-yl]amino]-4-pyridyl]amino]-N-methyl-benzamide | | 470.4 and 472.3 |
| 3.06 | (2-methoxyethyl)(methyl)amino | 2-[[5-chloro-2-[[1-[2-(2-methoxyethyl-methyl-amino)-2-oxo-ethyl]pyrazol-4-yl]amino]-4-pyridyl]amino]-N-methyl-benzamide | 2.79 (3H, d), 3.33 (3H, s), 3.44-3.55 (4H, m), 5.04 (2H, m), 6.69 (1H, s), 7.11 (1H, dd), 7.35 (1H, d), 7.52 (1H, ddd), 7.59 (1H, dd), 7.71 (1H, dd), 7.83 (1H, d), 8.00 (1H, s), 8.65 (1H, q), 8.70 (1H, s), 10.06 (1H, s). | 472.4 and 474.3 |
| 3.07 | 4-methylpiperazin-1-yl | 2-[[5-chloro-2-[[1-[2-(4-methylpiperazin-1-yl)-2-oxo-ethyl]pyrazol-4-yl]amino]-4-pyridyl]amino]-N-methyl-benzamide | 2.23 (3H, br. s), 2.34 (3H, br. m), 2.79 (3H, d), 3.48 (4H, br. m), 5.05 (2H, s), 6.69 (1H, s), 7.11 (1H, ddd), 7.36 (1H, d), 7.52 (2H, ddd), 7.59 (1H, d), 7.71 (1H, dd), 7.85 (1H, s), 8.00 (1H, s), 8.65 (1H, q), 8.70 (1H, s), 10.07 (1H, s). | 483.4 and 485.3 |

Example 3.08

2-[[5-Chloro-2-[(5-methoxy-2-methylpyrazol-3-yl)amino]pyridin-4-yl]amino]-N-methylbenzamide

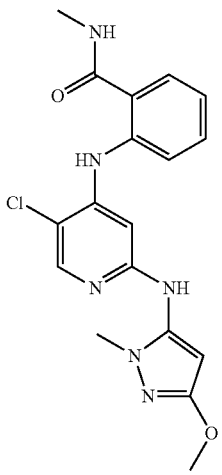 [SMILES: CNC(=O)c1ccccc1Nc1cc(Nc2cc(OC)nn2C)ncc1Cl]

2-[(2,5-Dichloropyridin-4-yl)amino]-N-methylbenzamide (92 mg, 0.31 mmol) and 9,9-dimethyl-4,5-bis(diphenylphosphino)xanthene (36 mg, 0.062 mmol), 5-methoxy-2-methylpyrazol-3-amine (51 mg, 0.40 mmol) and sodium tert-butoxide (45 mg, 0.466 mmol) was added to anhydrous 1,4-dioxane (3 mL). The mixture was purged with nitrogen and then bis(dibenzylideneacetone)palladium (28 mg, 0.049 mmol) was added. The mixture was heated at 150° C. in a microwave reactor for 30 minutes. The mixture was allowed to cool to room temperature and then a solution of 2M HCl in MeOH (0.30 mL) was added. The mixture was loaded onto an SCX column. The mixture was eluted first with MeOH and then with 0.7M solution of $NH_3$ in MeOH. Fractions containing product were combined and then evaporated. The residue was purified by preparative HPLC and fractions containing product were combined and evaporated to afford example 3.08 (28 mg, 23% yield); $^1$H NMR spectrum: (300 MHz, DMSO) δ 2.78 (3H, d), 3.48 (3H, s), 3.71 (3H, s), 5.67 (1H, s), 6.80 (1H, s), 7.12 (1H, m), 7.49 (1H, d), 7.55 (1H, t), 7.71 (1H, d), 8.01 (1H, s), 8.62-8.70 (2H, m), 10.09 (1H, s); Mass spectrum: m/z (ESI+) (M+H)+=387.51 and 389.54.

The following compounds were prepared in an analogous way to example 3.08.

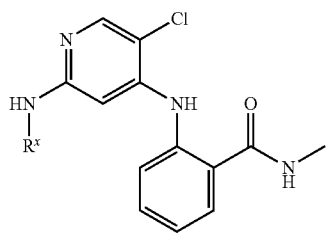

| # | R$^x$ | Name | $^1$H NMR spectrum (300 MHz, DMSO): δ | Mass spectrum m/z (ESI+) (M + H)$^+$ |
|---|---|---|---|---|
| 3.09 | | 2-[[5-chloro-2-[(2,5-dimethylpyrazol-3-yl)amino]-4-pyridyl]amino]-N-methyl-benzamide | 2.07 (3H, s), 2.75-2.78 (3H, d), 3.54 (3H, s), 5.98(1H, d), 6.77 (1H, d), 7.09-7.15 (1H, m), 7.48-7.53 (2H, m), 7.69-7.71 (1H, m), 7.99 (1H, s), 8.58 (1H, s), 8.65 (1H, d), 10.09 (1H, s) | 370.99 and 372.98 |
| 3.10 | | 2-[[5-chloro-2-[(1,5-dimethylpyrazol-3-yl)amino]-4-pyridyl]amino]-N-methyl-benzamide | 2.18 (3H, s), 2.78 (3H, d), 3.57 (3H, s), 5.88 (1H, s), 7.10 (1H, t), 7.53 (1H, m), 7.65-7.73 (3H, m), 7.97 (1H, s), 8.65 (1H, m), 8.96 (1H, s), 10.19 (1H, s) | 371.48 and 373.51 |
| 3.11 | | 2-[[5-chloro-2-[(1-methylpyrazol-4-yl)amino]-4-pyridyl]amino]-N-methyl-benzamide | 2.77 (3H, d), 3.77 (3H, s), 6.65 (1H, s), 7.10 (1H, t), 7.32 (1H, s), 7.50 (1H, t), 7.57 (1H, d), 7.68-7.71 (1H, m), 7.82 (1H, s), 7.98 (1H, s), 8.63 (2H, s), 10.04 (1H, s) | 357.07 and 359.03 |

-continued

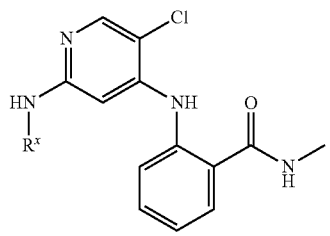

| # | R$^x$ | Name | $^1$H NMR spectrum (300 MHz, DMSO): δ | Mass spectrum m/z (ESI+) (M + H)$^+$ |
|---|---|---|---|---|
| 3.12 | | 2-[[5-chloro-2-[[1-(1-methyl-4-piperidyl)pyrazol-4-yl]amino]-4-pyridyl]amino]-N-methyl-benzamide | 1.82-1.88 (1H, m), 1.90-1.94 (4H, m), 1.98-2.06 (2H, m), 2.19 (3H, s), 2.73-2.81 (1H, m), 2.77 (3H, d), 2.85 (1H, s), 3.17 (1H, s), 4.02-4.07 (1H, m), 6.64 (1H, s), 7.07-7.12 (1H, m), 7.35-7.35 (1H, m), 7.46-7.50 (1H, m), 7.54-7.56 (1H, m), 7.68-7.71 (1H, m), 7.87 (1H, s), 7.98 (1H, s), 8.59 (1H, s), 8.63 (1H, t), 10.03 (1H, s) | 440.06 |
| 3.13$^a$ | | 2-[(2-[[1-(1-acetyl-4-piperidyl)pyrazol-4-yl]amino]-5-chloro-4-pyridyl]amino]-N-methyl-benzamide | 1.67-1.71 (1H, m), 1.84-1.88 (1H, m), 1.98 (1H, m), 1.98 (1H, m), 2.05 (3H, s), 2.79 (3H, d), 3.91 (2H, m), 4.33-4.39 (1H, m), 4.46 (2H, m), 6.66 (1H, s), 7.11 (1H, t), 7.38 (1H, s), 7.48-7.52 (1H, m), 7.58 (1H, d), 7.70-7.72 (1H, m), 7.91 (1H, s), 7.99 (1H, s), 8.64 (1H, d), 8.65 (1H, s), 10.05 (1H, s) | 468.55 and 470.54 |
| 3.14 | | 2-[[5-chloro-2-[(1,3-dimethylpyrazol-4-yl)amino]-4-pyridyl]amino]-N-methyl-benzamide | 2.06 (3H, s), 2.77 (3H, d), 3.69 (3H, s), 6.71 (1H, s), 7.06-7.11 (1H, m), 7.46-7.56 (2H, m), 7.68-7.70 (2H, m), 7.80 (1H, s), 7.94 (1H, s), 7.98 (1H, s), 8.63 (1H, q), 10.02 (1H, s) | 371.06 and 373.03 |
| 3.15$^b$ | | 2-[[5-chloro-2-[(1-tetrahydropyran-4-ylpyrazol-4-yl)amino]-4-pyridyl]amino]-N-methyl-benzamide | 1.89-1.93 (2H, m), 1.94-1.95 (2H, m), 2.79 (3H, d), 3.46-3.49 (2H, m), 3.95-3.97 (2H, m), 4.33 (1H, s), 6.66 (1H, s), 7.11 (1H, t), 7.38 (1H, s), 7.51 (1H, d), 7.58 (1H, d), 7.70-7.72 (1H, m), 7.91 (1H, s), 8.00 (1H, s), 8.63 (1H, d), 8.65 (1H, s), 10.05 (1H, s) | 427.50 and 429.50 |

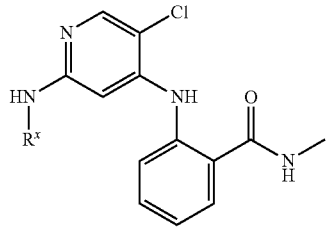

| # | R$^x$ | Name | $^1$H NMR spectrum (300 MHz, DMSO): δ | Mass spectrum m/z (ESI+) (M + H)$^+$ |
|---|---|---|---|---|
| 3.16 | | 2-[[5-Chloro-2-[(5-methyl-1H-pyrazol-3-yl)amino]pyridin-4-yl]amino]-N-methylbenzamide | 2.16 (3H, s), 2.79 (2H, d), 5.95 (1H, s), 7.10 (1H, t), 7.50 (1H, t), 7.58 (1H, s), 7.62, (2H, d), 7.71 (1H, d), 7.99 (1H, s), 8.64 (1H, t), 8.93 (1H, s), 10.15 (1H, s), 11.66 (1H, s) | 357.00 and 358.96 |
| 3.17 | | 2-[[5-chloro-2-[(5-cyclopropyl-1H-pyrazol-3-yl)amino]-4-pyridyl]amino]-N-methyl-benzamide | 0.61-0.66 (2H, m), 0.86-0.90 (2H, m), 1.78-1.86 (1H, m), 2.79 (3H, d), 5.83 (1H, s), 7.09 (1H, t), 7.46-7.54 (2H, m), 7.59-7.62 (1H, m), 7.68-7.71 (1H, m), 7.98 (1H, s), 8.64 (1H, d), 8.91 (1H, s), 10.14 (1H, s) | |
| 3.18 | | 2-[[5-chloro-2-[(1-methylimidazol-4-yl)amino]-4-pyridyl]amino]-N-methyl-benzamide | (400 MHz, DMSO) δ 2.79-2.80 (3H, m), 3.61 (3H, s), 7.00 (1H, s), 7.05-7.09 (1H, m), 7.10-7.11 (1H, m), 7.27-7.29 (1H, m), 7.45-7.49 (1H, m), 7.54-7.57 (1H, m), 7.66-7.69 (1H, m), 7.98 (1H, s), 8.61-8.65 (1H, m), 8.93 (1H, s), 10.11 (1H, s) | 357.34 and 359.36 |

$^a$The 1-[4-(4-aminopyrazol-1-yl)piperidin-1-yl)piperidin-1-yl]ethanone, used as starting material, was prepared as follows:

a) DIAD (3.40 mL, 17.25 mmol) was added dropwise to a stirred solution of 4-nitro-1H-pyrazole (1,3 g, 11.50 mmol), 1-(4-hydroxypiperidin-1-yl)ethanone (1.975 g, 13.80 mmol) and triphenylphosphine (3.77 mL, 17.25 mmol) in THF (25 mL) cooled to 0° C. under a nitrogen atmosphere. The resulting solution was stirred at 0° C. for 10 minutes and then allowed to warm to room temperature and stirred overnight. The mixture was diluted with CH$_2$Cl$_2$ (100 mL) and then washed with 2M HCl (100 mL). The aqueous layer was separated, basified with 2M NaOH and then extracted with CH$_2$Cl$_2$ (3x 100 mL). The combined organic layers were dried over MgSO$_4$ and then evaporated. The residue was purified by chromatography on silica, eluting with a gradient of 0-5% MeOH in CH$_2$Cl$_2$. Fractions containing product were combined and evaporated to afford 1-[4-(4-nitropyrazol-1-yl)piperidin-1-yl]ethanone (1.320 g, 48% yield); $^1$H NMR spectrum: (300 MHz, DMSO) δ 1.74-1.84 (1H, m), 1.89-1.95 (1H, m), 1.99-2.07 (3H, m), 2.12-2.15 (1H, m), 2.66-2.75 (1H, m), 3.15-3.24 (1H, m), 3.47-3.53 (1H, m), 3.87-3.95 (2H, m), 4.48-4.59 (2H, m), 8.28 (1H, s), 8.94 (1H, s); Mass spectrum: m/z (ESI+) (M + H)+ = 239.01.

b) A mixture of 1-[4-(4-nitropyrazol-1-yl)piperidin-1-yl]ethanone (1.32 g, 5.54 mmol), and 10% palladium on carbon (0.147 g, 0.139 mmol) in EtOH (100 mL) was stirred under an atmosphere of hydrogen for 18 hours. The mixture was filtered through Celite and the filtrate added directly to an SCX column. The desired product was eluted using a 7M solution of NH$_3$ in MeOH. Fractions containing were combined and evaporated to afford 1-[4-(4-aminopyrazol-1-yl)piperidin-1-yl]ethanone (0.724 g, 63% yield); $^1$H NMR spectrum: (300 MHz, DMSO) δ 1.46-1.91 (3, m), 2.02 (3H, s), 2.63-2.72 (1H, m), 3.11-3.18 (1H, m), 3.34-3.41 (1H, m), 3.77 (2H, s), 3.87 (1H, d), 4.14-4.24 (1H, m), 4.40 (1H, d), 6.91 (1H, s), 7.06 (1H, s); Mass spectrum: m/z (ESI+) (M + H)+ = 209.06.

$^b$The 1-tetrahydropyran-4-ylpyrazol-4-amine, used as starting material, was prepared as follows:

a) A solution of DIAD (2.95 mL, 15.00 mmol) in THF (5 mL) was added to a stirred solution of tetrahydro-2H-pyran-4-ol (1.226 g, 12.00 mmol), triphenylphosphine (3.93 g, 15.00 mmol) and 4-nitro-1H-pyrazole (1.131 g, 10 mmol) in THF (15 mL) cooled to 0° C., over a period of 60 minutes under an atmosphere of nitrogen. The resulting solution was stirred at 0° C. for 1 hour and then allowed to warm to room temperature and stirred overnight. The mixture was concentrated in vacuo and then a mixture of 20% EtOAc in isohexane (40 mL) was added to the residue with rapid stirring. The mixture was stirred for 20 minutes and then filtered. The filtrate was evaporated and the residue purified by chromatography on silica, eluting with a gradient of 30-55% EtOAc in isohexane. Fractions containing product were combined and evaporated. The residue was dissolved in EtOAc (100 mL) and washed sequentially with a solution of NaOH (2 x 75 mL), water (2 x 50 mL), and finally with a saturated solution of NaCl (2 x 50 mL). The organic layer was dried over MgSO$_4$ and then evaporated to leave 4-nitro-1-(tetrahydro-2H-pyran-4-yl)-1H-pyrazole (1.77 g, 90% yield) which was used in the next step without further purification; Mass spectrum: m/z (ESI−) (M − H)− = 196.41.

b) A mixture of 10% palladium on carbon (177 mg, 0.17 mmol) and 4-nitro-1-(tetrahydro-2H-pyran-4-yl)-1H-pyrazole (1.77 g, 8.98 mmol) in EtOH (50 mL) was stirred at room temperature under an atmosphere of hydrogen for 20 hours. The mixture was filtered through Celite and then evaporated. The residue was loaded onto an SCX column and the product eluted first with MeOH and then with a solution of 0.7M NH$_3$ in MeOH. Fractions containing product were combined and evaporated to afford 1-tetrahydropyran-4-ylpyrazol-4-amine (1.123 g, 75% yield); $^1$H NMR spectrum: (300 MHz, DMSO) δ 1.97 (4H, m), 3.44 (2H, m), 4.01 (2H, dt), 4.15 (1H, dquintet), 6.99 (1H, s), 7.10 (1H, s); Mass spectrum: m/z (ESI+) (M + H)+ = 168.39.

Example 3.19

2-[[5-Chloro-2-[[1-(4-piperidyl)pyrazol-4-yl]amino]-4-pyridyl]amino]-N-methyl-benzamide

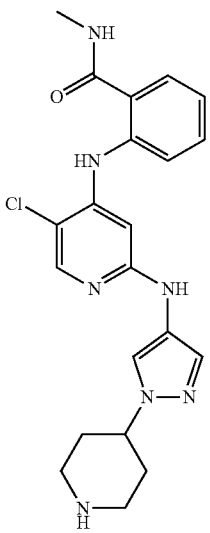 [SMILES: CNC(=O)c1ccccc1Nc1cc(Nc2cnn(C3CCNCC3)c2)ncc1Cl]

A mixture of 2-[(2,5-dichloropyridin-4-yl)amino]-N-methylbenzamide (100 mg, 0.34 mmol), tert-butyl 4-(4-aminopyrazol-1-yl)piperidine-1-carboxylate (90 mg, 0.34 mmol), palladium(II) acetate (3.03 mg, 0.01 mmol), cesium carbonate (220 mg, 0.68 mmol) and 9,9-dimethyl-4,5-bis(diphenylphosphino)xanthene (11.72 mg, 0.02 mmol) was suspended in DMA (2 mL). The mixture was heated at 150° C. for 3 hours in a microwave reactor and then allowed to cool to room temperature. The mixture was loaded onto an SCX column and eluted first with MeOH and then with a 7M solution of $NH_3$ in MeOH. Fractions containing product were combined and then evaporated. The residue was stirred in a 1.0M solution of HCl in $Et_2O$ at room temperature overnight. The mixture was evaporated and the residue purified by preparative HPLC. Fractions containing product were combined and evaporated to afford example 3.19 (9 mg, 6% yield); $^1$H NMR spectrum: (300 MHz, DMSO) δ 2.16-2.24 (4H, m), 2.78 (3H, d), 3.03-3.08 (2H, m), 3.37-3.42 (2H, m), 4.39-4.47 (1H, m), 6.63 (1H, s), 6.95 (1H, t), 7.42 (1H, s), 7.45-7.52 (2H, m), 7.72 (1H, d), 7.85 (1H, s), 7.98 (1H, s), 8.20-8.32 (2H, m), 10.03 (1H, s); Mass spectrum: m/z (ESI+) (M+H)+= 426.0 and 428.0.

The tert-butyl 4-(4-aminopyrazol-1-yl)piperidine-1-carboxylate, used as starting material, was prepared as follows:
a) DIAD (3.92 mL, 19.90 mmol) was added dropwise to a stirred solution of 4-nitro-1H-pyrazole (1.5 g, 13.27 mmol), tert-butyl 4-hydroxypiperidine-1-carboxylate (2.67 g, 13.27 mmol) and triphenylphosphine (5.22 g, 19.90 mmol) in THF (30 mL) cooled to 0° C. under a nitrogen atmosphere. The resulting solution was stirred at 0° C. for 10 minutes then allowed to warm to room temperature and stirred overnight. The mixture was diluted with isohexane (80 mL) and EtOAc (20 mL) and then stirred vigorously. The mixture was filtered and the solid washed with isohexane (20 mL). The combined filtrates were evaporated and the residue was purified by chromatography on silica, eluting with a gradient of 20-50% EtOAc in isohexane. Fractions containing product were combined and evaporated to afford tert-butyl 4-(4-nitropyrazol-1-yl)piperidine-1-carboxylate (3.63 g, 92% yield); $^1$H NMR spectrum: (300 MHz, DMSO) 1.42 (9H, s), 1.79-1.84 (2H, m), 2.01-2.05 (2H, m), 2.87-2.98 (2H, m), 4.40-4.47 (1H, m), 8.28 (1H, s), 8.95 (1H, s).

b) A mixture of tert-butyl 4-(4-nitropyrazol-1-yl)piperidine-1-carboxylate (3.63 g, 12.25 mmol) and 10% palladium on carbon (0.326 g, 0.31 mmol) in EtOH (200 mL) were stirred under an atmosphere of hydrogen for 18 hours. The mixture was filtered through Celite and the filtrate loaded onto an SCX column. The mixture was eluted first with MeOH and then with a 7M solution of $NH_3$ in MeOH. Fractions containing product were combined and evaporated to afford tert-butyl 4-(4-aminopyrazol-1-yl)piperidine-1-carboxylate (2.100 g, 64% yield); $^1$H NMR spectrum: (300 MHz, DMSO) δ 1.41 (9H, s), 1.65-1.74 (2H, m), 1.89-1.92 (2H, m), 2.81-2.93 (2H, m), 3.75 (2H, s), 3.99 (2H, d), 4.09-4.16 (1H, m), 6.91 (1H, s), 7.06 (1H, s); Mass spectrum: m/z (ESI+) (M+H)+=211.0.

Example 3.20

2-[[5-Chloro-2-[[1-(1-methyl-4-piperidyl)pyrazol-4-yl]amino]-4-pyridyl]amino]-N-methoxy-N-methyl-benzamide

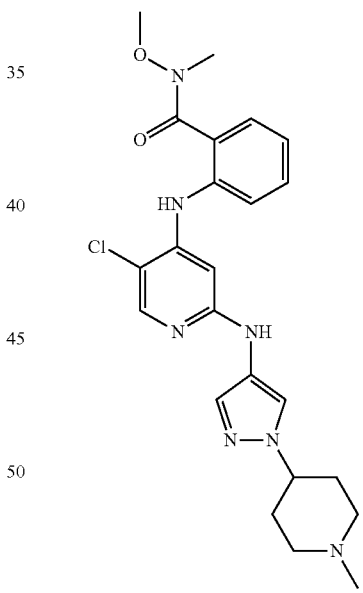

2-[(2,5-Dichloropyridin-4-yl)amino]-N-methoxy-N-methylbenzamide (0.1 g, 0.31 mmol), 1-(1-methylpiperidin-4-yl)pyrazol-4-amine (0.083 g, 0.46 mmol), 9,9-dimethyl-4,5-bis(diphenylphosphino)xanthene (10.64 mg, 0.02 mmol), cesium carbonate (0.200 g, 0.61 mmol) and palladium(II) acetate (2.75 mg, 0.01 mmol) were suspended in DMA (2 mL). The mixture was heated at 150° C. for 2 hours in a microwave reactor. A further portion of 9,9-dimethyl-4,5-bis(diphenylphosphino)xanthene (10.64 mg, 0.02 mmol) and palladium(II) acetate (2.75 mg, 0.01 mmol) were added and the mixture was heated at 150° C. for 1 hour in the microwave reactor. The mixture was allowed to cool to room temperature and then loaded onto an SCX column. The product was eluted first with MeOH and then with a solution of 7M NH₃ in MeOH. Fractions containing product were combined and evaporated. The residue was purified by preparative HPLC and fractions containing product were combined and evaporated to afford example 3.20 (21 mg, 14% yield); ¹H NMR spectrum: (300 MHz, DMSO) δ 1.82-2.05 (6H, m), 2.17 (3H, s), 2.80-2.88 (2H, m), 3.23 (3H, s), 3.48 (3H, s), 3.94-4.02 (1H, m), 6.26 (1H, d), 7.21-7.27 (1H, m), 7.32 (1H, s), 7.46-7.53 (3H, m), 7.81-7.85 (2H, m), 7.93 (1H, s), 8.51 (1H, s); Mass spectrum: m/z (ESI+) (M+H)+=470.08 and 472.02.

The 2-[(2,5-dichloropyridin-4-yl)amino]-N-methoxy-N-methylbenzamide, used as starting material, was prepared as follows:

a) Palladium(II) acetate (0.066 g, 0.29 mmol) was added to 2,5-dichloro-4-iodopyridine (2 g, 7.30 mmol), 2-amino-N-methoxy-N-methylbenzamide (1.316 g, 7.30 mmol), cesium carbonate (4.76 g, 14.60 mmol) and 9,9-dimethyl-4,5-bis(diphenylphosphino)xanthene (0.254 g, 0.44 mmol) in dioxane (100 mL) under an atmosphere of nitrogen. The resulting suspension was heated at 80° C. for 18 hours and then allowed to cool to room temperature. The mixture was filtered and the filtrate evaporated. The residue was purified by chromatography on silica, eluting with a gradient of 0-5% MeOH in CH₂Cl₂. Fractions containing product were combined and evaporated to afford 2-[(2,5-dichloropyridin-4-yl)amino]-N-methoxy-N-methylbenzamide (0.775 g, 33% yield); ¹H NMR spectrum: (300 MHz, DMSO) δ 3.18 (3H, s), 3.48 (3H, s), 6.61 (1H, d), 7.34-7.40 (1H, m), 7.45-7.47 (1H, m), 7.54-7.57 (2H, m), 8.19 (1H, s), 8.47 (1H, s); Mass spectrum: m/z (ESI+) (M+H)+=326.0 and 328.0 and 330.0.

The following compounds were prepared in an analogous way to example 3.20.

Example 3.22

6-[[5-Chloro-2-[(1,3-dimethylpyrazol-4-yl)amino]-4-pyridyl]amino]-4-methyl-2,3-dihydro-1,4-benzoxazepin-5-one

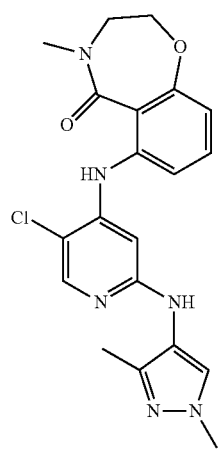 [SMILES: Cc1nn(C)cc1Nc1cc(Nc2cccc3c2C(=O)N(C)CCO3)c(Cl)cn1]

6-[(2,5-Dichloropyridin-4-yl)amino]-4-methyl-2,3-dihydro-1,4-benzoxazepin-5-one (118 mg, 0.35 mmol), 1,3-dimethylpyrazol-4-amine (58.2 mg, 0.52 mmol), 9,9-dimethyl-4,5-bis(diphenylphosphino)xanthene (40.4 mg, 0.07 mmol) and sodium tert-butoxide (50.3 mg, 0.52 mmol) were suspended in dioxane (5 mL). The mixture was degassed with nitrogen and then bis(dibenzylideneacetone)palladium (32.0 mg, 0.056 mmol) was added. The mixture was heated at 150° C. for 30 minutes in a microwave reactor and then allowed to cool to room temperature. The mixture was loaded onto an

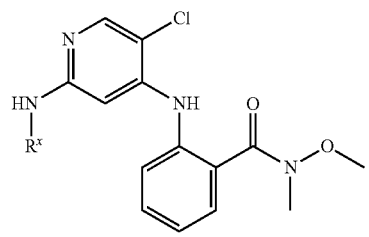

| # | Rˣ | Name | ¹H NMR spectrum (300 MHz, DMSO): δ | Mass spectrum m/z (ESI+) (M + H)⁺ |
|---|---|---|---|---|
| 3.21 | | 2-[[5-chloro-2-[(1,3-dimethylpyrazol-4-yl)amino]-4-pyridyl]amino]-N-methoxy-N-methyl-benzamide | | 401.08 and 403.04 |

SCX column and the product was eluted first with MeOH and then using a 7M solution of NH₃ in MeOH. Fractions containing product were combined and evaporated. The residue was purified by preparative HPLC. Fractions containing product were combined and evaporated to afford example 3.22 (39.0 mg, 27% yield); ¹H NMR spectrum: (300 MHz, DMSO) δ 2.06 (3H, s), 3.12 (3H, s), 3.50 (2H, t), 3.69 (3H, s), 4.32 (2H, t), 6.66 (1H, s), 6.77-6.80 (1H, m), 7.32-7.34 (1H, m), 7.46 (1H, t), 7.80 (1H, s), 7.93 (1H, s), 7.98 (1H, s), 9.00 (1H, s); Mass spectrum: m/z (ESI+) (M+H)+=413.05 and 415.02.

The 6-[(2,5-dichloropyridin-4-yl)amino]-4-methyl-2,3-dihydro-1,4-benzoxazepin-5-one, used as starting material, was prepared as follows:

a) 2,5-Dichloro-4-iodopyridine (0.2 g, 0.73 mmol), 6-amino-4-methyl-2,3-dihydro-1,4-benzoxazepin-5-one (0.140 g, 0.73 mmol), palladium(II) acetate (6.56 mg, 0.03 mmol), 9,9-dimethyl-4,5-bis(diphenylphosphino)xanthene (0.025 g, 0.04 mmol) and cesium carbonate (0.476 g, 1.46 mmol) were suspended in dioxane (5 mL). The mixture was heated at 100° C. for 30 minutes in a microwave reactor and then allowed to cool to room temperature. The mixture was loaded onto an SCX column and the product eluted first with MeOH and then with a 7M solution of NH₃ in MeOH. Fractions containing product were combined and evaporated. The residue was purified by chromatography on silica, eluting with a gradient of 0-5% MeOH in CH₂Cl₂. Fractions containing product were combined and evaporated to afford 6-[(2,5-dichloropyridin-4-yl)amino]-4-methyl-2,3-dihydro-1,4-benzoxazepin-5-one (0.118 g, 48% yield); ¹H NMR spectrum: (300 MHz, DMSO) δ 3.10 (3H, s), 3.55 (2H, t), 4.34 (2H, t), 6.88-6.91 (1H, m), 7.13 (1H, s), 7.36-7.39 (1H, m), 7.50 (1H, t), 8.26 (1H, s), 9.31 (1H, s); Mass spectrum: m/z (ESI+) (M+H)+ = 337.96 and 339.99 and 341.96.

The 6-amino-4-methyl-2,3-dihydro-1,4-benzoxazepin-5-one, used as starting material, was prepared as follows:

a) Sodium hydride (8.81 g, 220.38 mmol) was added portionwise to 2-(methylamino)ethanol (16.55 g, 220.38 mmol) in THF (500 mL) at 0° C. over a period of 10 minutes under an atmosphere of argon. The resulting solution was stirred at 0° C. for 1 hour and then 2-amino-6-fluorobenzonitrile (20 g, 146.92 mmol) was added in one portion and the mixture heated at 85° C. for 2 hours. The mixture was quenched with water and then evaporated. The residue was dissolved in EtOAc (300 mL), and the mixture washed sequentially with water (2×300 mL), and then with a saturated solution of NaCl (300 mL). The organic layer was dried over MgSO₄, and then evaporated. The residue was purified by chromatography on silica, eluting with a gradient of 0-10%, of a 7M solution of NH₃ in MeOH, in CH₂Cl₂. Fractions containing product were evaporated to afford 2-amino-6-(2-methylaminoethoxy)benzonitrile (12.08 g, 43% yield); Mass spectrum: m/z (ESI+) (M+H)+=192.43.

b) Potassium hydroxide (32 g, 570.35 mmol) was added in one portion to 2-amino-6-(2-methylaminoethoxy)benzonitrile (16 g, 83.67 mmol) in ethanol (160 mL). The resulting mixture was heated at 90° C. for 2 days. The mixture was then diluted with water (1000 mL) and acidified to ~pH1 with 2M HCl. The mixture was loaded onto an SCX column and the product was eluted first using MeOH and then with a 7M solution of NH₃ in MeOH. Fractions containing product were combined and evaporated to afford 2-amino-6-(2-methylaminoethoxy)benzoic acid which was used without further purification.

c) HATU (35.0 g, 92.04 mmol) was added in one portion to 2-amino-6-(2-methylaminoethoxy)benzoic acid (17.59 g, 83.67 mmol) and DIPEA (15.92 mL, 92.04 mmol) in DMF (200 mL) and the resulting solution was stirred for 1 hour. The mixture was evaporated and the residue dissolved in EtOAc (500 mL). The mixture was washed sequentially with a saturated solution of Na₂CO₃ (500 mL), water (500 mL), and finally with a saturated solution of NaCl (500 mL). The organic layer was dried over MgSO₄, and then evaporated. The residue was purified by chromatography on silica, eluting with a gradient of 0-100% EtOAc in isohexane. Fractions containing product were combined and evaporated to afford 6-amino-4-methyl-2,3-dihydro-1,4-benzoxazepin-5-one (1.635 g, 10% yield); ¹H NMR spectrum: (300 MHz, DMSO) δ 3.09 (s, 3H), 3.44 (t, 2H), 4.20 (t, 2H), 5.74 (br s, 2H), 6.22 (dd, 1H), 6.52 (dd, 1H), 7.08 (appt t, 1H); Mass spectrum: m/z (ESI+) (M+H)+=193.41.

Example 3.23

8-[[5-Chloro-2-[[1-(2-oxo-2-pyrrolidin-1-yl-ethyl)pyrazol-4-yl]amino]-4-pyridyl]amino]-2-methyl-3,4-dihydroisoquinolin-1-one

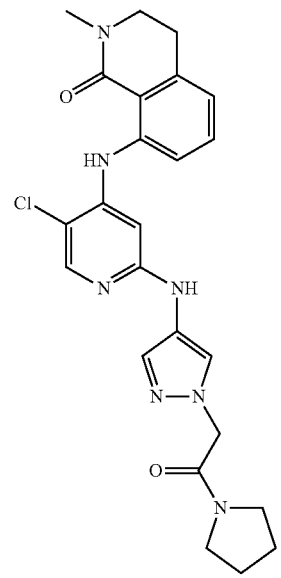 [SMILES: CN1CCc2cccc(Nc3cc(Nc4cnn(CC(=O)N5CCCC5)c4)ncc3Cl)c2C1=O]

A mixture of 2-[4-[[5-chloro-4-[(2-methyl-1-oxo-3,4-dihydroisoquinolin-8-yl)amino]pyridin-2-yl]amino]pyrazol-1-yl]acetic acid (60 mg, 0.141 mmol) was suspended in DMA (4 mL). Pyrrolidine (71 µl, 0.843 mmol) was added, followed by the dropwise addition of a solution of HATU (64 mg, 0.169 mmol) in DMA (1 mL). The mixture was stirred at 22° C. for 16 hours and then evaporated. The residue was partitioned between CH₂Cl₂ (10 mL) and water (10 mL). The aqueous layer was separated and extracted with CH₂Cl₂ (10 mL). The combined organic extracts were evaporated and the residue purified by chromatography on silica, eluting with a mixture of 2-4% (containing 10% aqueous NH₃) in CH₂Cl₂. Fractions containing product were combined and evaporated to afford example 3.23 (37 mg, 55% yield); ¹H NMR spectrum: (400 MHz, DMSO) δ 1.80 (2H, m), 1.93 (2H, m), 2.99 (2H, t), 3.07 (3H, s), 3.33 (2H, t), 3.49 (2H, t), 3.59 (2H, t), 5.00 (2H, s), 6.79 (1H, s), 7.03 (1H, d), 7.48-7.55 (3H, m), 7.88 (1H, s), 8.06 (1H, s), 9.19 (1H, s), 11.70 (1H, s); Mass spectrum: m/z (ESI+) (M+H)+=480.4 and 482.3.

The 2-[4-[[5-chloro-4-[(2-methyl-1-oxo-3,4-dihydroisoquinolin-8-yl)amino]pyridin-2-yl]amino]pyrazol-1-yl]acetic acid, used as starting material, was prepared as follows:

a) Sodium tert-butoxide (805 mg, 8.38 mmol) was added to a suspension of 2-(4-aminopyrazol-1-yl)acetic acid dihydrochloride (498 mg, 2.33 mmol) in 1,4-dioxane (15 mL) at 22° C. under an atmosphere of nitrogen. The mixture was stirred and sonicated for 5 minutes and then 8-[(2,5-dichloropyridin-4-yl)amino]-2-methyl-3,4-dihydroisoquinolin-1-one (300 mg, 0.93 mmol) and 9,9-dimethyl-4,5-bis(diphenylphosphino)xanthene (86 mg, 0.15 mmol) were added and the resulting suspension was purged with nitrogen. tris(dibenzylideneacetone)dipalladium(0) (68.2 mg, 0.075 mmol) was added and the mixture purged with nitrogen. The mixture was heated at 150° C. for 60 minutes in a microwave reactor and then allowed to cool to room temperature. The mixture was evaporated and the residue partitioned between $CH_2Cl_2$ (150 mL) and a 0.1N solution of NaOH (150 mL). The aqueous layer was separated, washed with $CH_2Cl_2$ (100 mL) and then adjusted to pH4 with 2N HCl solution. The aqueous solution was washed with $CH_2Cl_2$ (100 mL), filtered and then evaporated. The residue was triturated with a 1:1 mixture of $CH_2Cl_2$/MeOH (150 mL) and the resulting solid filtered and then washed with a 1:1 mixture of $CH_2Cl_2$/MeOH. The combined filtrates were evaporated to leave 2-[4-[[5-chloro-4-[(2-methyl-1-oxo-3,4-dihydroisoquinolin-8-yl)amino]pyridin-2-yl]amino]pyrazol-1-yl]acetic acid (250 mg, 63% yield); $^1$H NMR spectrum: (300 MHz, DMSO) δ 2.96 (2H, t), 3.06 (3H, s), 3.57 (2H, t), 4.71 (2H, s), 6.81 (1H, s), 6.89 (1H, d), 7.40 (1H, s), 7.43-7.50 (2H, m), 7.90 (1H, d), 8.01 (1H, s), 8.86 (1H, s), 11.23 (1H, s); Mass spectrum: m/z (ESI+) (M+H)+= 427.33 and 429.29.

The 8-[(2,5-dichloropyridin-4-yl)amino]-2-methyl-3,4-dihydroisoquinolin-1-one, used as starting material, was prepared as follows:

a) Palladium(II) acetate (0.093 g, 0.41 mmol) was added to 9,9-dimethyl-4,5-bis(diphenylphosphino)xanthene (0.360 g, 0.62 mmol), cesium carbonate (6.76 g, 20.74 mmol), 2,5-dichloro-4-iodopyridine (2.84 g, 10.37 mmol) and 8-amino-2-methyl-3,4-dihydroisoquinolin-1-one (1.827 g, 10.37 mmol) in dioxane (100 mL) under an atmosphere of nitrogen. The resulting suspension was heated at 80° C. for 18 hours then allowed to cool to room temperature. The mixture was filtered and then evaporated. The residue was dissolved in EtOAc (100 mL), and washed sequentially with a saturated solution of $NaHCO_3$ (50 mL), water (50 mL), and finally with a saturated solution of NaCl (50 mL). The organic layer was separated, dried over $MgSO_4$, and then evaporated. The residue was triturated with $Et_2O$ to leave a solid. The solid was purified by chromatography on silica, eluting with a gradient of 0-5% MeOH in $CH_2Cl_2$. Fractions containing product were combined and evaporated to afford 8-[(2,5-dichloropyridin-4-yl)amino]-2-methyl-3,4-dihydroisoquinolin-1-one (2.398 g, 72% yield); $^1$H NMR spectrum: (300 MHz, DMSO) δ 2.97 (2H, t), 3.05 (3H, s), 3.57 (2H, t), 7.00 (1H, m), 7.34 (1H, s), 7.44-7.51 (2H, m), 8.31 (1H, s), 11.63 (1H, s); Mass spectrum: m/z (ESI+) (M+H)+=322.29 and 324.28 and 326.29.

The following compounds were prepared in an analogous way to example 3.23.

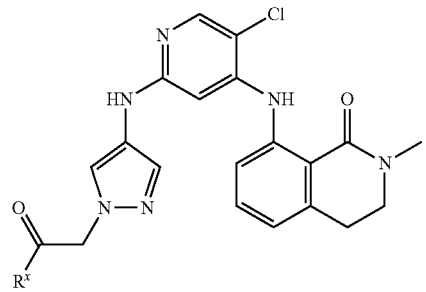

| # | R$^x$ | Name | $^1$H NMR spectrum (400 MHz, DMSO): δ | Mass spectrum m/z (ESI+) (M + H)$^+$ |
|---|---|---|---|---|
| 3.24 | —O\~\~\~N(H)— | 2-[4-[[5-chloro-4-[(2-methyl-1-oxo-3,4-dihydroisoquinolin-8-yl)amino]-2-pyridyl]amino]pyrazol-1-yl]-N-(2-methoxyethyl)acetamide | 3.01 (2H, t), 3.11 (3H, s), 3.30-3.33 (5H, m), 3.42 (2H, t), 3.62 (2H, t), 4.78 (2H, s), 6.83 (1H, s), 6.95 (1H, dd), 7.45 (1H, s), 7.49-7.50 (2H, m), 7.96 (1H, s), 8.07 (1H, s), 8.09 (1H, t), 8.79 (1H, s), 11.29 (1H, s) | 484.4 and 486.3 |
| 3.25 | —O\~\~\~N(Me)— | 2-[4-[[5-chloro-4-[(2-methyl-1-oxo-3,4-dihydroisoquinolin-8-yl)amino]-2-pyridyl]amino]pyrazol-1-yl]-N-(2-methoxyethyl)-N-methyl-acetamide | | 498.4 and 500.3 |

-continued

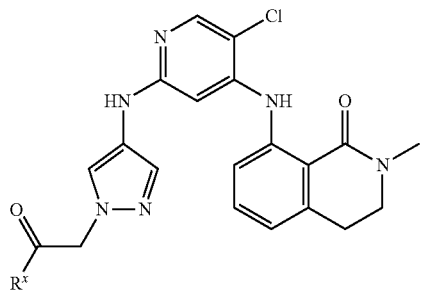

| # | R$^x$ | Name | $^1$H NMR spectrum (400 MHz, DMSO): δ | Mass spectrum m/z (ESI+) (M + H)$^+$ |
|---|---|---|---|---|
| 3.26 | ![structure: -N(CH3)CH2CH2NH-] | 2-[4-[[5-chloro-4-[(2-methyl-1-oxo-3,4-dihydroisoquinolin-8-yl)amino]-2-pyridyl]amino]pyrazol-1-yl]-N-(2-dimethylaminoethyl)acetamide | | 497.5 and 499.3 |
| 3.27 | ![structure: morpholino-] | 8-[[5-chloro-2-[[1-(2-morpholino-2-oxo-ethyl)pyrazol-4-yl]amino]-4-pyridyl]amino]-2-methyl-3,4-dihydroisoquinolin-1-one | (400 MHz, CDCl$_3$) δ 2.95 (4H, m), 3.16 (3H, s), 3.55 (4H, m), 3.59-3.67 (4H, m), 4.92 (2H, s), 6.00 (1H, s), 6.66 (1H, s), 6.72 (1H, d), 7.29 (1H, dd), 7.36 (1H, d), 7.45 (1H, s), 7.70 (1H, s), 8.01 (1H, s), 11.15 (1H, s) | 496.4 and 498.32 |

Example 3.28

8-[[5-Chloro-2-[(1-methylpyrazol-4-yl)amino]-4-pyridyl]amino]-2-methyl-3,4-dihydroisoquinolin-1-one

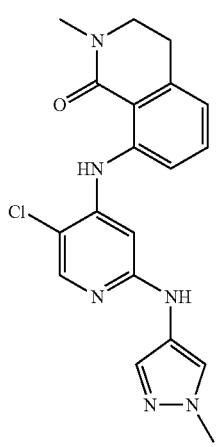 [SMILES: CN1CCc2cccc(Nc3cc(Nc4cnn(C)c4)ncc3Cl)c2C1=O]

1-Methylpyrazol-4-amine (39.2 mg, 0.40 mmol), 8-[(2,5-dichloropyridin-4-yl)amino]-2-methyl-3,4-dihydroisoquinolin-1-one (100 mg, 0.31 mmol), 9,9-dimethyl-4,5-bis(diphenylphosphino)xanthene (35.9 mg, 0.06 mmol) and sodium tert-butoxide (44.7 mg, 0.47 mmol) were suspended in dioxane (3.5 mL). The mixture was degassed with nitrogen and then bis(dibenzylideneacetone)palladium (28.2 mg, 0.049 mmol) was added. The mixture was heated at 150° C. for 30 minutes in a microwave reactor and then allowed to cool to room temperature. The mixture was loaded onto an SCX column and the product was eluted first with MeOH and then with a 0.7M solution of NH$_3$ in MeOH. Fractions containing product were evaporated and the residue purified by preparative HPLC. Fractions containing product were combined and evaporated to afford example 3.28 (12.90 mg, 11% yield); $^1$H NMR spectrum: (300 MHz, DMSO) δ 3.02 (2H, t), 3.12 (3H, s), 3.62 (2H, t), 3.84 (3H, s), 6.81 (1H, s), 6.95 (1H, dd), 7.40 (1H, d), 7.50 (2H, m), 7.90 (1H, s), 8.06 (1H, s), 8.72 (1H, s), 11.27 (1H, s); Mass spectrum: m/z (ESI+) (M+H)+= 383.03 and 384.99.

The following compounds were prepared in an analogous way to example 3.28.

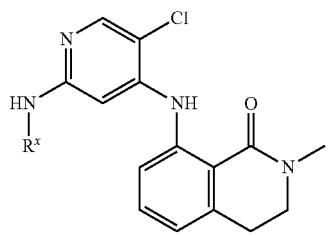

| # | Rˣ | Name | ¹H NMR spectrum (300 MHz, DMSO): δ | Mass spectrum m/z (ESI+) (M + H)+ |
|---|---|---|---|---|
| 3.29 | | 8-[[5-chloro-2-[[1-(1-methyl-4-piperidyl)pyrazol-4-yl]amino]-4-pyridyl]amino]-2-methyl-3,4-dihydroisoquinolin-1-one | 1.95 (2H, m), 2.00-2.04 (2H, m), 2.21 (3H, s), 2.83-2.86 (2H, m), 2.96 (2H, t), 3.06 (3H, s), 3.18 (3H, d), 3.57 (2H, t), 4.08 (1H, m), 6.75 (1H, s), 6.88-6.90 (1H, m), 7.38 (1H, d), 7.43 (1H, d), 7.90 (1H, d), 8.01 (1H, s), 8.63 (1H, s), 11.21 (1H, s) | 466.41 |
| 3.30 | | 8-[[5-chloro-2-[(1,5-dimethylpyrazol-3-yl)amino]-4-pyridyl]amino]-2-methyl-3,4-dihydroisoquinolin-1-one | 2.20 (3H, s), 2.97 (2H, t), 3.07 (3H, s), 3.58 (5H, m), 5.90 (1H, s), 6.90- 6.92 (1H, m), 7.48 (1H, d), 7.56 (1H, d), 7.79 (1H, s), 8.00 (1H, s), 8.99 (1H, s), 11.35 (1H, s) | 397.4 and 399.4 |
| 3.31 | | 8-[[2-[[1-(1-acetyl-4-piperidyl)pyrazol-4-yl]amino]-5-chloro-4-pyridyl]amino]-2-methyl-3,4-dihydroisoquinolin-1-one | 1.68-1.88 (2H, m), 1.96-2.00 (2H, m), 2.05 (3H, s), 2.67-2.69 (1H, m), 2.71 (1H, s), 2.96 (2H, t), 3.06 (3H, s), 3.57 (2H, t), 3.92 (1H, d), 4.33-4.39 (1H, m), 4.46 (1H, d), 6.76 (1H, s), 6.89-6.91 (1H, m), 7.39-7.39 (1H, m), 7.40-7.45 (2H, m), 7.92 (1H, s), 8.01 (1H, s), 8.66 (1H, s), 11.22 (1H, s) | 494.43 |
| 3.32 | | 8-[[5-chloro-2-[(1,3-dimethylpyrazol-4-yl)amino]-4-pyridyl]amino]-2-methyl-3,4-dihydroisoquinolin-1-one | 2.09 (3H, s), 2.96 (2H, s), 3.06 (3H, s), 3.56 (2H, s), 3.71 (3H, s), 6.80 (1H, s), 6.88-6.90 (1H, m), 7.42-7.43 (2H, m), 7.83 (1H, s), 7.97 (1H, s), 8.02 (1H, s), 11.18 (1H, s) | 397.41 |

Example 3.33

8-[[5-Chloro-2-[[1-(4-piperidyl)pyrazol-4-yl]amino]-4-pyridyl]amino]-2-methyl-3,4-dihydroisoquinolin-1-one

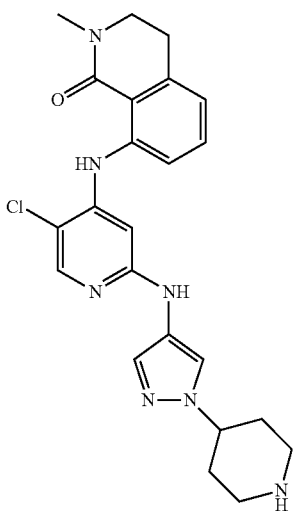 [SMILES: CN1CCc2cccc(Nc3cc(Nc4cnn(C5CCNCC5)c4)ncc3Cl)c2C1=O]

8-[(2,5-Dichloropyridin-4-yl)amino]-2-methyl-3,4-dihydroisoquinolin-1-one (70 mg, 0.22 mmol), tert-butyl 4-(4-aminopyrazol-1-yl)piperidine-1-carboxylate (145 mg, 0.54 mmol), 9,9-dimethyl-4,5-bis(diphenylphosphino)xanthene (25.1 mg, 0.04 mmol) and sodium tert-butoxide (31.3 mg, 0.33 mmol) were suspended in dioxane (6 mL). The mixture was degassed with nitrogen and then tris(dibenzylideneacetone)dipalladium(0) (19.90 mg, 0.022 mmol) was added. The mixture was heated at 150° C. for 30 minutes in a microwave reactor and then allowed to cool to room temperature. A 4M solution of HCl in 1,4-dioxane (1 mL) was added and the mixture was stirred at room temperature for 16 hours. The mixture was evaporated and the residue loaded onto an SCX column. The product was eluted first with MeOH and then with a 0.35M solution of $NH_3$ in MeOH. Fractions containing product were combined and evaporated. The residue was purified by preparative HPLC and fractions containing product were combined and evaporated to afford example 3.33 (13 mg, 13% yield); $^1$H NMR spectrum: (300 MHz, DMSO) δ 1.72-1.76 (2H, m), 1.89-1.92 (2H, m), 2.53 (2H, m), 2.96 (2H, m), 3.02-3.04 (2H, m), 3.06 (3H, s), 3.57 (2H, t), 4.09-4.15 (1H, m), 6.75 (1H, s), 6.88-6.91 (1H, m), 7.36-7.37 (1H, m), 7.42-7.45 (2H, m), 7.88 (1H, s), 8.01 (1H, s), 8.63 (1H, s), 11.21 (1H, s); Mass spectrum: m/z (ESI+) (M+H)+=452.44.

The following compounds were prepared in an analogous way to example 3.33.

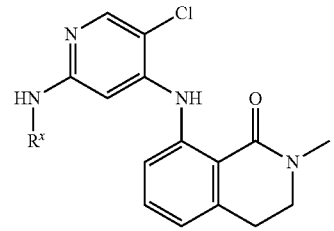

| # | $R^x$ | Name | $^1$H NMR spectrum (300 MHz, DMSO): δ | Mass spectrum m/z (ESI+) (M + H)$^+$ |
|---|---|---|---|---|
| 3.34$^a$ | (3-piperidyl)pyrazole | 8-[[5-chloro-2-[[1-(3-piperidyl)pyrazol-4-yl]amino]-4-pyridyl]amino]-2-methyl-3,4-dihydroisoquinolin-1-one | 1.47-1.50 (1H, m), 1.69 (1H, t), 1.82-1.85 (1H, m), 2.06 (1H, t), 2.87 (2H, d), 2.96 (2H, t), 3.06 (3H, s), 3.10-3.13 (1H, m), 3.18 (1H, d), 3.57 (2H, t), 4.03-4.07 (1H, m), 6.75 (1H, s), 6.88-6.91 (1H, m), 7.37-7.45 7.45 (3H, m), 7.89 (1H, s), 8.01 (1H, s), 8.62 (1H, s), 11.21 (1H, s) | 452.44 |

$^a$The tert-butyl 3-(4-aminopyrazol-1-yl)piperidine-1-carboxylate, used as starting material, was prepared as follows:

a) A solution of DIAD (2.95 mL, 15.00 mmol) in THF (5 mL) was added over a period of 60 minutes to a stirred solution of tert-butyl 3-hydroxypiperidine-1-carboxylate (2.415 g, 12.00 mmol), triphenylphosphine (3.93 g, 15.00 mmol) and 4-nitro-1H-pyrazole (1.131 g, 10 mmol) in THF (15 mL) cooled to 0° C. under an nitrogen atmosphere. The resulting solution was stirred at 0° C. for 1 hour and then allowed to warm to room temperature and stirred overnight. The mixture was concentrated in vacuo and then a mixture of 20% EtOAc in isohexane (40 mL) was added with rapid stirring. After 20 minutes the mixture was filtered and the filtrate evaporated. The residue was purified by chromatography on silica, eluting with a gradient of 0-40% EtOAc in isohexane. Fractions containing product were combined and evaporated. Mixed fractions were combined and evaporated and the residue purified by chromatography on silica, eluting with a gradient of 0-40% EtOAc in isohexane. Fractions containing product were combined and evaporated to afford tert-butyl 3-(4-nitropyrazol-1-yl)piperidine-1-carboxylate (2.045 g, 69% yield); Mass spectrum: m/z (ESI−) (M − H)− = 295.45.

b) A mixture of 10% palladium on carbon (0.048 g, 0.045 mmol) was added to tert-butyl 3-(4-nitropyrazol-1-yl)piperidine-1-carboxylate (475 mg, 1.60 mmol) in EtOH (16 mL) and the mixture was stirred at room temperature under an atmosphere of hydrogen for 20 hours. The mixture was filtered through Celite and the filtrate evaporated. The residue was loaded onto an SCX column and the product eluted first with MeOH and then with a 0.7M solution of $NH_3$ in MeOH. Fractions containing product were combined and evaporated to afford tert-butyl 3-(4-aminopyrazol-1-yl)piperidine-1-carboxylate (213 mg, 50% yield); $^1$H NMR spectrum: (300 MHz, DMSO) δ 1.39 (9H, s), 1.44-1.57 (1H, m), 1.68-1.75 (1H, m), 1.83-2.01 (1H, m), 2.06-2.15 (1H, m), 2.78 (1H, m), 3.06 (1H, dd), 3.82-4.02 (2H, m), 4.14 (1H, m), 6.99 (1H, d), 7.10 (1H, d); Mass spectrum: m/z (ESI+) (M + H)+ = 267.46.

Example 3.35

7-[[5-Chloro-2-[(1,3-dimethylpyrazol-4-yl)amino]-4-pyridyl]amino]-2-methyl-isoindolin-1-one

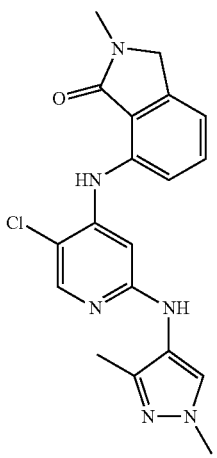 [SMILES: Cc1nn(C)cc1Nc1cc(Nc2cccc3c2C(=O)N(C)C3)c(Cl)cn1]

7-[(2,5-Dichloropyridin-4-yl)amino]-2-methyl-3H-isoindol-1-one (156 mg, 0.51 mmol), 1,3-dimethylpyrazol-4-amine (84 mg, 0.76 mmol), 9,9-dimethyl-4,5-bis(diphenylphosphino)xanthene (58.6 mg, 0.10 mmol) and sodium tert-butoxide (73.0 mg, 0.76 mmol) were suspended in dioxane (5 mL). The mixture was degassed with nitrogen and then bis(dibenzylideneacetone)palladium (46.4 mg, 0.081 mmol) was added and the mixture heated at 150° C. for 30 minutes in a microwave reactor. The mixture was allowed to cool to room temperature and then loaded onto an SCX column and the product eluted first with MeOH and then with a 7M solution of $NH_3$ in MeOH. Fractions containing product were combined and evaporated. The residue was purified by preparative HPLC. Fractions containing product were combined and evaporated to afford example 3.35 (27.0 mg, 14% yield); $^1$H NMR spectrum: (300 MHz, DMSO) δ 2.11 (3H, s), 3.07 (3H, s), 3.71 (3H, s), 4.47 (2H, s), 7.00 (1H, s), 7.15 (1H, d), 7.44-7.47 (1H, m), 7.54 (1H, d), 7.87 (1H, s), 8.00 (1H, s), 8.14 (1H, s), 9.53 (1H, s); Mass spectrum: m/z (ESI+) (M+H)+=383.05 and 385.02.

The 7-[(2,5-dichloropyridin-4-yl)amino]-2-methyl-3H-isoindol-1-one, used as starting material, was prepared as follows:

a) A mixture of 2,5-dichloro-4-iodopyridine (0.2 g, 0.73 mmol), 7-amino-2-methyl-3H-isoindol-1-one (0.118 g, 0.73 mmol), palladium(II) acetate (6.56 mg, 0.03 mmol), 9,9-dimethyl-4,5-bis(diphenylphosphino)xanthene (0.025 g, 0.04 mmol) and cesium carbonate (0.476 g, 1.46 mmol) were suspended in dioxane (5 mL). The mixture was heated at 100° C. for 30 minutes in a microwave reactor and then allowed to cool to room temperature. The mixture was loaded onto an SCX column and the product eluted first with MeOH and then with a 7M solution of $NH_3$ in MeOH. Fractions containing product were combined and evaporated. A solid recovered from the top of the column was washed with water, dried in vacuo, and combined with the evaporated residue to afford 7-[(2,5-dichloropyridin-4-yl)amino]-2-methyl-3H-isoindol-1-one (0.160 g, 71% yield); $^1$H NMR spectrum: (300 MHz, DMSO) δ 3.07 (3H, s), 4.50 (2H, s), 7.25-7.28 (1H, m), 7.48 (1H, s), 7.56-7.63 (2H, m), 8.36 (1H, s), 9.80 (1H, s); Mass spectrum: m/z (ESI+) (M+H)+=308.01 and 309.97 and 311.99.

The 7-amino-2-methyl-3H-isoindol-1-one, used as starting material, can be prepared as described in the literature (Garcia-Echeverria, C.; Kanazawa, T.; Kawahara, E.; Masuya, K.; Matsuura, N.; Miyake, T.; Ohmori, O.; Umemura, I. Preparation of novel 2,4-di(phenylamino)pyrimidines useful in the treatment of neoplastic diseases, inflammatory and immune system disorders. WO2004080980).

Example 3.36

2-[[5-Chloro-2-[(1,5-dimethylpyrazol-3-yl)amino]-4-pyridyl]amino]-N-methyl-5-(4-methylpiperazin-1-yl)benzamide

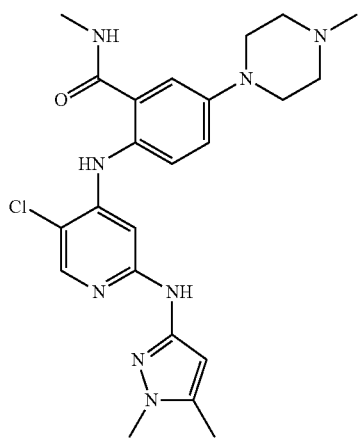 [SMILES: CNC(=O)c1cc(N2CCN(C)CC2)ccc1Nc1cc(Nc2cc(C)n(C)n2)ncc1Cl]

A mixture of 2-[(2,5-dichloropyridin-4-yl)amino]-N-methyl-5-(4-methylpiperazin-1-yl)benzamide (0.15 g, 0.38 mmol), 1,5-dimethylpyrazol-3-amine (0.042 g, 0.38 mmol), 9,9-dimethyl-4,5-bis(diphenylphosphino)xanthene (0.013 g, 0.02 mmol), cesium carbonate (0.248 g, 0.76 mmol) and palladium(II) acetate (3.42 mg, 0.02 mmol) was suspended in DMA (2 mL). The mixture was heated at 150° C. for 1 hour in a microwave reactor and then allowed to cool to room temperature. The mixture was loaded onto an SCX column and the product eluted first with MeOH and then with a 7M solution of NH₃ in MeOH. Fractions containing product were combined and evaporated. The residue was purified by preparative HPLC and fractions containing product were combined and evaporated to afford example 3.36 (0.013 g, 7% yield); $^1$H NMR spectrum: (300 MHz, DMSO) δ 2.17 (3H, s), 2.41 (3H, s), 2.68-2.77 (4H, m), 2.73 (2H, d), 3.17-3.30 (4H, m), 3.56 (3H, s), 5.86 (1H, s), 7.13-7.21 (2H, m), 7.44-7.49 (2H, m), 7.89 (1H, s), 8.59 (1H, d), 8.86 (1H, s), 9.56 (1H, s); Mass spectrum: m/z (ESI+) (M+H)+=469.2 and 471.1.

The 2-[(2,5-dichloropyridin-4-yl)amino]-N-methyl-5-(4-methylpiperazin-1-yl)benzamide, used as starting material, was prepared as follows:

a) A mixture of 2,5-dichloro-4-iodopyridine (0.56 g, 2.04 mmol), 2-amino-N-methyl-5-(4-methylpiperazin-1-yl)benzamide (0.508 g, 2.04 mmol), 9,9-dimethyl-4,5-s bis(diphenylphosphino)xanthene (0.071 g, 0.12 mmol), cesium carbonate (1.332 g, 4.09 mmol) and palladium(II) acetate (0.018 g, 0.08 mmol) was suspended in DMA (15 mL). The mixture was heated at 100° C. for 1 hour in a microwave reactor and then allowed to cool to room temperature. The mixture was loaded onto an SCX column and the product eluted first using MeOH and then with a 7M solution of NH₃ in MeOH. Fractions containing product were combined and evaporated to afford 2-[(2,5-dichloropyridin-4-yl)amino]-N-methyl-5-(4-methylpiperazin-1-yl)benzamide as a DMA adduct (0.990 g); $^1$H NMR spectrum: (300 MHz, DMSO) δ 2.23 (3H, s), 2.44-2.50 (4H, m), 2.73 (3H, d), 3.16-3.21 (4H, m), 6.90 (1H, s), 7.10-7.14 (1H, m), 7.20 (1H, d), 7.40 (1H, d), 8.19 (1H, s), 8.58 (1H, d), 9.67 (1H, s); Mass spectrum: m/z (ESI+) (M+H)+=394.09.

The 2-amino-N-methyl-5-(4-methylpiperazin-1-yl)benzamide, used as starting material, can be prepared as described in the literature (Imbach, P.; Kawahara, E.; Konishi, K.; Matsuura, N.; Miyake, T.; Ohmori, O.; Roesel, J.; Teno, N.; Umemura, I. Preparation of bis(arylamino)pyrimidine derivatives as antitumor agents. WO2006021454).

The following compounds were prepared in an analogous way to example 3.36.

| # | R$^x$ | Name | $^1$H NMR spectrum (300 MHz, DMSO): δ | Mass spectrum m/z (ESI+) (M + H)+ |
|---|---|---|---|---|
| 3.37 | (1,3-dimethylpyrazol-4-yl) | 2-[[5-chloro-2-[(1,3-dimethylpyrazol-4-yl)amino]-4-pyridyl]amino]-N-methyl-5-(4-methylpiperazin-1-yl)benzamide | 2.05 (3H, s), 2.24 (3H, s), 2.43-2.52 (4H, m), 2.74 (3H, d), 3.14-3.23 (4H, m), 3.69 (3H, s), 6.48 (1H, s), 7.09-7.12 (1H, m), 7.18 (1H, d), 7.36 (1H, d), 7.77 (1H, s), 7.85-7.88 (2H, m), 8.54 (1H, d), 9.31 (1H, s) | 469.1 and 471.1 |

Example 3.38

7-[[5-Chloro-2-[(1,3-dimethylpyrazol-4-yl)amino]-4-pyridyl]amino]-4-(4-isopropylpiperazin-1-yl)-2-methyl-isoindolin-1-one

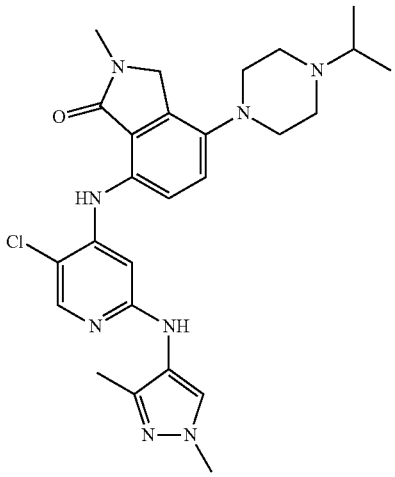 [SMILES: Cc1nn(C)cc1Nc1cc(Nc2ccc(N3CCN(C(C)C)CC3)c3c2C(=O)N(C)C3)c(Cl)cn1]

A mixture of 7-[(2,5-dichloropyridin-4-yl)amino]-2-methyl-4-(4-propan-2-ylpiperazin-1-yl)-3H-isoindol-1-one (0.20 g, 0.46 mmol), 1,3-dimethylpyrazol-4-amine (0.061 g, 0.55 mmol), 9,9-dimethyl-4,5-bis(diphenylphosphino)xanthene (0.053 g, 0.09 mmol) and sodium tert-butoxide (0.066 g, 0.69 mmol) was suspended in dioxane (5 mL). The mixture was degassed with nitrogen and then bis(dibenzylideneacetone)palladium (0.042 g, 0.073 mmol) was added. The mixture was heated at 150° C. for 30 minutes in a microwave reactor and then allowed to cool to room temperature. The mixture was loaded onto an SCX column and the product eluted first using MeOH and then with a 0.35M solution of $NH_3$ in MeOH. Fractions containing product were combined and evaporated. The residue was purified by preparative HPLC and fractions containing product were combined and evaporated to afford example 3.38 (0.050 g, 21% yield); $^1$H NMR spectrum: (300 MHz, DMSO) δ 1.00-1.03 (6H, m), 2.10 (3H, s), 2.55-2.62 (4H, m), 2.65-2.72 (1H, m), 2.98-3.01 (4H, m), 3.06 (3H, s), 3.71 (3H, s), 4.48 (2H, s), 6.91 (1H, s), 7.14 (1H, d), 7.41 (1H, d), 7.85 (1H, s), 7.95 (1H, s), 8.07 (1H, s), 9.32 (1H, s); Mass spectrum: m/z (ESI+) (M+H)+=509.06.

The 7-[(2,5-dichloropyridin-4-yl)amino]-2-methyl-4-(4-propan-2-ylpiperazin-1-yl)-3H-isoindol-1-one, used as starting material, was prepared as follows:

a) A mixture of 2,5-dichloro-4-iodopyridine (0.40 g, 1.46 mmol), 7-amino-2-methyl-4-(4-propan-2-ylpiperazin-1-yl)-3H-isoindol-1-one (0.421 g, 1.46 mmol), 9,9-dimethyl-4,5-bis(diphenylphosphino)xanthene (0.051 g, 0.09 mmol), cesium carbonate (0.952 g, 2.92 mmol) and palladium(II) acetate (0.013 g, 0.06 mmol) was suspended in DMA (15 mL). The mixture was heated at 100° C. for 1 hour in a microwave reactor and then allowed to cool to room temperature. The mixture was loaded onto an SCX column and the product eluted first with MeOH and then with a 7M solution of $NH_3$ in MeOH. Fractions containing product were combined and evaporated to afford 7-[(2,5-dichloropyridin-4-yl)amino]-2-methyl-4-(4-propan-2-ylpiperazin-1-yl)-3H-isoindol-1-one (0.630 g, 99% yield); $^1$H NMR spectrum: (300 MHz, DMSO) δ 1.01-1.18 (3H, d), 2.60-2.64 (4H, m), 3.04-3.09 (5H, m), 4.51 (2H, s), 7.16 (1H, d), 7.29 (1H, s), 7.50 (1H, d), 8.28 (1H, s), 9.59 (1H, s); Mass spectrum: m/z (ESI+) (M+H)=434.0 and 436.0 and 438.0.

Example 3.39

2-[[5-Chloro-2-[(1,3-dimethylpyrazol-4-yl)amino]-4-pyridyl]amino]-3-fluoro-N-methyl-benzamide

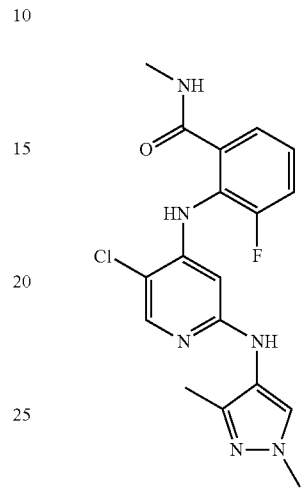

1,3-Dimethylpyrazol-4-amine (53.1 mg, 0.48 mmol), 2-[(2,5-dichloropyridin-4-yl)amino]-3-fluoro-N-methylbenzamide (100 mg, 0.32 mmol), 9,9-dimethyl-4,5-bis(diphenylphosphino)xanthene (36.8 mg, 0.06 mmol) and sodium tert-butoxide (45.9 mg, 0.48 mmol) were suspended in dioxane (3 mL). The mixture was degassed with nitrogen and then bis(dibenzylideneacetone)palladium (28 mg, 0.049 mmol) was added and the mixture was heated at 150° C. for 30 minutes in a microwave reactor. The mixture was allowed to cool to room temperature and then loaded onto an SCX column. The product was eluted first with MeOH and then with a 0.7M solution of $NH_3$ in MeOH and pure fractions were evaporated. The residue was purified by preparative HPLC to afford example 3.39 (37.7 mg, 30% yield); $^1$H NMR spectrum: (300 MHz, DMSO) δ 1H NMR (300.132 MHz, DMSO) δ 2.02 (3H, s), 2.75 (3H, s), 3.67 (3H, s), 5.84 (1H, d), 7.31 (1H, td), 7.45-7.54 (2H, m), 7.74 (1H, s), 7.88 (1H, s), 7.91 (1H, s), 8.63-8.95 (2H, m); Mass spectrum: m/z (ESI+) (M+H)$^+$ =389.3 and 391.3.

The 2-[(2,5-dichloropyridin-4-yl)amino]-3-fluoro-N-methylbenzamide, used as starting material, was prepared as follows:

a) Palladium(II) acetate (35.9 mg, 0.16 mmol) was added to 9,9-dimethyl-4,5-bis(diphenylphosphino)xanthene (139 mg, 0.24 mmol), cesium carbonate (2604 mg, 7.99 mmol), 2,5-dichloro-4-iodopyridine (1094 mg, 4.00 mmol) and 2-amino-3-fluoro-N-methylbenzamide (672 mg, 4.00 mmol) in dioxane (20 mL) under an atmosphere of nitrogen. The resulting suspension was heated at 80° C. for 24 hours and then allowed to cool to room temperature. The mixture was evaporated and the residue dissolved in EtOAc (150 mL) and then washed sequentially with a saturated solution of $NaHCO_3$ (100 mL), water (100 mL), and then with a saturated solution of NaCl (100 mL). The organic layer was dried over $MgSO_4$ and then evaporated. The residue was purified by chromatography on silica, eluting with a gradient of 0-100% EtOAc in isohexane. Fractions containing product were evaporated to afford 2-[(2,5-dichloropyridin-4-yl)amino]-3-fluoro-N-methylbenzamide (624 mg, 50% yield); ¹H NMR spectrum: (300 MHz, DMSO) δ 1H NMR (300.132 MHz, DMSO) δ 2.74 (3H, d), 6.39 (1H, d), 7.42 (1H, td), 7.49-7.59 (2H, m), 8.25 (1H, s), 8.64 (1H, m), 9.31 (1H, s); Mass spectrum: m/z (ESI+) (M+H)⁺ =314.20 and 316.20 and 318.17.

The 2-amino-3-fluoro-N-methylbenzamide, used as starting material, was prepared as follows:

a) 1,1'-Carbonyldiimidazole (1.946 g, 12.00 mmol) was added in one portion to 2-amino-3-fluorobenzoic acid (1.551 g, 10 mmol) in THF (25 mL) at room temperature and the resulting suspension stirred for 18 hours. A 2N solution of methylamine in THF (7.50 mL, 15.00 mmol) was added and the resulting solution stirred at room temperature for 1 hour. The mixture was evaporated and the residue dissolved in EtOAc (100 mL). The solution was washed sequentially with water (2×50 mL) and a saturated solution of NaCl (50 mL). The organic layer was dried over MgSO₄ and then evaporated. The residue was dissolved in EtOAc (100 mL) and the mixture washed sequentially with a 2M solution of NaOH (50 mL), water (50 mL), and then with a saturated solution of NaCl (50 mL). The organic layer was dried over MgSO₄ and then evaporated to afford 2-amino-3-fluoro-N-methylbenzamide (1.349 g, 80% yield); ¹H NMR spectrum: (300 MHz, CDCl₃) δ 2.91 (3H, d), 5.52 (2H, s), 5.97 (1H, s), 6.49 (1H, td), 6.93-7.04 (2H, m); Mass spectrum: m/z (ESI+) (M+H)⁺ = 169.34.

Example 3.40

2-[[5-Chloro-2-[(1,3-dimethylpyrazol-4-yl)amino]-4-pyridyl]amino]-6-fluoro-N-methyl-benzamide

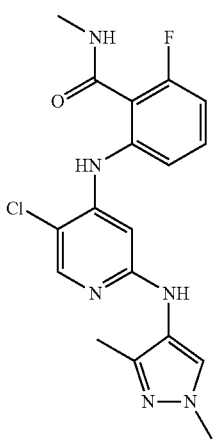 [SMILES: CNC(=O)c1c(F)cccc1Nc1cc(Nc2cn(C)nc2C)ncc1Cl]

1,3-Dimethylpyrazol-4-amine (70.8 mg, 0.64 mmol), 2-[(2,5-dichloropyridin-4-yl)amino]-6-fluoro-N-methylbenzamide (100 mg, 0.32 mmol), 9,9-dimethyl-4,5-bis(diphenylphosphino)xanthene (36.8 mg, 0.06 mmol) and sodium tert-butoxide (45.9 mg, 0.48 mmol) were suspended in dioxane (3 mL). The mixture was degassed with nitrogen and then bis(dibenzylideneacetone)palladium (28 mg, 0.049 mmol) was added and the mixture heated at 150° C. for 1 hour in a microwave reactor. The mixture was allowed to cool to room temperature and the mixture was acidified with a 2M solution of HCl in MeOH. The mixture was loaded onto an SCX column and the product eluted first with MeOH and then with a 0.7M solution of NH₃ in MeOH. Fractions containing product were combined and evaporated to afford example 3.40 (46.4 mg, 38% yield); ¹H NMR is spectrum: (300 MHz, DMSO) δ 1.99 (3H, s), 2.71 (3H, d), 3.62 (3H, s), 6.53 (1H, d), 6.92 (1H, m), 7.26 (1H, d), 7.42 (1H, td), 7.73 (1H, s), 7.87 (1H, s), 7.93 (1H, s), 8.49 (1H, m), 8.68 (1H, s); Mass spectrum: m/z (ESI+) (M+H)⁺ =389.3 and 391.3.

The 2-[(2,5-dichloropyridin-4-yl)amino]-6-fluoro-N-methylbenzamide, used as starting material, was prepared as follows:

a) A mixture of palladium(II) acetate (53.4 mg, 0.24 mmol), 9,9-dimethyl-4,5-bis(diphenylphosphino)xanthene (206 mg, 0.36 mmol), cesium carbonate (3875 mg, 11.89 mmol), 2-amino-6-fluoro-N-methylbenzamide (1000 mg, 5.95 mmol) and 2,5-dichloro-4-iodopyridine (1710 mg, 6.24 mmol) in dioxane (50 mL) under an atmosphere of nitrogen was heated at 80° C. for 18 hours. The mixture was allowed to cool to room temperature, filtered and then evaporated. The residue was dissolved in EtOAc (150 mL) and the mixture washed sequentially with a saturated solution of NaHCO₃ (2×100 mL), water (100 mL) and then with a saturated solution of NaCl (100 mL). The organic layer was dried over MgSO₄ and then evaporated. The residue was purified by chromatography on silica, eluting with a gradient of 0-100% EtOAc in isohexane. Fractions containing product were combined and evaporated to afford 2-[(2,5-dichloropyridin-4-yl)amino]-6-fluoro-N-methylbenzamide (486 mg, 26% yield); ¹H NMR spectrum: (300 MHz, DMSO) δ 2.74 (3H, d), 6.96 (1H, d), 7.15 (1H, ddd), 7.37 (1H, d), 7.54 (1H, td), 8.26 (1H, s), 8.54 (1H, m), 9.09 (1H, s); Mass spectrum: m/z (ESI+) (M+H)⁺ =314.26 and 316.21 and 318.23.

The 2-amino-6-fluoro-N-methylbenzamide, used as starting material, can be prepared as described in the literature (Engelhardt, H.; Reiser, U.; Zahn, S. K.; Hauptmann, R.; Steegmaier, M.; Guertler, U.; Hoffmann, M.; Grauert, M.; Stadtmueller, H. Preparation of 2-arylaminopyrimidines as polo-like kinase inhibitors. EP1598343).

Example 3.41

2-[[5-chloro-2-[(1,3-dimethylpyrazol-4-yl)amino]-4-pyridyl]amino]-5-fluoro-N-methyl-benzamide

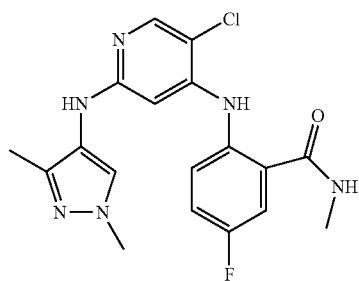 [SMILES: CNC(=O)c1cc(F)ccc1Nc1cc(Nc2cn(C)nc2C)ncc1Cl]

1,3-Dimethyl-1H-pyrazol-4-amine and 2-(2,5-dichloropyridin-4-ylamino)-5-fluoro-N-methylbenzamide were reacted according to the procedure of example 3.40 to afford 2-(5-chloro-2-(1,3-dimethyl-1H-pyrazol-4-ylamino)pyridin-4-ylamino)-5-fluoro-N-methylbenzamide (16.1 mg) as a beige solid. $^1$H NMR spectrum: (300 MHz, DMSO) δ 2.06 (3H, s), 2.77 (3H, d), 3.69 (3H, s), 6.60 (1H, s), 7.40 (1H, m), 7.55 (2H, m), 7.81 (1H, s), 7.93 (1H, s), 8.01 (1H, s), 8.72 (1H, m), 9.70 (1H, s); Mass spectrum: m/z (ESI+) (M+H)$^+$ =389

The 2-(2,5-dichloropyridin-4-ylamino)-5-fluoro-N-methylbenzamide used as starting material was prepared from 2-amino-5-fluoro-N-methylbenzamide (585 mg, 3.48 mmol; prepared from 2-amino-5-fluorobenzoic acid according to the procedure of example 3.39, starting material; Mass spectrum: m/z (ESI+) (M+H)$^+$ =169) and 2,5-dichloro-4-iodopyridine (1000 mg, 3.65 mmol) according to the procedure of example 3.40, starting material: 145 mg, solid. $^1$H NMR spectrum: (300 MHz, DMSO) δ 2.76 (3H, d), 7.05 (1H, d), 7.42 (1H, td), 7.57 (1H, m), 7.63 (1H, m), 8.26 (1H, s), 8.72 (1H, m), 9.99 (1H, s); Mass spectrum: m/z (ESI+) (M+H)$^+$ =314.

Example 3.42

2-[[5-chloro-2-[(1,3-dimethylpyrazol-4-yl)amino]-4-pyridyl]amino]-4-fluoro-N-methyl-benzamide

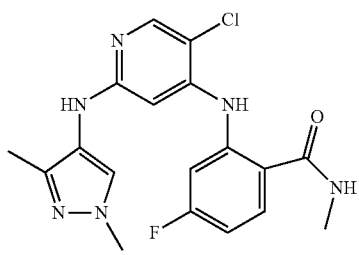 [SMILES: CNC(=O)c1ccc(F)cc1Nc1cc(Nc2cn(C)nc2C)ncc1Cl]

1,3-Dimethylpyrazol-4-amine and 2-(2,5-dichloropyridin-4-ylamino)-4-fluoro-N-methylbenzamide were reacted according to the procedure of example 3.40 to afford 2-(5-chloro-2-(1,3-dimethyl-1H-pyrazol-4-ylamino)pyridin-4-ylamino)-4-fluoro-N-methylbenzamide (23 mg) as a beige solid. $^1$H NMR spectrum: (300 MHz, DMSO) δ 2.02 (3H, s), 2.71 (3H, d), 3.64 (3H, s), 6.72 (1H, d), 6.86 (1H, td), 7.27 (1H, dd), 7.71 (1H, dd), 7.79 (1H, s), 7.92 (1H, s), 8.04 (1H, s), 8.63 (1H, m), 10.43 (1H, s); Mass spectrum: m/z (ESI+) (M+H)$^+$ =389

The 2-(2,5-dichloropyridin-4-ylamino)-4-fluoro-N-methylbenzamide used as starting material was prepared from 2-amino-4-fluoro-N-methylbenzamide (585 mg, 3.48 mmol; prepared from 2-amino-4-fluorobenzoic acid according to the procedure of example 3.39, starting material; Mass spectrum: m/z (ESI+) (M+H)$^+$ =169) and 2,5-dichloro-4-iodopyridine (1000 mg, 3.65 mmol) according to the procedure of example 3.40, starting material: 120 mg, solid. $^1$H NMR spectrum: (300 MHz, DMSO) δ 2.77 (3H, d), 7.03 (1H, td), 7.35 (1H, d), 7.48 (1H, ddd), 7.80 (1H, dd), 8.32 (1H, s), 8.73 (1H, m), 10.78 (1H, s); Mass spectrum: m/z (ESI+) (M+H)$^+$ =314.

Example 4.01

2-[[5-Fluoro-2-[[1-(2-oxo-2-pyrrolidin-1-yl-ethyl)pyrazol-4-yl]amino]-4-pyridyl]amino]-N-methylbenzamide

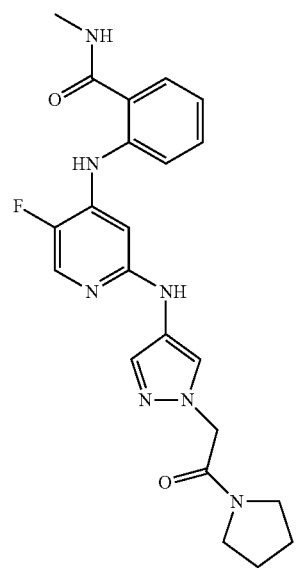 [SMILES: CNC(=O)c1ccccc1Nc1cc(Nc2cnn(CC(=O)N3CCCC3)c2)ncc1F]

2-[4-[[5-Fluoro-4-[[2-(methylcarbamoyl)phenyl]amino]pyridin-2-yl]amino]pyrazol-1-yl]acetic acid (60 mg, 0.156 mmol) was dissolved in DMA (4 mL). Pyrrolidine (78 μl, 0.936 mmol) was added, followed by dropwise addition of a solution of HATU (71 mg, 0.187 mmol) in DMA (1 mL). The mixture was stirred at 22° C. for 16 hours and then evaporated. The residue was partitioned between CH$_2$Cl$_2$ (10 mL) and water (10 mL). The aqueous layer was separated and then extracted with CH$_2$Cl$_2$ (10 mL). The combined extracts were evaporated and the residue purified by chromatography on silica, eluting with a mixture of 2-4% MeOH (containing 10% aqueous NH3) in CH$_2$Cl$_2$. Fractions containing product were combined and evaporated to afford example 4.01 (29 mg, 42% yield); $^1$H NMR spectrum: (300 MHz, DMSO) δ 1.90 (4H, m), 2.79 (3H, d), 3.44 (4H, m), 4.93 (2H, s), 6.70 (1H, d), 7.09 (1H, dd), 7.35 (1H, s), 7.52 (1H, dd), 7.56 (1H, d), 7.72 (1H, d), 7.89 (1H, s), 7.94 (1H, d), 8.57 (1H, s), 8.66 (1H, q), 10.11 (1H, s); Mass spectrum: m/z (ESI+) (M+H)+=438.5.

The 2-[4-[[5-fluoro-4-[[2-(methylcarbamoyl)phenyl]amino]pyridin-2-yl]amino]pyrazol-1-yl]acetic acid, used as starting material, was prepared as follows:

a) Reaction performed in 2 batches: Sodium tert-butoxide (773 mg, 8.05 mmol) was added to a suspension of 2-(4-aminopyrazol-1-yl)acetic acid dihydrochloride (0.478 g, 2.23 mmol) in 1,4-dioxane (15 mL) at 22° C. under an atmosphere of nitrogen. The mixture was stirred and sonicated for 5 minutes and then 2-[(2-chloro-5-fluoropyridin-4-yl)amino]-N-methylbenzamide (250 mg, 0.90 mmol) and 9,9-dimethyl-4,5-bis(diphenylphosphino)xanthene (82 mg, 0.15 mmol) were added and the resulting suspension was purged with nitrogen. Tris(dibenzylideneacetone)dipalladium (65 mg, 0.071 mmol) was added and the mixture was purged with nitrogen. The mixture was heated to 150° C. for 60 minutes in a microwave reactor and then allowed to cool to room temperature. Both batches were combined and then evaporated. The residue was partitioned between $CH_2Cl_2$ (150 mL) and a 0.1N solution of NaOH (150 mL). The aqueous layer was separated, washed with $CH_2Cl_2$ (100 mL) and then adjusted to pH4 by the addition of a 2N solution of HCl. The aqueous mixture was washed with $CH_2Cl_2$ (100 mL), filtered and then evaporated. The residue was triturated with a 1:1 mixture of $CH_2Cl_2$/MeOH (150 mL) and the resulting mixture filtered. The solid was washed with a 1:1 mixture of $CH_2Cl_2$/MeOH (3×150 mL) and the combined filtrates evaporated to afford 2-[4-[[5-fluoro-4-[[2-(methylcarbamoyl)phenyl]amino]pyridin-2-yl]amino]pyrazol-1-yl]acetic acid (440 mg, 64% yield); $^1$H NMR spectrum: (300 MHz, DMSO) δ 2.79 (3H, d), 4.69 (2H, s), 6.70 (1H, d), 7.08 (1H, ddd), 7.33 (1H, s), 7.51 (1H, d), 7.55 (1H, ddd), 7.73 (1H, dd), 7.88 (1H, s), 7.93 (1H, d), 8.57 (1H, s), 8.70 (1H, q), 10.10 (1H, d); Mass spectrum: m/z (ESI+) (M+H)+=385.34.

The 2-[(2-chloro-5-fluoropyridin-4-yl)amino]-N-methyl-benzamide, used as starting material, was prepared as follows:

a) Cesium carbonate (651 mg, 2.00 mmol) was added to a mixture of 2-amino-N-methylbenzamide (150 mg, 1.00 mmol), 2-chloro-5-fluoro-4-iodopyridine (257 mg, 1.00 mmol), 9,9-dimethyl-4,5-bis(diphenylphosphino)xanthene (35 mg, 0.06 mmol) and palladium(II) acetate (9 mg, 0.04 mmol) in dioxane (10 mL) under an atmosphere of nitrogen and the resulting suspension was heated at 80° C. for 24 hours. The mixture was filtered through Celite and the residue washed with $CH_2Cl_2$ (20 mL). The filtrate was evaporated and the residue was then dissolved in $CH_2Cl_2$ (40 mL) and washed sequentially with a saturated solution of $NaHCO_3$ (25 mL), water (25 mL), and finally with a saturated solution of NaCl (25 mL). The organic layer was dried over $MgSO_4$ and then evaporated to leave a solid. The solid was triturated in $CH_2Cl_2$ to afford 2-(2-chloro-5-fluoropyridin-4-ylamino)-N-methyl-benzamide (231 mg, 83% yield); $^1$H NMR spectrum (300.132 MHz, $d_6$ DMSO+$d_4$ Acetic acid): δ 2.76 (3H, s), 7.19 (1H, m), 7.22 (1H, d), 7.50-7.58 (2H, m), 7.71 (1H, dd), 8.19 (1H, d); Mass spectrum: m/z (ESI+) (M+H)+=280.0 and 282.0.

The following compounds were prepared in an analogous way to example 4.01.

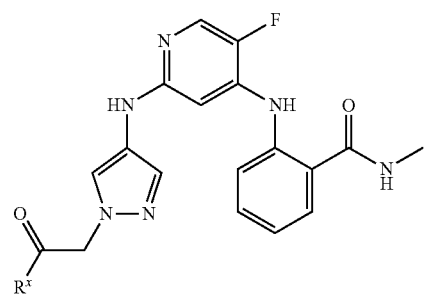

| # | R$^x$ | Name | $^1$H NMR spectrum (400 MHz, DMSO): δ | Mass spectrum m/z (ESI+) (M + H)$^+$ |
|---|---|---|---|---|
| 4.02 | (4-methyl-piperidin-1-yl-methyl)N— | 2-[[5-fluoro-2-[[1-[2-[methyl-(1-methyl-4-piperidyl)amino]-2-oxo-ethyl]pyrazol-4-yl]amino]-4-pyridyl]amino]-N-methyl-benzamide | 1.42-1.53 (2H, m), 1.73 (2H, m), 1.96 (2H, m), 2.17 (3H, s), 2.52 (3H, s), 2.79-2.83 (5H, m), 4.17 1H, m), 5.01 (1H, s), 5.07 (1H, s), 6.70 (1H, d), 7.09 (1H, dd), 7.34 (1H, d), 7.51 (1H, d), 7.55 (1H, dd), 7.72 (1H, d), 7.88 (1H, d), 7.93 (1H, d), 8.56 (1H, d), 10.11 (1H, s). | 495.5 |
| 4.03 | 2-methoxyethyl-methylamino— | 2-[[5-fluoro-2-[[1-[2-(2-methoxyethyl-methyl-amino)-2-oxo-ethyl]pyrazol-4-yl]4-pyridyl]amino]-N-methyl-benzamide | | 456.5 |
| 4.04 | (4-methyl-1,4-diazepan-1-yl)— | 2-[[5-fluoro-2-[[1-[2-(4-methyl-1,4-diazepan-1-yl)-2-oxo-ethyl]pyrazol-4-yl]amino]-4-pyridyl]amino]-N-methyl-benzamide | | 481.5 |
| 4.05 | morpholino— | 2-[[5-fluoro-2-[[1-(2-morpholino-2-oxo-ethyl)pyrazol-4-yl]amino]-4-pyridyl]amino]-N-methyl-benzamide | | 454.4 |

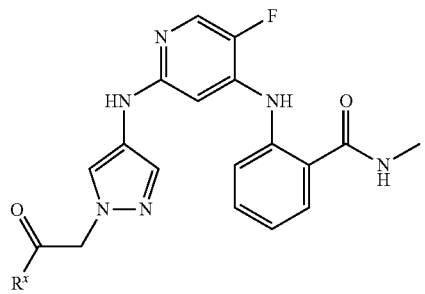

| # | R$^x$ | Name | $^1$H NMR spectrum (400 MHz, DMSO): δ | Mass spectrum m/z (ESI+) (M + H)$^+$ |
|---|---|---|---|---|
| 4.06 | (CH$_3$)$_2$N-piperidyl | 2-[[2-[[1-[2-(4-dimethylamino-1-piperidyl)-2-oxo-ethyl]pyrazol-4-yl]amino]-5-fluoro-4-pyridyl]amino]-N-methyl-benzamide | 1.22-1.39 (2H, m), 1.76 (2H, m), 2.20 (6H, s), 2.61-2.68 (2H, m), 2.79 (3H, d), 3.03 (1H, m), 3.91 (1H, m), 4.29 (1H, m), 4.98-5.09 (2H, m), 6.70 (1H, d), 7.09 (1H, dd), 7.34 (1H, s), 7.52 (1H, dd), 7.56 (1H, d), 7.72 (1H, d), 7.88 (1H, s), 7.94 (1H, d), 8.57 (1H, s), 8.66 (1H, d), 10.11 (1H, s). | 495.5 |
| 4.07 | 4-methylpiperazinyl | 2-[[5-fluoro-2-[[1-[2-(4-methylpiperazin-1-yl)-2-oxo-ethyl]pyrazol-4-yl]amino]-4-pyridyl]amino]-N-methyl-benzamide | | 467.5 |

Example 4.08

2-[[5-Fluoro-2-[(1-methylpyrazol-4-yl)amino]-4-pyridyl]amino]-N-methyl-benzamide

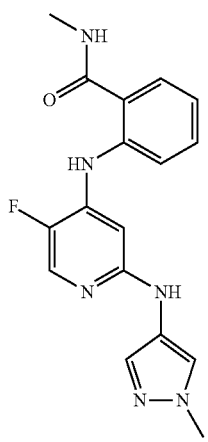 [SMILES: CNC(=O)c1ccccc1Nc1cc(Nc2cnn(C)c2)ncc1F]

A mixture of 1-methylpyrazol-4-amine (41.7 mg, 0.43 mmol), 9,9-dimethyl-4,5-bis(diphenylphosphino)xanthene (41.4 mg, 0.07 mmol), bis(dibenzylideneacetone)palladium (32.7 mg, 0.057 mmol), sodium tert-butoxide (51.5 mg, 0.54 mmol), and 2-[(2-chloro-5-fluoropyridin-4-yl)amino]-N-methylbenzamide (100 mg, 0.36 mmol) was suspended in dioxane (3 mL). The mixture was heated at 150° C. for 30 minutes in a microwave reactor and then allowed to cool to room temperature. The mixture was loaded onto an SCX column and the product eluted first with MeOH and then with a 7M solution of NH$_3$ in MeOH. Fractions containing product were combined and evaporated. The residue was purified by preparative HPLC and fractions containing product were combined and evaporated to afford example 4.08 (51.2 mg, 42% yield); $^1$H NMR spectrum: (300 MHz, DMSO) δ 2.78 (3H, d), 3.77 (3H, s), 6.66-6.68 (1H, m), 7.07-7.10 (1H, m), 7.31 (1H, s), 7.47-7.56 (2H, m), 7.69-7.72 (1H, m), 7.84 (1H, s), 7.91-7.92 (1H, m), 8.51 (1H, s), 8.64 (1H, q), 10.08 (1H, d); Mass spectrum: m/z (ESI+) (M+H)+=341.04.

The following compounds were prepared in an analogous way to example 4.08.

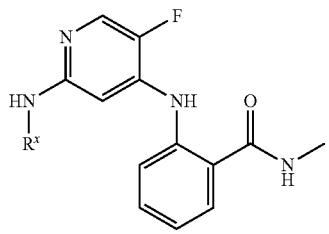

| # | $R^x$ | Name | $^1$H NMR spectrum (300 MHz, DMSO): δ | Mass spectrum m/z (ESI+) (M + H)$^+$ |
|---|---|---|---|---|
| 4.09 | | 2-[[5-fluoro-2-[(1-tetrahydropyran-4-ylpyrazol-4-yl)amino]-4-pyridyl]amino]-N-methyl-benzamide | 1.87-1.94 (4H, m), 2.77-2.78 (3H, m), 3.38-3.51 (2H, m), 3.93-3.97 (2H, m), 4.31-4.37 (1H, m), 6.67 (1H, d), 7.05-7.10 (1H, m), 7.36 (1H, s), 7.46-7.55 (2H, m), 7.69-7.72 (1H, m), 7.92 (2H, d), 8.49 (1H, s), 8.64 (1H, q), 10.08 (1H, d) | 411.13 |
| 4.10 | | 2-[[2-[(1,3-dimethylpyrazol-4-yl)amino]-5-fluoro-4-pyridyl]amino]-N-methyl-benzamide | 2.08 (3H, s), 2.77-2.79 (3H, m), 3.69 (3H, s), 6.74-6.77 (1H, m), 7.04-7.10 (1H, m), 7.47-7.54 (2H, m), 7.69-7.72 (1H, m), 7.84-7.89 (3H, m), 8.64 (1H, q), 10.08 (1H, d) | 355.11 |
| 4.11 | | 2-[[5-fluoro-2-[[1-(1-methyl-4-piperidyl)pyrazol-4-yl]amino]-4-pyridyl]amino]-N-methyl-benzamide | 1.83-2.07 (6H, m), 2.20 (3H, s), 2.78 (3H, m), 2.84 (2H, m), 4.02 (1H, m), 6.66 (1H, d), 7.08 (1H, ddd), 7.35 (1H, d), 7.49 (1H, m), 7.54 (1H, dd), 7.71 (1H, dd), 7.90 (1H, d), 7.93 (1H, d), 8.47 (1H, s), 8.65 (1H, m), 10.08 (1H, d) | 424.42 |

Example 4.12

8-[[2-[(1,3-Dimethylpyrazol-4-yl)amino]-5-fluoro-4-pyridyl]amino]-2-methyl-3,4-dihydroisoquinolin-1-one

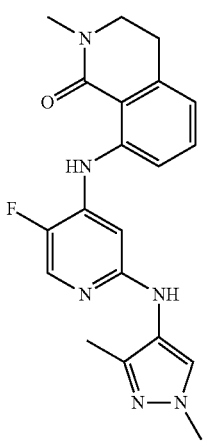 [SMILES: Cc1nn(C)cc1Nc1cc(Nc2cccc3c2C(=O)N(C)CC3)c(F)cn1]

A mixture of 8-[(2-chloro-5-fluoropyridin-4-yl)amino]-2-methyl-3,4-dihydroisoquinolin-1-one (100 mg, 0.33 mmol), 1,3-dimethylpyrazol-4-amine (48 mg, 0.43 mmol), sodium tert-butoxide (51.5 mg, 0.54 mmol) and 9,9-dimethyl-4,5-bis(diphenylphosphino)xanthene (41.4 mg, 0.07 mmol) in anhydrous dioxane (3 mL) was degassed with nitrogen and then bis(dibenzylideneacetone)palladium (32.7 mg, 0.057 mmol) was added. The mixture was heated at 150° C. for 30 minutes in a microwave reactor. MeOH was added and the mixture loaded onto an SCX column. The product was eluted first with MeOH and then with a 7M solution of NH$_3$ in MeOH. Fractions containing product were combined and evaporated. The residue was purified by preparative HPLC and fractions containing product were combined and evaporated to afford example 4.12 (50.1 mg, 40% yield); $^1$H NMR spectrum (300 MHz, DMSO): δ 2.09 (3H, s), 2.95 (2H, t), 3.05 (3H, s), 3.55 (2H, t), 3.70 (3H, s), 6.83-6.85 (2H, m), 7.38-7.43 (2H, m), 7.85 (1H, s), 7.89 (2H, t), 11.24 (1H, s); Mass spectrum: m/z (ESI+) (M+H)$^+$=381.56.

The 8-[(2-chloro-5-fluoropyridin-4-yl)amino]-2-methyl-3,4-dihydroisoquinolin-1-one, used as starting material, was prepared as follows:

(a) 8-amino-2-methyl-3,4-dihydroisoquinolin-1-one (1.369 g, 7.77 mmol), cesium carbonate (5.06 g, 15.54 mmol), 9,9-dimethyl-4,5-bis(diphenylphosphino)xanthene (0.270 g, 0.47 mmol), palladium(II) acetate (0.070 g, 0.31 mmol) were added in order to a mixture of 2-chloro-5-fluoro-4-iodopyridine (2.000 g, 7.77 mmol) in dioxane (150 mL) at 20° C. under an atmosphere of nitrogen. The resulting suspension was heated at 80° C. for 4 hours and then left to stand at room temperature overnight. The mixture was filtered through Celite and the residue washed with $CH_2Cl_2$ (20 mL). The filtrate was evaporated and the residue dissolved in $CH_2Cl_2$ (100 mL) and then washed sequentially with water (2×150 mL) and a saturated solution of NaCl (100 mL). The organic layer was dried over $Na_2SO_4$ and then evaporated to leave a solid. The solid was triturated with $Et_2O$ and then dried under vacuum to afford 8-[(2-chloro-5-fluoropyridin-4-yl)amino]-2-methyl-3,4-dihydroisoquinolin-1-one (2.117 g, 89% yield); $^1H$ NMR spectrum (300 MHz, DMSO): δ 2.97 (2H, t), 3.06 (3H, s), 3.57 (2H, t), 6.97 (1H, dd), 7.42 (1H, d), 7.47-7.49 (2H, m), 8.26 (1H, d), 11.66 (1H, s); Mass spectrum: m/z (ESI+) $(M+H)^+$ =306.39 and 308.36.

The following compounds were prepared in an analogous way to example 4.12.

| # | $R^x$ | Name | $^1H$ NMR spectrum (300 MHz, DMSO): δ | Mass spectrum m/z (ESI+) $(M + H)^+$ |
|---|---|---|---|---|
| 4.13[a] | (R)-5-(2-oxopiperidin-3-yl)pyrazol-1-yl substituent | 8-[[5-fluoro-2-[[1-[(3R)-6-oxopiperidin-3-yl]pyrazol-4-yl]amino]pyridin-4-yl]amino]-2-methyl-3,4-dihydroisoquinolin-1-one | 2.12-2.18 (2H, m), 2.95 (2H, t), 3.05 (3H, s), 3.42-3.53 (2H, m), 3.46-3.50 (2H, dd), 3.57 (2H, t), 4.53-4.60 (1H, m), 6.77 (1H, d), 6.87 (1H, dd), 7.39-7.46 (2H, m), 7.52 (1H, s), 7.94 (1H, s), 7.93-7.97 (1H, m), 8.58 (1H, s), 11.26 (1H, d) | 450.7 |
| 4.14 | 1-methylpyrazol-4-yl | 8-[[5-fluoro-2-[(1-methylpyrazol-4-yl)amino]-4-pyridyl]amino]-2-methyl-3,4-dihydroisoquinolin-1-one | 2.95 (2H, t), 3.05 (3H, s), 3.56 (2H, t), 3.77 (3H, s), 6.76 (1H, d), 6.85-6.86 (1H, m), 7.41 (1H, s), 7.39-7.46 (2H, m), 7.85 (1H, s), 7.93 (1H, d), 8.54 (1H, s), 11.25 (1H, d) | 367.56 |
| 4.15 | 1-(tetrahydropyran-4-yl)pyrazol-4-yl | 8-[[5-fluoro-2-[(1-tetrahydropyran-4-ylpyrazol-4-yl)amino]-4-pyridyl]amino]-2-methyl-3,4-dihydroisoquinolin-1-one | 1.87-1.95 (4H, m), 2.95 (2H, t), 3.05 (3H, s), 3.40-3.49 (2H, m), 3.54 (2H, t), 3.93-3.97 (2H, m), 4.32-4.36 (1H, m), 6.76 (1H, d), 6.85-6.90 (1H, m), 7.37-7.41 (2H, m), 7.43 (1H, t), 7.94 (2H, d), 8.52 (1H, s), 11.25 (1H, d) | 437.68 |
| 4.16 | 1-(1-methyl-4-piperidyl)pyrazol-4-yl | 8[[5-fluoro-2-[[1-(1-methyl-4-piperidyl)pyrazol-4-yl]amino]-4-pyridyl]amino]-2-methyl-3,4-dihydroisoquinolin-1-one | | 450.55 |

[a]The (R)-5-(4-amino-1H-pyrazol-1-yl)piperidin-2-one, used as starting material, was prepared as follows:

a) A solution of DIAD (2.95 mL, 15.00 mmol) in THF (5 mL) was added over a period of 60 minutes to a stirred solution of (S)-5-hydroxypiperidin-2-one (1.382 g, 12.00 mmol), triphenylphosphine (3.93 g, 15.00 mmol) and 4-nitro-1H-pyrazole (1.131 g, 10 mmol) in THF (15 mL) cooled to 0° C., under an atmosphere of nitrogen. The resulting solution was stirred at 0° C. for 1 hour and was then allowed to warm to room temperature and stirred overnight. The reaction mixture was concentrated in vacuo and a mixture of 20% EtOAc in isohexane (60 mL) was added with rapid stirring. The mixture was stirred for 20 minutes and then filtered. The solid was washed first with EtOAc and then with $Et_2O$ and then dried in air to afford (5R)-5-(4-nitropyrazol-1-yl)piperidin-2-one (1.623 g, 77% yield); $^1H$ NMR spectrum (300 MHz, DMSO): δ 2.29 (4H, m), 3.56 (2H, dd), 4.75 (1H, m), 7.59 (1H, s), 8.31 (1H, s), 8.96 (1H, s); Mass spectrum: m/z (ESI+) $(M + H)^+$ = 211.41.

b) A mixture of 10% palladium on carbon (118 mg, 0.11 mmol) and (5R)-5-(4-nitropyrazol-1-yl)piperidin-2-one (1.625 g, 7.73 mmol) in EtOH (50 mL) was stirred under a hydrogen atmosphere for 20 hours. The mixture was filtered through Celite and loaded onto an SCX column. The product was eluted first with MeOH and then with a 0.7M solution of $NH_3$ in MeOH. Fractions containing product were combined and evaporated to afford (R)-5-(4-amino-1H-pyrazol-1-yl)piperidin-2-one (1.343 g, 96% yield); $^1H$ NMR spectrum (300 MHz, DMSO): δ 2.12 (4H, m), 3.35 (2H, dd), 3.76 (2H, s), 4.33 (1H, m), 6.88 (1H, d), 7.03 (1H, d), 7.41 (1H, s, NH); Mass spectrum: m/z (ESI+) $(M + H)^+$ = 181.38.

Example 4.17

8-[[5-Fluoro-2-[[1-(4-piperidyl)pyrazol-4-yl]amino]-4-pyridyl]amino]-2-methyl-3,4-dihydroisoquinolin-1-one

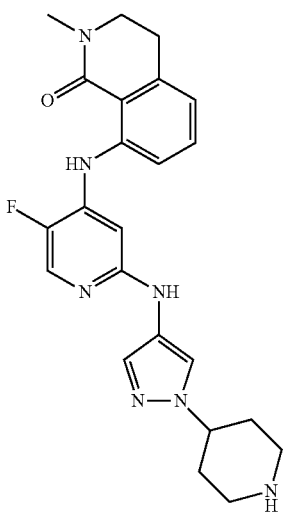

A mixture of 8-[(2-chloro-5-fluoropyridin-4-yl)amino]-2-methyl-3,4-dihydroisoquinolin-1-one (100 mg, 0.33 mmol), tent-butyl 4-(4-aminopyrazol-1-yl)piperidine-1-carboxylate (114 mg, 0.43 mmol), sodium tert-butoxide (51.5 mg, 0.54 mmol) and 9,9-dimethyl-4,5-bis(diphenylphosphino)xanthene (41.4 mg, 0.07 mmol) in anhydrous dioxane (3 mL) was degassed with nitrogen and then bis(dibenzylideneacetone) palladium (32.7 mg, 0.057 mmol) was added. The mixture was heated at 150° C. for 30 minutes in a microwave reactor. MeOH (0.40 mL) was added and the mixture loaded onto an SCX column. The product was eluted first with MeOH and then with a 7M solution of $NH_3$ in MeOH. Fractions containing product were combined and evaporated. The residue was stirred in a solution of HCl in dioxane (2 mL) overnight and then purified directly by preparative HPLC. Fractions containing product were combined and evaporated to afford example 4.17 (1.8 mg, 1% yield); $^1$H NMR spectrum (300 MHz, DMSO): δ 1.70-1.79 (2H, m), 1.89 (2H, d), 2.26-2.28 (2H, m), 2.54 (1H, d), 2.60-2.64 (1H, m), 2.71-2.74 (2H, m), 2.96 (1H, d), 3.00 (1H, s), 3.05 (3H, s), 3.55 (2H, t), 4.06-4.14; Mass spectrum: m/z (ESI+) (M+H)$^+$ =436.63.

The following compounds were prepared in an analogous way to example 4.17.

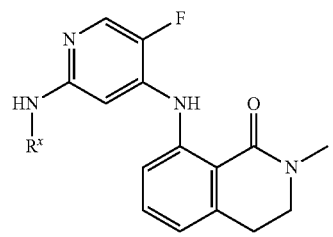

| # | R$^x$ | Name | $^1$H NMR spectrum (300 MHz, DMSO): δ | Mass spectrum m/z (ESI+) (M + H)$^+$ |
|---|---|---|---|---|
| 4.18 | ![pyrazolyl-piperidine] | 8-[[5-fluoro-2-[[1-(3-piperidyl)pyrazol-4-yl]amino]-4-pyridyl]amino]-2-methyl-3,4-dihydroisoquinolin-1-one | 1.50 (1H, t), 1.67 (1H, d), 1.80-1.85 (1H, m), 2.05 (1H, d), 2.26-2.28 (2H, m), 2.95 (2H, t), 3.05 (3H, s), 3.10-3.15 (2H, m), 3.55 (2H, t), 4.01-4.04 (1H, m), 6.75 (1H, dd), 6.86-6.87 (1H, m), 7.35-7.35 (1H, m), 7.41-7.43 (2H, m), 7.92 (1H, s), 7.95 (2H, d), 8.49 (1H, s), 11.25 (1H, s) | 436.14 |

| 4.19[a] | | 8-[[5-fluoro-2-[[1-(4-piperidyl)pyrazol-3-yl]amino]-4-pyridyl]amino]-2-methyl-3,4-dihydroisoquinolin-1-one | 1.72-1.82 (2H, m), 1.89-1.95 (2H, m), 2.26-2.28 (2H, m), 2.61-2.64 (2H, m), 2.96 (2H, t), 3.05 (3H, s), 3.56 (2H, t), 3.97-4.00 (1H, m), 6.01 (1H, d), 6.85-6.88 (1H, m), 7.53 (2H, t), 7.54 (1H, s), 7.87 (1H, d), 7.95 (1H, d), 8.96 (1H, s), 11.44 (1H, s) | 436.7 |
|---|---|---|---|---|

[a]The tert-butyl 4-(3-aminopyrazol-1-yl)piperidine-1-carboxylate, used as starting material, was prepared as follows:
a) DIAD (5.22 mL, 26.53 mmol) was added dropwise to a stirred solution of 3-nitro-1H-pyrazole (2 g, 17.69 mmol), tert-butyl 4-hydroxypiperidine-1-carboxylate (3.56 g, 17.69 mmol) and triphenylphosphine (5.80 mL, 26.53 mmol) in THF (30 mL) cooled to 0° C. under an atmosphere of nitrogen. The resulting solution was stirred at 0° C. for 10 minutes and then allowed to warm to room temperature and stirred overnight. The mixture was diluted with isohexane (80 mL) and EtOAc (20 mL) and stirred vigorously. The mixture was filtered and the residue washed with isohexane (20 mL). The combined filtrates were evaporated and the residue purified by chromatography on silica, eluting with a gradient of 20-100% EtOAc in isohexane. Fractions containing product were combined and evaporated to afford tert-butyl 4-(3-nitropyrazol-1-yl)piperidine-1-carboxylate (0.874 g, 17% yield); $^1$H NMR spectrum (300 MHz, DMSO): δ 1.42 (9H, s), 1.77-1.83 (2H, m), 2.04-2.09 (2H, m), 2.87-2.93 (2H, m), 4.04-4.09 (2H, m), 4.49-4.55 (1H, m), 7.07 (1H, d), 8.13 (1H, d); Mass spectrum: m/z (ESI+) (M-tBu + H)$^+$ = 240.98.
b) tert-butyl 4-(3-nitropyrazol-1-yl)piperidine-1-carboxylate (874 mg, 2.95 mmol), and 10% palladium on carbon (78 mg, 0.074 mmol) in EtOH (20 mL) were stirred under an atmosphere of hydrogen for 18 hours. The mixture was filtered through Celite and the filtrate evaporated. The residue was purified by chromatography on silica, eluting with a gradient of 0 to 10% MeOH in CH$_2$Cl$_2$. Fractions containing product were combined and evaporated to afford tert-butyl 4-(3-aminopyrazol-1-yl)piperidine-1-carboxylate as a CH$_2$Cl$_2$ adduct (820 mg); $^1$H NMR spectrum (300 MHz, DMSO): δ 1.41 (9H, s), 1.64-1.73 (2H, m), 1.88-1.91 (2H, m), 2.81-2.92 (2H, m), 3.97-4.01 (2H, m), 4.49 (2H, s), 5.37 (1H, d), 7.34 (1H, d); Mass spectrum: m/z (ESI+) (M-tBu + H)$^+$ = 211.43.

Example 4.20

8-[[5-Fluoro-2-[[1-(2-oxo-2-pyrrolidin-1-yl-ethyl)pyrazol-4-yl]amino]-4-pyridyl]amino]-2-methyl-3,4-dihydroisoquinolin-1-one

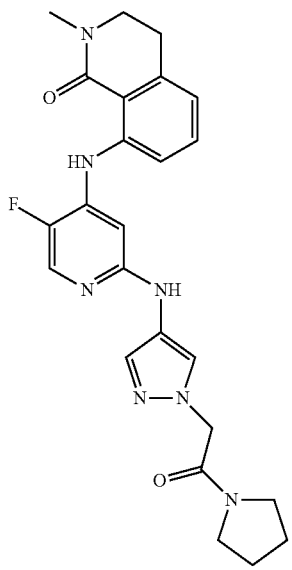 [SMILES: CN1CCc2cccc(Nc3cc(Nc4cnn(CC(=O)N5CCCC5)c4)ncc3F)c2C1=O]

2-[4-[[5-fluoro-4-[(2-methyl-1-oxo-3,4-dihydroisoquinolin-8-yl)amino]pyridin-2-yl]amino]pyrazol-1-yl]acetic acid (50 mg, 0.121 mmol) was dissolved in DMA (4 mL). Pyrrolidine (0.081 mL, 0.974 mmol) was added, followed by a dropwise addition of a solution of HATU (56 mg, 0.146 mmol) in DMA (1 mL). The mixture was stirred at 22° C. for 16 hours and then concentrated in vacuo. The residue was partitioned between CH$_2$Cl$_2$ (10 mL) and water (10 mL). The aqueous layer was separated and then extracted with CH$_2$Cl$_2$ (10 mL). The combined organics were evaporated and the residue was then purified by chromatography on silica, eluting with a mixture of 2-4% MeOH (containing 10% aqueous NH3) in CH$_2$Cl$_2$. Fractions containing product were combined and evaporated to afford example 4.20 (11 mg, 20% yield); $^1$H NMR spectrum (400 MHz, DMSO): δ 1.78 (2H, m), 1.90 (2H, m), 2.96 (2H, t), 3.06 (3H, s), 3.31 (2H, m), 3.46 (2H, m), 3.56 (2H, t), 4.93 (2H, s), 6.79 (1H, d), 6.87 (1H, dd), 7.35 (1H, s), 7.41-7.47 (2H, m), 7.89 (1H, s), 7.95 (1H, d), 8.59 (1H, s), 11.28 (1H, s); Mass spectrum: m/z (ESI+) (M+H)$^+$=464.4.

The 2-[4-[[5-fluoro-4-[(2-methyl-1-oxo-3,4-dihydroisoquinolin-8-yl)amino]pyridin-2-yl]amino]pyrazol-1-yl]acetic acid, used as starting material, was prepared as follows:
a) Reaction performed in 2 batches: sodium tert-butoxide (778 mg, 8.09 mmol) was added to a suspension of 2-(4-aminopyrazol-1-yl)acetic acid dihydrochloride (481 mg, 2.25 mmol) in 1,4-dioxane (15 mL) at 22° C. under an atmosphere of nitrogen. The mixture was stirred and sonicated for 5 minutes and then 8-[(2-chloro-5-fluoropyridin-4-yl)amino]-2-methyl-3,4-dihydroisoquinolin-1-one (275 mg, 0.90 mmol) and 9,9-dimethyl-4,5-bis(diphenylphosphino)xanthene (84 mg, 0.15 mmol) were added and the resulting suspension purged with nitrogen. Tris(dibenzylideneacetone)dipalladium (66 mg, 0.072 mmol) was added and the mixture was purged with nitrogen. The mixture was heated at 150° C. for 60 minutes in a microwave reactor and then allowed to cool to room temperature. The two batches were combined and the mixture was evaporated. The residue was partitioned between CH$_2$Cl$_2$ (150 mL) and a 0.1N solution of NaOH (150 mL). The aqueous layer was separated, washed with CH$_2$Cl$_2$ (100 mL) and then adjusted to pH4 with 2N HCl solution. The aqueous mixture was washed with CH$_2$Cl$_2$ (100 mL), filtered and then evaporated. The residue was triturated with a 1:1 mixture of CH$_2$Cl$_2$/MeOH (150 mL). The mixture was filtered and the residue washed with a 1:1 mixture of CH$_2$Cl$_2$/MeOH. The combined filtrates were evaporated to give 2-[4-[[5-fluoro-4-[(2-methyl-1-oxo-3,4-dihydroisoquinolin-8-yl)amino]pyridin-2-yl]amino]pyrazol-1-yl]acetic acid (400 mg, 54% yield); Mass spectrum: m/z (ESI+) (M+H)$^+$ =411.37.

The following compounds were prepared in an analogous way to example 4.20.

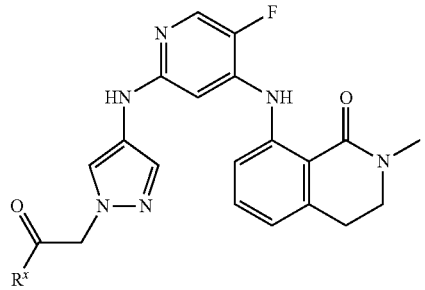

| # | R$^x$ | Name | $^1$H NMR spectrum (400 MHz, DMSO): δ | Mass spectrum m/z (ESI+) (M + H)$^+$ |
|---|---|---|---|---|
| 4.21 | | N-(3-dimethylaminopropyl)-2-[4-[[5-fluoro-4-[(2-methyl-1-oxo-3,4-dihydroisoquinolin-8-yl)amino]-2-pyridyl]amino]pyrazol-1-yl]acetamide | 1.53 (3H, tt), 2.08 (6H, s), 2.21 (2H, t), 2.97 (2H, t), 3.06 (1H, s), 3.11 (2H, dt), 3.57 (3H, t), 4.69 (2H, s), 6.80 (1H, d), 6.88 (1H, dd), 7.40 (1H, d), 7.44-7.47 (2H, m), 7.93 (1H, t), 7.94 (1H, d), 7.96 (1H, d), 8.63 (1H, s), 11.28 (1H, d). | 495.5 |
| 4.22 | | N-(2-dimethylaminoethyl)-2-[4-[[5-fluoro-4-[(2-methyl-1-oxo-3,4-dihydroisoquinolin-8-yl)amino]-2-pyridyl]amino]pyrazol-1-yl]acetamide | 2.19 (6H, s), 2.36 (2H, t), 2.97 (2H, t), 3.06 (3H, s), 3.19 (2H, dt), 3.57 (2H, t), 4.71 (2H, s), 6.80 (1H, d), 6.88 (1H, d), 7.39 (1H, s), 7.42-7.47 (2H, m), 7.87 (1H, t), 7.94 (1H, s), 7.96 (1H, d), 8.62 (1H, s), 11.28 (1H, s) | 481.5 |
| 4.23 | | 2-[4-[[5-fluoro-4-[(2-methyl-1-oxo-3,4-dihydroisoquinolin-8-yl)amino]-2-pyridyl]amino]pyrazol-1-yl]-N-(2-methoxyethyl)acetamide | 2.97 (2H, t), 3.06 (3H, s), 3.28-3.31 (5H, m), 3.37 (2H, t), 3.57 (2H, t), 4.72 (2H, s), 6.80 (1H, d), 6.88 (1H, dd), 7.39 (1H, s), 7.44 (1H, s), 7.45 (1H, d), 7.93 (1H, s), 7.96 (1H, d), 8.03 (1H, t), 8.61 (1H, s), 11.28 (1H, d). | 468.4 |
| 4.24 | | 2-[4-[[5-fluoro-4-[(2-methyl-1-oxo-3,4-dihydroisoquinolin-8-yl)amino]-2-pyridyl]amino]pyrazol-1-yl]-N-(2-methoxyethyl)-N-methyl-acetamide | | 482.5 |
| 4.25 | | 8-[[5-fluoro-2-[[1-(2-morpholino-2-oxo-ethyl)pyrazol-4-yl]amino]-4-pyridyl]amino]-2-methyl-3,4-dihydroisoquinolin-1-one | | 480.5 |
| 4.26 | | 8-[[5-fluoro-2-[[1-[2-(4-methylpiperazin-1-yl)-2-oxo-ethyl]pyrazol-4-yl]amino]-4-pyridyl]amino]-2-methyl-3,4-dihydroisoquinolin-1-one | | 493.5 |

Example 4.27

8-[[5-Fluoro-2-[[1-[2-(3-methylaminopyrrolidin-1-yl)-2-oxo-ethyl]pyrazol-4-yl]amino]-4-pyridyl]amino]-2-methyl-3,4-dihydroisoquinolin-1-one

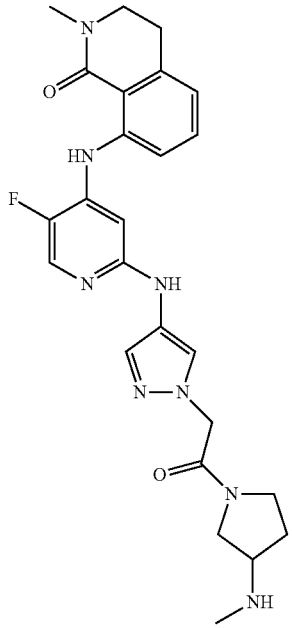 [SMILES: CNC1CCN(C(=O)Cn2cc(Nc3cc(Nc4cccc5c4C(=O)N(C)CC5)c(F)cn3)cn2)C1]

2-[4-[[5-fluoro-4-[(2-methyl-1-oxo-3,4-dihydroisoquinolin-8-yl)amino]pyridin-2-yl]amino]pyrazol-1-yl]acetic acid (50 mg, 0.121 mmol) was dissolved in DMA (4 mL). Tert-butyl N-methyl-N-pyrrolidin-3-ylcarbamate (0.195 g, 0.974 mmol) was added, followed by a dropwise addition of a solution of HATU (56 mg, 0.146 mmol) in DMA (1 mL). The mixture was stirred at 22° C. for 16 hours and then concentrated in vacuo. The residue was partitioned between $CH_2Cl_2$ (10 mL) and water (10 mL). The aqueous layer was separated and then extracted with $CH_2Cl_2$ (10 mL). The combined organics were evaporated and the residue was then purified by chromatography on silica, eluting with a mixture of 2-4% MeOH (containing 10% aqueous NH3) in $CH_2Cl_2$. Fractions containing product were combined and evaporated. The residue was dissolved in a 1:1 mixture of $CH_2Cl_2$/MeOH (5 mL) and 4M HCl in dioxane (1 mL) and the mixture stirred for 16 hours at 22° C. The mixture was evaporated and the residue dissolved in $CH_2Cl_2$/MeOH and loaded onto an SCX column (which had been equilibrated with 30% MeOH in DCM). The product was eluted with a mixture of 30% MeOH in $CH_2Cl_2$ and then with a mixture of 30% MeOH (containing 3M $NH_3$) in $CH_2Cl_2$. Fractions containing product were combined and evaporated to afford example 4.27 (36 mg, 60% yield); Mass spectrum: m/z (ESI+) $(M+H)^+$ =493.5.

Example 4.28

7-[[2-[(1,3-Dimethylpyrazol-4-yl)amino]-5-fluoro-4-pyridyl]amino]-4-(4-isopropylpiperazin-1-yl)-2-methyl-isoindolin-1-one

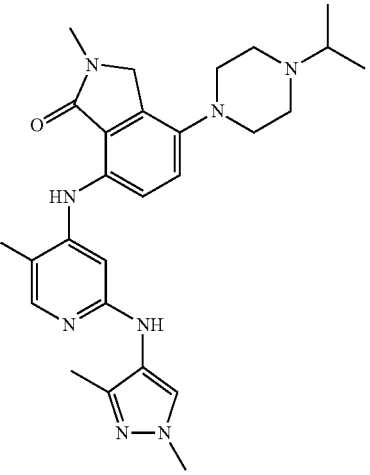

A mixture of 7-[(2-chloro-5-fluoropyridin-4-yl)amino]-2-methyl-4-(4-propan-2-ylpiperazin-1-yl)-3H-isoindol-1-one (150 mg, 0.36 mmol), 1,3-dimethylpyrazol-4-amine (80 mg, 0.72 mmol), cesium carbonate (234 mg, 0.72 mmol), 9,9-dimethyl-4,5-bis(diphenylphosphino)xanthene (24.92 mg, 0.04 mmol) and palladium(II) acetate (6.45 mg, 0.03 mmol) was suspended in DMA (2 mL) under an atmosphere of nitrogen. The mixture was heated at 150° C. for 60 minutes in a microwave reactor and then allowed to cool to room temperature. The mixture was filtered and the filtrate evaporated. The residue was dissolved in MeOH (20 mL) and the solution made acidic (pH6) by the addition of 2M HCl. The mixture was loaded onto an SCX column and the product eluted first with MeOH and then with a 0.7M solution of $NH_3$ in MeOH. Fractions containing product were combined and evaporated and the residue was then purified by preparative HPLC. Fractions containing product were combined and evaporated to afford example 4.28 (45.4 mg, 26% yield); $^1$H NMR spectrum (300 MHz, DMSO): δ 1.02 (6H, d), 2.11 (3H, s), 2.60 (4H, t), 2.70 (1H, m), 2.99 (4H, m), 3.06 (3H, s), 3.70 (3H, s), 4.48 (2H, s), 6.92 (1H, d), 7.15 (1H, d), 7.39 (1H, d), 7.86-7.93 (3H, m), 9.26 (1H, d); Mass spectrum: m/z (ESI+) $(M+H)^+$ =493.44.

The 7-[(2-chloro-5-fluoropyridin-4-yl)amino]-2-methyl-4-(4-propan-2-ylpiperazin-1-yl)-3H-isoindol-1-one, used as starting material, was prepared as follows:
a) Cesium carbonate (960 mg, 2.95 mmol) was added to 7-amino-2-methyl-4-(4-propan-2-ylpiperazin-1-yl)-3H-isoindol-1-one (425 mg, 1.47 mmol), 2-chloro-5-fluoro-4-iodopyridine (379 mg, 1.47 mmol), 9,9-dimethyl-4,5-bis(diphenylphosphino)xanthene (51.2 mg, 0.09 mmol) and palladium(II) acetate (13.23 mg, 0.06 mmol) in dioxane (15 mL) under an atmosphere of nitrogen. The resulting suspension was heated at 80° C. for 18 hours and then allowed to cool to room temperature. The mixture was filtered and then filtrate evaporated. The residue was dissolved in EtOAc (150 mL), and the solution washed sequentially with a saturated solution of $NaHCO_3$ (75 mL), water (75 mL), and finally with a saturated solution of NaCl (75 mL). The organic layer was dried over MgSO₄ and then evaporated. The residue was triturated with Et₂O and dried to afford 7-[(2-chloro-5-fluoropyridin-4-yl)amino]-2-methyl-4-(4-propan-2-ylpiperazin-1-yl)-3H-isoindol-1-one (432 mg, 70% yield); ¹H NMR spectrum (300.132 MHz, CDCl₃): δ 1.11 (6H, d), 2.70 (4H, m), 2.76 (1H, m), 3.07 (4H, m), 3.18 (3H, s), 4.37 (2H, s), 7.14 (1H, d), 7.33-7.41 (2H, m), 8.06 (1H, d), 9.40 (1H, d); Mass spectrum: m/z (ESI+) (M+H)⁺ =418.31.

Example 4.29

3-[[5-Fluoro-4-[(2-methyl-1-oxo-3,4-dihydroisoquinolin-8-yl)amino]-2-pyridyl]amino]-5-(4-methylpiperazin-1-yl)-1H-pyrazole-4-carbonitrile

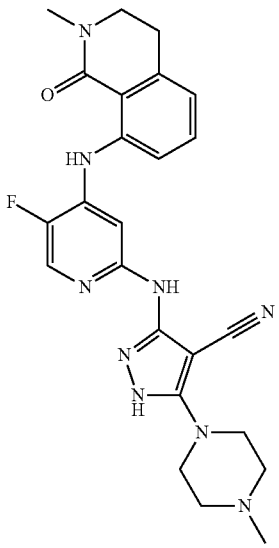 [SMILES: CN1CCN(c2[nH]nc(Nc3cc(Nc4cccc5c4C(=O)N(C)CC5)c(F)cn3)c2C#N)CC1]

A mixture of 3-amino-5-(4-methylpiperazin-1-yl)-1H-pyrazole-4-carbonitrile (68 mg, 0.33 mmol), 8-[(2-chloro-5-fluoropyridin-4-yl)amino]-2-methyl-3,4-dihydroisoquinolin-1-one (100 mg, 0.33 mmol), 9,9-dimethyl-4,5-bis(diphenylphosphino)xanthene (23 mg, 0.04 mmol), palladium(II) acetate (6 mg, 0.026 mmol) and cesium carbonate (215 mg, 0.66 mmol) in DMA (2 mL) was heated for 1 hour in a microwave reactor. The mixture was allowed to cool to room temperature, diluted with DMA and then loaded onto an SCX column. The mixture was eluted first with water followed by MeOH before eluting with a 0.7N solution of NH₃ in MeOH. Fractions containing product were combined and evaporated. The residue was purified by preparative HPLC and fractions containing product were combined and evaporated to afford example 4.29; ¹H NMR spectrum (300.132 MHz, DMSO): δ 2.20 (3H, s), 2.41 (4H, t), 2.98 (2H, t), 3.06 (3H, s), 3.29 (4H?, m, concealed under water peak), 3.58 (2H, t), 6.97 (1H, dd), 7.44-7.51 (2H, m), 7.76 (1H, d), 7.96 (2H, s), 8.25 (1H, d), 11.56 (1H, d); Mass spectrum: m/z (ESI+) (M+H)⁺ =476.76.

The 3-amino-5-(4-methylpiperazin-1-yl)-1H-pyrazole-4-carbonitrile, used as starting material, can be prepared as described in the literature (Tomcufcik, A. S.; Meyer, W. E.; Tseng, S. S. Pyrazolylpiperazines. U.S. Pat. No. 4,562,189).

Example 5.01

8-[[2-[(1,3-dimethylpyrazol-4-yl)amino]-5-(trifluoromethyl)-4-pyridyl]amino]-2-methyl-3,4-dihydroisoquinolin-1-ne

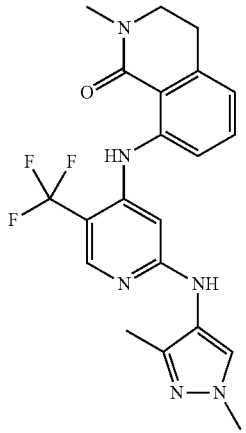 [SMILES: Cc1nn(C)cc1Nc1cc(Nc2cccc3c2C(=O)N(C)CC3)c(C(F)(F)F)cn1]

A suspension of 8-amino-2-methyl-3,4-dihydroisoquinolin-1-one (23.06 mg, 0.13 mmol), N-(1,3-dimethylpyrazol-4-yl)-4-iodo-5-(trifluoromethyl)pyridin-2-amine (50 mg, 0.13 mmol, Ex. 2.02), palladium(II) acetate (1.469 mg, 6.54 µmol), 9,9-dimethyl-4,5-bis(diphenylphosphino)xanthene (7.57 mg, 0.01 mmol) and cesium carbonate (85 mg, 0.26 mmol) in dioxane (1 ml) was stirred at 80° C. overnight under nitrogen. The same reactants were dissolved in DMA (1 mL) and sealed into a microwave tube. Argon was bubbled through the reaction mixture then the reaction was heated to 150° C. over a period of 30 minutes in a microwave reactor. The crudes were combined, poured onto a silica gel column and purified by flash chromatography eluting with 0 to 5% MeOH in EtOAc/DCM (1:1). The solvent was evaporated to dryness. Trituration with a few drops of MeCN gave a solid which was taken up into Et₂O, collected by filtration and dried to afford the title compound (19 mg, 33.7%) as a white solid. ¹H NMR spectrum (500 MHz, CDCl₃): 2.16 (s, 3H), 2.90-2.99 (m, 2H), 3.14 (s, 3H), 3.51-3.58 (m, 2H), 3.79 (s, 3H), 5.94 (s, 1H), 6.42 (s, 1H), 6.90 (d, 1H), 7.20 (dd, 1H), 7.29 (d, 1H), 7.37 (s, 1H), 8.26 (s, 1H), 11.13 (s, 1H); Mass spectrum: ESI+ MH⁺ 431.

Example 5.02

2-[[2-[(1,3-dimethylpyrazol-4-yl)amino]-5-(trifluoromethyl)-4-pyridyl]amino]-6-methoxy-N-methylbenzamide

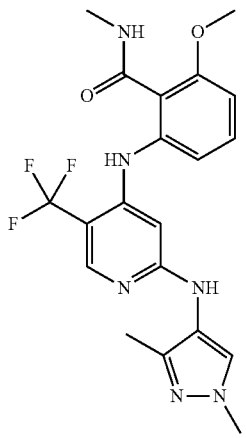 [SMILES: CNC(=O)c1c(Nc2cc(Nc3cn(C)nc3C)ncc2C(F)(F)F)cccc1OC]

A suspension of 2-amino-6-methoxy-N-methylbenzamide (2.48 g, 13.8 mmol), N-(1,3-dimethylpyrazol-4-yl)-4-iodo-5-(trifluoromethyl)pyridin-2-amine (2.63 g, 6.88 mmol), palladium(II) acetate (0.077 g, 0.34 mmol), 9,9-dimethyl-4,5-bis(diphenylphosphino)xanthene (0.398 g, 0.69 mmol) and cesium carbonate (4.48 g, 13.77 mmol) in dioxane (37 mL) was degassed with argon and stirred at 100° C. for 3 hours. The reaction mixture was concentrated to dryness, diluted with EtOAc (80 ml), washed with water (1×50 ml) and brine, dried over magnesium sulfate and concentrated to afford an oil. The crude product was purified by flash chromatography on silica gel eluting with EtOAc and then 3 to 8% MeOH in EtOAc. The solvent was evaporated to dryness to afford a foam which was dissolved in DCM (12 ml). A solid formed after a few minutes and this was filtered and dried to give the title compound as a white solid (1.570 g, 52.5%). $^1$H NMR spectrum (500 MHz, CDCl$_3$): 2.15 (s, 3H), 2.97 (d, 3H), 3.79 (s, 3H), 3.91 (s, 3H), 5.99 (s, 1H), 6.32 (s, 1H), 6.56 (d, 1H), 7.05 (d, 1H), 7.20 (dd, 1H), 7.34 (s, 1H), 7.44 (q, 1H), 8.23 (s, 1H), 10.56 (s, 1H); Mass spectrum: ESI+435.

The most prominent X-ray powder diffraction peaks for this crystalline material are listed below:

| Angle 2-Theta ° | Intensity % |
|---|---|
| 2.656 | 14.7 |
| 5.952 | 10.6 |
| 6.004 | 8.4 |
| 7.509 | 19 |
| 7.819 | 12.1 |
| 9.194 | 29.4 |
| 9.878 | 44.4 |
| 12.661 | 24 |
| 13.231 | 22.7 |
| 14.05 | 14.6 |
| 14.399 | 57.2 |
| 14.869 | 42.1 |
| 14.98 | 36.5 |
| 15.66 | 100 |
| 15.865 | 43.8 |
| 16.05 | 31.3 |
| 16.958 | 24.9 |
| 17.844 | 15.6 |
| 17.893 | 18.8 |
| 18.429 | 53.6 |
| 18.762 | 36.2 |
| 19.343 | 14.5 |
| 19.849 | 40 |
| 20.098 | 45.2 |
| 20.417 | 27.3 |
| 20.52 | 29.7 |
| 21.181 | 57.2 |
| 21.255 | 56.7 |
| 21.765 | 38 |
| 22.287 | 26 |
| 22.555 | 18.6 |
| 22.572 | 17.6 |
| 22.793 | 34 |
| 23.513 | 23.2 |
| 23.657 | 32.5 |
| 24.153 | 13.8 |
| 24.99 | 21.1 |
| 25.047 | 18.9 |
| 25.367 | 24.3 |
| 25.435 | 29.5 |
| 25.686 | 27.6 |
| 26.097 | 17.8 |
| 26.644 | 15.6 |
| 26.805 | 22.8 |
| 27.774 | 22.4 |
| 27.815 | 23.2 |
| 28.088 | 16.2 |
| 28.678 | 15.3 |
| 30.34 | 10.1 |
| 33.009 | 8.9 |
| 33.026 | 9.3 |
| 39.597 | 7.4 |

2-Amino-6-methoxy-N-methylbenzamide used as starting material was prepared as follows:

Phosgene (4.72 ml, 8.97 mmol; 20% in toluene) was added dropwise to a solution of 2-amino-6-methoxybenzoic acid (1 g, 5.98 mmol) in 2N aqueous sodium hydroxide (6.28 ml, 12.56 mmol) and water (15 ml) cooled to 0° C. over a period of 15 minutes, maintaining the temperature at 0-5° C. The resulting suspension was stirred at 0° C. for 15 minutes. The precipitate was collected by filtration, washed with water, followed by a small amount of acetonitrile and ether and dried under vacuum at 40° C. to afford 5-methoxy-1H-3,1-benzoxazine-2,4-dione (0.760 g, 65.8%) as a beige solid. 40% aqueous methylamine (1.57 ml, 18.1 mmol) was added to a stirred suspension of 5-methoxy-1H-3,1-benzoxazine-2,4-dione (700 mg, 3.62 mmol;) in water (5 ml). The resulting solution was stirred at room temperature for 36 hours. The mixture was diluted with EtOAc, washed sequentially with saturated aqueous sodium carbonate, water and brine. The organic layer was dried over MgSO$_4$ and evaporated to afford 2-amino-6-methoxy-N-methylbenzamide (457 mg, 70.0%) as a white solid. $^1$H NMR spectrum (500 MHz, DMSO): 2.73 (d, 3H), 3.73 (s, 3H), 5.79 (bs, 2H), 6.19 (d, 1H), 6.30 (d, 1H), 6.99 (dd, 1H), 7.98 (q, 1H).

Example 5.03

6-[[2-[(1,3-dimethylpyrazol-4-yl)amino]-5-(trifluoromethyl)-4-pyridyl]amino]-4-methyl-2,3-dihydro-1,4-benzoxazepin-5-one

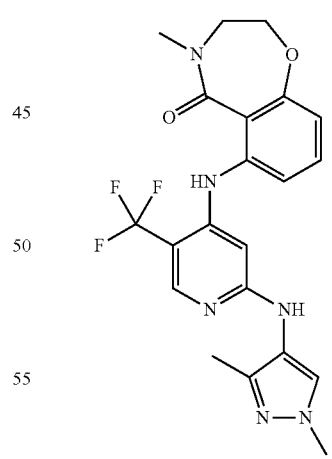

6-Amino-4-methyl-2,3-dihydro-1,4-benzoxazepin-5-one (151 mg, 0.79 mmol, see Example 3.22) and N-(1,3-dimethylpyrazol-4-yl)-4-iodo-5-(trifluoromethyl)pyridin-2-amine (150 mg, 0.39 mmol) were reacted using the procedure in Example 5.02. The reaction mixture was purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent, followed by flash chromatography on silica gel eluting with 0 to 5% MeOH in EtOAc/DCM (1:1). The solvent was evaporated to dryness and triturated in a mixture of 30% tBuOMe in pentane to give the title compounds as a light white foam (95 mg, 54%). $^1$H NMR spectrum (500 MHz, CDCl$_3$): 2.15 (s, 3H), 3.21 (s, 3H), 3.50 (t, 2H), 3.81 (s, 3H), 4.35 (t, 2H), 6.19 (s, 1H), 6.30 (s, 1H), 6.70 (dd, 1H), 7.19 (dd, 1H), 7.23 (dd, 1H), 7.38 (s, 1H), 8.20 (s, 1H), 9.21 (s, 1H); Mass spectrum: ESI+ MH$^+$ 447.

Example 6.01

8-[[5-chloro-2-[(2-methylpyrazol-3-yl)amino]-4-pyridyl]amino]-2-methyl-3,4-dihydroisoquinolin-1-one

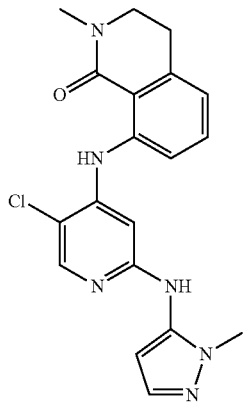 [SMILES: CN1CCc2cccc(Nc3cc(Nc4ccnn4C)ncc3Cl)c2C1=O]

8-[(2,5-Dichloropyridin-4-yl)amino]-2-methyl-3,4-dihydroisoquinolin-1-one (100 mg, 0.31 mmol, example 3.23), 1-Methylpyrazol-5-amine (60.3 mg, 0.62 mmol), cesium carbonate (121 mg, 0.37 mmol), 9,9-dimethyl-4,5-bis(diphenylphosphino)xanthene (28.7 mg, 0.05 mmol) and palladium (II) acetate (5.57 mg, 0.02 mmol) were suspended in dioxane (2 mL) and sealed in a tube. The reaction was degased, purged with nitrogen and heated to 100° C. for 12 hours. The reaction mixture was filtered, washed with DCM and concentrated to dryness. The reaction mixture was purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness to afford 8-(5-chloro-2-(1-methyl-1H-pyrazol-5-ylamino)pyridin-4-ylamino)-2-methyl-3,4-dihydroisoquinolin-1(2H)-one (83 mg, 69.8%) as a grey solid. $^1$H NMR spectrum (500 MHz, DMSO): 2.95 (t, 2H), 3.05 (s, 3H), 3.56 (t, 2H), 3.63 (s, 3H), 6.19 (d, 1H), 6.86 (s, 1H), 6.91 (dd, 1H), 7.29 (d, 1H), 7.42 (s, 1H), 7.43 (d, 1H), 8.02 (s, 1H), 8.68 (s, 1H), 11.26 (s, 1H); Mass spectrum: ESI+ MH$^+$ 383.

The following examples were made by reaction of 8-[(2,5-dichloropyridin-4-yl)amino]-2-methyl-3,4-dihydroisoquinolin-1-one and the corresponding aminoheteroaryl using the procedure above, except that the mixture was heated for 18 hours:

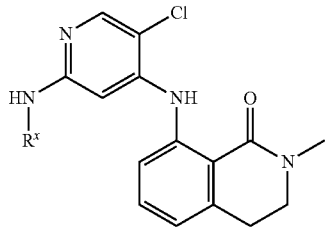

| # | R$^x$ | Name | Mass spectrum: ESI+ MH$^+$ | $^1$H NMR spectrum (500 MHz, DMSO) |
|---|---|---|---|---|
| 6.02 | | 8-[[5-chloro-2-[(2,5-dimethylpyrazol-3-yl)amino]-4-pyridyl]amino]-2-methyl-3,4-dihydroisoquinolin-1-one | 397 | 2.08 (s, 3H), 2.96 (t, 2H), 3.06 (s, 3H), 3.55 (s, 3H), 3.56 (t, 2H), 6.01 (s, 1H), 6.86 (s, 1H), 6.92 (dd, 1H), 7.39-7.48 (m, 2H), 8.02 (s, 1H), 8.64 (s, 1H), 11.26 (s, 1H) |
| 6.03 | | 8-[[5-chloro-2-[(1,5-dimethylpyrazol-4-yl)amino]-4-pyridyl]amino]-2-methyl-3,4-dihydroisoquinolin-1-one | 397 | 2.12 (s, 3H), 2.94 (t, 2H), 3.05 (s, 3H), 3.55 (t, 2H), 3.69 (s, 3H), 6.61 (s, 1H), 6.87 (d, 1H), 734-7.42 (m, 2H), 7.43 (s, 1H), 7.91 (s, 1H), 7.92 (s, 1H), 11.14 (s, 1H) |

-continued

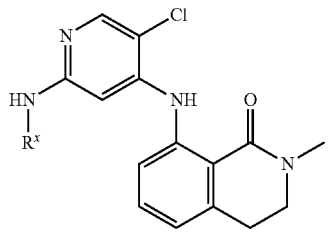

| # | R$^x$ | Name | Mass spectrum: ESI+ MH$^+$ | $^1$H NMR spectrum (500 MHz, DMSO) |
|---|---|---|---|---|
| 6.04$^a$ | (1-ethyl-3-methyl-pyrazol-4-yl) | 8-[[5-chloro-2-[(1-ethyl-3-methyl-pyrazol-4-yl)amino]-4-pyridyl]amino]-2-methyl-3,4-dihydroisoquinolin-1-one | 411 | 1.32 (t, 3H), 2.09 (s, 3H), 2.95 (t, 2H), 3.05 (s, 3H), 2.56 (t, 2H), 3.99 (q, 2H), 6.79 (s, 1H), 6.89 (dd, 1H), 7.39-7.44 (m, 2H), 7.87 (s, 1H), 7.97 (s, 1H), 8.02 (s, 1H), 11.19 (s, 1H) |
| 6.05 | (5-cyclopropyl-2-methyl-pyrazol-3-yl) | 8-[[5-chloro-2-[(5-cyclopropyl-2-methyl-pyrazol-3-yl)amino]-4-pyridyl]amino]-2-methyl-3,4-dihydroisoquinolin-1-one | 423 | 0.56-0.62 (m, 2H), 0.77-0.84 (m, 2H), 1.73-1.81 (m, 1H), 2.96 (t, 2H), 3.05 (s, 3H), 3.54 (s, 3H), 3.56 (t, 2H), 5.92 (s, 1H), 6.84 (s, 1H), 6.92 (dd, 1H), 7.42 (d, 1H), 7.43 (s, 1H), 802 (s, 1H), 8.62 (bs, 1H), 11.25 (s, 1H) |
| 6.06 | (2-ethylpyrazol-3-yl) | 8-[[5-chloro-2-[(2-ethylpyrazol-3-yl)amino]-4-pyridyl]amino]-2-methyl-3,4-dihydroisoquinolin-1-one | 397 | 1.26 (t, 3H), 2.96 (t, 2H), 3.06 (s, 3H), 3.56 (t, 2H), 3.99 (q, 2H), 6.20 (d, 1H), 6.84 (s, 1H), 6.90 (dd, 1H), 7.34 (d, 1H), 7.39-7.46 (m, 2H), 8.02 (s, 1H), 8.60 (bs, 1H), 11.26 (s, 1H) |

-continued

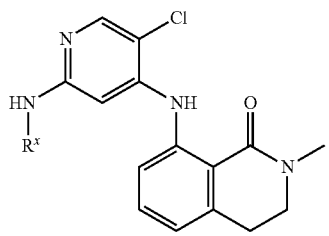

| # | R$^x$ | Name | Mass spectrum: ESI+ MH$^+$ | $^1$H NMR spectrum (500 MHz, DMSO) |
|---|---|---|---|---|
| 6.07 | | 8-[[5-chloro-2-[(1-methylpyrazol-3-yl)amino]-4-pyridyl]amino]-2-methyl-3,4-dihydroisoquinolin-1-one | 383 | 2.97 (t, 2H), 3.07 (s, 3H), 3.57 (t, 2H), 3.72 (s, 3H), 6.07 (d, 1H), 6.91 (d, 1H), 7.47 (dd, 1H), 7.49 (s, 1 H), 7.56 (d, 1H), 7.78 (s, 1H), 8.01 (s, 1H), 9.13 (s, 1H), 11.36 (s, 1H) |
| 6.08 | | 8-[[2-[(2-tert-butyl-5-ethyl-4-methyl-pyrazol-3-yl)amino]-5-chloro-4-pyridyl]amino]-2-methyl-3,4-dihydroisoquinolin-1-one | 467 | 1.12 (t, 3H), 1.45 (s, 9H), 1.71 (s, 3H), 2.46 (q, 2H), 2.94 (t, 2H), 3.05 (s, 3H), 3.55 (t, 2H), 6.87 (d, 1H), 7.24 (bs, 1H), 7.33 (dd, 1H), 7.39 (d, 1H), 7.97 (s, 1H), 8.12 (s, 1H), 11.23 (s, 1H) |
| 6.09 | | 8-[[5-chloro-2-[(1-isobutylpyrazol-4-yl)amino]-4-pyridyl]amino]-2-methyl-3,4-dihydroisoquinolin-1-one | 425 | 0.84 (d, 6H), 2.04-2.14 (m, 1H), 2.98 (t, 2H), 3.06 (s, 3H), 3.58 (t, 2H), 3.87 (d, 2H), 6.75 (s, 1H), 6.99 (d, 1H), 7.41-7.48 (m, 3H), 7.88 (s, 1H), 8.05 (s, 1H), 9.02 (bs, 1H), 11.53 (bs, 1H) |

$^a$1-ethyl-3-methylpyrazol-4-amine hydrochloride salt was used instead of the free base and cesium carbonate (303 mg, 0.93 mmol, 3 equivalents compared to 8-[(2,5-dichloropyridin-4-yl)amino]-2-methyl-3,4-dihydroisoquinolin-1-one) was used.

Example 8.01

N-methyl-2-[[2-[(2-methylpyrazol-3-yl)amino]-5-(trifluoromethyl)-4-pyridyl]amino]benzamide

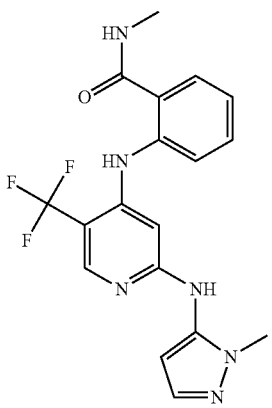 [SMILES: CNC(=O)c1ccccc1Nc1cc(Nc2ccnn2C)ncc1C(F)(F)F]

2-[[2-chloro-5-(trifluoromethyl)pyridin-4-yl]amino]-N-methylbenzamide (100 mg, 0.30 mmol, Example 2.01), 1-methylpyrazol-5-amine (58.9 mg, 0.61 mmol), cesium carbonate (119 mg, 0.36 mmol), 9,9-dimethyl-4,5-bis(diphenylphosphino)xanthene (28.1 mg, 0.05 mmol) and palladium (II) acetate (5.45 mg, 0.02 mmol) were suspended in dioxane (1.5 mL) in a sealed tube. The reaction was degased, purged with nitrogen and heated to 100° C. for 18 hours. The reaction mixture was filtered and purified by preparative HPLC using a Waters X-Bridge reverse-phase column (C-18, 5 microns silica, 19 mm diameter, 100 mm length, flow rate of 40 ml/minute) and decreasingly polar mixtures of water (containing 0.2% ammonium carbonate) and acetonitrile as eluent. The fractions containing the desired compound were evaporated to dryness to afford the title compound (62 mg, 52.4%) as a pale orange solid. $^1$H NMR spectrum (500 MHz, DMSO): 2.77 (d, 3H), 3.63 (s, 3H), 6.21 (d, 1H), 6.70 (s, 1H), 7.13 (ddd, 1H), 7.32 (d, 1H), 7.49 (ddd, 1H), 7.55 (d, 1H), 7.71 (dd, 1H), 8.25 (s, 1H), 8.68 (q, 1H), 9.03 (s, 1H), 10.20 (s, 1H); Mass spectrum: ESI+ MH$^+$ 391.

The following examples were made by reaction of 2-[[2-chloro-5-(trifluoromethyl)pyridin-4-yl]amino]-N-methyl-benzamide and the corresponding aminoheteroaryl using the procedure above:

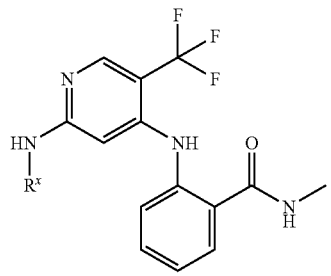

| # | Rx | Name | Mass spectrum: ESI+ MH$^+$ | $^1$H NMR spectrum (500 MHz, DMSO) |
|---|---|---|---|---|
| 8.02$^a$ | | 2-[[2-[(2,5-dimethylpyrazol-3-yl)amino]-5-(trifluoromethyl)-4-pyridyl]amino]-N-methyl-benzamide | 405 | 2.08 (s, 3H), 2.76 (d, 3H), 3.54 (s, 3H), 6.01 (s, 1H), 6.70 (s, 1H), 7.13 (dd, 1H), 7.50 (dd, 1H), 7.56 (d, 1H), 7.71 (d, 1H), 8.24 (s, 1H), 8.68 (q, 1H), 8.99 (s, 1H), 10.19 (s, 1H) |
| 8.03 | | 2-[[2-[(1,5-dimethylpyrazol-4-yl)amino]-5-(trifluoromethyl)-4-pyridyl]amino]-N-methyl-benzamide | 405 | 2.11 (s, 3H), 2.76 (d, 3H), 3.69 (s, 3H), 6.46 (bs, 1H), 7.08 (dd, 1H), 7.43 (s, 1H), 7.46 (d, 1H), 7.50 (d, 1H), 7.69 (d, 1H), 8.16 (s, 1H), 8.35 (s, 1H), 8.65 (q, 1H), 10.08 (s, 1H) |
| 8.04$^b$ | | 2-[[2-[(1-ethyl-3-methyl-pyrazol-4-yl)amino]-5-(trifluoromethyl)-4-pyridyl]amino]-N-methyl-benzamide | 419 | 1.31 (t, 3H), 2.07 (s, 3H), 2.76 (d, 3H), 3.99 (q, 2H), 6.62 (bs, 1H), 7.09 (dd, 1H), 7.47 (dd, 1H), 7.52 (d, 1H), 7.70 (d, 1H), 7.88 (s, 1H), 8.20 (s, 1H), 8.41 (s, 1H), 8.66 (q, 1H), 10.11 (s, 1H) |

-continued

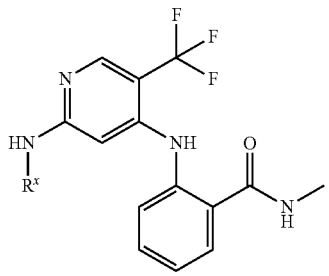

| # | Rx | Name | Mass spectrum: ESI+ MH+ | $^1$H NMR spectrum (500 MHz, DMSO) |
|---|---|---|---|---|
| 8.05[b] | (1-ethyl-pyrazol-4-yl) | 2-[[2-[(1-ethylpyrazol-4-yl)amino]-5-(trifluoromethyl)-4-pyridyl]amino]-N-methyl-benzamide | 405 | 1.34 (t, 3H), 2.77 (d, 3H), 4.07 (q, 2H), 6.61 (s, 1H), 7.10 (dd, 1H), 7.39 (s, 1H), 7.48 (dd, 1H), 7.56 (d, 1H), 7.71 (d, 1H), 7.90 (s, 1H), 8.24 (s, 1H), 8.67 (q, 1H), 9.03 (bs, 1H), 10.13 (s, 1H) |
| 8.06 | (1-ethyl-pyrazol-3-yl) | 2-[[2-[(1-ethylpyrazol-3-yl)amino]-5-(trifluoromethyl)-4-pyridyl]amino]-N-methyl-benzamide | 405 | 1.27 (t, 3H), 2.77 (d, 3H), 3.95 (q, 2H), 6.09 (s, 1H), 7.11 (ddd, 1H), 7.49 (ddd, 1H), 7.54 (d, 1H), 7.62 (d, 1H), 7.63 (bs, 1H), 7.70 (dd, 1H), 8.23 (s, 1H), 8.68 (q, 1H), 9.52 (s, 1H), 10.28 (s, 1H) |
| 8.07 | (5-cyclopropyl-2-methyl-pyrazol-3-yl) | 2-[[2-[(5-cyclopropyl-2-methyl-pyrazol-3-yl)amino]-5-(trifluoromethyl)-4-pyridyl]amino]-N-methyl-benzamide | 431 | 0.54-0.60 (m, 2H), 0.76-0.84 (m, 2H), 1.72-1.80 (m, 1H), 2.75 (d, 3H), 3.52 (s, 3H), 5.91 (s, 1H), 6.66 (s, 1H), 7.13 (ddd, 1H), 7.48 (ddd, 1H), 7.55 (d, 1H), 7.70 (dd, 1H), 8.23 (s, 1H), 8.67 (q, 1H), 8.97 (s, 1H), 10.17 (s, 1H) |
| 8.08 | (2-ethyl-pyrazol-3-yl) | 2-[[2-[(2-ethylpyrazol-3-yl)amino]-5-(trifluoromethyl)-4-pyridyl]amino]-N-methyl-benzamide | 405 | 1.24 (t, 3H), 2.76 (d, 3H), 3.96 (q, 2H), 6.19 (s, 1H), 6.66 (s, 1H), 7.11 (dd, 1H), 7.35 (d, 1H), 7.47 (dd, 1H), 7.53 (d, 1H), 7.70 (d, 1H), 8.23 (s, 1H), 8.68 (q, 1H), 8.96 (s, 1H), 10.20 (s, 1H) |
| 8.09 | (1-isobutyl-pyrazol-4-yl) | 2-[[2-[(1-isobutylpyrazol-4-yl)amino]-5-(trifluoromethyl)-4-pyridyl]amino]-N-methyl-benzamide | 433 | 0.81 (d, 6H), 2.01-2.12 (m, 1H), 2.76 (d, 3H), 3.84 (d, 2H), 6.59 (s, 1H), 7.09 (ddd, 1H), 7.39 (s, 1H), 7.46 (ddd, 1H), 7.54 (d, 1H), 7.70 (dd, 1H), 7.87 (s, 1H), 8.24 (s, 1H), 8.66 (q, 1H), 9.02 (bs, 1H), 10.14 (s, 1H) |

-continued

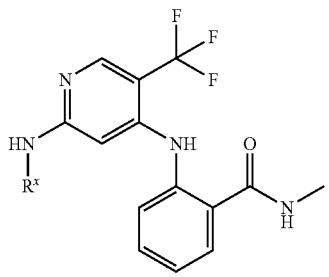

| # | Rx | Name | Mass spectrum: ESI+ MH+ | ¹H NMR spectrum (500 MHz, DMSO) |
|---|---|---|---|---|
| 8.10 | (1,3,5-trimethylpyrazol-4-yl) | N-methyl-2-[[5-(trifluoromethyl)-2-[(1,3,5-trimethylpyrazol-4-yl)amino]-4-pyridyl]amino]benzamide | 419 | 1.92 (s, 3H), 2.02 (s, 3H), 2.75 (d, 3H), 3.60 (s, 3H), 6.17 (bs, 1H), 7.07 (dd, 1H), 7.43 (bs, 2H), 6.67 (d, 1H), 8.13 (d, 1H), 8.14 (s, 1H), 8.64 (q, 1H), 10.05 (s, 1H) |
| 8.11[c] | (1-isopropylpyrazol-4-yl) | 2-[[2-[(1-isopropylpyrazol-4-yl)amino]-5-(trifluoromethyl)-4-pyridyl]amino]-N-methyl-benzamide | 419 | 1.37 (d, 6H), 2.76 (d, 3H), 4.38-4.47 (m, 1H), 6.59 (s, 1H), 7.09 (ddd, 1H), 7.38 (s, 1H), 7.47 (ddd, 1H), 7.55 (d, 1H), 7.70 (dd, 1H), 7.90 (s, 1H), 8.24 (s, 1H), 8.66 (q, 1H), 8.99 (bs, 1H), 10.12 (s, 1H) |
| 8.12[d] | (1-methyl-3-(trifluoromethyl)pyrazol-4-yl) | N-methyl-2-[[2-[[1-methyl-3-(trifluoromethyl)pyrazol-4-yl]amino]-5-(trifluoromethyl)-4-pyridyl]amino]benzamide | 459 | 2.76 (d, 3H), 3.89 (s, 3H), 6.84 s, 1H), 7.11 (ddd, 1H), 7.46-7.55 (m, 2H), 7.71 (dd, 1H), 8.22 (s, 2H), 8.59 (s, 1H), 8.68 (q, 1H), 10.20 (bs, 1H) |

The most prominent X-ray powder diffraction peaks for this crystalline material are listed below:

| Angle 2-Theta ° | Intensity % |
|---|---|
| 6.889 | 34.2 |
| 9.872 | 3.4 |
| 10.948 | 1.9 |
| 11.612 | 19.1 |
| 11.953 | 61.8 |
| 13.708 | 13.6 |
| 13.903 | 4.4 |
| 14.588 | 16.5 |
| 14.907 | 15.8 |
| 15.897 | 3 |
| 16.362 | 13.9 |
| 16.498 | 8.7 |
| 18.509 | 7.9 |
| 19.502 | 23.3 |
| 19.635 | 26.3 |
| 20.043 | 5.7 |
| 20.085 | 5.4 |
| 20.487 | 62.1 |
| 20.595 | 100 |
| 21.301 | 10.2 |
| 21.475 | 25 |
| 21.528 | 17.9 |
| 21.637 | 10.7 |
| 21.85 | 18.1 |
| 22.258 | 5.9 |
| 22.321 | 7.7 |
| 22.387 | 8.8 |
| 22.447 | 5.7 |
| 22.604 | 5 |
| 22.675 | 3.6 |
| 23.078 | 3.1 |
| 23.139 | 3.6 |
| 23.804 | 5.9 |
| 23.861 | 4.4 |
| 24.232 | 6 |
| 24.284 | 9.7 |
| 24.334 | 10.3 |
| 24.4 | 8.3 |
| 24.627 | 3 |
| 24.845 | 4 |
| 25.118 | 4.3 |
| 25.319 | 6.2 |
| 25.379 | 5.5 |
| 25.797 | 16.6 |

151
-continued

| Angle 2-Theta ° | Intensity % |
|---|---|
| 26.084 | 8.7 |
| 26.165 | 6.9 |
| 26.474 | 3 |
| 26.93 | 3.7 |
| 27.14 | 3.4 |
| 27.26 | 3.4 |
| 27.324 | 2.3 |
| 28.064 | 3 |
| 28.139 | 4.7 |
| 28.302 | 4.1 |
| 28.975 | 2.4 |
| 29.013 | 2.5 |
| 29.913 | 7.6 |
| 29.958 | 7.5 |
| 30.055 | 5.3 |
| 30.318 | 2.1 |
| 30.517 | 4.1 |
| 30.573 | 5 |
| 30.66 | 4.5 |
| 31.092 | 2.2 |
| 32.116 | 2.5 |
| 32.564 | 6.4 |
| 32.644 | 2.6 |
| 33.426 | 3.1 |
| 33.495 | 2.4 |
| 33.676 | 2.3 |
| 33.807 | 5.7 |
| 33.895 | 3.6 |
| 34.593 | 3.3 |
| 34.954 | 4.4 |
| 35.427 | 2.2 |
| 35.851 | 1.6 |
| 36.337 | 2.5 |
| 36.44 | 2.4 |
| 37.056 | 1.7 |
| 38.205 | 2 |
| 38.753 | 3.3 |
| 38.886 | 3 |
| 39.346 | 3 |
| 39.607 | 2.2 |

The filtrate was concentrated to dryness and the residue was purified by preparative HPLC using a Waters X-Bridge reverse-phase column (5 microns silica, 30 mm diameter, 150 mm length) and decreasingly polar mixtures of water (containing 0.2% ammonium carbonate) and acetonitrile as eluent. The fractions were evaporated to dryness and the remaining solid was crystallised from acetonitrile. The resulting crystalline solid was collected by filtration, washed with acetonitrile and dried to a constant weight in a vacuum oven at 60° C. to afford more title compound (0.309 g, 0.764 mmol, 7.50%) as a white solid.

152
Example 10

NMR spectra in Examples 10.01 to 10.13 were recorded on a NMR Spectrometer JEOL Eclipse270 working at 270 MHz (at about 20° C.).

Example 10.01

2-[[2-[(1,3-dimethylpyrazol-4-yl)amino]-5-(trifluoromethyl)-4-pyridyl]amino]-5-methoxy-N-methyl-benzamide

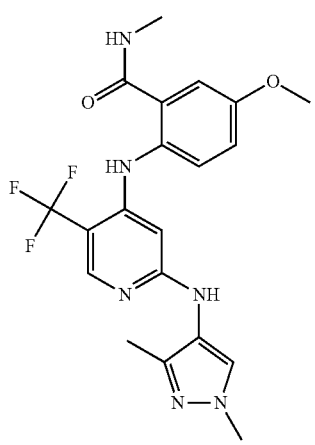 [SMILES: CNC(=O)c1cc(OC)ccc1Nc1cc(Nc2cn(C)nc2C)ncc1C(F)(F)F]

Nitrogen gas was bubbled into 9,9-dimethyl-4,5-bis (diphenylphosphino)xanthene (19 mg) and palladium(II) acetate (4 mg) in dioxane (4 mL) for 5 minutes. 2-Amino-5-methoxy-N-methylbenzamide (101 mg), N-(1,3-dimethylpyrazol-4-yl)-4-iodo-5-(trifluoromethyl)pyridin-2-amine (126 mg) and cesium carbonate (215 mg) were then added and the reaction was heated at an oil bath temperature of 90° C. overnight. The reaction was cooled to room temperature and DCM (15 mL) was added. After stirring for 5 minutes the suspension was filtered and the filter cake washed with DCM (15 mL). The filtrate was concentrated in vacuo and the residue was purified by column chromatography on silica gel (eluent: 3% to 6% MeOH in DCM). The product containing fractions were combined and concentrated in vacuo. After drying for 3 days at 40° C., the title compound was obtained as a pale red-brown solid (121 mg, 85% yield).

$^1$H NMR spectrum (270 MHz, CDCl$_3$): 2.11 (s, 3H), 2.92 (d, 3H), 3.77 (s, 3H), 3.81 (s, 3H), 5.86 (s, 1H), 5.99 (s, 1H), 6.30 (q, 1H), 6.93 (dd, 1H), 7.09 (d, 1H), 7.26 (d, 1H), 7.37 (s, 1H), 8.18 (s, 1H), 8.34 (bs, 1H); Mass spectrum: ESI+ MH$^+$ 435.

The following compounds were obtained using the corresponding aniline according to the procedure in Example 10.01:

Example 10.02

2-[[2-[(1,3-Dimethylpyrazol-4-yl)amino]-5-(trifluoromethyl)-4-pyridyl]amino]-N,4-dimethyl-benzamide

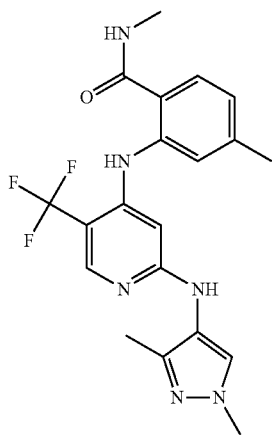 [SMILES: CNC(=O)c1ccc(C)cc1Nc1cc(Nc2cn(C)nc2C)ncc1C(F)(F)F]

Aniline used: 2-amino-N,4-dimethylbenzamide

The reaction was heated at an oil bath temperature of 95° C. for 90 minutes then for a further 90 minutes and stirred overnight. Additional degassed dioxane (3.7 mL) was added and the reaction heated for a further 3 hours at an oil bath temperature of 95° C.

Eluent: 2% to 5% MeOH in DCM for purification. 95 mg, 68% yield of title compound as a brick red solid. $^1$H NMR spectrum (270 MHz, CDCl$_3$): 2.15 (s, 3H), 2.28 (s, 3H), 2.94 (d, 3H), 3.78 (s, 3H), 6.00 (s, 1H), 6.14 (q, 1H), 6.27 (s, 1H), 6.78 (d, 1H), 7.23 (d, 1H), 7.33 (s, 1H), 7.34 (d, 1H), 8.21 (s, 1H), 9.75 (s, 1H); Mass spectrum: ESI+ MH$^+$ 419.

Example 10.03

2-[[2-[(1,3-dimethylpyrazol-4-yl)amino]-5-(trifluoromethyl)-4-pyridyl]amino]-N,5-dimethyl-benzamide

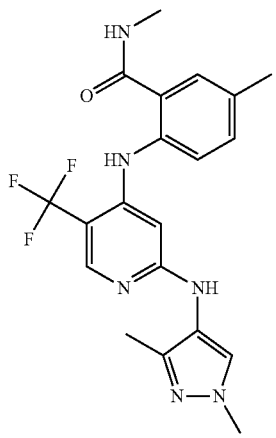 [SMILES: CNC(=O)c1cc(C)ccc1Nc1cc(Nc2cn(C)nc2C)ncc1C(F)(F)F]

Aniline used: 2-amino-N,5-dimethylbenzamide 119 mg, 86% yield of title compound as an off-white solid. $^1$H NMR spectrum (270 MHz, CDCl$_3$): 2.13 (s, 3H), 2.31 (s, 3H), 2.95 (d, 3H), 3.78 (s, 3H), 5.85 (s, 1H), 6.13 (q, 1H), 6.19 (s, 1H), 7.15 (d, 1H), 7.28 (d. 1H), 7.30 (d, 1H), 7.36 (s, 1H), 8.21 (s, 1H), 9.28 (bs, 1H); Mass spectrum: ESI+ MH$^+$ 419.

Example 10.04

2-[[2-[(1,3-dimethylpyrazol-4-yl)amino]-5-(trifluoromethyl)-4-pyridyl]amino]-4-methoxy-N-methyl-benzamide

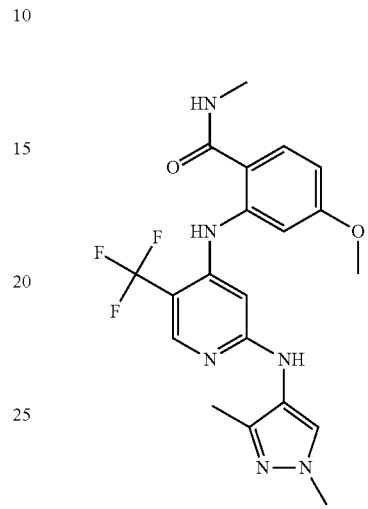

Aniline used: 2-amino-4-methoxy-N-methylbenzamide

Eluent: 2% to 10% MeOH in DCM for purification. 113 mg, 79% yield of title compound as an off-white solid. $^1$H NMR spectrum (270 MHz, CDCl$_3$): 2.13 (s, 3H), 2.94 (d, 3H), 3.72 (s, 3H), 3.79 (s, 3H), 5.93 (s, 1H), 6.03 (q, 1H), 6.39 (s, 1H), 6.49 (dd, 1H), 6.89 (d, 1H), 7.37 (s, 1H), 7.39 (d, 1H), 8.24 (s, 1H), 10.09 (bs, 1H); Mass spectrum: ESI+ MH$^+$ 435.

Example 10.05

2-[[2-[(1,3-dimethylpyrazol-4-yl)amino]-5-(trifluoromethyl)-4-pyridyl]amino]-4-fluoro-N-methyl-benzamide

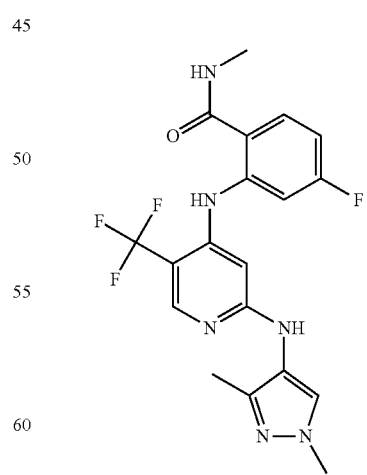

Aniline used: 2-amino-4-fluoro-N-methylbenzamide

Eluent: 2% to 10% MeOH in DCM for purification. 108 mg, 78% yield of title compound as an off-white solid. $^1$H NMR spectrum (270 MHz, CDCl$_3$): 2.15 (s, 3H), 2.96 (d, 3H), 3.81 (s, 3H), 5.97 (s, 1H), 6.02 (bs, 1H), 6.34 (bs, 1H), 6.65 (ddd, 1H), 7.10 (dd, 1H), 7.39 (s, 1H), 7.44 (dd, 1H), 8.26 (s, 1H), 10.11 (bs, 1H); Mass spectrum: ESI+ MH+ 423.

Example 10.06

2-[[2-[(1,3-dimethylpyrazol-4-yl)amino]-5-(trifluoromethyl)-4-pyridyl]amino]-3-fluoro-N-methyl-benzamide

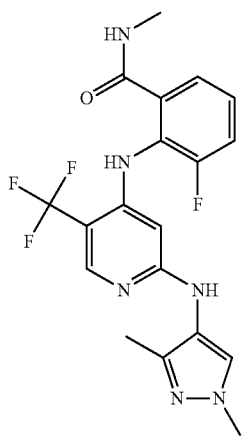 [SMILES: CNC(=O)c1cccc(F)c1Nc1cc(Nc2cn(C)nc2C)ncc1C(F)(F)F]

Aniline used: 2-amino-3-fluoro-N-methylbenzamide
Eluent: 3% to 5.5% MeOH in DCM for purification. 72 mg, 52% yield of title compound as an off-white solid. $^1$H NMR spectrum (270 MHz, DMSO): 2.01 (s, 3H), 2.74 (d, 3H), 3.68 (s, 3H), 5.87 (bs, 1H), 7.24-7.40 (m, 1H), 7.43-7.62 (m, 2H), 7.78 (bs, 1H), 8.14 (s, 1H), 8.39 (s, 1H), 8.73 (q, 1H), 9.19 (s, 1H); Mass spectrum: ESI+ MH+ 423.

Example 10.07

5-chloro-2-[[2-[(1,3-dimethylpyrazol-4-yl)amino]-5-(trifluoromethyl)-4-pyridyl]amino]-N-methyl-benzamide

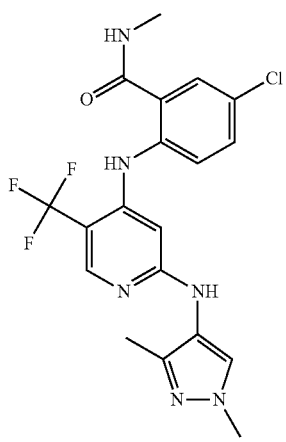 [SMILES: CNC(=O)c1cc(Cl)ccc1Nc1cc(Nc2cn(C)nc2C)ncc1C(F)(F)F]

Aniline used: 2-amino-5-chloro-N-methylbenzamide
Eluent: 3% to 5.5% MeOH in DCM for purification. 127 mg, 88% yield of title compound as a beige solid. $^1$H NMR spectrum (270 MHz, DMSO): 2.05 (s, 3H), 2.74 (d, 3H), 3.69 (s, 3H), 6.61 (bs, 1H), 7.23 (s, 2H), 7.77 (s, 1H), 7.84 (s, 1H), 8.20 (s, 1H), 8.45 (s, 1H), 8.80 (q, 1H), 10.07 (s, 1H); Mass spectrum: ESI+ MH+ 439.

Example 10.08

2-[[2-[(1,3-dimethylpyrazol-4-yl)amino]-5-(trifluoromethyl)-4-pyridyl]amino]-N-methoxy-benzamide

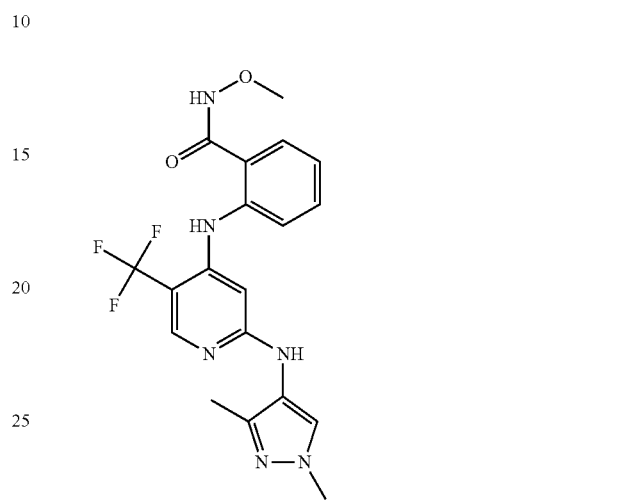

Aniline used: 2-amino-N-methoxybenzamide
Eluent: 3% to 6% MeOH in DCM for purification on silica gel—followed by preparative HPLC. 67 mg, 48% yield of title compound as a beige solid. $^1$H NMR spectrum (270 MHz, DMSO): 2.05 (s, 3H), 3.68 (s, 3H), 3.69 (s, 3H), 6.60 (bs, 1H), 7.07 (ddd, 1H), 7.45-7.60 (m, 3H), 7.83 (s, 1H), 8.19 (s, 1H), 8.45 (s, 1H), 9.52 (bs, 1H), 11.93 (bs, 1H); Mass spectrum: ESI+ MH+ 421.

Crystalline material was prepared as follows:
9,9-dimethyl-4,5-bis(diphenylphosphino)xanthene (0.303 g, 0.52 mmol), palladium(II) acetate (0.059 g, 0.26 mmol), 2-amino-N-methoxybenzamide (1.479 g, 8.90 mmol), N-(1,3-dimethylpyrazol-4-yl)-4-iodo-5-(trifluoromethyl)pyridin-2-amine (2 g, 5.23 mmol) and cesium carbonate (3.41 g, 10.47 mmol) were weighed out in a round bottom flask. Dioxane (60 mL) was added and argon was bubbled through the mixture for 10 minutes. The suspension was stirred at 100° C. overnight. The reaction mixture was allowed to cool to room temperature with stirring, diluted with DCM and MeOH. Silica gel was added and the mixture was concentrated. The crude product was purified by flash chromatography on silica gel (150 g) eluting with 0 to 5% MeOH in EtOAc/DCM (1:1). The solvent was evaporated to dryness, giving. 35 mL of tBuOMe was added and the resulting solution was stirred at room temperature for 3 hours. The resulting precipitate was collected by filtration, washed with tBuOMe and dried to a constant weight to afford the title compound (1.53 g, 3.64 mmol, 69.5%) as a white solid. This solid was taken up into a minimum of acetonitrile, heated to 100° C. and more acetonitrile was added until complete solubilisation was achieved. The solution was filtered and left to cool to room temperature overnight. The resulting crystals were collected by filtration and dried to constant weight under high vacuum ($7.10^{-2}$ mbar) at 50° C. for 1 hour, to give the title compound (1.2 g, 2.63 mmol, 50.2%) as a crystalline white solid.

The most prominent X-ray powder diffraction peaks for this crystalline material are listed below:

| Angle 2-Theta ° | Intensity % |
|---|---|
| 7.81 | 23.8 |
| 8.382 | 100 |
| 11.174 | 10.5 |
| 11.533 | 7.6 |
| 11.977 | 2.2 |
| 12.946 | 11.6 |
| 13.302 | 16 |
| 13.548 | 5.5 |
| 14.709 | 2.3 |
| 15.311 | 16.4 |
| 15.484 | 8.9 |
| 16.244 | 16.5 |
| 16.985 | 2.6 |
| 17.472 | 6.9 |
| 17.784 | 3.8 |
| 18.111 | 10 |
| 18.269 | 5.1 |
| 18.655 | 22.5 |
| 19.055 | 5 |
| 19.186 | 4.4 |
| 19.643 | 9.9 |
| 20.311 | 15.4 |
| 20.574 | 16.3 |
| 20.719 | 6.9 |
| 21.118 | 13.3 |
| 22.106 | 9.2 |
| 22.316 | 5.3 |
| 22.629 | 16.9 |
| 23.053 | 21.9 |
| 23.602 | 5.2 |
| 24.222 | 8.3 |
| 24.476 | 5.8 |
| 24.613 | 8.7 |
| 24.872 | 9.7 |
| 25.074 | 38.1 |
| 25.357 | 8.6 |
| 25.54 | 23.8 |
| 25.783 | 6.2 |
| 25.936 | 11 |
| 26.146 | 9.1 |
| 27.183 | 2.7 |
| 27.352 | 3.2 |
| 27.697 | 5.5 |
| 27.871 | 11.4 |
| 28.141 | 8.7 |
| 28.43 | 3.2 |
| 28.692 | 3.2 |
| 29.038 | 3.2 |
| 29.298 | 2.7 |
| 29.868 | 2.7 |
| 30.32 | 2.7 |
| 30.644 | 2.9 |
| 30.729 | 2.5 |
| 30.868 | 2.3 |
| 31.141 | 5 |
| 32.267 | 2.8 |
| 32.824 | 2.6 |
| 32.91 | 2.3 |
| 33.648 | 4.7 |
| 34.672 | 4.1 |
| 35.239 | 4.9 |
| 35.313 | 3.7 |
| 35.673 | 2.9 |
| 36.112 | 3.6 |
| 37.128 | 2.2 |
| 38.142 | 2 |
| 39.581 | 2.5 |

Example 10.09

4-chloro-2-[[2-[(1,3-dimethylpyrazol-4-yl)amino]-5-(trifluoromethyl)-4-pyridyl]amino]-N-methyl-benzamide

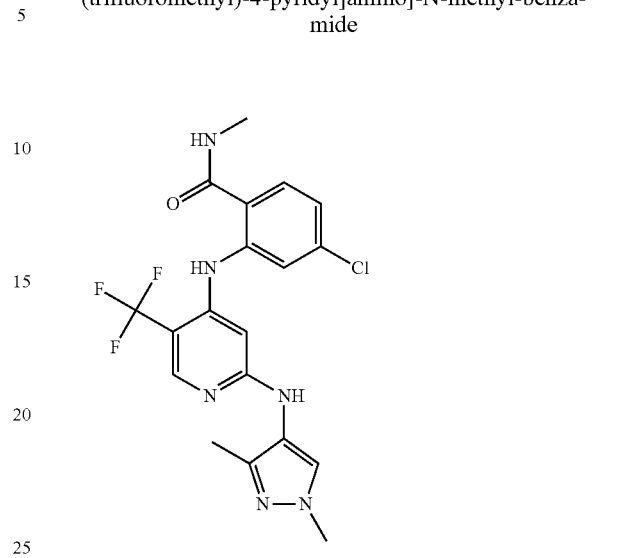

Aniline used: 2-amino-4-chloro-N-methylbenzamide

Eluent: 3% to 5.5% MeOH in DCM. 127 mg, 88% yield of title compound as a beige solid. $^1$H NMR spectrum (270 MHz, DMSO): 2.06 (s, 3H), 2.74 (d, 3H), 3.70 (s, 3H), 7.12 (dd, 1H), 7.51 (d, 1H), 7.70 (d, 1H), 7.83 (s, 1H), 8.22 (s, 1H), 8.51 (s, 1H), 8.75 (q, 1H), 10.39 (s, 1H); Mass spectrum: ESI+ MH$^+$ 439.

Example 10.10

2-[[2-[(1,3-dimethylpyrazol-4-yl)amino]-5-(trifluoromethyl)-4-pyridyl]amino]-N-methyl-5-methylsulfanyl-benzamide

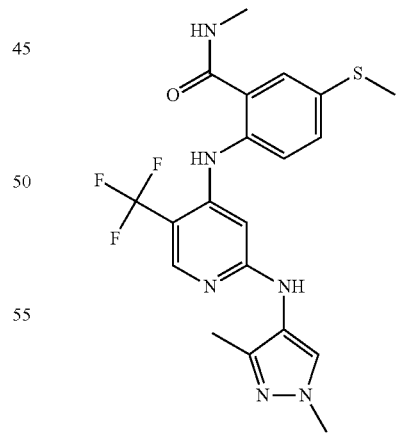

Aniline used: 2-amino-4-methylsulfanyl-N-methylbenzamide

Eluent: 3% to 5.5% MeOH in DCM. 68 mg, 46% yield of title compound as a beige solid. $^1$H NMR spectrum (270 MHz, CDCl$_3$): 2.14 (s, 3H), 2.48 (s, 3H), 2.96 (d, 3H), 3.79 (s, 3H), 6.14 (q, 1H), 6.18 (s, 1H), 6.50 (bs, 1H), 7.31 (s, 1H), 7.33-7.37 (m, 2H), 7.40 (d, 1H), 8.18 (s, 1H), 9.48 (bs, 1H); Mass spectrum: ESI+ MH+ 451.

Example 10.11

2-[[2-[(1,3-dimethylpyrazol-4-yl)amino]-5-(trifluoromethyl)-4-pyridyl]amino]-N-methyl-5-morpholino-benzamide

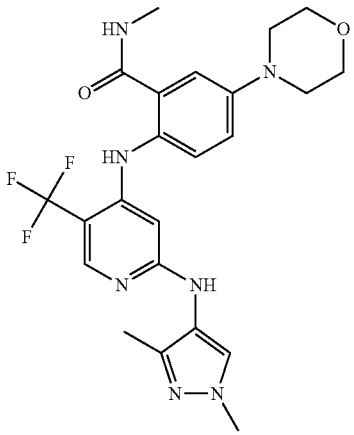 [SMILES: CNC(=O)c1cc(N2CCOCC2)ccc1Nc1cc(Nc2cn(C)nc2C)ncc1C(F)(F)F]

Aniline used: 2-amino-N-methyl-5-(4-morpholino)benzamide

Eluent: 3% to 8% MeOH in DCM. 179 mg, quantitative yield of title compound as a light brown-green solid. $^1$H NMR spectrum (270 MHz, DMSO): 2.03 (s, 3H), 2.72 (d, 3H), 3.04-3.22 (m, 4H), 3.68 (s, 3H), 3.71-3.87 (m, 4H), 6.41 (bs, 1H), 7.11 (dd, 1H), 7.17 (d, 1H), 7.36 (d, 1H), 7.80 (s, 1H), 8.10 (s, 1H), 8.33 (s, 1H), 8.59 (q, 1H), 9.41 (s, 1H); Mass spectrum: ESI+ MH+ 490.

Example 10.13

2-[[2-[(1,3-dimethylpyrazol-4-yl)amino]-5-(trifluoromethyl)-4-pyridyl]amino]-N-methyl-4-methylsulfonyl-benzamide

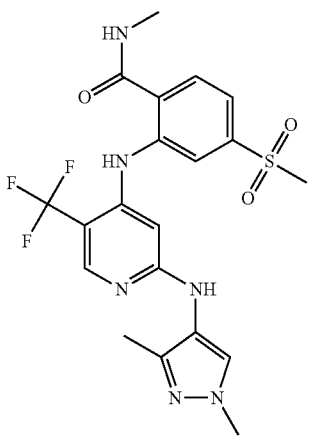 [SMILES: CNC(=O)c1ccc(S(C)(=O)=O)cc1Nc1cc(Nc2cn(C)nc2C)ncc1C(F)(F)F]

Aniline used: 2-amino-4-methylsulfonyl-N-methylbenzamide

Eluent: 3% to 6% MeOH in DCM. 124 mg, 78 yield of title compound as a light tan solid. $^1$H NMR spectrum (270 MHz, CDCl$_3$): 2.09 (s, 3H), 2.94 (d, 3H), 2.99-3.16 (m, 4H), 3.79 (s, 3H), 3.79-3.90 (m, 4H), 5.90 (s, 1H), 6.02 (q, 1H), 6.35 (s, 1H), 6.47 (d, 1H), 6.78 (d, 1H), 7.32 (s, 1H), 7.36 (d, 1H), 8.23 (s, 1H), 10.07 (bs, 1H); Mass spectrum: ESI+ MH+ 483.

The anilines used in Examples 10.01 to 10.13 were commercially available or made from the corresponding anthranilic acid:

2-amino-4-fluoro-N-methylbenzamide (used in example 10.05)

Carbonyl-1,1'-diimidazole (1.26 g) was added to 2-amino-4-fluorobenzoic acid (1.0 g) in THF (16.3 mL). After stirring overnight a solution of methylamine in THF (2M, 4.9 mL) was added and the reaction stirred for 3 hours. The reaction was concentrated in vacuo and the residue dissolved in EtOAc (100 mL) and saturated aqueous sodium bicarbonate solution (100 mL). The phases were separated and the organics were washed with water (2×100 mL) and then saturated aqueous brine (30 mL). The organics were dried (MgSO$_4$, 15 g), filtered and concentrated in vacuo to give crude product (0.9 g). This material was purified by column chromatography (SiO$_2$, 40 g, eluent 3% MeOH in DCM) to give 2-amino-4-fluoro-N-methylbenzamide (0.6 g). $^1$H NMR spectrum (270 MHz, DMSO): 2.69 (d, 3H), 6.28 (ddd, 1H), 6.42 (dd, 1H), 6.74 (bs, 2H), 7.48 (dd, 1H), 8.16 (q, 1H); Mass spectrum: ESI+ MH+ 169.

2-amino-N-methoxybenzamide (Used in Example 10.08)

O-methylhydroxylamine hydrochloride (1.79 g) was added to isatoic anhydride (2.34 g) in THF (72 mL) and DIPEA (4 mL). The reaction was stirred for 3 hours and then heated to reflux overnight. The reaction was then cooled and concentrated in vacuo and the residue dissolved in EtOAc (100 mL) and saturated aqueous sodium bicarbonate solution (100 mL). The phases were separated and the organics were washed with saturated aqueous sodium bicarbonate solution (2×100 mL). The organics were extracted with 1 M HCl (4×25 mL), the aqueous phase basified with potassium carbonate (~15 g) and the organics discarded. The aqueous was then extracted with EtOAc (3×75 mL). The combined organics were dried (MgSO$_4$, 20 g) and concentrated. The product was dried overnight at 40° C. under vacuum to give 2-amino-N-methoxybenzamide (1.18 g, 50% yield).

$^1$H NMR spectrum (270 MHz, DMSO): 3.66 (s, 3H), 6.29 (bs, 2H), 6.47 (dd, 1H), 6.69 (d, 1H), 7.14 (ddd, 1H), 7.29 (dd, 1H), 11.40 (bs, 1H; Mass spectrum: ESI+ MH+ 167.

2-amino-4-chloro-N-methylbenzamide (Used in Example 10.09)

Carbonyl-1,1'-diimidazole (1.70 g) was added to 2-amino-4-chlorobenzoic acid (1.50 g) in THF (22.2 mL). After stirring overnight a solution of methylamine in THF (2M, 6.6 mL) was added and the reaction stirred for 3 hours. The reaction was concentrated in vacuo and the residue dissolved in EtOAc (100 mL) and saturated aqueous sodium bicarbonate solution (50 mL). The organics were then washed with saturated aqueous sodium bicarbonate solution (50 mL) and then water (2×100 mL). The organics were extracted with 1 M HCl (4×25 mL, then 2×100 mL then 50 mL), the aqueous phase basified with potassium carbonate (~50 g) and the organics discarded. The aqueous was then extracted with EtOAc (2×50 mL). The combined organics were dried (MgSO$_4$, 10 g) and concentrated to give 2-amino-4-chloro-N-methylbenzamide (1.2 g, 74%).

According to procedures described above, the following intermediates were prepared from the appropriate material:

From 2-amino-5-methoxybenzoic acid (2.16 g); 2-amino-5-methoxy-N-methylbenzamide 1.41 g (61% yield). $^1$H NMR spectrum (270 MHz, DMSO): 2.71 (d, 3H), 3.66 (s, 3H), 5.95 (bs, 2H), 6.62 (d, 1H), 6.81 (dd, 1H), 7.01 (d, 1H), 8.18 (q, 1H); Mass spectrum: ESI+ MH+ 181.

From 2-amino-4-methylbenzoic acid (3.06 g); 2-amino-N,4-dimethylbenzamide as a beige solid 2.4 g, (72% yield). ¹H NMR spectrum (270 MHz, DMSO): 2.14 (s, 3H), 2.68 (d, 3H), 6.30 (d, 1H), 6.39 (bs, 2H), 6.46 (s, 1H), 7.33 (d, 1H), 8.06 (q, 1H); Mass spectrum: ESI+ MH+ 165.

From 2-amino-5-methylbenzoic acid (1.17 g); 2-amino-N,5-dimethylbenzamide 0.98 g (77% yield). ¹H NMR spectrum (270 MHz, DMSO): 2.14 (s, 3H), 2.69 (d, 3H), 6.15 (bs, 2H), 6.57 (d, 1H), 6.93 (dd, 1H), 7.24 (d, 1H), 8.11 (q, 1H); Mass spectrum: ESI+ MH+ 165.

From 4-methoxyanthranilic acid (2.16 g); 2-amino-4-methoxy-N-methylbenzamide 0.78 g, (33% yield). ¹H NMR spectrum (270 MHz, DMSO): 2.67 (d, 3H), 3.67 (s, 3H), 6.07 (dd, 1H), 6.19 (d, 1H), 6.60 (bs, 2H), 7.39 (d, 1H), 7.97 (q, 1H); Mass spectrum: ESI+ MH+ 181.

From 2-amino-3-fluorobenzoic acid (1.03 g); 2-amino-3-fluoro-N-methylbenzamide 0.856 g (77% yield).

From 2-amino-5-chlorobenzoic acid (1.46 g); 2-amino-5-chloro-N-methylbenzamide 1.4 g (89% yield).

From 2-amino-4-(methylsulfanyl)benzoic acid (0.20 g); 2-amino-4-(methylsulfanyl)-N-methylbenzamide 0.11 g (51% yield).

From 2-amino-4-(methylsulfonyl)benzoic acid (1.51 g); 2-amino-4-(methylsulfonyl)-N-methylbenzamide 1.1 g (69% yield). ¹H NMR spectrum (270 MHz, CD₃OD): 2.88 (s, 3H), 3.08 (s, 3H), 3.31 (s partially hidden by CD₂HOH, 3H), 7.06 (dd, 1H), 7.27 (d, 1H), 7.57 (d, 1H); Mass spectrum: ESI+ MH+ 229.

2-amino-N-methyl-5-(4-morpholino)-benzamide

Morpholine (2.87 mL) was added to a solution of 5-fluoro-2-nitrobenzoic acid (3.03 g) in DMSO (16.3 mL) and the reaction was heated to 90° C. for 14 hours. The reaction was cooled and water (100 mL) was added. After stirring for 10 minutes the mixture was filtered and the filter cake was washed with water (50 mL). Citric acid (4 g) was charged to the filtrate, causing more of the product to precipitate. The filter cake was washed with more water (500 mL) then the acidified filtrate filtered and washed with water (300 mL). The solid was dried overnight at 40° C. under vacuum to give 5-(4-morpholino)-2-nitrobenzoic acid (3.05 g, 74% yield).

Carbonyl-1,1'-diimidazole (2.65 g) was added to 5-(4-morpholino)-2-nitrobenzoic acid (3.44 g) in THF (34 mL). After stirring overnight a solution of methylamine in THF (2M, 10.2 mL) was added and the reaction stirred for 3 hours. The reaction was concentrated in vacuo and the residue partitioned between EtOAc (150 mL) and saturated aqueous sodium bicarbonate solution (75 mL) in water (75 mL). The phases were separated and the aqueous was washed with EtOAc (2×100 mL). The combined organics were dried (MgSO₄, 30 g) and concentrated to give 3.3 g of material. This material was stirred in a solution of methylamine in THF (2M, 25 mL) in THF (25 mL) overnight. The reaction was concentrated in vacuo and the residue partitioned between EtOAc (350 mL) and saturated aqueous sodium bicarbonate solution (75 mL). The phases were separated and the aqueous was washed with EtOAc (2×100 mL). The combined organics were dried (MgSO₄, 30 g) and concentrated in vacuo. When a volume of approximately 20 mL was reached the suspension was filtered. The resulting solid was dried to give N-methyl-5-(4-morpholino)-2-nitrobenzamide (1.6 g, 44%).

A solution of N-methyl-5-(4-morpholino)-2-nitrobenzamide (1.6 g) in MeOH (120 mL) was stirred with 10% palladium on carbon (1 g) under hydrogen overnight. The reaction was then filtered and washed with MeOH (120 mL). The filtrate was concentrated in vacuo to give 2-amino-N-methyl-5-(4-morpholino)-benzamide as a brown solid which was dried at 40° C. overnight (1.47 g, quantitative yield). ¹H NMR spectrum (270 MHz, DMSO): 2.70 (d, 3H), 2.88-2.94 (m, 4H), 3.66-3.74 (m, 4H), 5.94 (bs, 2H), 6.61 (d, 1H), 6.88 (dd, 1H), 6.97 (d, 1H), 8.15 (q, 1H); Mass spectrum: ESI+ MH+ 236.

Example 11

2-[[2-[(2,5-dimethylpyrazol-3-yl)amino]-5-(trifluoromethyl)-4-pyridyl]amino]-6-methoxy-N-methylbenzamide

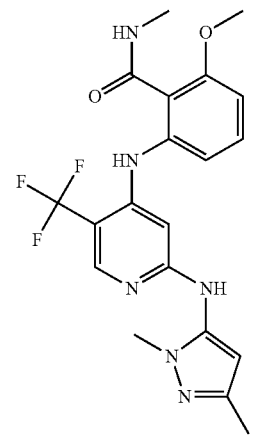 [SMILES: CNC(=O)c1c(Nc2cc(Nc3cc(C)nn3C)ncc2C(F)(F)F)cccc1OC]

2-(2-Chloro-5-(trifluoromethyl)pyridin-4-ylamino)-6-methoxy-N-methylbenzamide (305 mg, 0.85 mmol), 1,3-dimethylpyrazol-5-amine (94 mg, 0.85 mmol), palladium(II) acetate (15.23 mg, 0.07 mmol), 9,9-dimethyl-4,5-bis(diphenylphosphino)xanthene (78 mg, 0.14 mmol) and cesium carbonate (331 mg, 1.02 mmol) were mixed together in dioxane (6 mL). The reaction mixture was degassed with argon and was stirred at 90° C. for 8 hours under argon. After cooling, the reaction mixture was filtered and washed with DCM. The filtrate was concentrated to dryness and was purified by flash chromatography on silica gel eluting with 1 to 5% MeOH in DCM. The solvent was evaporated to dryness to afford the title compound (118 mg, 32%) as a pale beige-pink solid.

This compound was crystallised from chloroform and the resulting crystalline solid was collected by filtration, washed with chloroform and dried to a constant weight in a vacuum oven at 60° C. to afford (79 mg, 0.182 mmol, 21.45%) as a white crystalline solid. ¹H NMR spectrum (500 MHz, DMSO): 2.08 (s, 3H), 2.73 (d, 3H), 3.54 (s, 1H), 3.82 (s, 1H), 5.97 (s, 1H), 6.48 (s, 1H), 6.88 (d, 1H), 7.08 (d, 1H), 7.41 (dd, 1H), 8.19 (s, 1H), 8.28 (q, 1H), 8.83 (s, 1H), 8.95 (s, 1H); Mass spectrum: ESI+ MH+ 435.

The following crystalline form was characterised:
2-(2-Chloro-5-(trifluoromethyl)pyridin-4-ylamino)-6-methoxy-N-methylbenzamide (1.66 g, 4.61 mmol), 1,3-dimethylpyrazol-5-amine (0.523 g, 4.71 mmol), palladium(II) acetate (0.083 g, 0.37 mmol), 9,9-dimethyl-4,5-bis(diphenylphosphino)xanthene (0.427 g, 0.74 mmol) and cesium carbonate (1.804 g, 5.54 mmol) were mixed together in dioxane (30 mL). The reaction was degassed with argon and was stirred at 90° C. for 3 hours under argon. The mixture was filtered, the filtrate concentrated and purified twice by flash chromatography on silica gel eluting with 0 to 4% MeOH in DCM/EtOAc (60:40). The solvent was evaporated to dryness to afford 2-(2-(1,3-dimethyl-1H-pyrazol-5-ylamino)-5-(trifluoromethyl)pyridin-4-ylamino)-6-methoxy-N-methylbenzamide (0.882 g, 44.0%) as a beige solid. 150 mg of this material was dissolved in acetonitrile, concentrated and diluted with DCM. Crystals appeared slowly. The resulting crystalline solid was collected by filtration, washed with DCM and dried to a constant weight to afford 2-[[2-[(2,5-dimethylpyrazol-3-yl)amino]-5-(trifluoromethyl)-4-pyridyl]amino]-6-methoxy-N-methyl-benzamide (110 mg, 32.3%) as a white crystalline solid. Melting onset of 163° C.

The most prominent X-ray powder diffraction peaks for this crystalline material are listed below:

| Angle 2-Theta ° | Intensity % |
| --- | --- |
| 2.361 | 15.9 |
| 6.937 | 6.1 |
| 7.541 | 9.8 |
| 7.796 | 16.8 |
| 9.31 | 15.5 |
| 9.637 | 8.8 |
| 9.841 | 44.4 |
| 12.539 | 16.2 |
| 13.389 | 13 |
| 13.885 | 13.5 |
| 14.389 | 66.6 |
| 15.067 | 43.3 |
| 15.589 | 100 |
| 15.932 | 19.8 |
| 16.214 | 17.2 |
| 16.554 | 6.5 |
| 16.982 | 13.3 |
| 17.416 | 6.6 |
| 17.987 | 10.6 |
| 18.327 | 11.6 |
| 18.648 | 48.2 |
| 18.972 | 17.7 |
| 19.331 | 8 |
| 19.74 | 25.5 |
| 19.906 | 17.8 |
| 20.082 | 41.4 |
| 20.413 | 13.8 |
| 20.506 | 12.9 |
| 20.876 | 26.1 |
| 21.283 | 15.4 |
| 21.379 | 20.1 |
| 21.849 | 35.3 |
| 22.093 | 18.5 |
| 22.691 | 17.2 |
| 22.898 | 19.9 |
| 23.314 | 14.4 |
| 23.474 | 19.6 |
| 23.584 | 25.1 |
| 23.949 | 12.6 |
| 24.368 | 10.4 |
| 24.871 | 12 |
| 24.883 | 11.8 |
| 25.21 | 22.7 |
| 25.829 | 7.4 |
| 26.034 | 16.9 |
| 26.525 | 9.7 |
| 26.542 | 9.5 |
| 26.708 | 11.2 |
| 27.853 | 9.2 |
| 27.93 | 11.9 |
| 28.113 | 15.8 |
| 28.964 | 11.3 |
| 29.409 | 9.9 |
| 30.299 | 8.7 |
| 30.497 | 8.1 |
| 32.912 | 7.3 |
| 33.777 | 4 |
| 36.072 | 7.3 |
| 36.175 | 8.3 |

2-(2-Chloro-5-(trifluoromethyl)pyridin-4-ylamino)-6-methoxy-N-methylbenzamide used as starting material was made as follows:

2-Chloro-4-iodo-5-(trifluoromethyl)pyridine (420 mg, 1.37 mmol), 2-amino-6-methoxy-N-methylbenzamide (246 mg, 1.37 mmol), palladium(II) acetate (24.54 mg, 0.11 mmol), 9,9-dimethyl-4,5-bis(diphenylphosphino)xanthene (126 mg, 0.22 mmol) and cesium carbonate (534 mg, 1.64 mmol) were mixed together in dioxane (8 mL). Reaction was degassed with argon and was stirred at 90° C. overnight (15 hours) under argon. The reaction mixture was filtered, washed with DCM and the filtrate was concentrated to dryness. The crude product was purified by flash chromatography on silica gel eluting with 10 to 30% EtOAc in petroleum ether. The solvent was evaporated to dryness to afford 2-(2-chloro-5-(trifluoromethyl)pyridin-4-ylamino)-6-methoxy-N-methylbenzamide (325 mg, 66%) as a white solid. $^1$H NMR spectrum (500 MHz, DMSO): 2.68 (d, 3H), 3.83 (s, 3H), 6.84 (s, 1H), 7.03 (d, 1H), 7.08 (d, 1H), 7.47 (dd, 1H), 8.19 (q, 1H), 8.42 (s, 1H), 9.15 (s, 1H); Mass spectrum: ESI+ MH$^+$ 360.

Example 12

NMR spectra for examples 12.01 to 12.12 were recorded on a NMR Spectrometer JEOL Eclipse 270 working at 270 MHz (at about 20° C.).

General Procedure

8-[(2,5-dichloropyridin-4-yl)amino]-2-methyl-3,4-dihydroisoquinolin-1-one (120 mg), palladium(II) acetate (7 mg, 8 mol %), 9,9-dimethyl-4,5-bis(diphenylphosphino)xanthene (34 mg, 17 mol %), cesium carbonate (140 mg, 1.2 equiv.) and the appropriate amine (2 equiv.) were suspended in dioxane (5 ml) in a sealed tube. The mixture was degassed with nitrogen for 5 minutes, the vessel purged with nitrogen and the mixture stirred at 100° C. for 16-60 hours [Note: if reaction was incomplete after this period either further palladium(II) acetate (7 mg) was added or the suspended inorganics were filtered off, followed by re-introduction of 9,9-dimethyl-4,5-bis(diphenylphosphino)xanthene (34 mg), cesium carbonate (140 mg) and palladium(II) acetate (7 mg) to the reaction mixture]. Upon completion, the reaction mixture was passed through a plug of silica gel (2 g) washing with DCM (50 ml) and the solvent concentrated under vacuum. The crude material was dissolved in DMF:water, 1:1 (6 ml) and purification via prep. HPLC performed (MeOH:TFA; 99.9:0.1).

The following examples were obtained:

Example 12.01

4-[[5-chloro-4-[(2-methyl-1-oxo-3,4-dihydroiso-quinolin-8-yl)amino]-2-pyridyl]amino]-N,1-dimethyl-pyrazole-3-carboxamide

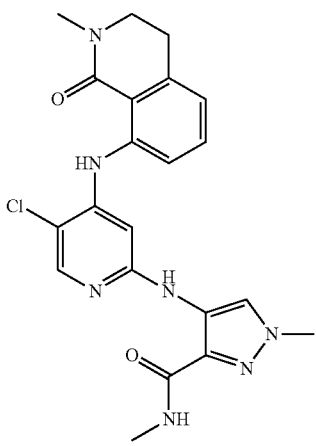 [SMILES: CNC(=O)c1nn(C)cc1Nc1cc(Nc2cccc3c2C(=O)N(C)CC3)c(Cl)cn1]

Example 12.02

4-[[5-chloro-4-[(2-methyl-1-oxo-3,4-dihydroiso-quinolin-8-yl)amino]-2-pyridyl]amino]-N,N,1-trimethyl-pyrazole-3-carboxamide

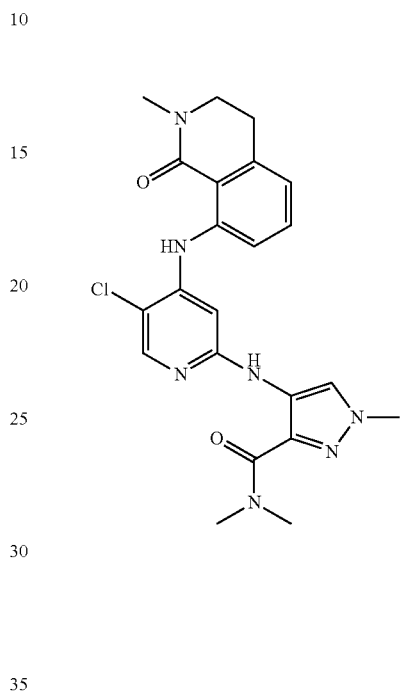

Obtained from 4-amino-N,1-dimethylpyrazole-3-carboxamide; 55 mg.

$^1$H NMR spectrum (CDCl$_3$) 2.96 (d, 3H), 2.97 (t, 2H), 3.16 (s, 1H), 3.56 (t, 2H), 3.87 (s, 3H), 6.75-6.80 (m, 3H), 7.32 (dd, 1H), 7.43 (d, 1H), 8.08 (s, 1H), 8.26 (s, 1H), 8.68 (s, 1H), 11.12 (s, 1H); Mass spectrum: ESI+ MH$^+$ 440.

The starting material, 4-amino-N,1-dimethylpyrazole-3-carboxamide, was prepared as follows:

To 1-methyl-4-nitropyrazole-3-carboxylic acid (2.0 g) in THF (30 ml) was charged carbonyl-1,1'-diimidazole (1.9 g) over 1 hour at room temperature. The reaction was stirred overnight before cooling to 0° C. A solution of methylamine in THF (12 ml of a 2M solution) was added and the reaction stirred for 1 hour. The THF layer was separated and concentrated in vacuo. The crude oil was purified by column chromatography on silica (25 g), eluting with 100% EtOAc (500 ml) to give N,1-dimethyl-4-nitropyrazole-3-carboxamide, 976 mg.

N,1-Dimethyl-4-nitropyrazole-3-carboxamide (1.23 g) was dissolved in MeOH (30 ml) and 10% Pd/C (0.3 g, 50% wet) was added. The mixture was stirred under a hydrogen atmosphere overnight and the catalyst filtered off. The solvent was removed in vacuo to yield 4-amino-N,1-dimethylpyrazole-3-carboxamide, 1.1 g. NMR Spectrum: (CDCl$_3$) 2.93 (s, 3H), 3.76 (s, 3H), 4.41 (m, 2H), 6.62 (m, 1H), 6.89 (s, 1H); Mass spectrum: MH$^+$ 155

Obtained from 4-amino-N,N,1-trimethylpyrazole-3-carboxamide; 46 mg; purified via column chromatography (4 g SiO$_2$; EtOAc:heptane, 1:1).

$^1$H NMR spectrum (CDCl$_3$) 2.96 (t, 2H), 3.08 (s, 3H), 3.16 (s, 3H), 3.54 (s, 3H), 3.56 (t, 2H), 3.89 (s, 3H), 7.70 (s, 1H), 7.74 (d, 1H), 7.34 (dd, 1H), 7.43 (d, 1H), 8.07 (s, 1H), 8.31 (s, 1H), 8.97 (s, 1H), 11.10 (s, 1H); Mass spectrum: ESI+ MH$^+$ 454.

The starting material, 4-amino-N,N,1-trimethylpyrazole-3-carboxamide, was is prepared as follows:

To 1-methyl-4-nitropyrazole-3-carboxylic acid (2.0 g) in THF (30 ml) was charged carbonyl-1,1'-diimidazole (1.9 g) over 1 hour at room temperature. The reaction was stirred overnight before cooling to 0° C. A solution of dimethylamine in THF (12 ml of a 2M solution) was added and the reaction stirred for 1 hour. The THF layer was separated and concentrated in vacuo. The crude product was purified by column chromatography on silica (30 g), eluting with 100% EtOAc (300 ml) to give N,N,1-trimethyl-4-nitropyrazole-3-carboxamide, 1235 mg.

N,N,1-Trimethyl-4-nitropyrazole-3-carboxamide (1.22 g) was dissolved in MeOH (35 ml) and 10% Pd/C (0.3 g, 50% wet) was added. The mixture was stirred under a hydrogen atmosphere overnight and the catalyst filtered off. The solvent was removed in vacuo to yield 4-amino-N,N,1-trimethylpyrazole-3-carboxamide, 810 mg. NMR Spectrum: (CDCl$_3$) 3.06 (m, 3H), 3.44 (m, 3H), 3.78 (s, 3H), 4.51 (m, 2H), 6.90 (s, 1H); Mass spectrum: MH$^+$ 169

Example 12.03

8-[[5-chloro-2-[(3-methyl-1H-pyrazol-4-yl)amino]-
4-pyridyl]amino]-2-methyl-3,4-dihydroisoquinolin-
1-one

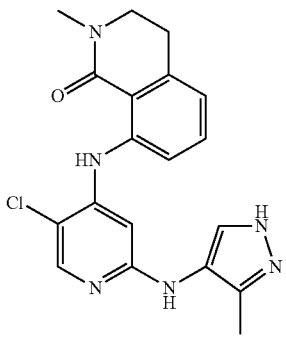 [SMILES: Cc1n[nH]cc1Nc1cc(Nc2cccc3c2C(=O)N(C)CC3)c(Cl)cn1]

Using the general procedure of Example 12, tert-butyl 4-[[5-chloro-4-[(2-methyl-1-oxo-3,4-dihydroisoquinolin-8-yl)amino]pyridin-2-yl]amino]-3-methylpyrazole-1-carboxylate, 68 mg was obtained from tert-butyl 4-amino-3-methylpyrazole-1-carboxylate. To a stirred solution of tert-butyl 4-[[5-chloro-4-[(2-methyl-1-oxo-3,4-dihydroisoquinolin-8-yl)amino]pyridin-2-yl]amino]-3-methylpyrazole-1-carboxylate (68 mg) in EtOAc (0.6 ml) was added HCl/EtOAc (4M, 1.0 ml) and the mixture stirred at room temperature for 2.5 hours. The reaction mixture was diluted with EtOAc (5 ml) and quenched with aq. potassium bicarbonate (0.53 g, 3 ml). The aqueous phase was extracted with EtOAc (2×5 ml), the combined organic extracts dried (Na$_2$SO$_4$), filtered and concentrated under reduced pressure. Purification via a 'catch and release' method (2 g isolute flash SCX-2, eluting with 100% MeOH then methanolic ammonia 0.5M→7M) afforded the title compound which was combined with a second batch; 59 mg. $^1$H NMR spectrum (methanol-d3) 2.03 (s, 3H), 2.84 (t, 2H), 3.00 (s, 3H), 3.46 (t, 2H), 6.47 (s, 1H), 6.72 (dd, 1H), 7.19 (dd, 1H), 7.23 (dd, 1H), 7.44 (bs, 1H), 7.71 (s, 1H); Mass spectrum: ESI+ MH$^+$ 383.

The starting material, tert-butyl 4-amino-3-methylpyrazole-1-carboxylate, was prepared as follows:

To 3-methyl-4-nitropyrazole (0.5 g) in THF (20 ml) was added triethylamine (0.55 ml) followed by a solution of di-tert-butyl dicarbonate (0.86 g) in THF (5 ml). The reaction was stirred for 16 hours, water (10 ml) was added and the mixture was extracted with EtOAc (2×30 ml). The combined organics were washed with brine (15 ml), dried, filtered and the solvent removed in vacuo to yield crude material (1.1 g) as a pink solid. Column chromatography on silica (25 g), eluting with 1:2 EtOAc-Heptane (300 ml) gave tert-butyl 3-methyl-4-nitropyrazole-1-carboxylate, 815 mg, 91% yield.

tert-Butyl 3-methyl-4-nitropyrazole-1-carboxylate (815 mg) was dissolved in MeOH (20 ml) and hydrogenated at room temperature for 40 hours with 10% Pd/C (0.2 g, 50% wet). The catalyst was filtered off and the solvent removed in vacuo. Column chromatography on silica (4 g), eluting with 1:1 EtOAc-heptane (500 ml) gave tert-butyl 4-amino-3-methylpyrazole-1-carboxylate (400 mg).

Example 12.04

8-[[5-chloro-2-[[3-(methoxymethyl)-1-methyl-pyrazol-4-yl]amino]-4-pyridyl]amino]-2-methyl-3,4-dihydroisoquinolin-1-one

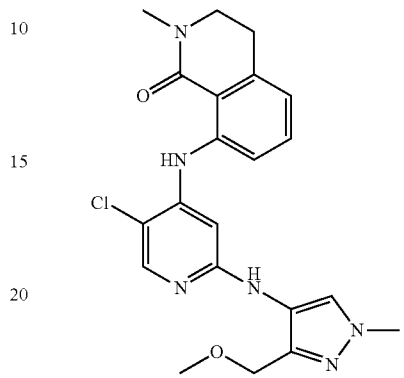

Obtained from 3-(methoxymethyl)-1-methylpyrazol-4-amine, 43 mg $^1$H NMR spectrum (CDCl$_3$) 2.96 (t, 2H), 3.16 (s, 3H), 3.35 (s, 3H), 3.55 (t, 2H), 3.83 (s, 3H), 4.52 (s, 2H), 6.60 (s, 1H), 6.75 (d, 1H), 7.30 (bs, 1H), 7.31 (dd, 1H), 7.41 (d, 1H), 7.79 (s, 1H), 8.03 (s, 1H), 11.14 (s, 1H); Mass spectrum: ESI+ MH$^+$ 427.

The starting material, 3-(methoxymethyl)-1-methylpyrazol-4-amine, was prepared as follows:

Concentrated H$_2$SO$_4$ (0.4 ml) was added to 1-methyl-4-nitropyrazole-3-carboxylic acid (2.02 g) in MeOH (40 ml) and the mixture heated to reflux for 4 hours. After cooling to room temperature, the reaction was concentrated in vacuo. The crude material was dissolved in EtOAc (60 ml) then washed with water (10 ml) and brine (10 ml). The organic layer was dried, filtered and concentrated to give methyl 1-methyl-4-nitropyrazole-3-carboxylate, 1.96 g.

Diisobutyl aluminum hydride (34.2 ml of a 1 M solution in toluene) was added to a solution of methyl 1-methyl-4-nitropyrazole-3-carboxylate (2.92 g) in anhydrous THF (100 ml) at −20° C. over a period of 5 minutes. The reaction was stirred at room temperature overnight and then poured into sat. citric acid (100 ml). The organic phase was separated and the aqueous washed with EtOAc (4×100 ml). The combined organic phases were washed with brine (100 ml), dried, filtered and concentrated in vacuo. The crude material was columned on silica (50 g), eluting with EtOAc. The product fractions were combined and washed with sat. aq. potassium sodium L-tartrate solution (3×100 ml) and brine (100 ml). The solvent was removed in vacuo to yield (1-methyl-4-nitropyrazol-3-yl)methanol as a pale yellow solid, 2.0 g, 74%.

(1-Methyl-4-nitropyrazol-3-yl)methanol (2.0 g) was dissolved in THF (80 ml) and NaH (0.6 g, 60% in oil) added at <5° C. After 30 minutes, dimethylsulfate (1.92 g) was added and the reaction stirred overnight at room temperature. An additional 0.5 eq NaH was charged and the reaction warmed to 50° C. for 30 minutes. The reaction was cooled to room temperature, and water added dropwise (10 ml), then the mixture was poured into 5% aq. ammonia (100 ml). The organic phase was separated and the aqueous extracted with EtOAc (4×50 ml). The combined organic phases were washed with 5% aq. ammonia (2×50 ml), brine (50 ml), then dried, filtered and concentrated in vacuo to yield 3-(methoxymethyl)-1-methyl-4-nitropyrazole, 2.03 g, 94%.

10% wt Pd/C (50% wet) (2 g) was added to a stirred solution of 3-(methoxymethyl)-1-methyl-4-nitropyrazole (2.02 g) in MeOH (60 ml) and the mixture stirred under an atmosphere of hydrogen overnight. The reaction mixture was filtered through a plug of celite, and the cake washed with EtOAc (200 ml). The volatiles were removed under reduced pressure to give the crude product as a brown oil. Subsequent column chromatography ($SiO_2$; 100% EtOAc) of the crude material gave 3-(methoxymethyl)-1-methylpyrazol-4-amine (1.18 g, 70%) as a brown liquid. NMR Spectrum: ($CDCl_3$) 2.9 (m, 2H), 3.35 (s, 3H), 3.74 (s, 3H), 4.46 (s, 2H), 6.91 (s, 1H)

Example 12.05

4-[[5-chloro-4-[(2-methyl-1-oxo-3,4-dihydroisoquinolin-8-yl)amino]-2-pyridyl]amino]-1-methyl-pyrazole-3-carbonitrile

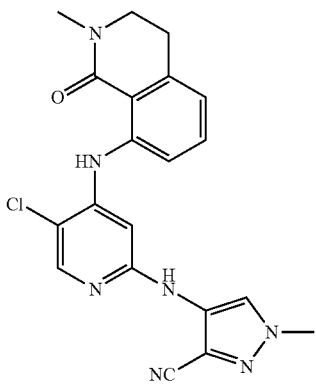 [SMILES: CN1CCc2cccc(Nc3cc(Nc4cn(C)nc4C#N)ncc3Cl)c2C1=O]

Obtained from 4-amino-1-methylpyrazole-3-carbonitrile, 55 mg; purified via column chromatography (neutral alumina 5 g; EtOAc:heptane 1:1).

$^1$H NMR spectrum ($CDCl_3$) 2.98 (t, 2H), 3.17 (s, 3H), 3.58 (t, 2H), 3.93 (s, 3H), 6.17 (s, 1H), 6.72 (s, 1H), 6.82 (d, 1H), 7.39 (dd, 1H), 7.46 (d, 1H), 8.08 (s, 1H), 8.20 (s, 1H), 11.21 (s, 1H); Mass spectrum: ESI+ MH$^+$ 408.

The starting material, 4-amino-1-methylpyrazole-3-carbonitrile, was prepared as follows:

1-Methyl-4-nitropyrazole-3-carbonitrile (2.0 g) was dissolved in DCM (30 ml) and 10% Pd/C (0.3 g, 50% wet) added. The mixture was stirred under a hydrogen atmosphere overnight. The catalyst was filtered off and the solution poured on to a silica column (15 g). The product was eluted with 100% EtOAc (100 ml) to yield 4-amino-1-methylpyrazole-3-carbonitrile, 1.277 g. Mass spectrum: MH$^+$ 123

Example 12.06

8-[[5-chloro-2-[(3-methoxy-1-methyl-pyrazol-4-yl)amino]-4-pyridyl]amino]-2-methyl-3,4-dihydroisoquinolin-1-one

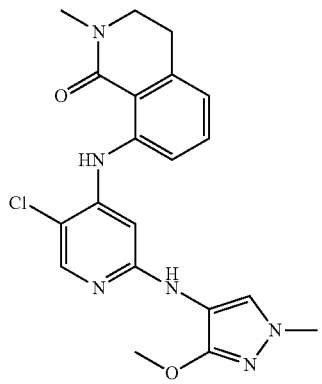 [SMILES: COc1nn(C)cc1Nc1cc(Nc2cccc3c2C(=O)N(C)CC3)c(Cl)cn1]

Obtained from 3-methoxy-1-methylpyrazol-4-amine, 53 mg.

$^1$H NMR spectrum ($CDCl_3$) 2.95 (t, 2H), 3.15 (s, 3H), 3.55 (t, 2H), 3.70 (s, 3H), 3.94 (s, 3H), 5.66 (s, 1H), 6.55 (s, 1H), 6.71 (d, 1H), 7.25 (t partially hidden by $CHCl_3$, 1H), 7.40 (d, 1H), 7.41 (s, 1H), 8.01 (s, 1H), 11.12 (s, 1H); Mass spectrum: ESI+ MH$^+$ 413.

The starting material, 3-methoxy-1-methylpyrazol-4-amine was prepared as follows:

Potassium carbonate (4.42 g) was added to a solution of 3-methoxy-4-nitro-1H-pyrazole (3.05 g) in DMF (35 ml) and the reaction mixture stirred at room temperature for 5 minutes. Methyl iodide (6.6 ml) was added slowly and the solution stirred for a further 3 hours at room temperature. The reaction mixture was poured into water (50 ml) and the aqueous phase extracted with EtOAc (4×50 ml). The combined organic extracts were washed with water (50 ml), brine (50 ml) and dried (magnesium sulfate). The solvent was removed in vacuo to give 3-methoxy-1-methyl-4-nitropyrazole as a pale yellow solid (3.90 g, containing ~20% wt DMF).

3-Methoxy-1-methyl-4-nitropyrazole (2.9 g) was dissolved in MeOH (100 ml) at room temperature and Pd/C (0.58 g, 50% wet) was added. The solution was purged with nitrogen for 10 minutes, followed by hydrogen for 2.5 hours. The reaction mixture was filtered through a cake of celite, washed with EtOAc (200 ml) and the volatiles removed under vacuum to give the crude product as a deep red oil. Column chromatography ($SiO_2$; 50:50, EtOAc:heptane), followed by further purification via a 'catch and release' method (2 g isolute flash SCX-2, eluting with 100% MeOH then methanolic ammonia (0.5 M to 7 M) furnished 3-methoxy-1-methylpyrazol-4-amine as a deep blue liquid (0.551 g). NMR Spectrum: ($CDCl_3$) 2.35 (m, 2H), 3.62 (s, 3H), 3.94 (s, 3H), 6.83 (s, 1H); Mass spectrum: MH$^+$ 128.

Similarly from 2-[[2-chloro-5-(trifluoromethyl)pyridin-4-yl]amino]-N-methylbenzamide and the appropriate amine, the following compounds were obtained:

Example 12.07

N,1-dimethyl-4-[[4-[[2-(methylcarbamoyl)phenyl]amino]-5-(trifluoromethyl)-2-pyridyl]amino]pyrazole-3-carboxamide

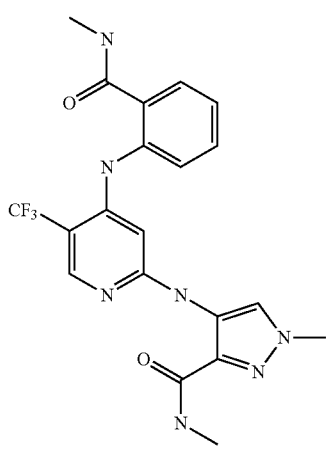 [SMILES: CNC(=O)c1ccccc1Nc1cc(Nc2cn(C)nc2C(=O)NC)ncc1C(F)(F)F]

60 mg; $^1$H NMR spectrum (CDCl$_3$) 2.95 (d, 3H), 2.98 (d, 3H), 3.88 (s, 3H), 6.15 (q, 1H), 6.60 (s, 1H), 7.75 (q, 1H), 7.04 (dd, 1H), 7.31-7.57 (m, 3H), 8.30 (s, 1H), 8.33 (s, 1H), 8.88 (s, 1H), 9.65 (s, 1H); Mass spectrum: ESI+ MH$^+$ 448.

Example 12.08

N,N,1-trimethyl-4-[[4-[[2-(methylcarbamoyl)phenyl]amino]-5-(trifluoromethyl)-2-pyridyl]amino]pyrazole-3-carboxamide

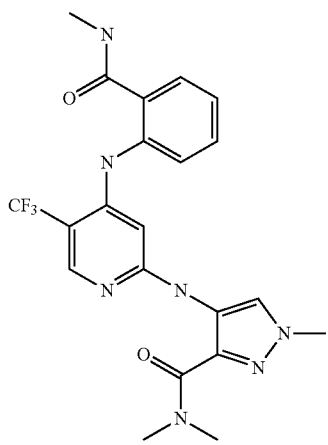 [SMILES: CNC(=O)c1ccccc1Nc1cc(Nc2cn(C)nc2C(=O)N(C)C)ncc1C(F)(F)F]

64 mg; $^1$H NMR spectrum (CDCl$_3$) 2.98 (d, 3H), 3.08 (s, 3H), 3.55 (s, 3H), 3.91 (s, 3H), 6.14 (q, 1H), 6.54 (s, 1H), 7.03 (dd, 1H), 7.43 (dd, 1H), 7.47 (d, 1H), 7.52 (d, 1H), 8.33 (s, 1H), 8.35 (s, 1H), 9.23 (s, 1H), 9.62 (s, 1H); Mass spectrum: ESI+ MH$^+$ 462; purified via column chromatography (4 g silica; EtOAc:heptane, 1:1).

Example 12.09

N-methyl-2-[[2-[(3-methyl-1H-pyrazol-4-yl)amino]-5-(trifluoromethyl)-4-pyridyl]amino]benzamide

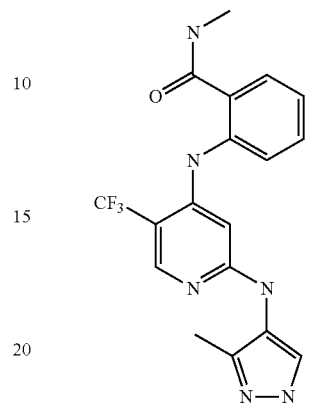

From tert-butyl 4-amino-3-methylpyrazole-1-carboxylate was obtained tert-butyl 3-methyl-4-[[4-[[2-(methylcarbamoyl)phenyl]amino]-5-(trifluoromethyl)pyridin-2-yl]amino]pyrazole-1-carboxylate (72 mg). This compound (72 mg) was dissolved in EtOAc (2 ml) in a sealed tube and HCl/EtOAc (4M, 2.3 ml) added dropwise. The mixture was stirred at room temperature for 2 hours followed by the steady addition of DCM (3 ml) and aq. potassium carbonate (2.8 g in 4.8 ml water). The aqueous phase was extracted with EtOAc (2×5 ml), the combined organic extracts dried (Na$_2$SO$_4$) and concentrated under vacuum to give the crude product as yellow solid. The crude product was re-dissolved in DCM/MeOH (15:1) and stirred with potassium carbonate (0.1 g) for 30 minutes then filtered and concentrated in vacuo to give the final product as a white solid (40 mg). $^1$H NMR spectrum (methanol-d3) 2.02 (s, 3H), 2.74 (s, 3H), 6.26 (s, 1H), 6.97 (ddd, 1H), 7.29 (ddd, 1H), 7.34 (d, 1H), 7.43 (s, 1H), 7.47 (dd, 1H), 7.95 (s, 1H); Mass spectrum: ESI+ MH$^+$ 391.

Example 12.10

2-[[2-[[3-(methoxymethyl)-1-methyl-pyrazol-4-yl]amino]-5-(trifluoromethyl)-4-pyridyl]amino]-N-methyl-benzamide

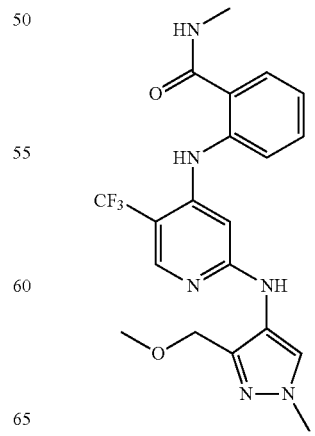

63 mg; ¹H NMR spectrum (CDCl₃) 2.97 (d, 3H), 3.34 (s, 3H), 3.83 (s, 3H), 4.51 (s, 2H), 6.17 (q, 1H), 6.43 (s, 1H), 6.54 (s, 1H), 7.04 (dd, 1H), 7.40 (ddd, 1H), 7.48 (s, 1H), 7.51 (d, 1H), 7.81 (s, 1H), 8.28 (s, 1H), 9.59 (s, 1H); Mass spectrum: ESI+ MH⁺ 435.

Example 12.11

2-[[2-[(3-cyano-1-methyl-pyrazol-4-yl)amino]-5-(trifluoromethyl)-4-pyridyl]amino]-N-methyl-benzamide

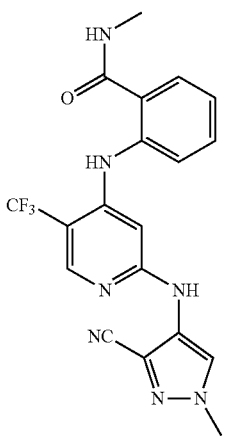 [SMILES: CNC(=O)c1ccccc1Nc1cc(Nc2cn(C)nc2C#N)ncc1C(F)(F)F]

89 mg; purified via column chromatography (neutral alumina 5 g; EtOAc:heptane 1:1); ¹H NMR spectrum (DMSO) 2.75 (d, 3H), 3.90 (s, 3H), 6.94 (s, 1H), 7.12 (dd, 1H), 7.51 (dd, 1H), 7.57 (d, 1H), 7.71 (d, 1H), 8.26 (s, 1H), 8.32 (s, 1H), 7.73 (q, 1H), 9.42 (s, 1H), 10.26 (s, 1H); Mass spectrum: ESI+ MH⁺ 416.

Example 12.12

2-[[2-[(3-methoxy-1-methyl-pyrazol-4-yl)amino]-5-(trifluoromethyl)-4-pyridyl]amino]-N-methyl-benzamide

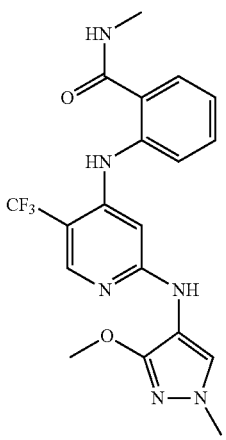 [SMILES: CNC(=O)c1ccccc1Nc1cc(Nc2cn(C)nc2OC)ncc1C(F)(F)F]

82 mg, ¹H NMR spectrum (CDCl₃) 2.97 (d, 3H), 3.69 (s, 3H), 3.92 (s, 3H), 5.91 (s, 1H), 6.12 (q, 1H), 7.38 (s, 1H), 7.00 (dd, 1H), 7.39 (ddd, 1H), 7.41 (s, 1H), 7.48 (ddd, 1H), 7.51 (d, 1H), 8.24 (s, 1H), 9.64 (s, 1H); Mass spectrum: ESI+ MH⁺ 421.

Example 13

NMR spectra for example 13.01 to 13.06 were recorded on a NMR Spectrometer JEOL Eclipse 270 working at 270 MHz (at about 20° C.)

General Procedure

8-[(2,5-dichloropyridin-4-yl)amino]-2-methyl-3,4-dihydroisoquinolin-1-one or 2-[[2-chloro-5-(trifluoromethyl)pyridin-4-yl]amino]-N-methylbenzamide (120 mg), palladium (II) acetate (7 mg, 8 mol %), 9,9-dimethyl-4,5-bis(diphenylphosphino)xanthene (34 mg, 17 mol %), cesium carbonate (140 mg, 1.2 equiv.) and the appropriate pyrazole amine (2 equiv.) were suspended in dioxane (5 ml) in a sealed tube. The mixture was degassed with nitrogen for 5 minutes, the vessel purged with nitrogen and the mixture stirred at 100° C. for 60 hours [Note: if reaction was incomplete after this period either further palladium(II) acetate (7 mg) was added or the suspended inorganics were filtered off, followed by re-introduction of 9,9-dimethyl-4,5-bis(diphenylphosphino)xanthene (34 mg), cesium carbonate (140 mg) and palladium (II) acetate (7 mg) to the reaction mixture]. Upon completion, the reaction mixture was dissolved in MeOH (30 mL) and adsorbed onto SiO₂ (2 g)

The appropriate pyrazole amines were prepared from the corresponding nitropyrazoles as follows:

The corresponding nitropyrazole (1.2 mmol) was dissolved in MeOH (5 mL). Pd/C (10%, 20% w/w) was added and rinsed into the vessel with MeOH (1 mL). The vessel was purged with nitrogen for 5 minutes followed by hydrogen and then stirred under an atmosphere of hydrogen overnight. [Note: If the reaction was incomplete after this time, the catalyst was filtered off and fresh catalyst added and the hydrogenation procedure repeated as above]. Upon completion of the reaction, the reaction mixture was filtered through a silica plug (0.5 g) and the solvent removed in vacuo. This procedure was used to prepare:

2-(4-amino-3-methyl-pyrazol-1-yl)ethanol (171 mg) from 240 mg of 2-(3-methyl-4-nitropyrazol-1-yl)ethanol, Mass spectrum: MH⁺ 142

1-isopropyl-3-methyl-pyrazol-4-amine (133 mg) from 220 mg of 1-isopropyl-3-methyl-4-nitropyrazole NMR Spectrum: (CDCl₃) 1.38-1.47 (m, 3H), 1.56 (s, 3H), 2.16 (s, 3H), 2.69 (m, 2H), 4.29 (m, 1H), 6.98 (s, 1H); and 1-(difluoromethyl)-3-methyl-pyrazol-4-amine (210 mg) from 270 mg of 3-methyl-4-nitro-1-(difluoromethyl)pyrazole.

Example 13.01

8-[[5-chloro-2-[(1-isopropyl-3-methyl-pyrazol-4-yl)amino]-4-pyridyl]amino]-2-methyl-3,4-dihydroisoquinolin-1-one

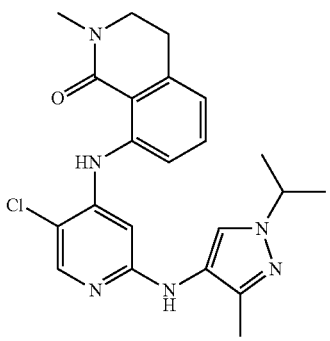 [SMILES: Cc1nn(C(C)C)cc1Nc1cc(Nc2cccc3c2C(=O)N(C)CC3)c(Cl)cn1]

This compound was prepared from 8-[(2,5-dichloropyridin-4-yl)amino]-2-methyl-3,4-dihydroisoquinolin-1-one and 1-isopropyl-3-methyl-pyrazol-4-amine.

Column chromatography (SiO$_2$, 20 equiv.; 95:5; DCM:MeOH) followed by preparative TLC performed (SiO$_2$: 20×20 cm; 1000 μM, Analtech, 100% EtOAc). Obtained from this was 25 mg of the title compound.

$^1$H NMR spectrum (CDCl$_3$) 1.43 (d, 6H), 2.13 (s, 3H), 2.92 (t, 2H), 3.12 (s, 3H), 3.52 (t, 2H), 4.29-4.43, (m, 1H), 5.89 (s, 1H), 6.43 (s, 1H), 6.67 (dd, 1H), 7.15 (dd, 1H) 7.24 (d, 1H), 7.25 (s, 1H), 7.39 (s, 1H), 7.96 (s, 1H); Mass spectrum: ESI+ MH$^+$ 425.

1-isopropyl-3-methyl-pyrazol-4-amine was obtained from 1-isopropyl-3-methyl-4-nitropyrazole. This starting material was prepared as follows:

To a stirred of solution of 3-methyl-4-nitro-1H-pyrazole (0.3 g, 2.4 mmol) in DMF (10 mL) was added potassium carbonate (0.4 g, 2.9 mmol) and 2-iodopropane (0.72 mL, 7.2 mmol). The solution was stirred at room temperature for 3 hours. The reaction mixture was poured into water (50 mL) and extracted into ether (4×30 mL). The combined ethereal extracts were dried (MgSO$_4$) and the solvent removed under vacuum to give a pale yellow oil. Several purifications were performed via column chromatography (SiO$_2$; 200 equiv. 100% DCM) to give 1-isopropyl-3-methyl-4-nitropyrazole (11 mg, 93% isomeric purity). This was combined with another batch (110 mg, purified identically).

Example 13.02

2-[[2-[(1-isopropyl-3-methyl-pyrazol-4-yl)amino]-5-(trifluoromethyl)-4-pyridyl]amino]-N-methyl-benzamide

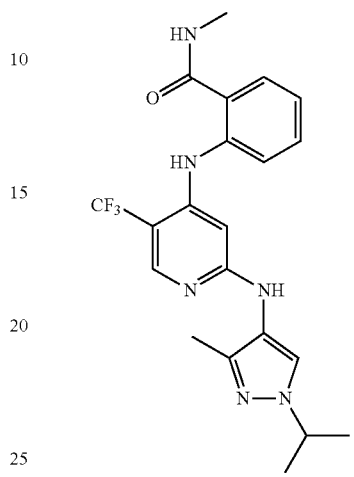

This compound was prepared from 2-[[2-chloro-5-(trifluoromethyl)pyridin-4-yl]amino]-N-methylbenzamide and 1-isopropyl-3-methyl-pyrazol-4-amine.

Column chromatography of crude material (SiO$_2$, 20 equiv.; 95:5; EtOAc:MeOH) followed by 2 prep. TLC was performed (SiO$_2$: 20×20 cm; 1000 μM, Analtech, 95:5; EtOAc:MeOH and SiO$_2$: 20×20 cm; 1000 μM, Analtech, 100% ether); 12 mg $^1$H NMR spectrum (methanol-D3) 1.33 (d, 6H), 2.01 (s, 3H), 1.91 (s, 3H), 2.77 (s, 3H), 4.27-4.30 (m, 1H), 6.29 (s, 1H), 7.03 (ddd, 1H), 7.32 (ddd, 1H), 7.33 (dd, 1H), 7.51 (dd, 1H), 7.58 (s, 1H), 8.00 (s, 1H); Mass spectrum: ESI+ MH$^+$ 433

Example 13.03

2-[[2-[[1-(difluoromethyl)-3-methyl-pyrazol-4-yl]amino]-5-(trifluoromethyl)-4-pyridyl]amino]-N-methyl-benzamide

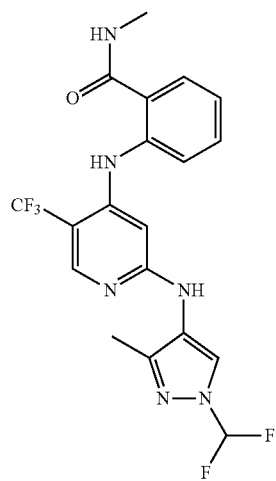 [SMILES: CNC(=O)c1ccccc1Nc1cc(Nc2cn(C(F)F)nc2C)ncc1C(F)(F)F]

This compound was prepared from 2-[[2-chloro-5-(trifluoromethyl)pyridin-4-yl]amino]-N-methylbenzamide and 1-(difluoromethyl)-3-methyl-pyrazol-4-amine. Column chromatography performed (SiO$_2$, 50 equiv.; 50:50; EtOAc:MeOH) followed by SCX-2 'catch and release' (2 g isolute flash SCX-2, eluting with 100% MeOH then methanolic ammonia 0.5 M→7 M) and further column chromatography (SiO$_2$, 50 equiv.; DCM:MeOH; 95:5) to give 38 mg of product.

$^1$H NMR spectrum (CDCl$_3$) 2.20 (s, 3H), 2.95 (d, 3H), 6.17 (s, 1H), 6.22 (q, 1H), 6.41 (s, 1H), 7.03 (dd, 1H), 7.04 (t, 1H), 7.36 (dd, 1H), 7.40-7.50 (m, 2H), 7.98 (s, 1H), 8.27 (s, 1H), 9.63 (s, 1H); Mass spectrum: ESI+ MH$^+$ 441

1-(difluoromethyl)-3-methyl-pyrazol-4-amine was obtained from 3-methyl-4-nitro-1-(difluoromethyl)pyrazole. This starting material was prepared as follows:

3-Methyl-4-nitro-1H-pyrazole (0.35 g, 2.8 mmol) was dissolved in DMF (10 mL), Potassium carbonate (0.86 g, 6.2 mmol) was added and the mixture stirred at room temperature for 5 minutes. The resulting solution was purged with chlorodifluoromethane for 5 hours after which time no starting material remained. The mixture was cautiously poured into H$_2$O (100 mL) and extracted into ether (5×30 mL). The combined ethereal extracts were dried (MgSO$_4$) and the solvent removed to give a yellow oil (0.65 g). Column chromatography (SiO$_2$; 100 g, 50/50: DCM:heptane) was performed to give 3-methyl-4-nitro-1-(difluoromethyl)pyrazole as a colourless oil (200 mg)

Example 13.04

8-[[5-chloro-2-[[1-(difluoromethyl)-3-methyl-pyrazol-4-yl]amino]-4-pyridyl]amino]-2-methyl-3,4-dihydroisoquinolin-1-one

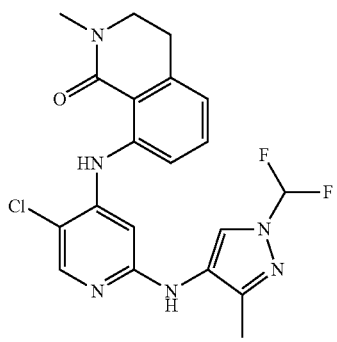 [SMILES: Cc1nn(C(F)F)cc1Nc1cc(Nc2cccc3c2C(=O)N(C)CC3)c(Cl)cn1]

This compound was prepared from 8-[(2,5-dichloropyridin-4-yl)amino]-2-methyl-3,4-dihydroisoquinolin-1-one and 1-(difluoromethyl)-3-methyl-pyrazol-4-amine. Column chromatography (SiO$_2$, 50 equiv.; 50:50; EtOAc:MeOH) followed by re-crystallisation from warm MeOH (1-2 mL) furnished 64 mg of the desired product.

$^1$H NMR spectrum (CDCl$_3$) 2.22 (s, 3H), 2.96 (t, 2H), 3.15 (s, 3H), 3.55 (t, 2H), 5.73 (s, 1H), 6.60 (s, 1H), 6.75 (d, 1H), 7.04 (t, 1H), 7.25 (dd partially hidden by CHCl$_3$, 1H), 7.35 (dd, 1H), 7.99 (s, 1H), 8.05 (s, 1H), 11.15 (s, 1H); Mass spectrum: ESI+ MH$^+$ 433

Example 13.05

8-[[5-chloro-2-[[1-(2-hydroxyethyl)-3-methyl-pyrazol-4-yl]amino]-4-pyridyl]amino]-2-methyl-3,4-dihydroisoquinolin-1-one

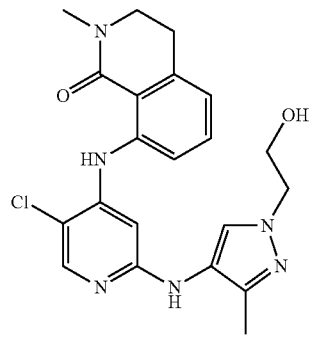 [SMILES: Cc1nn(CCO)cc1Nc1cc(Nc2cccc3c2C(=O)N(C)CC3)c(Cl)cn1]

This compound was prepared from 8-[(2,5-dichloropyridin-4-yl)amino]-2-methyl-3,4-dihydroisoquinolin-1-one and 2-(4-amino-3-methyl-pyrazol-1-yl)ethanol. Column chromatography (SiO$_2$, 50 equiv.; 95:5; EtOAc:MeOH) followed by prep. TLC (SiO$_2$: 20×20 cm; 1000 µM, Analtech, EtOAc:MeOH; 95:5) furnished 45 mg of the desired compound. $^1$H NMR spectrum (CDCl$_3$) 2.09 (s, 3H), 2.91 (t, 2H), 3.11 (s, 3H), 3.25 (bs, 1H), 3.51 (t, 2H), 3.86-3.95 (m, 2H), 4.05-4.10 (m, 2H), 5.89 (s, 1H), 6.44 (s, 1H), 6.68 (d, 1H), 7.14-7.29 (m, 2H), 7.44 (s, 1H), 7.88 (s, 1H), 11.09 (s, 1H); Mass spectrum: ESI+ MH$^+$ 427

2-(4-Amino-3-methyl-pyrazol-1-yl)ethanol was obtained from 2-(3-methyl-4-nitropyrazol-1-yl)ethanol. This starting material was prepared as follows:

To a stirred solution of 3-methyl-4-nitro-1H-pyrazole (15.7 g) in toluene (525 mL) was added potassium carbonate (20.5 g). The suspension was stirred for 20 minute at room temperature followed by the addition of ethyl bromoacetate (16.5 mL). The mixture was heated to 80° C. and stirred overnight. Further ethyl bromo acetate (6.5 mL) was added and the reaction mixture stirred for a further 12 h at 80° C. Upon cooling, the mixture was filtered from suspended solids, washing with DCM (100 mL) and dried (Na$_2$SO$_4$). Volatiles were removed in vacuo to give a yellow oil (35 g). Dry column (SiO$_2$, 420 g; 14-40 µM, Merck, 100% DCM) chromatography was performed on the bulk material (25 g) giving material enriched in the desired isomer.

Dry flash column chromatography was repeated on the material enriched in the desired isomer until 2.4 g of ethyl 2-(3-methyl-4-nitropyrazol-1-yl)acetate (>90% isomerically purity material) was obtained.

To a stirred solution of the ethyl 2-(3-methyl-4-nitropyrazol-1-yl)acetate (0.69 g, 3.24 mmol) in THF (24 mL) at −20° C. under N$_2$ was added diisobutylaluminum hydride (1M in toluene, 6.5 mL) over 5 min. maintaining the temperature below −20° C. The solution was allowed to warm to room temperature overnight. The reaction mixture was poured into sat. aq. citric acid (60 mL). The phases were separated and the aqueous phase extracted with EtOAc (4×30 mL). The combined organic phase was washed with sat. aq. sodium potassium L-tartrate (3×20 mL) and brine (30 mL), dried (MgSO$_4$)

and the solvent removed to give 2-(3-methyl-4-nitropyrazol-1-yl)ethanol as a pale yellow oil (0.50 g, 91%). Mass spectrum: MH+ 172

Example 13.06

2-[[2-[[1-(2-hydroxyethyl)-3-methyl-pyrazol-4-yl]amino]-5-(trifluoromethyl)-4-pyridyl]amino]-N-methyl-benzamide

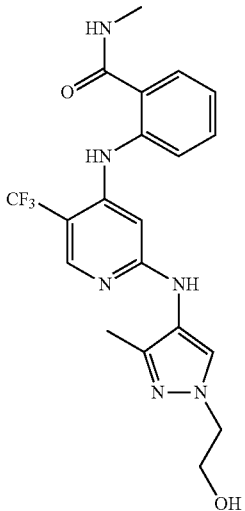 [SMILES: CNC(=O)c1ccccc1Nc1cc(Nc2cn(CCO)nc2C)ncc1C(F)(F)F]

This compound was prepared from 2-[[2-chloro-5-(trifluoromethyl)pyridin-4-yl]amino]-N-methylbenzamide and 2-(4-amino-3-methyl-pyrazol-1-yl)ethanol.

Prep. TLC performed (SiO$_2$: 20×20 cm; 1000 µM, Analtech, eluted twice with DCM:MeOH; 95:5). Obtained was 45 mg of product.

$^1$H NMR spectrum (CDCl$_3$) 2.11 (s, 3H), 2.92 (d, 3H), 3.40 (bs, 1H), 3.92 (t, 2H), 4.10 (t, 2H), 5.96 (s, 1H), 6.18 (s, 1H), 6.25 (q, 1H), 7.03 (ddd, 1H), 7.28-7.37 (m, 2H), 7.46 (s, 1H), 7.49 (d, 1H), 8.01 (s, 1H), 9.22 (s, 1H); Mass spectrum: ESI+ MH+ 435

Example 14

NMR spectra for examples 14.01 to 14.03 were recorded on a BRUKER AVANCE 500 MHz at 24° C.

Example 14.01

2-[[2-[(1,3-dimethylpyrazol-4-yl)amino]-5-(trifluoromethyl)-4-pyridyl]amino]-N,6-dimethoxy-benzamide

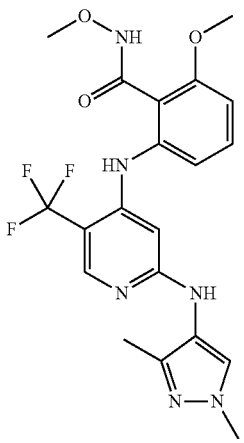 [SMILES: CONC(=O)c1c(Nc2cc(Nc3cn(C)nc3C)ncc2C(F)(F)F)cccc1OC]

9,9-dimethyl-4,5-bis(diphenylphosphino)xanthene (34.1 mg, 0.06 mmol), palladium(II) acetate (7.93 mg, 0.04 mmol), 2-amino-N,6-dimethoxybenzamide (131 mg, 0.67 mmol), N-(1,3-dimethylpyrazol-4-yl)-4-iodo-5-(trifluoromethyl)pyridin-2-amine (150 mg, 0.39 mmol) and cesium carbonate (256 mg, 0.79 mmol) were weighed out in a microwave vial, sealed and dioxane (5 mL) was added. Argon was bubbled through the mixture for 5 minutes. The reaction was stirred at 90° C. overnight. The reaction mixture was allowed to cool to room temperature, diluted with DCM and MeOH. Silica gel was added and the mixture was concentrated. The crude product was purified by flash chromatography on silica gel (25 g) eluting with 0 to 5% MeOH in EtOAc/DCM (1:1). The solvent was evaporated to dryness. The residue was triturated in Et$_2$O and the resulting precipitate was collected by filtration, washed with Et$_2$O and dried to a constant weight to afford the title compound (131 mg, 74.1%) as a off-white solid. NMR Spectrum: (DMSOd$_6$) 2.04 (s, 3H), 3.62 (s, 3H), 3.69 (s, 3H), 3.81 (s, 3H), 6.31 (bs, 1H), 6.89 (d, 1H), 7.06 (d, 1H), 7.43 (dd, 1H), 7.79 (s, 1H), 7.86 (s, 1H), 8.14 (s, 1H), 8.38 (s, 1H), 11.38 (s, 1H); Mass spectrum: MH+ 451.

The 2-amino-N,6-dimethoxybenzamide used as starting material was made as follows:

A mixture of 2-amino-6-methoxybenzoic acid (4.6 g, 27.52 mmol) and carbonyl-1,1'-dimidazole (5.35 g, 33.02 mmol) in THF (70 ml) was stirred at 21° C. under nitrogen for 3 days. N,N-diisopropyl-N-ethyl-amine (1.667 ml, 9.57 mmol) and O-methylhydroxylaminehydrochloride (0.545 ml, 7.18 mmol) were added. The solution was heated to 50° C. for 3 hours. After cooling and concentration under vacuum, the reaction mixture was diluted with EtOAc, washed with a saturated aqueous solution of sodium hydrogencarbonate, water and brine, dried over magnesium sulfate, concentrated under vacuum. The residue was purified by flash chromatography on silica gel eluting with 10 to 20% EtOAc in DCM to afford 2-amino-N,6-dimethoxybenzamide (318 mg, 33.9%) as a white solid. Mass spectrum: MH+ 197; NMR Spectrum: (DMSOd$_6$) 3.67 (s, 3H), 3.71 (s, 3H), 5.57 (bs, 2H), 6.19 (d, 1H), 6.31 (d, 1H), 7.02 (dd, 1H)

The following compounds were obtained from N-(1,3-dimethylpyrazol-5-yl)-4-iodo-5-(trifluoromethyl)pyridin-2-amine (150 mg, 0.39 mmol) and the corresponding aniline using the procedure in Example 14.01:

Example 14.02

2-[[2-[(2,5-dimethylpyrazol-3-yl)amino]-5-(trifluoromethyl)-4-pyridyl]amino]-N-methoxy-benzamide

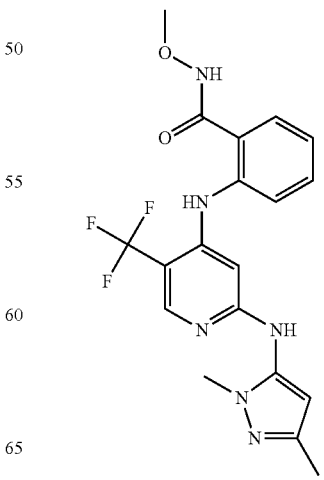

Triturated in Et$_2$O 99 mg as a off-white solid, 60%; NMR Spectrum: (DMSOd$_6$) 2.07 (s, 3H), 3.54 (s, 3H), 3.70 (s, 3H), 6.00 (s, 1H), 6.65 (s, 1H), 7.14 (dd, 1H), 7.53 (dd, 1H), 7.55-7.63 (m, 2H), 8.24 (s, 1H), 9.00 (s, 1H), 9.58 (bs, 1H), 11.92 (bs, 1H); Mass spectrum: MH$^+$ 421

Example 14.03

2-[[2-[(2,5-dimethylpyrazol-3-yl)amino]-5-(trifluoromethyl)-4-pyridyl]amino]-N,6-dimethoxy-benzamide

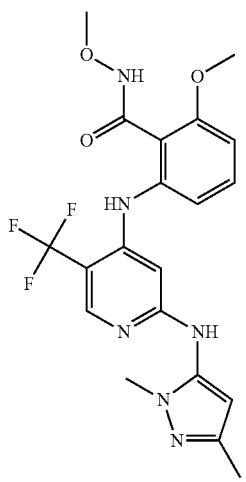 [SMILES: CONC(=O)c1c(Nc2cc(Nc3cc(C)nn3C)ncc2C(F)(F)F)cccc1OC]

Triturated in tBuOMe 124 mg as a off-white solid, 70%; NMR Spectrum: (DMSOd$_6$) 2.06 (s, 3H), 3.52 (s, 3H), 3.62 (s, 3H), 3.81 (s, 3H), 5.96 (s, 1H), 6.34 (s, 1H), 6.93 (d, 1H), 7.08 (d, 1H), 7.45 (dd, 1H), 7.95 (s, 1H), 8.17 (s, 1H), 8.94 (s, 1H), 11.36 (s, 1H); Mass spectrum: MH$^+$ 451

The N-(1,3-dimethylpyrazol-5-yl)-4-iodo-5-(trifluoromethyl)pyridin-2-amine used as starting material was made as follows:

A suspension of 2,5-dimethylpyrazol-3-amine (1 g, 9.00 mmol), potassium acetate (0.971 g, 9.90 mmol) and acetic anhydride (1.002 mL, 9.00 mmol) in EtOAc (25 mL) was stirred at 25° C. overnight. Silica gel was added and the mixture was concentrated. The crude product was purified by flash chromatography on silica gel eluting with 0 to 5% MeOH in DCM. The solvent was evaporated to dryness to afford N-(2,5-dimethylpyrazol-3-yl)acetamide (1.400 g, 102%) as a pale yellow oil. Mass spectrum: MH$^+$ 154 Sodium hydride (0.385 g, 9.14 mmol) was added to N-(2,5-dimethylpyrazol-3-yl)acetamide (1.4 g, 9.14 mmol) dissolved in THF (20 mL) under nitrogen. The resulting light suspension was stirred at 35° C. for 30 minutes then 2-chloro-4-iodo-5-(trifluoromethyl)pyridine (1.338 g, 4.35 mmol) was added. DMF (2 mL) was added and the mixture was stirred at 80° C. for 18 hours. The reaction mixture was cooled to room temperature, quenched with water (20 mL). Lithium hydroxide hydrate (0.548 g, 13.06 mmol) was added and the mixture was stirred at room temperature for 1.5 hours. The mixture was diluted with EtOAc and water, the phases were separated and the organic phase washed with brine, dried over magnesium sulfate and concentrated. The residue was purified by flash chromatography on silica gel (40 g) eluting with 0 to 50% EtOAc in DCM. After collection of the fractions and evaporation of the solvents, the resulting solid was triturated in petroleum ether, collected by filtration, washed with petroleum ether and dried to a constant weight to afford N-(2,5-dimethylpyrazol-3-yl)-4-iodo-5-(trifluoromethyl)pyridin-2-amine (900 mg, 54.1%) as an off-white solid.

NMR Spectrum: (CDCl$_3$) 2.29 (s, 3H), 3.69 (s, 3H), 5.98 (s, 1H), 6.56 (bs, 1H), 7.08 (s, 1H), 8.30 (s, 1H); Mass spectrum: MH$^+$ 383

Example 15

NMR spectra for examples 15.01 to 15.08 were recorded on a BRUKER AVANCE 500 MHz at 24° C.

Example 15.01

2-[[2-[(1,3-dimethylpyrazol-4-yl)amino]-5-(trifluoromethyl)-4-pyridyl]amino]-4-fluoro-N-methoxybenzamide

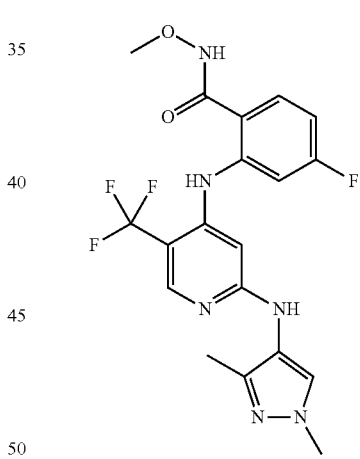

2-amino-4-fluoro-N-methoxybenzamide (90 mg, 0.49 mmol) and N-(1,3-dimethylpyrazol-4-yl)-4-iodo-5-(trifluoromethyl)pyridin-2-amine (110 mg, 0.29 mmol) were reacted according to the procedure of example 14.01. After chromatography, the solvent was evaporated to dryness, the residue triturated in tBuOMe and the resulting precipitate was collected by filtration and dried to a constant weight to afford the title compound (50 mg, 39.6%) as a white solid. NMR Spectrum: (DMSO-d$_6$) 2.08 (s, 3H), 3.70 (s, 3H), 3.71 (s, 3H), 6.71 (bs, 1H), 6.93 (ddd, 1H), 7.36 (dd, 1H), 7.66 (dd, 1H), 7.87 (s, 1H), 8.24 (1, 1H), 8.52 (s, 1H), 9.99 (bs, 1H), 11.95 (s, 1H); Mass spectrum: MH$^+$ 439

The 2-amino-4-fluoro-N-methoxybenzamide used as starting material was prepared as follows:

Bis(trichloromethyl) carbonate (3.73 g, 12.57 mmol) was added to a solution of 2-amino-4-fluorobenzoic acid (1.3 g, 8.38 mmol) in sodium hydroxide (2N in water) (8.80 mL, 17.60 mmol) and water (9 mL) at room temperature. The resulting suspension was stirred for 15 minutes then toluene (9.00 mL) was added. The mixture was stirred at room temperature for 18 hours. The resulting precipitate was collected by filtration, washed with water, followed by 20% acetonitrile in Et$_2$O (10 mL) and dried under vacuum at 40° C. to afford 7-fluoro-1H-3,1-benzoxazine-2,4-dione (0.852 g, 56.1%) as a off-white solid.

NMR Spectrum: (DMSO-d$_6$) 6.88 (dd, 1H), 7.21 (ddd, 1H), 8.00 (dd, 1H), 11.87 (s, 1H). 7-fluoro-1H-3,1-benzoxazine-2,4-dione (0.85 g, 4.69 mmol) was added to stirred solution of O-methylhydroxylamine hydrochloride (1.960 g, 23.47 mmol) in a 2N aqueous solution of sodium hydroxide (11.73 ml, 23.47 mmol) at 25° C. The resulting solution was stirred at room temperature for 2 hours. The solution was diluted with EtOAc, washed sequentially with water and brine. The organic layer was dried over magnesium sulfate and evaporated. The crude product was purified by flash chromatography on silica gel eluting with 0 to 5% MeOH in DCM to afford 2-amino-4-fluoro-N-methoxybenzamide (0.390 g, 45.1%) as a white crystalline solid. NMR Spectrum: (DMSOd$_6$) 3.67 (s, 3H), 6.30 (dd, 1H), 6.47 (ddd, 1H), 6.62 (bs, 2H), 7.37 (dd, 1H), 11.40 (s, 1H)

The compounds of example 15.02 to 15.08 were obtained using the procedure of example 14.01.

Example 15.02

2-[[2-[(2,5-dimethylpyrazol-3-yl)amino]-5-(trifluoromethyl)-4-pyridyl]amino]-4-fluoro-N-methoxybenzamide

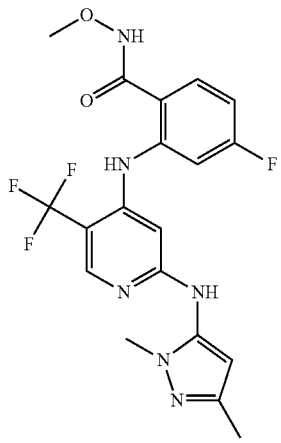 [SMILES: CONC(=O)c1ccc(F)cc1Nc1cc(Nc2cc(C)nn2C)ncc1C(F)(F)F]

This compound was prepared from N-(1,3-dimethylpyrazol-5-yl)-4-iodo-5-(trifluoromethyl)pyridin-2-amine and 2-amino-4-fluoro-N-methoxybenzamide. 81 mg, 48%; triturated in Et$_2$O; NMR Spectrum: (DMSOd$_6$) 2.08 (s, 3H), 3.55 (s, 3H), 3.70 (s, 3H), 6.04 (s, 1H), 6.74 (s, 1H), 6.97 (ddd, 1H), 7.43 (dd, 1H), 7.66 (dd, 1H), 8.28 (s, 1H), 9.07 (s, 1H), 10.04 (bs, 1H), 11.96 (bs, 1H); Mass spectrum: MH$^+$ 439.

Example 15.03

2-[[2-[(2,5-dimethylpyrazol-3-yl)amino]-5-(trifluoromethyl)-4-pyridyl]amino]-4-fluoro-N-methyl-benzamide

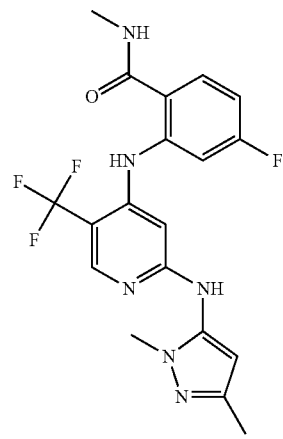 [SMILES: CNC(=O)c1ccc(F)cc1Nc1cc(Nc2cc(C)nn2C)ncc1C(F)(F)F]

This compound was prepared from N-(1,3-dimethylpyrazol-5-yl)-4-iodo-5-(trifluoromethyl)pyridin-2-amine and 2-amino-4-fluoro-N-methylbenzamide. 54 mg, 33%; triturated in tBuOMe; NMR Spectrum: (DMSOd$_6$) 2.08 (s, 3H), 2.76 (d, 3H), 3.55 (s, 3H), 6.04 (s, 1H), 6.76 (s, 1H), 6.95 (ddd, 1H), 7.39 (dd, 1H), 7.79 (dd, 1H), 8.27 (s, 1H), 8.69 (q, 1H), 9.06 (s, 1H), 10.65 (s, 1H); Mass spectrum: MH$^+$ 423.

Example 15.04

2-Methoxy-N-methyl-6-[[5-(trifluoromethyl)-2-[(1,3,5-trimethylpyrazol-4-yl)amino]-4-pyridyl]amino]benzamide

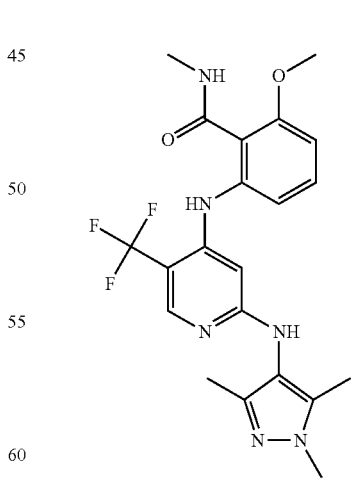

This compound was obtained from 4-iodo-5-(trifluoromethyl)-N-(1,3,5-trimethylpyrazol-4-yl)pyridin-2-amine and 2-amino-6-methoxy-N-methylbenzamide. Heated for 6 hours; trituration in pentane then washed with very little Et$_2$O; 89 mg, 68%; NMR Spectrum: (DMSOd$_6$) 1.92 (s, 3H), 2.02 (s, 3H), 2.72 (d, 3H), 3.60 (s, 3H), 3.80 (s, 3H), 6.02 (bs, 1H), 6.81 (d, 1H), 6.97 (bs, 1H), 7.34 (dd, 1H), 8.08 (s, 1H), 8.11 (s, 1H), 8.27 (q, 1H), 8.74 (s, 1H); Mass spectrum: MH+ 449.

The 4-iodo-5-(trifluoromethyl)-N-(1,3,5-trimethylpyrazol-4-yl)pyridin-2-amine used as starting material was made as follows:

A suspension of 1,3,5-trimethylpyrazol-4-amine (1 g, 7.99 mmol), potassium acetate (0.862 g, 8.79 mmol) and acetic anhydride (0.889 mL, 7.99 mmol) in EtOAc (25 mL) was stirred at 25° C. overnight. Silica gel was added and the mixture was concentrated. The crude product was purified by flash chromatography on silica gel eluting with 0 to 5% MeOH in DCM. The solvent was evaporated to dryness to afford N-(1,3,5-trimethylpyrazol-4-yl)acetamide (1.390 g, 104%) as a off-white solid. Mass spectrum: MH+ 168

N-(1,3,5-trimethylpyrazol-4-yl)acetamide (1.142 g, 6.83 mmol) was added to sodium hydride (0.288 g, 6.83 mmol) suspended in nitrogen-degassed DMF (5 mL) under nitrogen. The resulting light suspension was stirred at 35° C. for 30 minutes then 2-chloro-4-iodo-5-(trifluoromethyl)pyridine (1 g, 3.25 mmol) was added. The reaction mixture was allowed to cool to room temperature, stirred for 1 hour and quenched with water (20 mL). Lithium hydroxide hydrate (0.409 g, 9.76 mmol) was added, the mixture was stirred at room temperature for 1.5 hour and then diluted with EtOAc and water. The phases were separated and the organic phase was washed with brine, dried over magnesium sulfate and concentrated. The crude product was purified by flash chromatography on silica gel (40 g) eluting with 0 to 50% EtOAc in DCM to afford 4-iodo-5-(trifluoromethyl)-N-(1,3,5-trimethylpyrazol-4-yl)pyridin-2-amine (350 mg, 27.2%) as an off-white solid.

NMR Spectrum: (CDCl₃ at 297° K) 2.10 (s, 3H), 2.13 (s, 3H), 3.77 (s, 3H), 6.16 (bs, 1H), 6.81 (s, 1H), 8.24 (s, 1H); Mass spectrum: MH+ 397.

Example 15.05

N,2-dimethoxy-6-[[5-(trifluoromethyl)-2-[(1,3,5-trimethylpyrazol-4-yl)amino]-4-pyridyl]amino]benzamide

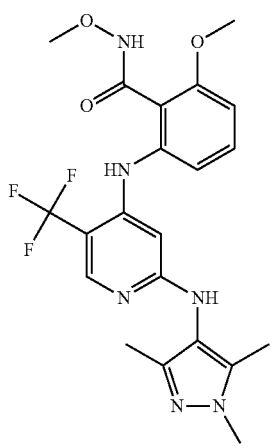 [SMILES: CONC(=O)c1c(Nc2cc(Nc3c(C)nn(C)c3C)ncc2C(F)(F)F)cccc1OC]

This compound was obtained from 4-iodo-5-(trifluoromethyl)-N-(1,3,5-trimethylpyrazol-4-yl)pyridin-2-amine and 2-amino-N,6-dimethoxybenzamide. 81 mg, 60%; heated for 6 hours; trituration in Et₂O; NMR Spectrum: (DMSOd₆) 1.91 (s, 3H), 2.02 (s, 3H), 3.59 (s, 3H), 3.63 (s, 3H), 3.80 (s, 3H), 5.95 (bs, 1H), 6.85 (d, 1H), 6.98 (bs, 1H), 7.39 (dd, 1H), 7.86 (s, 1H), 8.08 (s, 1H), 8.12 (s, 1H), 11.39 (s, 1H); Mass spectrum: MH+ 465.

Example 15.06

N-methoxy-2-[[5-(trifluoromethyl)-2-[(1,3,5-trimethylpyrazol-4-yl)amino]-4-pyridyl]amino]benzamide

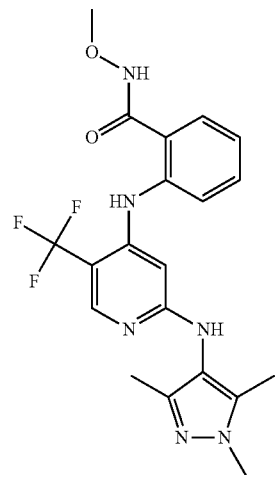 [SMILES: CONC(=O)c1ccccc1Nc1cc(Nc2c(C)nn(C)c2C)ncc1C(F)(F)F]

This compound was obtained from 4-iodo-5-(trifluoromethyl)-N-(1,3,5-trimethylpyrazol-4-yl)pyridin-2-amine and 2-amino-N-methoxybenzamide. Heated for 18 hours; trituration in Et₂O, 79 mg, 62%; NMR Spectrum: (DMSOd₆) 1.93 (s, 3H), 2.02 (s, 3H), 3.60 (s, 3H), 3.69 (s, 3H), 6.21 (bs, 1H), 7.08 (dd, 1H), 7.47 (bs, 2H), 7.56 (d, 1H), 8.13 (s, 1H), 8.16 (s, 1H), 9.50 (s, 1H), 11.89 (s, 1H); Mass spectrum: MH+ 435;

Example 15.07

2-[[2-[(2,5-dimethylpyrazol-3-yl)amino]-5-(trifluoromethyl)-4-pyridyl]amino]-N-ethoxy-benzamide

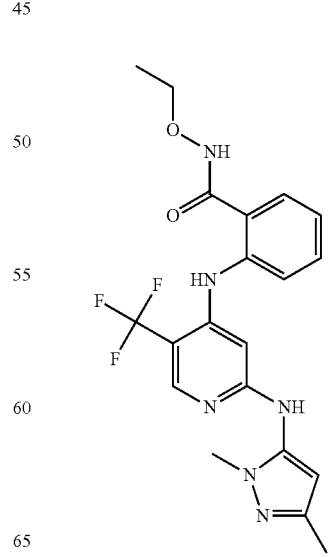

This compound was obtained from 4-iodo-5-(trifluoromethyl)-N-(1,3-dimethylpyrazol-5-yl)pyridin-2-amine and 2-amino-N-ethoxybenzamide. Heated for 14 hours (addition of more catalyst after 12 hours); dissolved in Et$_2$O and precipitated by addition of petroleum ether; 127 mg, 74.5% as a white solid. NMR Spectrum: (DMSOd$_6$) 1.19 (t, 3H), 2.07 (s, 3H), 3.53 (s, 3H), 3.92 (q, 2H), 6.00 (s, 1H), 6.64 (s, 1H), 7.14 (dd, 1H), 7.52 (dd, 1H), 7.57 (d, 1H), 7.60 (d, 1H), 8.23 (s, 1H), 8.99 (s, 1H), 9.56 (bs, 1H), 11.80 (bs, 1H); Mass spectrum: MH$^+$ 435

The 2-amino-N-ethoxybenzamide used as starting material was prepared as follows:

1H-3,1-benzoxazine-2,4-dione (372 mg, 2.28 mmol) was added portionwise to a stirred solution of O-ethylhydroxylamine hydrochloride (890 mg, 9.12 mmol) and sodium hydroxide 2N (4.56 mL, 9.12 mmol) in water (15 mL) cooled with an ice bath. The resulting solution was stirred for 2 hours leaving the ice bath to warm slowly. The reaction was stirred at room temperature for 2 hours. EtOAc (20 mL) was added and the 2 phases were separated. Aqueous layer was extracted with EtOAc (3×10 mL). The combined organic layers were washed with brine, dried over magnesium sulfate and concentrated to dryness. The crude product was purified by flash chromatography on silica gel eluting with 0 to 30% EtOAc in DCM. The solvent was evaporated to dryness to afford 2-amino-N-ethoxybenzamide (339 mg, 82%) as a pale yellow oil which crystallised on standing.

NMR Spectrum: (DMSOd$_6$) 1.19 (t, 3H), 3.89 (q, 2H), 6.25 (bs, 2H), 6.48 (dd, 1H), 6.70 (d, 1H), 7.14 (dd, 1H), 7.32 (d, 1H), 11.28 (bs, 1H); Mass spectrum: M–H$^-$ 179.

Example 15.08

2-[[2-[(2,5-dimethylpyrazol-3-yl)amino]-5-(trifluoromethyl)-4-pyridyl]amino]-N-(2-hydroxyethoxy)benzamide

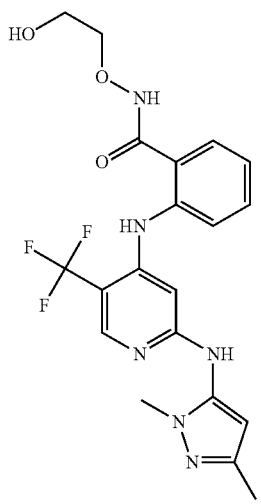 [SMILES: Cc1cc(Nc2cc(Nc3ccccc3C(=O)NOCCO)c(C(F)(F)F)cn2)n(C)n1]

This compound was obtained from 4-iodo-5-(trifluoromethyl)-N-(1,3-dimethylpyrazol-5-yl)pyridin-2-amine and 2-amino-N-(2-hydroxyethoxy)benzamide. Heated for 14 hours (addition of more catalyst after 12 hours); triturated in Et$_2$O and petroleum ether and the resulting precipitate was sonicated for 10 minutes, 86 mg, 49% as a yellow solid. NMR Spectrum: (DMSOd$_6$) 2.07 (s, 3H), 3.54 (s, 3H), 3.57-3.64 (m, 2H), 3.87-3.95 (m, 2H), 4.74 (bs, 1H), 6.00 (s, 1H), 6.65 (s, 1H), 7.13 (dd, 1H), 7.51 (dd, 1H), 7.57 (d, 1H), 7.62 (d, 1H), 8.24 (s, 1H), 8.99 (s, 1H), 9.57 (bs, 1H), 11.91 (bs, 1H); Mass spectrum: MH$^+$ 451

The 2-amino-N-(2-hydroxyethoxy)benzamide used as starting material was made as follows:

1H-3,1-benzoxazine-2,4-dione (320 mg, 1.96 mmol) and 2-(aminooxy)ethanol hemisulfate (990 mg, 3.92 mmol) were reacting using the procedure of example 15.07, starting material. The crude product was purified by flash chromatography on silica gel eluting with 0 to 80% EtOAc in DCM. The solvent was evaporated to dryness to afford 2-amino-N-(2-hydroxyethoxy)benzamide (256 mg, 66.5%) as a pale yellow oil which solidified on standing. NMR Spectrum: (DMSOd$_6$) 3.57-3.64 (m, 2H), 3.85-3.92 (m, 2H), 4.75 (bs, 1H), 6.27 (bs, 2H), 6.49 (dd, 1H), 6.71 (d, 1H), 7.15 (ddd, 1H), 7.34 (dd, 1H), 11.39 (bs, 1H); Mass spectrum: MH$^+$ 197

Example 16

The appropriate pyrazole amine (0.36 mmol), palladium (II) acetate (5.43 mg, 0.02 mmol), 9,9-dimethyl-4,5-bis(diphenylphosphino)xanthene (28.0 mg, 0.05 mmol) and cesium carbonate (118 mg, 0.36 mmol) were weighed out in a microwave vial and sealed. 2-[[2-chloro-5-(trifluoromethyl)-4-pyridyl]amino]-5-fluoro-N-methoxybenzamide (110 mg, 0.30 mmol) dissolved in dioxane (4 mL) was added and argon was bubbled through the mixture for 5 minutes. The resulting mixture was stirred at 95° C. The reaction mixture was allowed to cool to room temperature, silica gel was added and the mixture was concentrated to afford the crude product, was purified by flash chromatography on silica gel eluting with 0 to 5% MeOH in EtOAc/DCM (1:1). The solvent was evaporated to dryness, the resulting gummy residue was triturated in a specified solvent, collected by filtration and dried to afford the desired compound as a solid.

Example 16.01

2-[[2-[(2,5-dimethylpyrazol-3-yl)amino]-5-(trifluoromethyl)-4-pyridyl]amino]-5-fluoro-N-methoxybenzamide

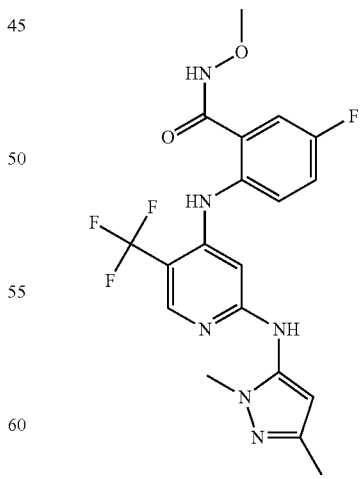

This compound was prepared using 1,3-dimethylpyrazole-5-amine. Heating time: 2 hours; triturated in tBuOMe/pentane (1:1); 55 mg, 39%; NMR Spectrum: (DMSOd$_6$) 2.07 (s, 3H), 3.53 (s, 3H), 3.58 (s, 3H), 5.98 (s, 1H), 5.49 (s, 1H), 7.42

(dd. 1H), 7.46 (dd, 1H), 7.60 (dd, 1H), 8.22 (s, 1H), 8.96 (s, 1H), 9.20 (bs, 1H), 11.94 (bs, z1H); Mass spectrum: MH+ 439

The 2-[[2-chloro-5-(trifluoromethyl)-4-pyridyl]amino]-5-fluoro-N-methoxybenzamide used as starting material was prepared as follows:

Using the procedure in example 15.01, 2-amino-5-fluorobenzoic acid (1.5 g, 9.67 mmol) was converted into 6-fluoro-1H-3,1-benzoxazine-2,4-dione (1.2 g, 68.5%) as an pale yellow solid; and 6-fluoro-1H-3,1-benzoxazine-2,4-dione (1.05 g, 5.80 mmol) converted into 2-amino-5-fluoro-N-methoxybenzamide (0.344 g, 32.2%) as a yellow pale solid after purification by 2 flash chromatographies on silica gel (eluting with 0 to 50% EtOAc in DCM; eluting with 20% EtOAc in DCM). NMR Spectrum: (DMSOd$_6$) 3.68 (s, 3H), 6.19 (bs, 2H), 6.72 (dd, 1H), 7.07 (ddd, 1H), 7.15 (dd, 1H), 11.48 (bs, 1H) 2-chloro-4-iodo-5-(trifluoromethyl)pyridine (0.502 g, 1.63 mmol), 2-amino-5-fluoro-N-methoxybenzamide (0.344 g, 1.68 mmol), palladium(II) acetate (0.029 g, 0.13 mmol), 9,9-dimethyl-4,5-bis(diphenylphosphino)xanthene (0.151 g, 0.26 mmol) and cesium carbonate (0.638 g, 1.96 mmol) were weighed out in a microwave vial and sealed. Dioxane (10.3 ml) was added and argon bubbled through the reaction mixture followed by stirring at 90° C. for 5 hours. The reaction mixture was allowed to cool to room temperature, silica gel was added and the mixture was concentrated to afford the crude, which was purified by flash chromatography on silica gel eluting with 20 to 50% EtOAc. The solvent was evaporated to dryness to afford 2-[[2-chloro-5-(trifluoromethyl)-4-pyridyl]amino]-5-fluoro-N-methoxy-benzamide (0.240 g, 40%) as an yellow oil which crystallised on standing. NMR Spectrum: (DMSOd$_6$) 3.62 (s, 3H), 6.85 (s, 1H), 7.43-7.51 (m, 2H), 7.60 (dd, 1H), 7.44 (s, 1H), 9.37 (bs, 1H), 11.88 (bs, 1H); Mass spectrum: MH+ 364

Example 16.02

2-[[2-[(1,3-dimethylpyrazol-4-yl)amino]-5-(trifluoromethyl)-4-pyridyl]amino]-5-fluoro-N-methoxy-benzamide

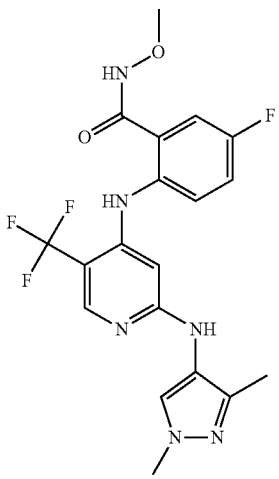 [SMILES: CONC(=O)c1cc(F)ccc1Nc1cc(Nc2cn(C)nc2C)ncc1C(F)(F)F]

This compound was prepared using 1,3-dimethylpyrazole-4-amine. Heating time: 3.5 hours; triturated in Et$_2$O; 57 mg, 40%; NMR Spectrum: (DMSOd$_6$) 2.05 (s, 3H), 3.69 (s, 3H), 3.70 (s, 3H), 6.45 (bs, 1H), 7.42 (dd, 1H), 7.45 (d, 1H), 7.56 (dd, 1H), 7.83 (s, 1H), 8.18 (s, 1H), 8.40 (s, 1H), 9.15 (s, 1H), 11.95 (bs, 1H); Mass spectrum: MH+ 439

The invention claimed is:
1. A compound of formula I:

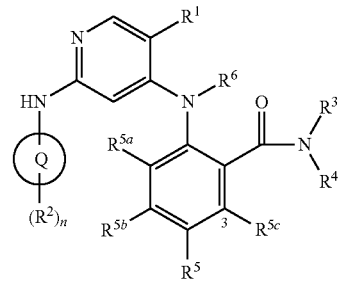

wherein:
ring Q is selected from pyrazolyl and imidazolyl;
$R^1$ is selected from halo, trifluoromethyl, cyclopropyl, cyano, $C_{1-4}$alkyl and $C_{1-4}$alkoxy;
n is 0, 1, 2 or 3; wherein the values of $R^2$ may be the same or different;
$R^2$ is selected from halo, nitro, cyano, hydroxy, trifluoromethoxy, amino, carboxy, carbamoyl, mercapto, ureido, sulfonylamino, $C_{1-6}$alkyl, $C_{2-6}$alkenyl, $C_{2-6}$alkynyl, $C_{1-6}$alkoxy, $C_{2-6}$alkenyloxy, $C_{2-6}$alkynyloxy, $C_{1-6}$alkanoyl, $C_{1-6}$alkanoyloxy, N—($C_{1-6}$alkyl)amino, N,N—($C_{1-6}$alkyl)$_2$-amino, N'—($C_{1-6}$alkyl)ureido, N',N'—($C_{1-6}$ alkyl)$_2$ureido, N'—($C_{1-6}$alkyl)-N—($C_{1-6}$alkyl) ureido, N',N'—($C_{1-6}$alkyl)$_2$-N—($C_{1-6}$alkyl)ureido, $C_{1-6}$alkanoylamino, N—($C_{1-6}$alkyl)-$C_{1-6}$alkanoylamino, N—($C_{1-6}$alkyl)carbamoyl, N,N—($C_{1-6}$alkyl)$_2$-carbamoyl, $C_{1-6}$alkylS(O)$_a$ wherein a is 0 to 2, $C_{1-6}$alkylsulfonylamino, N—($C_{1-6}$alkyl)aminosulfonyl, N,N—($C_1$-6alkyl)$_2$-aminosulfonyl, $C_{1-6}$alkoxycarbonyl, $C_{1-6}$alkoxycarbonylamino, N—($C_{1-6}$alkyl)$C_1$-6 alkoxycarbonylamino, $C_{1-6}$alkylsulfonylaminocarbonyl, N—($C_1$-6alkyl)$C_{1-6}$alkylsulfonylaminocarbonyl, carbocyclyl-$X^1$—, heterocyclyl-$X^2$— and heteroaryl-$X^3$—;
wherein $R^2$ may be optionally substituted on carbon by one or more $R^7$; and wherein if a heterocyclyl or heteroaryl within $R^2$ contains an —NH— moiety that nitrogen may be optionally substituted by a group selected from $R^8$;
and wherein any heterocyclyl within $R^2$ optionally bears 1 or 2 oxo or thioxo substituents;
or two adjacent $R^2$ groups together with the carbon atoms to which they are attached form a carbocyclic, heteroaromatic or heterocyclic ring, which carbocyclic, heterocyclic or heteroaromatic ring may be optionally substituted on carbon by one or more $R^9$; and wherein if said heterocyclic or heteroaromatic ring so formed contains an —NH— moiety that nitrogen may be optionally substituted by a group selected from $R^{10}$; and wherein a carbocyclic or heterocyclic so formed optionally bears 1 oxo substituent;
$R^3$ is selected from hydrogen, hydroxy, $C_{1-4}$alkyl and $C_{1-4}$alkoxy; and wherein $R^3$ may be optionally substituted on carbon by one or more substituents selected from hydroxy, amino, $C_{1-4}$alkoxy, N—($C_{1-4}$alkyl)amino and N,N—($C_{1-4}$alkyl)$_2$-amino;
$R^4$ is selected from hydrogen and $C_{1-4}$alkyl; and wherein $R^4$ may be optionally substituted on carbon by one or more substituents selected from hydroxy, amino, $C_{1-4}$-alkoxy, N—($C_{1-4}$alkyl)amino and N,N—($C_{1-4}$-alkyl)$_2$-amino;

or $R^3$ and $R^4$ together with the nitrogen atom to which they are attached form a 4 or 5 membered heterocyclyl ring, which heterocyclyl ring may be optionally substituted on carbon by one or more $C_{1-4}$alkyl;

or the —C(O)NR$^3$R$^4$ group together with the carbon atom to which it is attached and the R$^{5c}$ group together with the carbon atom to which it is attached (3-position of the phenyl ring) form a heterocyclic ring, which heterocyclic ring contains a —C(O)N(R$^3$)— group as a ring member; wherein R$^3$ is as hereinbefore defined, or the N(R$^3$) ring member together with an adjacent ring member together form a heterocyclic ring;

and wherein any heterocyclic ring so formed by the C(O)NR$^3$R$^4$ or NR$^3$ ring member may be optionally substituted on carbon by one or more $R^{3a}$ selected from $C_{1-4}$alkyl, $C_{1-4}$alkoxy, halo, cyano, hydroxy and oxo; and wherein if said heterocyclyl ring contains an —NH— moiety that nitrogen may be optionally substituted by $R^{3b}$ selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl and N,N—($C_{1-4}$-alkyl)carbamoyl;

R$^5$ is selected from hydrogen, halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$ alkanoylamino, N—($C_{1-6}$alkyl)carbamoyl, N,N—($C_{1-6}$alkyl)$_2$-carbamoyl, $C_{1-6}$alkylS(O)$_b$ wherein b is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl, $C_{1-6}$alkylsulfonylamino, carbocyclyl-X$^7$—, heterocyclyl-X$^8$— and heteroaryl-X$^9$—;

and wherein R$^5$ may be optionally substituted on carbon by one or more groups selected from halo, nitro, cyano, hydroxy, amino, $C_{1-4}$alkyl, $C_{1-4}$alkoxy, N—($C_{1-4}$alkyl)amino, N,N—($C_{1-4}$alkyl)$_2$-amino, carbocyclyl-X$^{10}$—, heterocyclyl-X$^{11}$— and heteroaryl-X$^{12}$—; and wherein if a heterocyclyl or heteroaryl within R$^5$ contains an —NH— moiety that nitrogen may be optionally substituted by a group selected from $C_{1-4}$alkyl, $C_{1-4}$alkanoyl, $C_{1-4}$alkylsulfonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulfonyl;

and wherein any heterocyclyl within R$^5$ optionally bears 1 or 2 oxo or thioxo substituents;

R$^{5a}$ is selected from hydrogen and halo;

R$^{5b}$ and R$^{5c}$ are independently selected from hydrogen, halo, nitro, cyano, hydroxy, amino, carboxy, carbamoyl, mercapto, sulfamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$-amino, $C_{1-4}$-alkanoylamino, N—($C_{1-4}$alkyl)carbamoyl, N,N—($C_{1-4}$alkyl)$_2$-carbamoyl, $C_{1-4}$alkylS(O)$_c$ wherein c is 0 to 2, $C_{1-4}$alkoxycarbonyl, $C_{1-4}$alkoxycarbonylamino, N—($C_{1-4}$alkyl)sulfamoyl, N,N—($C_{1-4}$alkyl)$_2$sulfamoyl and $C_{1-4}$alkylsulfonylamino; and wherein R$^{5b}$ and R$^{5c}$ may be independently optionally substituted on carbon by one or more groups selected from halo, nitro, cyano, hydroxy, amino, $C_{1-4}$alkoxy, N—($C_{1-4}$alkyl)amino and N,N—($C_{1-4}$-alkyl)$_2$-amino;

R$^6$ is selected from hydrogen and $C_{1-4}$alkyl;

R$^7$ and R$^9$ are independently selected from halo, nitro, cyano, hydroxy, amino, carboxy, carbamoyl, mercapto, sulfamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$-amino, $C_{1-6}$alkanoylamino, N—($C_{1-6}$alkyl)carbamoyl, N,N—($C_{1-6}$alkyl)$_2$-carbamoyl, $C_{1-6}$alkylS(O)$_d$ wherein d is 0 to 2, $C_{1-6}$alkoxycarbonyl, $C_{1-6}$alkoxycarbonylamino, N—($C_{1-6}$alkyl)sulfamoyl, N,N—($C_{1-6}$alkyl)$_2$sulfamoyl, $C_{1-6}$alkylsulfonylamino, carbocyclyl-X$^4$—, heterocyclyl-X$^5$— and heteroaryl-X$^6$—; wherein R$^7$ may be optionally substituted on carbon by one or more R$^{11}$; and wherein if any heterocyclyl in R$^7$ and R$^9$ contains an —NH— moiety that nitrogen may be optionally substituted by a group selected from R$^{12}$;

and wherein any heterocyclyl within R$^7$ and R$^9$ optionally bears 1 or 2 oxo or thioxo substituents;

R$^8$, R$^{10}$ and R$^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulfonyl; wherein R$^8$, R$^{10}$ and R$^{12}$ may be optionally substituted on carbon by one or more R$^{13}$; and R$^{11}$ and R$^{13}$ are independently selected from halo, nitro, cyano, hydroxy, trifluoromethoxy, trifluoromethyl, amino, carboxy, carbamoyl, mercapto, sulfamoyl, methyl, ethyl, cyclopropyl, cyclobutyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl and N-methyl-N-ethylsulfamoyl;

$X^1$, $X^2$ and $X^3$ are independently selected from a direct bond, —O—, —N(R$^{22}$)—, —S—, —C(O)—, —N(R$^{14}$)C(O)—, —C(O)N(R$^{14}$)—, —N(R$^{16}$)CON(R$^{17}$)—, —OC(R$^{18}$)$_2$—, —SC(R$^{19}$)$_2$— and —N(R$^{20}$)C(R$^{21}$)$_2$—;

$X^4$, $X^5$ and $X^6$ are independently selected from a direct bond, —O—, —N(R$^{22}$)—, —C(O)—, —N(R$^{14}$)C(O)—, —C(O)N(R$^{14}$)—, —S(O)$_e$—, —SO$_2$N(R$^{15}$)—, —N(R$^{15}$)SO$_2$—, —N(R$^{16}$)CON(R$^{17}$)—, —OC(R$^{18}$)$_2$—, —SC(R$^{19}$)$_2$— and —N(R$^{20}$)C(R$^{21}$)$_2$—;

$X^7$, $X^8$ and $X^9$ are independently selected from a direct bond, —O—, —N(R$^{22}$)—, —S—, —C(O)—, —N(R$^{14}$)C(O)—, —C(O)N(R$^{14}$)—, —N(R$^{16}$)CON(R$^{17}$)—, —OC(R$^{18}$)$_2$—, —SC(R$^{19}$)$_2$— and —N(R$^{20}$)C(R$^{21}$)$_2$—;

$X^{10}$, $X^{11}$ and $X^{12}$ are independently selected from a direct bond, —O—, —N(R$^{22}$)—, —C(O)—, —N(R$^{14}$)C(O)—, —C(O)N(R$^{14}$)—, —S(O)$_e$—, —SO$_2$N(R$^{15}$)—, —N(R$^{15}$)SO$_2$—, —N(R$^{16}$)CON(R$^{17}$)—, —OC(R$^{18}$)$_2$—, —SC(R$^{19}$)$_2$— and —N(R$^{20}$)C(R$^{21}$)$_2$—; and R$^{14}$, R$^{15}$, R$^{16}$, R$^{17}$, R$^{18}$, R$^{19}$, R$^{20}$, R$^{21}$ and R$^{22}$ are independently selected from hydrogen or $C_{1-6}$alkyl and e is independently 0-2; or a pharmaceutically acceptable salt thereof.

2. The compound according to claim 1, wherein the compound is 2-[[2-[(1,3-dimethylpyrazol-4-yl)amino]-5-(trifluoromethyl)-4-pyridyl]amino]-5-fluoro-N-methoxy-benzamide, or a pharmaceutically acceptable salt thereof.

3. A compound of formula I according to claim 1, or a pharmaceutically acceptable salt thereof, wherein:

R$^2$ is selected from cyano, $C_{1-6}$alkyl and $C_{1-6}$alkoxy, wherein $C_{1-6}$alkyl and $C_{1-6}$alkoxy may be optionally substituted on carbon by one or more R$^7$; or R$^2$ is selected from:

(i) $C_{3-7}$cycloalkyl-$X^1$—, wherein $X^1$ is selected from a direct bond, —O—, —$N(R^{14})C(O)$— and —$C(O)N(R^{14})$—, and $R^{14}$ is hydrogen or $C_{1-4}$alkyl;

(ii) heterocyclyl-$X^2$—, wherein $X^2$ is a direct bond, which heterocyclyl is carbon linked to $X^2$ and is selected from azetidinyl, tetrahydrofuranyl, tetrahydropyranyl, pyrrolidinyl, morpholinyl, thiomorpholinyl, thiomorpholinyl 1,1-dioxide, piperidinyl, piperazinyl, tetrahydrothienyl, tetrahydrothienyl 1,1-dioxide, homopiperidinyl, homopiperazinyl, quinuclidinyl and tetrahydropyridazinyl (such as 1,4,5,6-tetrahydropyridazin-3-yl); and which cycloalkyl or heterocyclyl may be optionally substituted on carbon by one or more $R^7$; and wherein if a heterocyclyl within $R^2$ contains an —NH— moiety that nitrogen may be optionally substituted by a group selected from $R^8$; and wherein any heterocyclyl within $R^2$ optionally bears 1 or 2 oxo substituents;

$R^7$ is selected from halo, hydroxy, amino, carbamoyl, $C_{1-6}$alkyl, $C_{3-7}$cycloalkyl, $C_{1-6}$alkoxy, $C_{1-6}$alkanoyl, N—($C_{1-6}$alkyl)amino, N,N—($C_{1-6}$alkyl)$_2$-amino, N—($C_{1-6}$alkyl)carbamoyl, N,N—($C_{1-6}$alkyl)$_2$-carbamoyl, $C_{3-7}$cycloalkyl and heterocyclyl, which heterocyclyl is selected from azetidinyl, tetrahydrofuranyl, tetrahydropyranyl, pyrrolidinyl, morpholinyl, piperidinyl, piperazinyl, homopiperidinyl, homopiperazinyl and diazepanyl;

and wherein $R^7$ may be independently optionally substituted on carbon by one or more $R^{11}$ selected from halo, amino, hydroxy, methyl, ethyl, cyclopropyl, cyclobutyl, methoxy, ethoxy, methylamino, ethylamino, dimethylamino, diethylamino and N-methyl-N-ethylamino; and wherein if any heterocyclyl in $R^7$ contains an —NH— moiety that nitrogen may be optionally substituted by a group selected from $R^{12}$; and wherein any heterocyclyl or cycloalkyl within $R^7$ optionally bears 1 or 2 oxo substituents;

$R^8$ and $R^{12}$ are independently selected from selected from $C_{1-6}$alkyl, $C_{1-6}$alkanoyl, $C_{1-6}$alkylsulfonyl, $C_{1-6}$alkoxycarbonyl, carbamoyl, N—($C_{1-6}$alkyl)carbamoyl and N,N—($C_{1-6}$alkyl)$_2$-carbamoyl; wherein $R^8$ and $R^{12}$ may be optionally substituted on carbon by one or more $R^{13}$ selected from halo, hydroxy, cyclopropyl, cyclobutyl, methoxy and ethoxy; and $R^{14}$ is selected from hydrogen or $C_{1-6}$alkyl.

4. A compound of formula I according to claim 1, or a pharmaceutically acceptable salt thereof, wherein $R^1$ is selected from halo, trifluoromethyl and cyano.

5. A compound of formula I according to claim 1, or a pharmaceutically acceptable salt thereof, wherein $R^1$ is chloro.

6. A compound of formula I according to claim 1, or a pharmaceutically acceptable salt thereof, wherein $R^3$ is $C_{1-4}$-alkoxy and $R^4$ is selected from hydrogen and $C_{1-4}$-alkyl.

7. A compound of formula I according to claim 1, or a pharmaceutically acceptable salt thereof, wherein $R^6$ is hydrogen.

8. A compound of formula I according to claim 1, or a pharmaceutically acceptable salt thereof; wherein:

ring Q is pyrazolyl;
$R^1$ is selected from fluoro and chloro;
n is 1 or 2;
$R^3$ is selected from hydrogen, $C_{1-3}$alkyl and $C_{1-3}$alkoxy;
$R^4$ is selected from hydrogen and $C_{1-3}$alkyl; or the $C(O)NR^3R^4$ group together with the carbon atom to which it is attached and the $R^{5c}$ group together with the carbon atom to which it is attached (at the 3-position on the phenyl ring) form a heterocyclic ring fused to the phenyl ring such that the aniline at the 4-position on the pyridine ring in formula I is selected from:

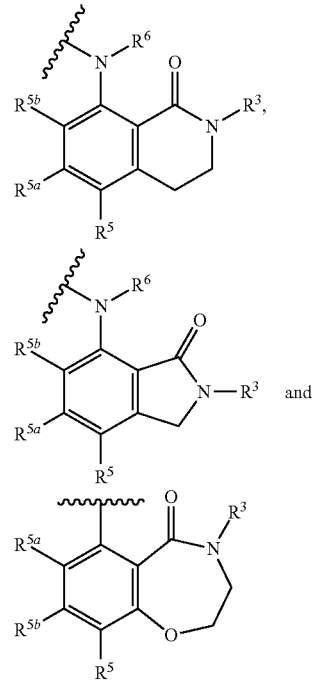

wherein the heterocyclic ring so formed by the $C(O)NR^3R^4$ ring member may be optionally substituted on carbon by one or more $R^{3a}$ selected from $C_{1-4}$alkyl, $C_{1-4}$alkoxy, halo, cyano, hydroxy and oxo; and $R^6$ is hydrogen.

9. A compound of formula I according to claim 1, or a pharmaceutically acceptable salt thereof, wherein $R^5$ is hydrogen, fluoro, 4-methylpiperazinyl or 4-isopropylpiperazinyl.

10. A compound of formula I according to claim 1, or a pharmaceutically acceptable salt thereof, wherein $R^5$ is hydrogen.

11. A compound of formula I according to claim 1, or a pharmaceutically acceptable salt thereof, wherein $R^{5a}$ is hydrogen or fluoro.

12. A compound of formula I according to claim 1, or a pharmaceutically acceptable salt thereof, wherein $R^{5a}$ is hydrogen.

13. A compound of formula I according to claim 1, or a pharmaceutically acceptable salt thereof, wherein $R^{5b}$ is hydrogen.

14. A compound of formula I according to claim 1, or a pharmaceutically acceptable salt thereof, wherein $R^{5c}$ is hydrogen, halo or $C_{1-4}$alkoxy.

15. A compound of formula I according to claim 1, or a pharmaceutically acceptable salt thereof, wherein $R^{5c}$ is hydrogen.

16. A pharmaceutical composition which comprises a compound of the formula, or a pharmaceutically acceptable thereof, as defined in claim 1 in association with a pharmaceutically-acceptable diluent or carrier.

17. A process for preparing a compound according to claim 1, or a pharmaceutically acceptable salt thereof, comprising: Process (a)

the palladium catalysed coupling, in the presence of a suitable base, of a compound of the formula II:

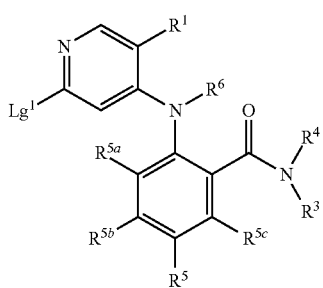

II wherein $R^1$, $R^3$, $R^4$, $R^5$, $R^{5a}$, $R^{5b}$, $R^{5c}$ and $R^6$ are as hereinbefore defined, except any functional group is protected if necessary, and $Lg^1$ is a suitable displaceable group,
with a compound of the formula III:

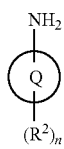

III wherein ring Q, $R^2$ and n are as hereinbefore defined, except any functional group is protected if necessary; or Process (b)
the palladium catalysed coupling in the presence of a suitable base of a compound of the formula IV:

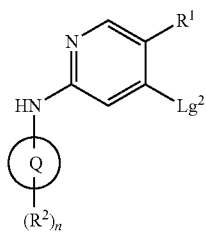

IV wherein ring Q, $R^1$, $R^2$ and n are as hereinbefore defined, except any functional group is protected if necessary, and $Lg^2$ is a suitable displaceable group,
with a compound of the formula V:

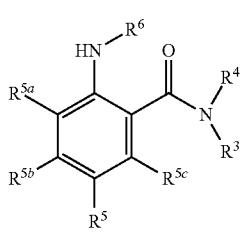

V wherein $R^3$, $R^4$, $R^5$, $R^{5a}$, $R^{5b}$, $R^{5c}$ and $R^6$ are as hereinbefore defined, except any functional group is protected if necessary; or Process (b')
the coupling of a compound of the formula IV (as shown above) with a compound of formula V (as shown above) under acidic conditions; or Process (c)
the coupling of a compound of the formula VI or a reactive derivative thereof:

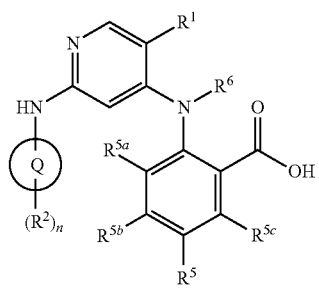

VI wherein ring Q, $R^1$, $R^2$, $R^5$, $R^{5a}$, $R^{5b}$, $R^{5c}$, $R^6$ and n are as hereinbefore defined, except any functional group is protected if necessary,
with an amine of the formula VII:

$HNR^3R^4$  VII wherein $R^3$ and $R^4$ are as hereinbefore defined, except any functional group is protected if necessary; or
for the preparation of those compounds of the formula I wherein an $R^2$ is linked to ring Q by a —$N(R^{14})C(O)$— group or a —$N(R^{14})C(O)CH_2$— group the coupling of a compound of the formula VIII, or a reactive derivative thereof:

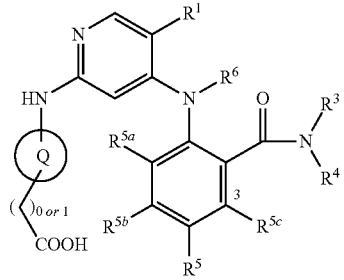

VIII wherein ring Q, $R^1$, $R^2$, $R^3$, $R^4$, $R^5$, $R^{5a}$, $R^{5b}$, $R^{5c}$ and $R^6$ are as hereinbefore defined, except any functional group is protected if necessary,
with an appropriate amine such that the coupling with the compound of formula VIII gives an amide linked $R^2$ substituent as hereinbefore defined;
and thereafter, if necessary (in any order):
(i) converting a compound of the formula I into another compound of the formula I;
(ii) removing any protecting groups; and
(iii) forming a pharmaceutically acceptable salt of the compound of formula I.

* * * * *